United States Patent
Merchant et al.

(10) Patent No.: US 11,542,312 B2
(45) Date of Patent: Jan. 3, 2023

(54) IL-2 SUPERAGONISTS IN COMBINATION WITH ANTI-PD-1 ANTIBODIES

(71) Applicant: Medicenna Therapeutics, Inc., Toronto (CA)

(72) Inventors: Fahar Merchant, Vancouver (CA); Shafique Fidai, Vancouver (CA)

(73) Assignee: Medicenna Therapeutics, Inc., Toronto (CA)

( * ) Notice: Subject to any disclaimer, the term of this patent is extended or adjusted under 35 U.S.C. 154(b) by 375 days.

(21) Appl. No.: 16/012,733

(22) Filed: Jun. 19, 2018

(65) Prior Publication Data

US 2019/0062395 A1    Feb. 28, 2019

Related U.S. Application Data

(60) Provisional application No. 62/521,957, filed on Jun. 19, 2017, provisional application No. 62/679,687, filed on Jun. 1, 2018.

(51) Int. Cl.

| | | |
|---|---|---|
| A61K 38/20 | (2006.01) | |
| A61K 39/395 | (2006.01) | |
| C07K 14/55 | (2006.01) | |
| C07K 16/28 | (2006.01) | |
| C07K 16/30 | (2006.01) | |
| C07K 19/00 | (2006.01) | |
| C07K 14/76 | (2006.01) | |
| A61P 35/00 | (2006.01) | |
| A61K 38/17 | (2006.01) | |
| A61K 39/00 | (2006.01) | |
| C12N 7/00 | (2006.01) | |
| A61K 35/76 | (2015.01) | |

(52) U.S. Cl.
CPC ......... *C07K 14/55* (2013.01); *A61K 38/1709* (2013.01); *A61K 38/2013* (2013.01); *A61K 39/0011* (2013.01); *A61K 39/3955* (2013.01); *A61K 39/39541* (2013.01); *A61P 35/00* (2018.01); *C07K 14/76* (2013.01); *C07K 16/283* (2013.01); *C07K 16/2818* (2013.01); *C07K 16/2896* (2013.01); *C07K 19/00* (2013.01); *C12N 7/00* (2013.01); *A61K 35/76* (2013.01); *A61K 2039/505* (2013.01); *A61K 2039/5256* (2013.01); *A61K 2039/55533* (2013.01); *C07K 2317/76* (2013.01); *C07K 2319/30* (2013.01); *C07K 2319/31* (2013.01); *C12N 2710/10034* (2013.01); *C12N 2710/10043* (2013.01); *C12N 2710/24134* (2013.01); *C12N 2710/24143* (2013.01)

(58) Field of Classification Search
CPC .... A61K 38/19; A61K 38/2013; A61K 39/00; A61K 39/3955; A61K 39/395; A61K 2039/505; A61K 2319/30; C07K 2319/00; C07K 14/54; C07K 16/2896; C07K 2317/76; C07K 16/22; C07K 16/24
See application file for complete search history.

(56) References Cited

U.S. PATENT DOCUMENTS

| | | |
|---|---|---|
| 4,522,811 A | 6/1985 | Eppstein et al. |
| 4,530,787 A | 7/1985 | Shaked et al. |
| 4,569,790 A | 2/1986 | Koths et al. |
| 4,572,798 A | 2/1986 | Koths et al. |
| 4,604,377 A | 8/1986 | Fernandes et al. |
| 4,656,132 A | 4/1987 | Ben-Bassat et al. |
| 4,738,927 A | 4/1988 | Taniguchi et al. |
| 4,748,234 A | 5/1988 | Dorin et al. |
| 4,816,249 A | 5/1989 | Levy et al. |
| 4,931,543 A | 6/1990 | Halenbeck et al. |
| 5,068,177 A | 11/1991 | Carson et al. |
| 5,122,464 A | 6/1992 | Wilson et al. |
| 5,227,159 A | 7/1993 | Miller |
| 5,538,866 A | 7/1996 | Israeli et al. |
| 6,011,002 A | 1/2000 | Pastan et al. |
| 6,451,308 B1 | 9/2002 | Strom et al. |
| 6,468,798 B1 | 10/2002 | Debs et al. |
| 6,617,135 B1 | 9/2003 | Gillies et al. |
| 6,682,736 B1 | 1/2004 | Hanson et al. |
| 6,984,720 B1 | 1/2006 | Korman et al. |
| 7,001,596 B1 | 2/2006 | Johnson et al. |
| 7,288,638 B2 | 10/2007 | Jure-Kunkel et al. |
| 7,741,465 B1 | 6/2010 | Eshhar et al. |

(Continued)

FOREIGN PATENT DOCUMENTS

| | | |
|---|---|---|
| EP | 338841 | 10/1989 |
| WO | WO 1991/02000 | 2/1991 |

(Continued)

OTHER PUBLICATIONS

Bolt et al. The generation of a humanized, non-mitogenic CD3 monoclonal antibody which retains in vitro immunosuppressive properties. Eur J Immunol 23: 403-411, 1993.*

(Continued)

*Primary Examiner* — Bridget E Bunner

(74) *Attorney, Agent, or Firm* — Morgan, Lewis & Bockius LLP

(57) ABSTRACT

Human interleukin-2 (IL-2) muteins or variants thereof are provided. In particular, provided are IL-2 muteins that have an increased binding capacity for IL-2Rβ receptor as compared to wild-type IL-2 for use in combination therapies with anti-PD-1 antibodies for the treatment of cancer. Also provided are pharmaceutical compositions that include such anti-PD-1 antibodies and the disclosed IL-2 muteins.

15 Claims, 18 Drawing Sheets

Specification includes a Sequence Listing.

(56) References Cited

U.S. PATENT DOCUMENTS

| | | | |
|---|---|---|---|
| 7,812,135 | B2 | 10/2010 | Smith et al. |
| 7,943,743 | B2 | 5/2011 | Korman et al. |
| 8,008,449 | B2 | 8/2011 | Korman et al. |
| 8,217,149 | B2 | 7/2012 | Irving et al. |
| 8,337,850 | B2 | 12/2012 | Ahrens et al. |
| 8,355,502 | B1 | 1/2013 | Donlin et al. |
| 8,821,867 | B2 | 9/2014 | Ahrens et al. |
| 8,962,804 | B2 | 2/2015 | Williams et al. |
| 9,428,567 | B2* | 8/2016 | Garcia ............... A61P 35/00 |
| 9,468,678 | B2 | 10/2016 | Ahrens et al. |
| 2002/0039581 | A1 | 4/2002 | Carreno et al. |
| 2002/0086014 | A1 | 7/2002 | Korman et al. |
| 2003/0138405 | A1 | 7/2003 | Fueyo et al. |
| 2005/0201994 | A1 | 9/2005 | Korman et al. |
| 2006/0147420 | A1 | 7/2006 | Fueyo et al. |
| 2006/0160187 | A1 | 7/2006 | Denis-Mize |
| 2006/0269515 | A1 | 11/2006 | Denis-Mize |
| 2010/0183545 | A1 | 7/2010 | Puri |
| 2010/0240732 | A1* | 9/2010 | Gilboa ............. A61K 31/7115 514/44 A |
| 2011/0150892 | A1 | 6/2011 | Thudium et al. |
| 2011/0017219 | A1 | 7/2011 | Merchant |
| 2011/0274650 | A1 | 11/2011 | Gavin et al. |
| 2011/0274685 | A1 | 11/2011 | Keler et al. |
| 2012/0213771 | A1 | 8/2012 | Keler et al. |
| 2012/0315245 | A1 | 12/2012 | Leon Monzon et al. |
| 2013/0022623 | A1 | 1/2013 | Karsunky et al. |
| 2013/0149236 | A1 | 6/2013 | Johnson et al. |
| 2014/0046026 | A1 | 2/2014 | Garcia |
| 2015/0203848 | A1* | 7/2015 | Yu ..................... C12N 15/1138 514/44 A |
| 2015/0268243 | A1* | 9/2015 | Hannani ......... G01N 33/57484 435/7.23 |
| 2016/0222117 | A1 | 8/2016 | Irving et al. |
| 2016/0257758 | A1 | 9/2016 | Gray et al. |
| 2017/0081409 | A1 | 3/2017 | Dijk et al. |
| 2017/0281764 | A1 | 10/2017 | Tso et al. |

FOREIGN PATENT DOCUMENTS

| | | |
|---|---|---|
| WO | WO 1999/45128 | 9/1999 |
| WO | WO 1999/60128 | 11/1999 |
| WO | WO 2001/027156 | 4/2001 |
| WO | WO 2001/036650 | 5/2001 |
| WO | WO 2003/048334 | 6/2003 |
| WO | WO 2005/007121 | 1/2005 |
| WO | WO 2006/029879 | 3/2006 |
| WO | WO 2006/081510 | 8/2006 |
| WO | WO 2008/039173 | 4/2008 |
| WO | WO 2010/077634 | 7/2010 |
| WO | WO 2010/096418 | 8/2010 |
| WO | WO 2012/032433 | 3/2012 |
| WO | WO 2012/054929 | 4/2012 |
| WO | WO 2012/088446 | 6/2012 |
| WO | WO 2010/085495 | 7/2012 |
| WO | WO 2012/119093 A1 | 9/2012 |
| WO | WO 2012/120125 | 9/2012 |
| WO | WO 2013/006490 | 1/2013 |
| WO | WO 2013/038066 | 3/2013 |
| WO | WO 2013/079174 | 6/2013 |
| WO | WO 2014/127261 | 8/2014 |
| WO | WO 2015/009856 | 1/2015 |
| WO | WO 2015/042707 | 4/2015 |
| WO | WO 2015/117229 | 8/2015 |
| WO | WO 2015/164815 | 10/2015 |
| WO | WO 2016/145085 | 9/2016 |
| WO | WO 2017/100541 | 6/2017 |

OTHER PUBLICATIONS

Borrok et al. An "Fc-silenced" IgG1 format with extended half-life designed for improved stability. J Pharmaceut Sci 106: 1008-1017, Jan. 2017.*

Carmenate et al. Human IL-2 mutein with higher antitumor efficacy than wild type IL-2. J Immunol 190: 6230-6238, 2013.*

Clinical Trial NCT02964078 history, dated Nov. 15, 2016 (10 total pages).*

Clinical Trial NCT02989714 history, dated Dec. 12, 2016 (8 total pages).*

Hamanishi et al. PD-1/PD-L1 blockade in cancer treatment: perspectives and issues. Int J Clin Oncol 21: 462-473, 2016.*

Huang et al. IL-2 synergizes with PD-1/PD-L1 blockade via CD28/CHK1 pathway to enhance CD81 T cell responses in lung squamous cell carcinoma. Annals Oncol 27(Suppl 9): ix123-ix125, abstract 653, 2016.*

Liu et al. Ongoing clinical trials of PD-1 and PD-L1 inhibitors for lung cancer in China. J Hematol Oncol 10: 136, 2017 (8 total pages).*

Ohaegbulam et al. Human cancer immunotherapy with antibodies to the PD-1 and PD-L1 pathway. Trends Mol Med 21(1): 24-33, 2015.*

West et al. PD-L1 blockade synergizes with IL-2 therapy in reinvigorating exhausted T cells. J Clin Invest 123(6): 2604-2615, 2013.*

Hannani et al. Anticancer therapy by CTLA-4 blockade: obligatory contribution of IL-2 receptor and negative prognostic impact of soluble CD25. Cell Res 25: 208-224, 2015.*

Ott et al. CTLA-4 and PD-1/PD-L1 blockade: new immunotherapeutic modalities with durable clinical benefit in melanoma patients. Clin Cancer Res 19(19): 5300-5309, 2013.*

Adams PD, et al. Identification of a cyclin-cdk2 recognition motif present in substrates and p21-like cyclin-dependent kinase inhibitors. Mol Cell Biol. 16(12), 6623-6633 (1996).

Adams PD, et al. Transcriptional control by E2F. Semin. Cancer Biol. 6(2), 99-108 (1995).

Allen C, et al. Interleukin-13 Displaying Retargeted Oncolytic Measles Virus Strains Have Significant Activity Against Gliomas With Improved Specificity. Mol Ther. 16(9), 1556-1564 (2008).

Baldari C, et al. A novel leader peptide which allows efficient secretion of a fragment of human interleukin 1 beta in *Saccharomyces cerevisiae*. EMBO J. 6(1), 229-234 (1987).

Batlevi CL, et al. Novel immunotherapies in lymphoid malignancies. Nat Rev Clin Oncol. 13(1), 25-40 (2016).

Berk AJ. Adenovirus Promoters and E1a Transactivation. Annual Review of Genetics. 20(1), 45-77 (1986).

Blanar MA, et al. Interaction cloning: identification of a helix-loop-helix zipper protein that interacts with c-Fos. Science. 256(5059), 1014-1018 (1992).

Boder ET, et al. Yeast surface display for screening combinatorial polypeptide libraries. Nat. Biotechnol. 15(6), 553-557 (1997).

Cate RL, et al. Isolation of the bovine and human genes for Müllerian inhibiting substance and expression of the human gene in animal cells. Cell. 45(5), 685-698 (1986).

Cheng G, et al. T cell tolerance and the multi-functional role of IL-2R signaling in T regulatory cells. Immunol Rev. 241(1), 63-76 (2011).

Freyer GA, et al. Characterization of the major mRNAs from adenovirus 2 early region 4 by cDNA cloning and sequencing. Nucleic Acids Res. 12(8), 3503-3519 (1984).

Fujita T, et al. Structure of the human interleukin 2 gene. Proceedings of the National Academy of Sciences. 80(24), 7437-7441 (1983).

Gilardi P, et al. The E4 transcriptional unit of Ad2: far upstream sequences are required for its transactivation by E1A. Nucleic Acids Res. 12(20), 7877-7888 (1984).

Gilardi P, et al. The E4 promoter of adenovirus type 2 contains an E1A dependent cis-acting element. Nucleic Acids Res. 14(22), 9035-9049 (1986).

Hanaka S, et al. Regulation of in vitro and in vivo transcription of early-region IV of adenovirus type 5 by multiple cis-acting elements. Mol Cell Biol. 7(7), 2578-2587 (1987).

Hatfield L, et al. The NFIII/OCT-1 binding site stimulates adenovirus DNA replication in vivo and is functionally redundant with adjacent sequences. J Virol. 67(7), 3931-3939 (1993).

(56) References Cited

OTHER PUBLICATIONS

Johnson DG, et al. Autoregulatory control of E2F1 expression in response to positive and negative regulators of cell cycle progression. Genes Dev. 8(13), 1514-1525 (1994).
Jones C, et al. E1A-mediated activation of the adenovirus E4 promoter can occur independently of the cellular transcription factor E4F. Mol Cell Biol. 11(9), 4297-4305 (1991).
Kahlon KS, et al. Specific Recognition and Killing of Glioblastoma Multiforme by Interleukin 13-Zetakine Redirected Cytolytic T Cells. Cancer Res. 64(24), 9160-9166 (2004).
Kaufman HL, et al. Oncolytic viruses: a new class of immunotherapy drugs. Nat Rev Drug Discov. 14(9), 642-662 (2015).
Kaufman RJ, et al. Construction of a modular dihydrofolate reductase cDNA gene: analysis of signals utilized for efficient expression. Mol Cell Biol. 2(11), 1304-1319 (1982).
Kaufman RJ, et al. Translational efficiency of polycistronic mRNAs and their utilization to express heterologous genes in mammalian cells. The EMBO Journal. 6(1), 187-193 (1987).
Kong S, et al. Suppression of Human Glioma Xenografts with Second-Generation IL13R-Specific Chimeric Antigen Receptor-Modified T Cells. Clin Cancer Res. 18(21), 5949-5960 (2012).
Kurjan J, et al. Structure of a yeast pheromone gene (MF alpha): a putative alpha-factor precursor contains four tandem copies of mature alpha-factor. Cell. 30(3), 933-943 (1982).
Leclair KP, et al. The p50 subunit of NF-kappa B associates with the NF-IL6 transcription factor. Proc Natl Acad Sci U S A. 89(17), 8145-8149 (1992).
Lee KA, et al. A cellular transcription factor E4F1 interacts with an E1a-inducible enhancer and mediates constitutive enhancer function in vitro. The EMBO Journal. 6(5), 1345-1353 (1987).
Lee SJ, et al. Proliferin secreted by cultured cells binds to mannose 6-phosphate receptors. J. Biol. Chem. 263(7), 3521-3527 (1988).
Lenardo MJ. Interleukin-2 programs mouse alpha beta T lymphocytes for apoptosis. Nature. 353(6347), 858-861 (1991).
Levin AM, et al. Exploiting a natural conformational switch to engineer an Interleukin-2 superkine. Nature. 484(7395), 529-533 (2012).
Liao W, et al. Interleukin-2 at the Crossroads of Effector Responses, Tolerance, and Immunotherapy. Immunity. 38(1), 13-25 (2013).
Liao W, et al. Cytokine receptor modulation by interleukin-2 broadly regulates T helper cell lineage differentiation. Nat Immunol. 12(6), 551-559 (2011).
Liao W, et al. Priming for T helper type 2 differentiation by interleukin 2-mediated induction of IL-4 receptor α chain expression. Nat Immunol. 9(11), 1288-1296 (2008).
Luckow VA, et al. High level expression of nonfused foreign genes with Autographa californica nuclear polyhedrosis virus expression vectors. Virology. 170(1), 31-39 (1989).
McCaffrey AP, et al. RNA interference in adult mice. Nature. 418(6893), 38-39 (2002).
Morgan DA, et al. Selective in vitro growth of T lymphocytes from normal human bone marrows. Science. 193(4257), 1007-1008 (1976).
Neuman E, et al. Transcription of the E2F-1 gene is rendered cell cycle dependent by E2F DNA-binding sites within its promoter. Mol Cell Biol. 15(8), 4660 (1995).
Neuman E, et al. Structure and partial genomic sequence of the human E2F1 gene. Gene. 173(2), 163-169 (1996).
Parr MJ, et al. Tumor-selective transgene expression in vivo mediated by an E2F-responsive adenoviral vector. Nat. Med. 3(10), 1145-1149 (1997).
Putnam DA. Antisense strategies and therapeutic applications. Am J Health Syst Pharm. 53(2), 151-160; quiz 182-183 (1996).
Rawlins DR, et al. Structure and function of the adenovirus origin of replication. Cell. 37(1), 309-319 (1984).
Rosenberg SA, et al. Biological activity of recombinant human interleukin-2 produced in *Escherichia coli*. Science. 223(4643), 1412-1414 (1984).
Rosenfeld PJ, et al. Sequence-specific interactions between cellular DNA-binding proteins and the adenovirus origin of DNA replication. Mol. Cell. Biol. 7(2), 875-886 (1987).

Schultz LD, et al. Expression and secretion in yeast of a 400-kDa envelope glycoprotein derived from Epstein-Barr virus. Gene. 54(1), 113-123 (1987).
Schmid S.I., et al. Selective encapsidation of adenovirus DNA. Current Topics In Microbiology And Immunology, 199(1), 67-80 (1995).
Seed B. An LFA-3 cDNA encodes a phospholipid-linked membrane protein homologous to its receptor CD2. Nature. 329(6142), 840-842 (1987).
Sellers WR, et al. A potent transrepression domain in the retinoblastoma protein induces a cell cycle arrest when bound to E2F sites. Proc Natl Acad Sci U S A. 92(25), 11544-11548 (1995).
Smith GE, et al. Modification and secretion of human interleukin 2 produced in insect cells by a baculovirus expression vector. Proc Natl Acad Sci U S A. 82(24), 8404-8408 (1985).
Smith GE, et al. Production of human beta interferon in insect cells infected with a baculovirus expression vector. Mol Cell Biol. 3(12), 2156-2165 (1983).
Taniguchi T, et al. Structure and expression of a cloned cDNA for human interleukin-2. Nature. 302(5906), 305-310 (1983).
Thaci B, et al. Significance of interleukin-13 receptor alpha 2-targeted glioblastoma therapy. Neuro Oncol. 16(10), 1304-1312 (2014).
Tigges MA, et al. Splice junctions in adenovirus 2 early region 4 mRNAs: multiple splice sites produce 18 to 24 RNAs. J Virol. 50(1), 106-117 (1984).
Twumasi-Boateng K, et al. Oncolytic viruses as engineering platforms for combination immunotherapy. Nat. Rev. Cancer. 18(7), 419-432 (2018).
Virtanen A, et al. mRNAs from human adenovirus 2 early region 4. J Virol. 51(3), 822-831 (1984).
Vogelstein B, et al. Cancer Genome Landscapes. Science. 339(6127), 1546-1558 (2013).
Wides RJ, et al. Adenovirus origin of DNA replication: sequence requirements for replication in vitro. Mol. Cell. Biol. 7(2), 864-874 (1987).
Xia H, et al. siRNA-mediated gene silencing in vitro and in vivo. Nat. Biotechnol. 20(10), 1006-1010 (2002).
Zhu J, et al. Differentiation of Effector CD4 T Cell Populations. Annu Rev Immunol. 28, 445-489 (2010).
Antignani et al., "A Chimeric Protein Induces Tumor Cell Apoptosis by Delivering the Human Bcl-2 Family BH3-Only Protein Bad", Biochemistry, vol. 44, 2005, p. 4074-4082.
Antignani et al., "The cytokine, Granulocyte-Macrophage Colony-Stimulating Factor (GM-CSF), Can Deliver Bxl-XL as an Extracellular Fusion Protein to Protect Cells from Apoptosis and Retain Differentiation Induction", The Journal of Biological Chemistry, vol. 282, No. 15, 2007, p. 11246-11254.
Aqeilan et al., "Interleukin 2-Bax: a novel prototype of human chimeric proteins for targeted therapy", FEBS Letters, vol. 457, 1999, pp. 271-276.
Aqeilan et al., "Mechanism of action of interleukin-2 (IL-2)-Bax, an apoptosis-inducing chimaeric protein targeted against cells expressing the IL-2 receptor", Biochemical Journal, vol. 370, 2003, pp. 129-140.
Argos "A possible homology between immunodeficiency virus p24 core protein and picornaviral VP2 coat protein: prediction of HIV p24 antigenic sites" EMBO Journal, vol. 8, No. 3, pp. 779-785 (1989).
Azar et al., "GnRH-Bik/Bax/Bak chimeric proteins target and kill adenocarcinoma cells; the general use of pro-apoptotic proteins of the Bcl-2 family as novel killing components of targeting chimeric proteins", Apoptosis, vol. 5, 2000, p. 531-542.
Beers & Berkow, The Merck Manual, 17*th* edition, pp. 986-995, (1999).
Bhatia et al. Innovative approaches for enhancing cancer gene therapy. Discovery Med 15(84): 309-317, 2013.
Blaser et al. "Donor-derived IL-15 is critical for acute allogeneic graft-versus-host disease" Blood, vol. 105, pp. 894-901 (2005).
Bork, P. Powers and pitfalls in sequence analysis: the 70% hurdle. Genome Res 10: 398-400, 2000.
Bork, et al. Go hunting in sequence databases but watch out for the traps. Trends in Genetics. 12(10): 425-427, 1996.

(56) References Cited

OTHER PUBLICATIONS

Boyman et al. "The role of interleukin-2 during homeostasis and activation of the immune system" Nature Reviews Immunology, vol. 12, pp. 180-190 (2012).
Brenner, S.E. Errors in genome function. Trends in Genetics 15(4): 132-133, 1999.
Buchli et al., "The Functional Display of Interleukin-2 on Filamentous Phage" Archives of Biochemistry and Biophysics, vol. 339, pp. 79-84 (1997).
Cao et al. In vivo delivery of a Bcl-xL fusion protein containing the TAT protein transduction domain protects against ischemic brani injury and neuronal apoptosis. J Neurosci 22(13): 5423-5431, 2002.
Cassell et al., Current Pharmaceutical Design, vol. 8, No. 24, Nov. 2002, pp. 2171-2183(13).
Ceretti et al., "Cloning, sequence, and expression of bovine interleukin 2", Proc. Natl. Acad. Sci. U.S.A. 83 (10), pp. 3223-3227. (1986) & CA Registry Nos. 103207-23-4 & 103219-24-5.
Doerks et al. Protein annotation: detective work for function prediction. Trends in Genetics 14(6): 248-250, 1998.
Dumont "Interleukin-2 Family Cytokines: Potential for Therapeutic Immunoregulation" Expert Opinion Therapeutic Patents, vol. 15, No. 5, pp. 521-554 (2005).
European Search Report dated Oct. 17, 2017, for EP Application No. 15782644.7, 8 pages.
GenBank Accession No. AAN76508, IL-2 (Bos taurus), Submission date Feb. 13, 2001.
GenBank Accession No. AAP83420, Interleukin-2 (Bos grunniens), Submission date May 7, 2003.
GenBank Accession No. AAW27917, Interleukin-2 (Moschus berezovskii), Submission date Nov. 26, 2004.
Genbank Accession No. NM_000206, *Homo sapiens* interleukin receptor subunit gamma [*homo sapiens*] Jun. 24, 2018.
Genbank Accession No. NM_000878, *Homo sapiens* interleukin 2 receptor subunit beta (IL2RB) [*homo sapiens*] Jun. 30, 2018.
Genbank Accession No. NM_013563, Mus musculus interleukin 2 receptor, gamma chain (ll2rg) [house mouse] Jul. 7, 2018.
Genbank Accession No. NP_000197, cytokine receptor common subunit gamma precursor [*homo sapiens*] Jun. 24, 2018.
Genbank Accession No. NP_000869, interleukin-2 receptor subunit beta precursor [*homo sapiens*] Jun. 30, 2018.
Genbank Accession No. NP_038591, cytokine receptor common subunit gamma isoform a precursor [house mouse] Jul. 7, 2018.
Grant, et al., "The interleukin 2 receptor (IL-2R): The IL-2R α subunit alters the function of the IL-2R β subunit to enhance IL-2 binding and signaling by mechaisms that do not require binding of IL-2 to IL-2R α subunit," Proc. Natl. Acad. Sci. USA, vol. 89, pp. 2165-2169 (1992).
Ju et al. "CP-690,550, a therapeutic agent, inhibits cytokine-mediated Jak3 activation and proliferation of T cells from patients withATL and HAM/TSP" Blood, vol. 117, No. 6, pp. 1938-1946 (2011).
Juengst, E.T. What next for gene therapy? BMJ 326: 1410-1411, 2003.
Kuziel et al. Unexpected effects of the IL-2 receptor alpha subunit on high affinity IL-2 receptor assembly and function detected with a mutant IL-2 analog. J Immunol 150; 3357-3365, 1993.
Lyu et al., "Bax345/BLyS: A novel, completely human fusion protein targeting malignant B cells and delivering a unique mitochondrial toxin", Cancer Letters, vol. 322, 2012, p. 159-168.
Mitra et al. "Interleukin-2 Activity Can Be Fine Tuned With Engineered Receptor Signaling Clamps", Cell Press, vol. 42, pp. 826-838, 2015.
Morris et al. "Preclinical and phase I clinical trial of blockade of IL-15 using Mik 1 monoclonal antibody in T cell large granular lymphocyte leukemia" PNAS, vol. 103, No. 2, pp. 401-406 (2006).
Murray, E.J. "Cloning Genes in Mammalian Cell-lines" in Molecular Biology and Biotechnology. Great Britain: The Royal Society of Chemistry, 2000, pp. 177-201.
Ngo et al. Computational complexity, protein structure prediction, and the Levinthal paradox. The Protein Folding Problem and Tertiary Structure Prediction, pp. 492-495, 1994.
Phillips. A. J. The challenge of gene therapy and DNA delivery. J Pharmacy Pharmacol 53: 1169-1174, 2001.
Rubanyi e, G.M. The future of human gene therapy. Mol Aspects Med 22: 113-142, 2001.
Segel et al., "Effect of IL-2-Bax, a novel interleukin-2-receptor-targeted chimeric protein, on bleomycin lung injury". Int'l Journal of Experimental Pathology, vol. 86, 2005, p. 279-288.
Shanafelt et al., "A T-cell-selective interleukin 2 mutein exhibits potent antitumor activity and is well tolerated in vivo," Nature Biotechnology, vol. 18, pp. 1197-1202 (2000).
Shevach "Application of IL-2 therapy to target T regulatory cell function" Trends in Immunology, vol. 33, No. 12, pp. 626-632 (2012).
Skolnick et al. From genes to protein structure and function: novel applications of computational approaches in the genomic era. Trends in Biotech 18(1): 34-39, 2000.
Spangler et al. Insights into cytokine-receptor interactions from cytokine engineering. Annu Rev Immunol 33: 139-167, 2015.
Strohl "Optimization of Fc-mediated effector functions of monoclonal antibodies" vol. 20, issue 6, pp. 685-691 (2009).
Tanaka et al. Structure-function analysis of the Bcl-2 oncoprotein. J Biol Chem 268(15): 10920-10926, 1993.
Tokuriki et al. Stability effects of mutations and protein evolvability. Curr Opin Structural Biol 19: 596-604, 2009.
Tsudo et al., "Characterization of the interleukin 2 receptor β chain using three distinct monoclonal antibodies," Proc. Natl. Acad. Sci. USA, vol. 86, pp. 1982-1986 (1989).
UNIPROTKB/Swiss Prot Accession Q07817, Feb. 1, 1995, 14 total pages.
Vallera et al., "Retroviral Immunotoxin Gene Therapy of Leukemia in Mice Using Leukemia-Specific T Cells Transduced with an Interleukin-3/Bax Fusion Protein Gene", Human Gene Therapy, vol. 14, 2003, p. 1787-1798.
Virdee et al., "Phosphorylation of the pro-apoptotic protein BAD on serine 155, a novel site, contributes to cell survival", Current Biology, vol. 10, No. 18, 2000, pp. 1151-1154.
Votavova et al. "Increasing the biological activity of IL-2 and IL-15 through complexing with anti-IL-2 mAbs and IL-15R[alpha]-Fc chimera" Immunology Letters, vol. 159, No. 1-2, pp. 1-10 (2014).
Wells, J.A. Additivity of mutational effects in proteins. Biochemistry 29 (37): 8509-8517, 1990.
Yan et al. Overexpression of the cell death suppressor Bcl-w in ischemic brain: implications for a neuroprotective role via the mitochondrial pathway. J Cerebral Blood Flow Metabol 20: 620-630, 2000.
Zurawski et al. Partial agonist/antagonist mouse interleukin-2 proteins indicate that a third component of the receptor complex functions in signal transduction. EMBO J 9(12): 3899-3905, 1990.

\* cited by examiner

CH1

| EU INDEX | 118 | 119 | 120 | 121 | 122 | 123 | 124 | 125 | 126 | 127 | 128 | 129 | 130 | 131 | 132 | 133 | 134 | 135 | 136 | 137 | 138 |
|---|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | E | S |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | E | S |

| EU INDEX | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU INDEX | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU INDEX | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | Y | C | N |
| IgG3 | S | L | S | S | V | V | T | V | P | S | S | S | L | G | T | Q | T | Y | Y | C | N |
| IgG4 | S | L | S | S | V | V | T | V | P | S | S | S | L | G | T | K | T | Y | T | C | N |

| EU INDEX | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|
| IgG1 | V | N | H | K | P | S | N | T | K | V | D | K | K | V | E | P | K | S | C |
| IgG2 | V | D | H | K | P | S | N | T | K | V | D | K | T | V | E | R | K | C | C |
| IgG3 | V | N | H | K | P | S | N | T | K | V | D | K | R | V | E | L | K | T | P |
| IgG4 | V | D | H | K | P | S | N | T | K | V | D | K | R | V | E | S | K | Y | G |

HINGE                                   Fc >

| EU INDEX | 221 | | 222 | 223 | 224 | 225 | 226 | 227 | 228 | | | | | | | | | | | | | |
|---|---|---|---|---|---|---|---|---|---|---|---|---|---|---|---|---|---|---|---|---|---|---|
| IgG1 | D | | K | T | H | T | C | P | P | | | | | | | | | | | | | |
| IgG2 | | | V | E | | | C | P | P | | | | | | | | | | | | | |
| IgG3 | L | G | D | T | T | H | T | C | P | R | C | P | E | P | K | S | C | D | T | P | P | |
| IgG4 | | | | | P | P | C | P | S | | | | | | | | | | | | | |

| EU INDEX | | | | | | | | | | | | | | | | | | | | | |
|---|---|---|---|---|---|---|---|---|---|---|---|---|---|---|---|---|---|---|---|---|---|
| IgG3 | P | C | P | R | C | P | E | P | K | S | C | D | T | P | P | C | P | R | C | P | |

Fc >

| EU INDEX | | | | | | | | | | | | | | 229 | 230 | 231 | 232 | 233 | 234 | 235 | 236 | |
|---|---|---|---|---|---|---|---|---|---|---|---|---|---|---|---|---|---|---|---|---|---|---|
| IgG1 | | | | | | | | | | | | | | C | P | A | P | E | L | L | G | SEQ ID. NO: 203 |
| IgG2 | | | | | | | | | | | | | | C | P | A | P | P | V | A | | SEQ ID. NO: 204 |
| IgG3 | E | P | K | S | C | D | T | P | P | P | C | P | R | C | P | A | P | E | L | L | G | SEQ ID. NO: 205 |
| IgG4 | | | | | | | | | | | | | | C | P | A | P | E | F | L | G | SEQ ID. NO: 206 |

H9-Fc Fusions

Annotation Key:
    Signal Peptide (MYRMQLLSCIALSLALVTNS) (SEQ ID NO:20)
    Gene of Interest
    Linker (GGGGSGGGGSGGGGS) (SEQ ID NO:17)
    Tag (Fc)
    H9 Mutations (L80F, R81D, L85V, I86V, and I92F)
    Other IL-2 Mutations (F42A, Y45A, E62A)
    Fc variant (N297A)

Protein: wtIL2-Fc (Native IL-2 ss, hIgG1 N297A) 3x GGGGS linker
Isotype: Human IgG1 (N297A)
MYRMQLLSCIALSLALVTNSAPTSSSTKKTQLQLEHLLLDLQMILNGINNYKNPKLTRMLTFKFYMPKKATELKHLQCLEE
ELKPLEEVLNLAQSKNFHLRPRDLISNINVIVLELKGSETTFMCEYADETATIVEFLNRWITFCQSIISTLTGGGGSGGGG
SGGGGSDKTHTCPPCPAPELLGGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK* (SEQ ID
NO:11)

Protein: H9-Fc (Native IL-2 ss, hIgG1 N297A) 3x GGGGS linker
Isotype: Human IgG1 (N297A)
MYRMQLLSCIALSLALVTNSAPTSSSTKKTQLQLEHLLLDLQMILNGINNYKNPKLTRMLTFKFYMPKKATELKHLQCLEE
ELKPLEEVLNLAQSKNFHFDPRDVVSNINVFVLELKGSETTFMCEYADETATIVEFLNRWITFCQSIISTLTGGGGSGGGG
SGGGGSDKTHTCPPCPAPELLGGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK* (SEQ ID
NO:12)

Protein: H9-FYAA-Fc (Native IL-2 ss, hIgG1 N297A) 3x GGGGS linker
Isotype: Human IgG1 (N297A)
MYRMQLLSCIALSLALVTNSAPTSSSTKKTQLQLEHLLLDLQMILNGINNYKNPKLTRMLTAKFAMPKKATELKHLQCLEE
ELKPLEEVLNLAQSKNFHFDPRDVVSNINVFVLELKGSETTFMCEYADETATIVEFLNRWITFCQSIISTLTGGGGSGGGG
SGGGGSDKTHTCPPCPAPELLGGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK* (SEQ ID
NO:13)

Protein: H9-FEAA-Fc (Native IL-2 ss, hIgG1 N297A) 3x GGGGS linker
Isotype: Human IgG1 (N297A)
MYRMQLLSCIALSLALVTNSAPTSSSTKKTQLQLEHLLLDLQMILNGINNYKNPKLTRMLTAKFYMPKKATELKHLQCLEE
ALKPLEEVLNLAQSKNFHFDPRDVVSNINVFVLELKGSETTFMCEYADETATIVEFLNRWITFCQSIISTLTGGGGSGGGG
SGGGGSDKTHTCPPCPAPELLGGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK* (SEQ ID
NO:14)

Protein: H9-FYEAAA-Fc (Native IL-2 ss, hIgG1 N297A) 3x GGGGS linker
Isotype: Human IgG1 (N297A)
MYRMQLLSCIALSLALVTNSAPTSSSTKKTQLQLEHLLLDLQMILNGINNYKNPKLTRMLTAKFAMPKKATELKHLQCLEE
ALKPLEEVLNLAQSKNFHFDPRDVVSNINVFVLELKGSETTFMCEYADETATIVEFLNRWITFCQSIISTLTGGGGSGGGG
SGGGGSDKTHTCPPCPAPELLGGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK* (SEQ ID
NO:15)

| | 10 | 11 | 14 | 18 | 86 | 87 | 88 | 89 | 101 | 104 | 105 | 107 | 108 | IL-13Rα1 binding constants | | | | IL-13Rα2 binding constants | | | |
|---|---|---|---|---|---|---|---|---|---|---|---|---|---|---|---|---|---|---|---|---|---|
| | | | | | | | | | | | | | | K1 (M-1s-1) | K1 (s-1) | KD (kinetic) | KD (eq) | K1 (M-1s-1) | K1 (s-1) | KD (kinetic) | KD (eq) |
| IL-13 | L | R | I | V | R | D | T | K | L | K | F | M | R | 5.21E+06 | 2.20E-02 | 4.38 nM | - | 5.00E+07 | 8.40E-05 | 0.001 nM | 50 nM |
| A5 | - | - | - | - | K | G | S | - | H | R | A | M | - | 2.80E+06 | 8.20E-03 | 2.94 nM | - | - | - | - | - |
| A6 | - | - | L | - | M | K | S | - | H | R | A | - | - | 1.77E+06 | 3.30E-03 | 1.9 nM | - | 1.07E+07 | 2.80E-03 | 0.267 nM | - |
| A7 | - | - | - | - | - | G | S | - | H | R | A | - | - | 2.90E+06 | 3.40E-03 | 1.18 nM | - | 1.80E+07 | 4.10E-03 | 0.218 nM | - |
| A8 | V | - | - | - | - | S | S | - | H | R | T | - | - | 1.64E+06 | 3.30E-03 | 2.061 nM | - | 1.01E+07 | 2.60E-03 | 0.263 nM | - |
| A11 | - | - | - | - | - | S | S | R | F | R | T | - | - | 1.64E+07 | 1.30E-03 | 0.084 nM | - | 1.62E+07 | 6.00E-03 | 0.391 nM | - |
| B2 | - | S | - | - | T | G | S | - | Y | R | A | - | - | 6.30E+06 | 1.70E-03 | 0.275 nM | - | - | - | - | - |
| B4 | - | - | - | - | K | K | S | M | Y | R | T | - | - | 1.36E+06 | 2.40E-02 | 18 nM | - | 7.80E+06 | 1.00E-02 | 1.5 nM | - |
| B6 | T | - | - | - | - | G | G | K | Y | R | T | - | - | 1.40E+06 | 8.20E-03 | 5.9 nM | - | - | - | - | 108 nM |
| C2 | D | - | - | - | K | K | K | R | N | R | - | - | K | - | - | - | 4000 nM | 6.60E+06 | 1.50E-04 | 0.025 nM | 53 nM |
| C3 | A | - | - | - | T | G | - | R | N | R | A | - | K | - | - | - | 15000 nM | 6.00E+06 | 2.00E-03 | 0.379 nM | - |
| C4 | V | - | - | - | - | - | - | - | - | - | E | - | T | - | - | - | 36000 nM | 1.94E+06 | 7.64E-04 | 0.393 nM | - |
| C7 | H | - | - | - | K | E | S | R | N | - | E | - | K | - | - | - | 35000 nM | 2.10E+06 | 5.70E-04 | 0.272 nM | - |
| C9 | H | M | - | - | M | - | - | - | - | R | T | - | K | - | - | - | 31000 nM | 2.03E+06 | 5.29E-04 | 0.259 nM | - |
| C10 | H | - | - | - | T | G | G | - | - | - | - | - | K | - | - | - | 264 nM | 1.19E+06 | 6.10E-03 | 5 nM | - |
| C11 | H | L | - | - | M | - | R | R | - | - | A | - | K | - | - | - | 1600 nM | 6.41E+06 | 9.18E-07 | 0.0001 nM | - |
| C12 | H | L | - | - | K | K | S | R | - | - | - | - | K | - | - | - | 15000 nM | 7.61E+06 | 4.04E-04 | 0.053 nM | - |
| D7 | A | - | - | F | - | - | - | - | - | R | - | - | K | - | - | - | 4100 nM | 1.77E+07 | 5.37E-05 | 0.003 nM | - | a: IL-13Rα1 specific (A5–B6); IL-13Rα2 specific (C2–D7)

Pembrolizumab (Anti-PD1 hIgG4)

| What | sequence | SEQ ID NO: |
|---|---|---|
| Variable heavy (vh) domain | EVQLVLSGGGFVQPGGSLKLSCAASGFTFSSYAMSWVRQNPERRLVWVATITGGGRNTYYPDSVKGRFTIS RDNAKNTLYLQMSSLRSEDTAMYYCTRQGYDGYTWFAYWGQGTLVTVSS | |
| Full length HC | EVQLVLSGGGFVQPGGSLKLSCAASGFTFSSYAMSWVRQNPERRLVWVATITGGGRNTYYPDSVKGRFTIS RDNAKNTLYLQMSSLRSEDTAMYYCTRQGYDGYTWFAYWGQGTLVTVSSASTKGPSVFPLAPCSRSTSEST AALGCLVKDYFPEPVTVSWNSGALTSGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYSRLTVDKSRWQEGNVFSCSVM HEALHNHYTQKSLSLSPGK | |
| Variable light (vl) domain | DIVLTQSPTSLAVSLGQRATISCRASESVDNSGISFMNWFQQKPGQPPKLLIYAASNPGSGVPARFSGSGSGT DFSLNIHPMEEDTAMYFCQQSKEVPWTFGGGTELEIKR | |
| Full length light chain | DIVLTQSPTSLAVSLGQRATISCRASESVDNSGISFMNWFQQKPGQPPKLLIYAASNPGSGVPARFSGSGSGT DFSLNIHPMEEDTAMYFCQQSKEVPWTFGGGTELEIKRTVAAPSVFIFPPSDEQLKSGTASVVCLLNNFYPR EAKVQWKVDNALQSGNSQESVTEQDSKDSTYSLSSTLTLSKADYEKHKVYACEVTHQGLSSPVTKSFNRGE C | |

Pembrolizumab (Anti-PD1 from WO2016028656)

| What | sequence | SEQ ID NO: |
|---|---|---|
| Full length HC (SEQ ID NO:33 from WO2016028656) | QVQLVQSGVEVKKPGASVKVSCKASGYTFTNYYMYWRQAPGQGLEWMGGINPSNGGTNFNEKFKNRVTL TTDSSTTTAYMELKSLQFDDTAVYYCARRDYRFDMGFDYWGQGTTVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVSQEDPEVQFNWYVDGVEV HNAKTKPREEQFNSTYRVVSVLTVLHQDWLNGKEYKCKVSNKGLPSSIEKTISKAKGQPREPQVYTLPPSQE E MTKNQVSLTCLVKGFYPSDIAVEWESNGQPENNYKTTPPVLDSDGSFFLYSRLTVDKSRWQEGNVFSCSVM HEALHNHYTQKSLSLSLGK | |
| Full length light chain (SEQ ID NO:34 from WO2016028656) | EIVLTQSPATLSLSPGERATLSCRASKGVSTSGYSYLHWYQQKPGQAPRLLIYLASYLESGVPARFSGSGSGT DFTLTISSLEPEDFAVYYCQHSRDLPLTFGGGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSSPVTKSFNRGEC | |

*Figure 7B*

| | | SEQ ID NO: |
|---|---|---|
| Nivolumab (Anti-PD1 hIgG4) | | |
| What | sequence | |
| Variable heavy (vh) domain | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS | |
| Full length HC | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSRWQEGNVFSCSVMHEALHNHYTQKSLSLSLGK | |
| Variable light (vl) domain | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKR | |
| Full length light chain | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | |

| | | SEQ ID NO: |
|---|---|---|
| Nivolumab (Anti-PD1 from WO2016028656) | | |
| What | sequence | |
| Full length heavy chain (SEQ ID NO:35 from WO2016028656) | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | |
| Full length light chain (SEQ ID NO:36 from WO2016028656) | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | |

*Figure 7C*

Cemiplimab (REGN2810; anti-PD1)

| What | sequence | SEQ ID NO: |
|---|---|---|
| Variable heavy (vh) domain (SEQ ID NO:1 from US20170174779) | EVQLLESGGVLVQPGGSLRLSCAASGFTFSNFGMTWVRQAPGKGLEWVSGISGGGRDTYF ADSVKGRFTISRDNSKNTLYLQMNSLKGEDTAVYYCVKWGNIYFDYWGQGTLVTVSS | |
| Variable light (vl) domain (SEQ ID NO:2 from US20170174779) | DIQMTQSPSSLSASVGDSITITCRASLSINTFLNWYQQKPGKAPNLLIYAASSLHGGVPS RFSGSGSGTDFTLTIRTLQPEDFATYYCQQSSNTPFTFGPGTVVDFR | |

Cemiplimab (REGN2810; anti-PD1)

| What | sequence | SEQ ID NO: |
|---|---|---|
| Full length heavy chain (SEQ ID NO:9 from US20170174779) | EVQLLESGGVLVQPGGSLRLSCAASGFTFSNFGMTWVRQAPGKGLEWVSGISGGGRDTYFADSVKGRFTIS RDNSKNTLYLQMNSLKGEDTAVYYCVKWGNIYFDYWGQGTLVTVSSASTKGPSVFPLAPCSRSTSESTAAL GCLVKDYFPEPVTVSWNSGALTSGVHTFPAVLQSSGLYSLSSVVTVPSSSLGTKTYTCNVDHKPSNTKVDKR VESKYGPPCPPCPAPEFLGGPSVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAKGQPREPQVYTLPPSQEEMTKN QVSLTCLVKGFYPSDIAVEWESNGQPENNYKTTPPVLDSDGSFFLYSRLTVDKSRWQEGNVFSCSVMHEAL HNHYTQKSLSLSLGK | |
| Full length light chain (SEQ ID NO:10 from US20170174779) | DIQMTQSPSSLSASVGDSITITCRASLSINTFLNWYQQKPGKAPNLLIYAASSLHGGVPSRFSGSGSGTDFTLTI RTLQPEDFATYYCQQSSNTPFTFGPGTVVDFRRTVAAPSVFIFPPSDEQLKSGTASVVCLLNNFYPREAKVQ WKVDNALQSGNSQESVTEQDSKDSTYSLSSTLTLSKADYEKHKVYACEVTHQGLSSPVTKSFNRGEC | |

*Figure 8A*

From WO2017100541 (Medimmune, LLC: also US20170306025; Durvalumab)

| What | sequence | SEQ ID NO: |
|---|---|---|
| Heavy chain (SEQ ID NO:2 from WO2017100541) | EVQLVESGGGLVQPGGSLRLSCAASGFTFSRYWMSWVRQAPGKGLEWVANIKQDGSEKYYVDSVKGR FTISRDNAKNSLYLQMNSLRAEDTAVYYCAREGGWFGELAFDYWGQGTLVTVSS | |
| Light chain (SEQ ID NO:1 from WO2017100541) | EIVLTQSPGTLSLSPGERATLSCRASQRVSSSYLAWYQQKPGQAPRLLIYDASSRATGIPDRFSGSGSGT DFTLTISRLEPEDFAVYYCQQYGSLPWTFGQGTKVEIK | |

From US20170281764 (JN Biosciences)

| What | sequence | SEQ ID NO: |
|---|---|---|
| Heavy chain (SEQ ID NO:34 from US20170281764) | EVQLVESGGGLVQPGGSLRLSCAASGFTFSDSWIHWVRQAPGKGLEWVAWISPYGGSTYYADSVKGR FTISADTSKNTAYLQMNSLRAEDTAVYYCARRHWPGGFDYWGQGTLVTVSAASTKGPSVFPLAPSSKST SGGTAALGCLVKDYFPEPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPEVTCVVVDVSHEDPEVK FNWYVDGVEVHNAKTKPREEQYASTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLYSKLTV DKSRWQQGNVFSCSVMHEALHNHYTQKSLSLSPG | |
| Light chain (SEQ ID NO:36 from US20170281764) | DIQMTQSPSSLSASVGDRVTITCRASQDVSTAVAWYQQKPGKAPKLLIYSASFLYSGVPSRFSGSGSGT DFTLTISSLQPEDFATYYCQQYLFTPPTFGQGTKVEIKRTVAAPSVFIFPPSDEQLKSGTASVVCLLNNFY PREAKVQWKVDNALQSGNSQESVTEQDSKDSTYSLSSTLTLSKADYEKHKVYACEVTHQGLSSPVTKS FNRGEC | |

*Figure 8B*

From WO2015009856 (GENENTECH, INC. and F. HOFFMANN-LA ROCHE AG)

| What | sequence | SEQ ID NO: |
|---|---|---|
| Heavy chain (SEQ ID NO:23 from WO2015009856) | EVQLVESGGGLVQPGGSLRLSCAASGFTFSDSWIHWVRQAPGKGLEWVAWISPYGGSTYYADSVKGR FTISADTSKNTAYLQMNSLRAEDTAVYYCARRHWPGGFDYWGQGTLVTVSA | |
| Light chain (SEQ ID NO:24 from WO2015009856) | DIQMTQSPSSLSASVGDRVTITCRASQDVSTAVAWYQQKPGKAPKLLIYSASFLYSGVPSRFSGSGSGT DFTLTISSLQPEDFATYYCQQYLYHPATFGQGTKVEIKR | |

From WO2015009856 (GENENTECH, INC. and F. HOFFMANN-LA ROCHE AG)

| What | sequence | SEQ ID NO: |
|---|---|---|
| Heavy chain (SEQ ID NO:40 from WO2015009856) | EVQLVESGGGLVQPGGSLRLSCAASGFTFSDSWIHWVRQAPGKGLEWV A WISPYGG STYY ADSVKGRFTISADTSKNTA YLQMNSLRAEDTA VYYCARRHWPGGFDYWGQG TLVTVSSASTK | |
| Light chain (SEQ ID NO:24 from WO2015009856) | DIQMTQSPSSLSASVGDRVTITCRASQDFTLTISSLQPEDF ATYCCQYL YHPATFGQGTKVEIKR | |

From WO2015009856 (GENENTECH, INC. and F. HOFFMANN-LA ROCHE AG)

| What | sequence | SEQ ID NO: |
|---|---|---|
| Heavy chain (SEQ ID NO:41 from WO2015009856) | EVQLVESGGGLVQPGGSLRLSCAASGFTFSDSWIHWVRQAPGKGLEWVAWISPYGG STYYADSVKGRFTISADTSKNTAYLQMNSLRAEDTA VYYCARRHWPGGFDYWGQG TLVTVSS | |
| Light chain (SEQ ID NO:24 from WO2015009856) | DIQMTQSPSSLSASVGDRVTITCRASQDVSTAVAWYQQKPGKAPKLLIYSASFLYSGVPSRFSGSGSGT DFTLTISSLQPEDFATYYCQQYLYHPATFGQGTKVEIKR | |

*Figure 8C*

| From US20160222117 (GENENTECH, INC.) | | |
|---|---|---|
| What | sequence | SEQ ID NO: |
| Heavy chain (SEQ ID NO:20 from US20160222117) | EVQLVESGGGLVQPGGSLRLSCAASGFTFSDSWIHWVRQAPGKGLEWVAWISPYGGSTYYADSVKGRFTISRDTSKNTAYLQMNSLRAEDTAVYYCARRHWPGGFDYWGQGTLVTVSA | |
| Heavy chain (SEQ ID NO:23 from US20160222117) | EVQLVESGGGLVQPGGSLRLSCAASGFTFSDSWIHWVRQAPGKGLEWVAWISPYGGSTYYADSVKGRFTISRDTSKNTAYLQMNSLRAEDTAVYYCARRHWPGGFDYWGQGTLVTVSA | |
| Heavy chain (SEQ ID NO:24 from US20160222117) | EVQLVESGGGLVQPGGSLRLSCAASGFTFSGSWIHWVRQAPGKGLEWVAWILPYGGSSYYADSVKGRFTISRDTSKNTAYLQMNSLRAEDTAVYYCARRHWPGGFDYWGQGTLVTVSA | |

| From US20160222117 (GENENTECH, INC.) | | |
|---|---|---|
| What | sequence | SEQ ID NO: |
| Light chain (SEQ ID NO:21 from US20160222117) | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIKR | |
| Light chain (SEQ ID NO:26 from US20160222117) | DIQMTQSPSSLSASVGDRVTITCRASQDVSTAVAWYQQKPGKAPKLLIYSASFLYSGVPSRFSGSGSGTDFTLTISSLQPEDFATYYCQQYNVPWTFGQGTKVEIKR | |
| Light chain (SEQ ID NO:27 from US20160222117) | DIQMTQSPSSLSASVGDRVTITCRASQDVSTAVAWYQQKPGKAPKLLIYSASFLYSGVPSRFSGSGSGTDFTLTISSLQPEDFATYYCQQYYAPPWTFGQGTKVEIKR | |

*Figure 8D*

From US20160222117 (GENENTECH, INC.)

| What | sequence | SEQ ID NO: |
|---|---|---|
| Light chain (SEQ ID NO:28 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQYTVPWTFGQGTKVEIKR | |
| Light chain (SEQ ID NO:29 from US20160222117) | DIQMTQSPSSLSASVGDRVTITCRASQVINTFLAWYQQKPGKAPKLLIYSASTLASGVPSRFSGSGSGTD FTLTISSLQPEDFATYYCQQYTVPRTFGQGTKVEIKR | |
| Light chain (SEQ ID NO:30 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQGYGVPRTFGQGTKVEIKR | |
| Light chain (SEQ ID NO:31 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQYLFTPPTFGQGTKVEIKR | |
| Light chain (SEQ ID NO:32 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQYFITPTTFGQGTKVEIKR | |
| Light chain (SEQ ID NO:33 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQYTPPTFGQGTKVEIKR | |
| Light chain (SEQ ID NO:34 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQFFYTPPTFGQGTKVEIKR | |

From WO2013079174 (Merck; Avelumab or A09-246- 2)

| What | sequence | SEQ ID NO: |
|---|---|---|
| Heavy chain (SEQ ID NO:32 from WO2013079174) | EVQLLESGGGLVQPGGSLRLSCAASGFTFSSYIMMWVRQAPGKGLEWVSSIYPSGGITFYADTVKGRFT ISRDNSKNTLYLQMNSLRAEDTAVYYCARIKLGTVTTVDYWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGK | |
| Light chain (SEQ ID NO:33 from WO2013079174) | QSALTQPASVSGSPGQSITISCTGTSSDVGGYNYVSWYQQHPGKAPKLMIYDVSNRPSGVSNRFSGSK SGNTASLTISGLQAEDEADYYCSSYTSSSTRVFGTGTKVTVLGQPKANPTVTLFPPSSEELQANKATLVC LISDFYPGAVTVAWKADGSPVKAGVETTKPSKQSNNKYAASSYLSLTPEQWKSHRSYSCQVTHEGSTV EKTVAPTECS | |

*Figure 8E*

| From US20160222117 (GENENTECH, INC.) | | |
|---|---|---|
| What | sequence | SEQ ID NO: |
| Light chain (SEQ ID NO:35 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQSLFTPPTFGQGTKVEIKR | |
| Light chain (SEQ ID NO:36 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQSLYTPPTFGQGTKVEIKR | |
| Light chain (SEQ ID NO:37 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQSWYHPPTFGQGTKVEIKR | |
| Light chain (SEQ ID NO:38 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQYFIPPTFGQGTKVEIKR | |
| Light chain (SEQ ID NO:39 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQYWYTPYTFGQGTKVEIKR | |
| Light chain (SEQ ID NO:40 from US20160222117) | DIQMTQSPSSLSASVGDRVTITCRASQDVSTAVAWYQQKPGKAPKLLIYSASFLYSGVPSRFSGSGSGT DFTLTISSLQPEDFATYYCQQSYFIPPTFGQGTKVEIKR | |

*Figure 8F*

From US8217149 (Hoffman La Roche; Atezolizumab)

| What | sequence | SEQ ID NO: |
|---|---|---|
| Heavy chain (VH) (SEQ ID NO:20 from US8217149) | EVQLVESGGGLVQPGGSLRLSCAASGFTFSDSWIHWVRQAPGKGLEWVAWISPYGGSTYYADSVKGR FTISADTSKNTAYLQMNSLRAEDTAVYYCARRHWPGGFDYWGQGTLVTVSA | |
| Light chain (VL) (SEQ ID NO:21 from US8217149) | DIQMTQSPSSLSASVGDRVTITCRASQDVSTAVAWYQQKPGKAPKWYSASFLYSGVPSRFSGSGSGTD FTLTISSLQPEDFATYYC QQYLYH PATFGQGTKVEIKR | |

Atezolizumab (alternate sequence)

| What | sequence | SEQ ID NO: |
|---|---|---|
| Heavy chain (from IMGT database or DrugBank database) | EVQLVESGGGLVQPGGSLRLSCAASGFTFSDSWIHWVRQAPGKGLEWVAWISPYGGSTYYADSVKGR FTISADTSKNTAYLQMNSLRAEDTAVYYCARRHWPGGFDYWGQGTLVTVSSASTKGPSVFPLAPSSKST SGGTAALGCLVKDYFPEPVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTPEVTCVVVDVSHEDPEVK FNWYVDGVEVHNAKTKPREEQYASTYRVVSVLTVLHQDWLNGKEYKCKVSNKALPAPIEKTISKAKGQP REPQVYTLPPSREEMTKNQVSLTCLVKGFYPSDIAVEWESNGQPENNYKTTPPVLDSDGSFFLYSKLTV DKSRWQQGNVFSCSVMHEALHNHYTQKSLSLSPGK | |
| Light chain (from IMGT database or DrugBank database) | DIQMTQSPSSLSASVGDRVTITCRASQDVSTAVAWYQQKPGKAPKLLIYSASFLYSGVPSRFSGSGSGT DFTLTISSLQPEDFATYYCQQYLYHPATFGQGTKVEIKRTVAAPSVFIFPPSDEQLKSGTASVVCLLNNFY PREAKVQWKVDNALQSGNSQESVTEQDSKDSTYSLSSTLTLSKADYEKHKVYACEVTHQGLSSPVTKS FNRGEC | |

Adenoviruses used as oncolytic agents

| Name (serotype) | Basis of tumor-selective propagation | Therapeutic traits |
|---|---|---|
| Ad wild type (various serotypes) | None | Oncolysis |
| Ad5/IFN (Ad5) | None | Oncolysis & immuno-stimulatory gene therapy |
| A1520 or Onyx015 < Ad2/5) | Elb55kDa-deletion abrogates p53 binding | Oncolysis |
| AdTKRC | ElbSSkDa-deletion abrogates p53 binding | Oncolysis & suicide gene therapy (TK) |
| Ad-5-CD-TKrep or FGR (ad5) | Elb5SkDa-deletion abrogates p53 binding | Oncolysis ft suicide gene therapy (CD +TK) |
| AdvElAdB-F/K20 (Ad5) | ElbSSkDa-deletion abrogates p53 binding | Oncolysis with enhanced infectivity |
| AxElAdB (Ad5) & AdCAhIL-2 (Ad5) | ElbSSkDa-deletion abrogates p53 binding | Oncolysis & immuno-slimulatory gene therapy |
| AdD24 (Ad5) | Ela deletion abrogates Rb binding | Oncolysis |
| CN706 (Ad5) | Regulation of Ela under the PSA promoter | Oncolysis |
| CN763 (Ad5) | Regulation of Ela under the kalikein 2 promoter | Oncolysis |
| CN764 (Ad5) | Regulation of Ela under the PSA promoter and Elb under the kalikrein 2 promoter | Oncolysis |
| CV739 | Regulation of Ela under rat probasin promoter and El binder human PSA promoter | Oncolysis |

Adenoviruses used as oncolytic agents

| Name (serotype) | Basis of tumor-selective propagation | Therapeutic traits |
|---|---|---|
| CV787 | Regulation of Ela under rat probasin promoter and Elb under human PSA promoter | Oncolysis (enhanced compared with CV739 due to the presence of E |
| AvEla041 | Regulation of Ela under the AFP promoter | Oncolysis |
| GT5610 (Ad5) + AdHB (Ad5) | Regulation of Ela under the AFP promoter | Oncolysis |
| Dl337 (Ad5) | None | Oncolysis(enhanced due to Elb-19 kDa deletion) |
| Dl316 (Ad5) | The complete deletion of Ela makes this mutant dependent on Nrinsic or ML-6-induced Ela-like activity | Oncolysis |
| Dl118 (Ad5) | The complete deletion of ELb abrogates p53 binding; however Ela-induced apoptosts is not inhibited by Elb-19 kDa | Oncolysis |

*Figure 9A*

Replication-Selective Viruses in Clinical Trials

| Parental Strain | Agent | Clinical phase | Tumor targets in clinical trials | Genetic alterations | Cell phenotype allowing selective replication |
|---|---|---|---|---|---|
| Engineered | | | | | |
| Adenovirus (2/5 chimera) | ONYX-015 | I-III | SCCHN, Colorectal, Ovarian, Pancreatic | E1B-55-kD gene deletion | Controversial cells lacking p53 function (for example, deletion, mutation), other? |
| Adenovirus (serotype 5) | CN706, CN787 | I, I | Prostate | E3-10.4/14.5 deletion, E1A expression driven by PSE element, E1A driven by rat probasin promoter/ E1B by PSE promoter/enhancer | Prostate cells (malignant, normal) |
| Adenovirus (2/5 chimera) | Ad5-CD/tk-rep | I | Prostate | E1B-55-kD gene deletion, Insertion of HSV-tk/CD fusion gene | Controversial cells lacking p53 function (for example, deletion, mutation), other? Proliferating cells |
| Herpes simplex virus-1 | G207 | I-II | GBM | ribonucleotide reductase disruption (lacZ insertion into ICP6 gene) neuropathogenesis gene mutation (γ-34.5 gene)–both copies | Proliferating cells |
| Herpes simplex virus-1 | NV1020 | I | Colorectal | neuropathogenesis gene mutation (γ-34.5 gene)–single copy | Unknown |
| Vaccinia virus | Wild-type ± GM-CSF | I | Melanoma | For selectivity: none or ⊘ deletion Immunostimulatory gene (GM-CSF) insertion | |
| Non-engineered | | | | | |
| Newcastle Disease virus | 73-T | I | Bladder, SCCHN, Ovarian | Unknown (serial passage on tumor cells) | Loss of IFN response in tumor cells |
| Autonomous parvoviruses | H-I | I | | None | Transformed cells ↑ proliferation ↓ differentiation ras, p53 mutation, Ras-pathway activation (for example, ras mutation, EGFR signaling) |
| Reovirus | Reolysin | I | SCCHN | None | |

*Figure 9B*

IL-2 SUPERAGONISTS IN COMBINATION WITH ANTI-PD-1 ANTIBODIES

CROSS REFERENCE TO RELATED APPLICATIONS

This application claims priority under 35 U.S.C. § 119 to U.S. Patent Application Nos. 62/521,957, filed on Jun. 19, 2017, and 62/679,687, filed on Jun. 1, 2018, all of which are expressly incorporated herein by reference in their entireties.

REFERENCE TO A "SEQUENCE LISTING," A TABLE, OR A COMPUTER PROGRAM, LISTING APPENDIX SUBMITTED ON A COMPACT DISK

This invention incorporated by reference Sequence Listing text copy submitted herewith, which was created on Dec. 15, 2020, entitled 117802-5001-US_Sequence_Listing.txt which is 416 kilobytes in size.

BACKGROUND

Interleukin 2 (IL-2) is a pluripotent cytokine produced primarily by activated CD4+ T cells, which plays a crucial role in producing a normal immune response. IL-2 promotes proliferation and expansion of activated T lymphocytes, potentiates B cell growth, and activates monocytes and natural killer cells. It was by virtue of these activities that IL-2 was tested and is used as an approved treatment of cancer (aldesleukin, Proleukin®). In eukaryotic cells, human IL-2 is synthesized as a precursor polypeptide of 153 amino acids, from which 20 amino acids are removed to generate mature secreted IL-2 (Taniguchi 1983). Recombinant human IL-2 has been produced in *E. coli* (Rosenberg 1984), in insect cells (Smith 1985) and in mammalian COS cells (Taniguchi 1983).

Interleukin-2 (IL-2) is a four $\alpha$-helical bundle type I cytokine first identified as a T cell growth factor (Morgan et al., *Science* 193: 1007 (1976)) but subsequently shown to have broad actions. IL-2 promotes T helper differentiation (Zhu et al., *Annual review of immunology* 28: 445 (2010); Liao et al., *Nat Immunol* 9: 1288 (2008); and Liao et al., *Nat Immunol* 12: 551 (2011)) and the development of regulatory T (Treg) cells (Cheng et al., *Immunol Rev* 241: 63 (2011)), induces natural killer and lymphokine activated killer activity (Liao et al., *Immunity* 38: 13 (2013)), and mediates activation-induced cell death (AICD) (Lenardo et al., *Nature* 353: 858 (1991)).

IL-2 works by interacting with three different receptors: the interleukin 2 receptor alpha (IL-2R$\alpha$; CD25), the interleukin 2 receptor beta (IL-2R$\beta$; CD122), and the interleukin 2 receptor gamma (IL-2R$\gamma$; CD132; common gamma chain). The first receptor to be identified was the IL-2R$\alpha$, which is a 55 kD polypeptide (p55) that appears upon T cell activation and was originally called Tac (for T activation) antigen. The IL-2R$\alpha$ binds IL-2 with a $K_d$ of approximately $10^{-8}$M, and is also known as the "low affinity" IL-2 receptor. Binding of IL-2 to cells expressing only the IL-2R$\alpha$ does not lead to any detectable biologic response. In most circumstances, IL-2 works through three different receptors: the IL-2R$\alpha$, the IL-2R$\beta$, and the IL-2R$\gamma$. Most cells, such as resting T cells, are not responsive to IL-2 since they only express the IL-2R$\beta$, and the IL-2R$\gamma$, which have low affinity for IL-2. Upon stimulation, resting T cells express the relatively high affinity IL-2 receptor IL-2R$\alpha$. Binding of IL-2 to the IL-2R$\alpha$ causes this receptor to sequentially engage the IL-2R$\beta$, and the IL-2R$\gamma$, bringing about T cell activation. IL-2 "superkines" with augmented action due to enhanced binding affinity for IL-2R$\beta$ were previously developed (Levin et al., *Nature* 484: 529 (2012)).

Despite the wealth of knowledge around IL-2, including IL-2 superagonists, there remains a need in the art for better combination therapies for the treatment of cancer, including combination therapies with anti-PD-1 antibodies as well as combinations with oncolytic viruses or CAR-T cells. The present invention meets this need, providing combination therapies of IL-2 superagonists or agonists for the treatment of cancer, in particular combinations of anti-PD-1 antibodies with IL-2 muteins comprising substitutions L80F, R81D, L85V, I86V and I92F, numbered in accordance with wild-type IL-2.

BRIEF SUMMARY

IL-2 exerts a wide spectrum of effects on the immune system, and it plays crucial roles in regulating both immune activation and homeostasis. As an immune system stimulator, IL-2 muteins of the present invention have found use in combination with anti-PD-1 antibodies for the treatment of cancer.

In another aspect, provided herein is a method of treating a subject having cancer comprising administering an IL-2 mutein in combination with an anti-PD-1 antibody or inhibitor. In some embodiments, the method comprises administering to the subject a therapeutically effective amount of a pharmaceutical composition comprising any one of the IL-2 muteins disclosed herein. In some embodiments, the pharmaceutical composition comprises an IL-2 mutein having the amino acid substitutions L80F, R81D, L85V, I86V, and I92F.

As such, in some embodiments, the present invention provides a method of treating cancer comprising administering a combination treatment comprising: (i) an anti-PD-1 antibody or inhibitor and (ii) an IL-2 mutein comprising the following amino acid substitutions L80F, R81D, L85V, I86V and I92F, wherein numbering is in accordance with the wild-type human IL-2 of SEQ ID NO:2.

In some embodiments, the anti-PD-1 antibody or inhibitor is selected from the group consisting of nivolumab, BMS-936558, MDX-1106, ONO-4538, AMP224, CT-011, MK-3475 (pembrolizumab), cemiplimab (REGN2810), SHR-1210 (CTR20160175 and CTR20170090), SHR-1210 (CTR20170299 and CTR20170322), JS-001 (CTR20160274), IBI308 (CTR20160735), BGB-A317 (CTR20160872) and a PD-1 antibody as recited in U.S. Patent Publication No. 2017/0081409. In some embodiments, the anti-PD-L1 antibody or inhibitor is selected from the group consisting of atezolizumab, avelumab, and Durvalumab.

In some embodiments, the IL-2 mutein further comprises F42A substitution, wherein numbering is in accordance with the wild-type human IL-2 of SEQ ID NO:2. In some embodiments, the IL-2 mutein further comprising a F42A substitution exhibits reduced binding affinity for CD25 as compared to wild-type human IL-2.

In some embodiments, the IL-2 mutein further comprises K43N substitution, wherein numbering is in accordance with the wild-type human IL-2 of SEQ ID NO:2. In some embodiments, the IL-2 mutein further comprising a K43N substitution exhibits reduced binding affinity for CD25 as compared to wild-type human IL-2.

In some embodiments, the IL-2 mutein further comprises Y45A substitution, wherein numbering is in accordance with the wild-type human IL-2 of SEQ ID NO:2. In some embodiments, the IL-2 mutein further comprising a Y45A substitution exhibits reduced binding affinity for CD25 as compared to wild-type human IL-2.

In some embodiments, the IL-2 mutein further comprises E62A substitution, wherein numbering is in accordance with the wild-type human IL-2 of SEQ ID NO:2. In some embodiments, the IL-2 mutein further comprising a E62A substitution exhibits reduced binding affinity for CD25 as compared to wild-type human IL-2.

In some embodiments, the IL-2 mutein is a fusion protein. In some embodiments, the fusion protein comprises said IL-2 linked to an albumin. In some embodiments, the fusion protein comprises said IL-2 linked to an Fc antibody fragment. In some embodiments, the Fc antibody fragment is a human Fc antibody fragment. In some embodiments, the Fc antibody fragment comprises a N297A substitution.

In some embodiments, the cancer is selected from the group consisting of prostate cancer, ovarian cancer, breast cancer, endometrial cancer, multiple myeloma, melanoma, lymphomas, lung cancers including small cell lung cancer, kidney cancer, liver cancer, colon cancer, colorectal cancer, pancreatic cancer, gastric cancer, and brain cancer. In some embodiments, the cancer is colon cancer.

In some embodiments, the IL-2 mutein exhibits increased binding capacity for IL-2Rβ as compared to wild-type human IL-2. In some embodiments, the IL-2 mutein exhibits a greater binding affinity for IL-2Rβ as compared to wild-type human IL-2.

The method of any one of claims 3 to 7, wherein said IL-2 mutein exhibits decreased binding affinity for CD25 as compared to wild-type human IL-2.

In another aspect, provided herein is a pharmaceutical composition comprising any one of the IL-2 muteins or the IL-2 mutein fusion protein described herein and a pharmaceutically acceptable carrier. In some embodiments, the pharmaceutical composition comprises an IL-2 mutein having the amino acid substitutions L80F, R81D, L85V, I86V, and I92F.

In some embodiments, the pharmaceutical composition comprises an anti-PD-1 antibody or inhibitor, any of the IL-2 muteins as described herein, and a pharmaceutically acceptable carrier.

The present invention also provides for an immune cell targeting or expression construct comprising: an interleukin-2 receptor β (IL-2Rβ) binding protein, wherein the equilibrium dissociation constant for the IL-2Rβ of said binding protein is less than that of wild-type human IL-2 (hIL-2); linked to an immune cell targeting or expression construct comprising at least one other targeting moiety.

In some embodiments, the immune cell targeting or expression construct exhibits a cyotoxic effect on a T-cell, for example a CD8+ T-cell or a CD4+ T-cell.

In some embodiments, the construct is a chimeric antigen receptor (CAR) and wherein the IL-2 mutein is fused to a transmembrane domain; linked to an intracellular signaling region. In some embodiments, the intracellular signaling region comprises a CD3 signaling domain. In some embodiments, the intracellular signaling region comprises one or more of a CD28 signaling domain, a CD137 signaling domain, an OX-40 signaling domain, an ICOS signaling domain, a DAP10 signaling domain.

In some embodiments, the IL-2 mutein or other targeting moiety is fused to a ligand that binds a protein associated with the TCR complex; fused to a T cell receptor signaling domain polypeptide.

In some embodiments, the protein associated with the TCR complex is CD3.

In some embodiments, the T cell receptor signaling domain polypeptide comprises CD4 cytosolic domain and CD4 transmembrane domain.

In some embodiments, the construct is an antibody coupled T cell receptors (ACTR), comprising a chimeric antigen receptor component that binds to the IL-2 or other targeting moiety mutein at a high affinity.

In some embodiments, the CAR component comprises CD16, and the IL-2 mutein or other targeting moiety is fused to an Fc sequence.

In some embodiments, the construct is a bispecific T cell exchanger (BiTE) comprising an IL-2 mutein fused to a variable region of an antibody that binds to a component of a T cell receptor.

In some embodiments, the BiTE component of a T cell receptor is CD3.

In some embodiments, the IL-2 mutein comprises the following amino acid substitutions: L80F, R81D, L85V, I86V, and I92F, numbered in accordance with wild-type hIL-2.

In some embodiments, a nucleic acid encoding a construct according to the above is provided.

In some embodiments, a vector comprising the nucleic acid is provided.

In some embodiments, a T cell comprising a construct or a vector according to the above is provided. In some embodiments, the the T cell is a CD4$^+$ T cell. In some embodiments, the T cell is a CD8$^+$ T cell.

In some embodiments, an NK cell comprising a construct or a vector according to the above is provided Also provided is an isolated population of immune cells according to the above.

Also provided is a pharmaceutical formulation comprising the immune cell population of according to the above.

In some embodiments, a method of targeting a cell expressing an IL-2 receptor, including a cell expressing an IL-2 receptor, is provided, wherein the method comprising contacting a cell with a formulation comprising the immune cell population of according to the above. In some embodiments, the contacting is in vitro. In some embodiments, the contacting is in vivo.

The present invention also provides a method of treating cancer, the method comprising contacting an individual having cancer with an effective dose of a formulation comprising the immune cell population of according to the above.

In some embodiments, the cancer is a leukemia, lymphoma, glioblastoma, medulloblastoma, breast cancer, head and neck cancer, kidney cancer, ovarian cancer, Kaposi's sarcoma, acute myelogenous leukemia, B-lineage malignancies, colorectal, pancreatic, kidney, or mesothelioma.

The present invention also provides methods for targeting an IL-2 mutein protein to a cancer cell comprising contacting said cancer cell with an IL-2 mutein oncolytic virus combination, wherein said combination comprises an IL-2 mutein conjugated to or expressed by an oncolytic virus, and wherein said oncolytic virus is capable of targeting a cancer cell.

In some embodiments, the contacting occurs in vitro. In some embodiments, the contacting occurs in vivo.

In some embodiments, the oncolytic virus is selected from the group consisting of an adenovirus, a self-replicating alphavirus, a vaccinia virus, a Seneca Valley Virus, a Newcastle disease Virus, a Maraba virus, vesicular stomatitis virus (VSV), a Herpes virus (including HSV-1 and HSV-2), a measles virus, a poliovirus, a reovirus, a coxsackie virus, a lentivirus, a morbillivirus, an influenza virus, Sinbis virus, myxoma virus, and a retrovirus.

In some embodiments, the vaccinia virus genome comprises thymidine kinase gene is inactivated by a substitution in the thymidine kinase (TK) gene and/or an open reading frame ablating deletion of at least one nucleotide providing a partially deleted thymidine kinase gene, the vaccinia growth factor gene is deleted, and the modified vaccinia virus vector comprises at least one nucleic acid sequence encoding an IL-2 mutein as described herein.

In some embodiments, the in vivo contacting results in an increased concentration of the IL-2 mutein protein in the tumor microenvironment as compared to the concentration of an IL-2 mutein protein not conjugated to an oncolytic virus.

In some embodiments, the modified oncolytic virus targets the IL-2 mutein to the immunosuppressive cells of the tumor microenvironment (TME), such as tumor associated macrophages and MDSCs (myeloid-derived suppressor cells) in order to have an improved therapeutic benefit.

In some embodiments, modified oncolytic virus targets the IL-2 mutein to one or more immunosuppressive cells expressing one or more tumor antigens.

In some embodiments, the modified oncolytic virus targets the IL-2 mutein to the TME.

In some embodiments, the IL-2 mutein protein enhances effector T cells and/or NK cells.

In some embodiments, the IL-2 mutein suppresses Treg activity.

In some embodiments, the IL-2 comprises the following amino acid substitutions L80F, R81D, L85V, I86V, and I92F, wherein numbering is in accordance with the wild-type human IL-2 of SEQ ID NO:2.

According to the present invention, also provided is a modified vaccinia virus vector, characterized in that the vector comprises vaccinia virus genome wherein the thymidine kinase gene is inactivated by a substitution in the thymidine kinase (TK) gene and/or an open reading frame ablating deletion of at least one nucleotide providing a partially deleted thymidine kinase gene, the vaccinia growth factor gene is deleted, and the modified vaccinia virus vector comprises at least one nucleic acid sequence encoding an IL-2 mutein as described herein.

According to the present invention, also provided is a modified oncolytic adenovirus comprising (i) a modified nucleic acid, wherein optionally the nucleotides encoding amino acids 122-129 of the encoded E1A polypeptide are deleted, and (ii) an expression cassette comprising a polynucleotide encoding an IL-2 mutein as described herein.

In some embodiments, the IL-2 mutein directs the modified oncolytic virus to the immunosuppressive cells of the tumor microenvironment (TME), such as tumor associated macrophages and MDSCs (myeloid-derived suppressor cells) in order to have an improved therapeutic benefit.

In some embodiments, the IL-2 mutein protein directs the modified oncolytic virus to one or more tumor antigens.

In some embodiments, the IL-2 mutein protein directs modified oncolytic virus to the TME.

In some embodiments, the IL-2 mutein protein enhances effector T cells and NK cells.

In some embodiments, the IL-2 mutein suppresses Treg activity.

The present invention also provides for a method of treating cancer comprising administering and oncolytic virus capable of expressing an IL-2 mutein to s subject in need thereof. In some embodiments, the IL-2 mutein comprises the following amino acid substitutions L80F, R81D, L85V, I86V, and I92F, wherein numbering is in accordance with the wild-type human IL-2 of SEQ ID NO:2. In some embodiments, the IL-2 the oncolytic virus is selected from the group consisting of an adenovirus, a self-replicating alphavirus, a vaccinia virus, a Seneca Valley Virus, a Newcastle disease Virus, a Maraba virus, vesicular stomatitis virus (VSV), a Herpes virus (including HSV-1 and HSV-2), a measles virus, a poliovirus, a reovirus, a coxsackie virus, a lentivirus, a morbillivirus, an influenza virus, Sinbis virus, myxoma virus, and a retrovirus.

BRIEF DESCRIPTION OF THE DRAWINGS

FIG. 2. Provides examples of IgG1, IgG2, IgG3, and IgG4 sequences.

FIG. 3. Provides exemplary H9-Fc fusion sequences.

FIG. 4. Comparative analysis of the IL-13Rα1- and the IL-13Rα2-selective IL-13 variants Human IL-13 and IL-13Rα1 and IL-13Rα2 selective variants sequences are given for the indicated residue numbers. Kinetic and affinity parameters were determined by surface plasmon resonance.

FIG. 7. Exemplary anti-PD-1 antibodies for use with the combinations of the invention.

FIG. 8. Exemplary anti-PD-L1 antibodies for use with the combinations of the invention.

FIG. 9: Exemplary oncolytic viruses.

DETAILED DESCRIPTION

Figure 1:
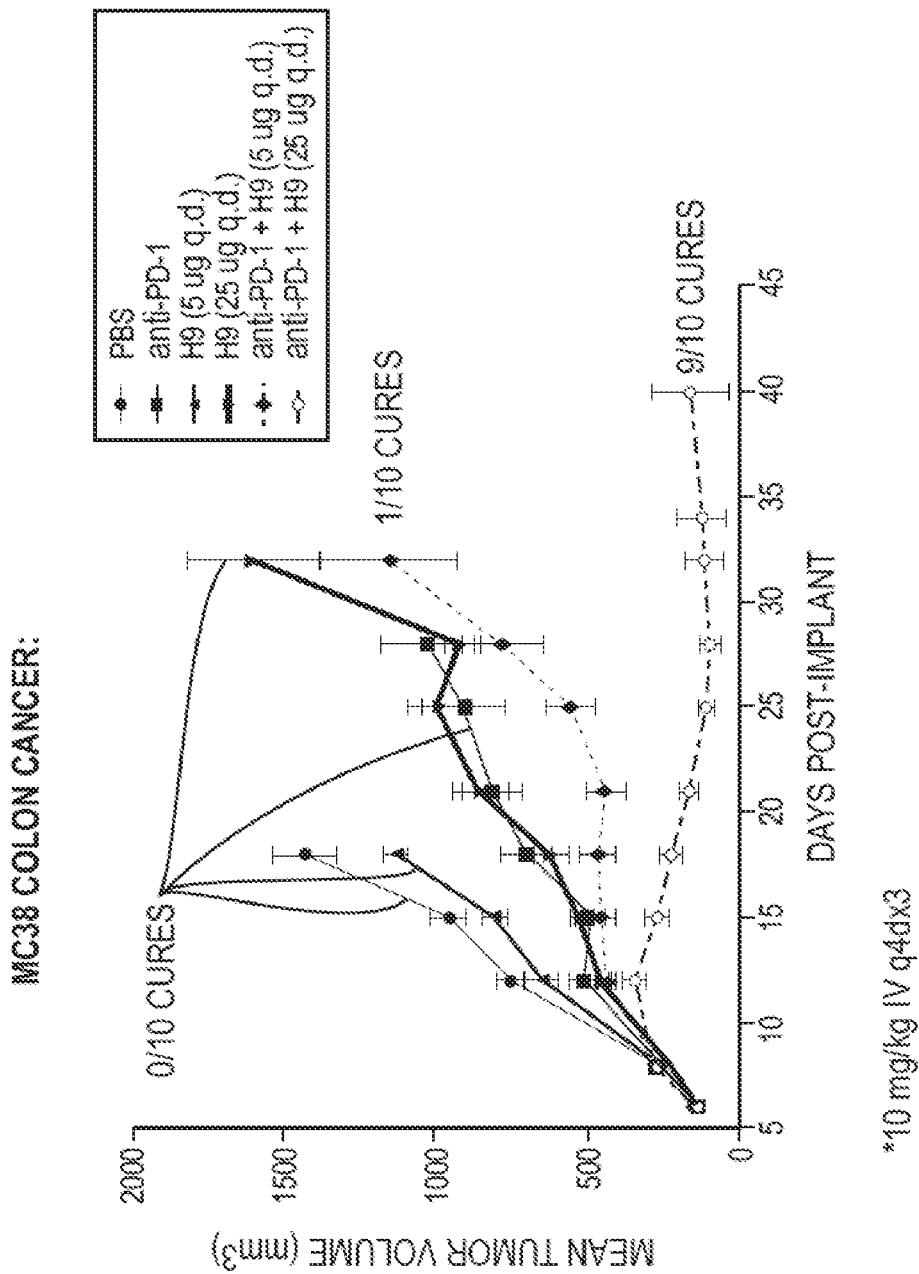
FIG. 1. H9 Synergizes with Anti-PD-1 Immunotherapy. Combination Therapy Produces Robust Responses in a Dose-Dependent Fashion. Anti-PD-1 antibody was administered at 10 mg/kg intravenously with 3 doses administered every 4 days (10 mg/kg IV q4dx3). H9 (IL-2 mutein having the amino acid substitutions L80F, R81D, L85V, I86V, and I92F, wherein numbering is in accordance with the wild-type human IL-2 of SEQ ID NO:2) was administered at the indicated dosage of 5 μg q.d. or 25 μg q.d. (dosing was μg/mouse), according to the same dosing regimen. MC38 colon cancer model mice were then monitored for up to 40 days post-tumor implant. The combination of anti-PD-1 antibody plus H9 resulted in an increase in the number of cures at both the low and high dose, with a substantial increase at the 25 ug q.d, dose of H9.
Figure 5:
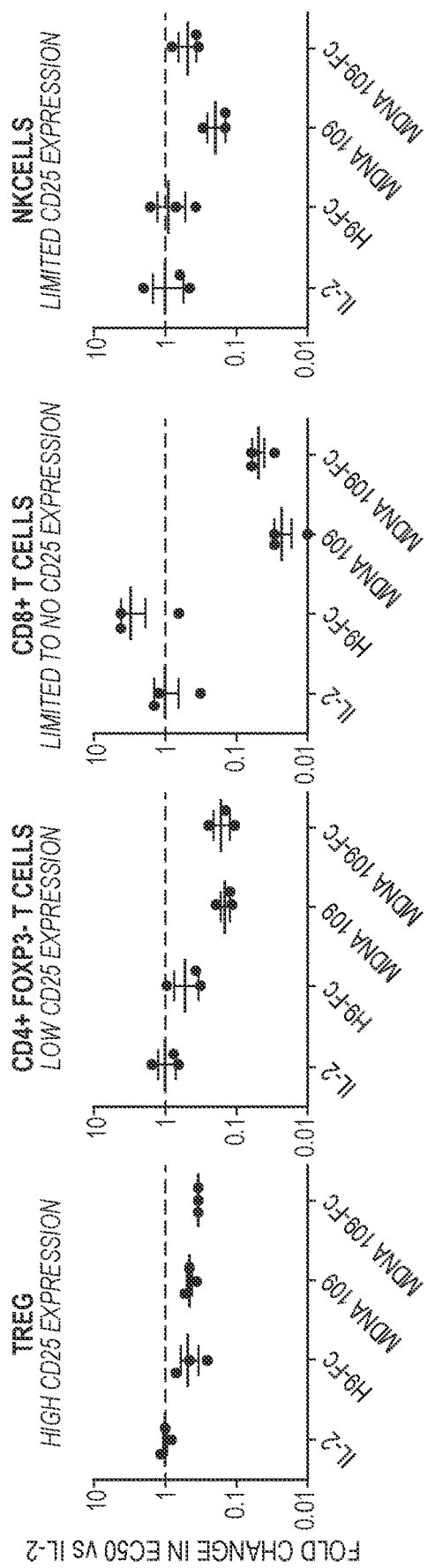
FIG. 5. H9-Fc has improved potency towards key immune cells H9 and H9-Fc have largely improved potency towards key effector T cells, particularly CD8+ T cells responsible for tumor cell killing. H9 and its Fc-variant do not lose potency towards Tregs, but enable a much increased relative activation of anti-tumor effector CD8+ T cells.
Figure 6:
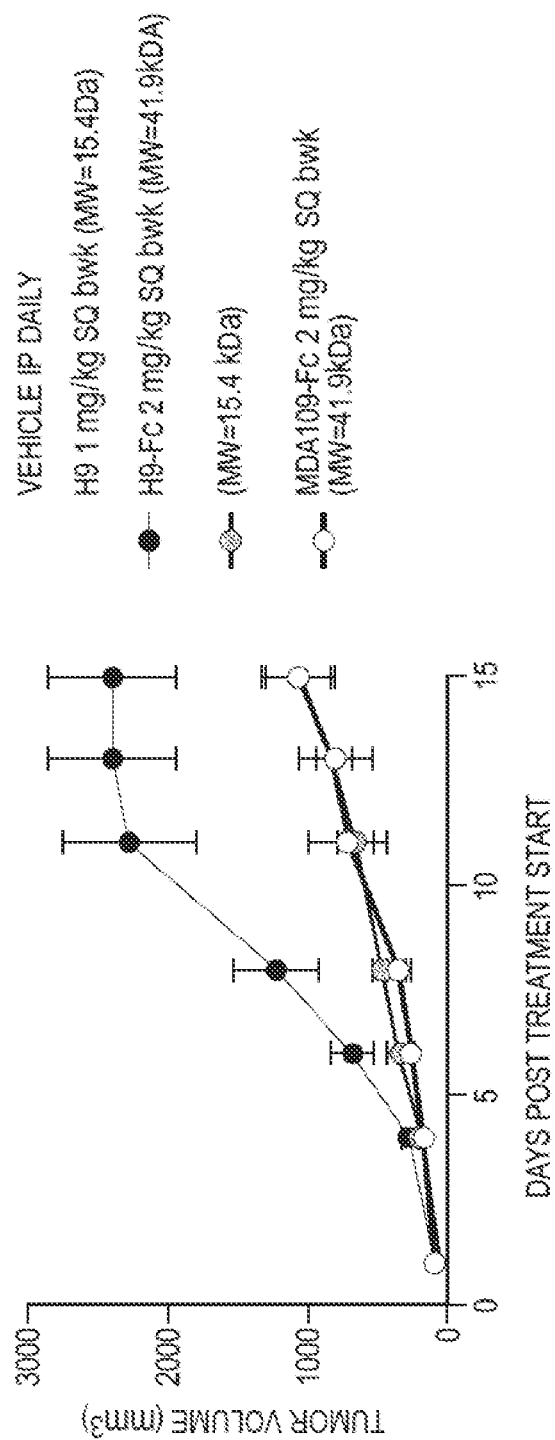
FIG. 6. H9-Fc has similar in vivo potency and extended PK profile vs H9. An optimized dose and schedule for the extended PK variant of H9 has been identified. H9-Fc enables effective B16F10 tumor control with a biweekly schedule, a similar schedule as anti-PD-1 antibodies used in mice. Accordingly, we predict weekly or once every two week administration of H9-Fc. Subcutaneous administration: Subcutaneous H9-Fc is an advantageous administration approach for a future immunotherapy drug. Checkpoint inhibitors, Proleukin and competitor IL-2 therapies (NKTR-214, ALKS 4230) all require IV infusion, with lengthy administration and monitoring time in the clinic. Subcutaneous administration offers fast and convenient administration that is typically preferred by patients for common targeted cancer therapies.

In order for the present disclosure to be more readily understood, certain terms and phrases are defined below as well as throughout the specification.

Definitions

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russell, *Molecular Cloning: A Laboratory Manual* 3rd ed., Cold Spring harbor Laboratory Press (Cold Spring Harbor, N.Y. 2001), provide one skilled in the art with a general guide to many terms used in the present disclosure. As appropriate, procedures involving the use of commercially available kits and reagents are generally carried out in accordance with manufacturer defined protocols and/or parameters unless otherwise noted.

As used herein, "IL-2" means wild-type IL-2, whether native or recombinant. Mature human IL-2 occurs as a 133 amino acid sequence (less the signal peptide, consisting of an additional 20 N-terminal amino acids), as described in Fujita, et. al., PNAS USA, 80, 7437-7441 (1983). The amino acid sequence of human IL-2 (SEQ ID NO:1; full length) is found in Genbank under accession locator NP_000577.2. The amino acid sequence of mature human IL-2 is depicted in SEQ ID NO:2 (human wild-type mature; position numbering of the substitutions is based on this sequence). The murine (*Mus musculus*) IL-2 amino acid sequence is found in Genbank under accession locator (SEQ ID NO:3). The amino acid sequence of mature murine IL-2 is depicted in SEQ ID NO:4.

```
                                         SEQ ID NO: 1
MYRMQLLSCIALSLALVTNSAPTSSSTKKTQLQLEHLLLDLQMILNG

INNYKNPKLTRMLTFKFYMPKKATELKHLQCLEEELKPLEEVLNLAQ

SKNFHLRPRDLISNINVIVLELKGSETTFMCEYADETATIVEFLNRW

ITFCQSIISTLT

SEQ ID NO: 2
APTSSSTKKTQLQLEHLLLDLQMILNGINNYKNPKLTRMLTFKFYMP

KKATELKHLQCLEEELKPLEEVLNLAQSKNFHLRPRDLISNINVIVL

ELKGSETTFMCEYADETATIVEFLNRWITFCQSIISTLT

SEQ ID NO: 3
MYSMQLASCVTLTLVLLVNSAPTSSSTSSSTAEAQQQQQQQQQQQQH

LEQLLMDLQELLSRMENYRNLKLPRMLTFKFYLPKQATELKDLQCLE

DELGPLRHVLDLTQSKSFQLEDAENFISNIRVTVVKLKGSDNTFECQ

FDDESATVVDFLRRWIAFCQSIISTSPQ

SEQ ID NO: 4
APTSSSTSSSTAEAQQQQQQQQQQQQHLEQLLMDLQELLSRMENYRN

LKLPRMLTFKFYLPKQATELKDLQCLEDELGPLRHVLDLTQSKSFQL

EDAENFISNIRVTVVKLKGSDNTFECQFDDESATVVDFLRRWIAFCQ

SIISTSPQ
```

As used herein, "IL-2 mutein" means an IL-2 polypeptide wherein specific substitutions to the interleukin-2 protein have been made. The IL-2 muteins are characterized by amino acid insertions, deletions, substitutions and modifications at one or more sites in or at the other residues of the native IL-2 polypeptide chain. In accordance with this disclosure, any such insertions, deletions, substitutions and modifications result in an IL-2 mutein that retains the IL-2Rβ binding activity. Exemplary muteins can include substitutions of 1, 2, 3, 4, 5, 6, 7, 8, 9, 10 or more amino acids.

Muteins also include conservative modifications and substitutions at other positions of IL-2 (i.e., those that have a minimal effect on the secondary or tertiary structure of the mutein). Such conservative substitutions include those described by Dayhoff in *The Atlas of Protein Sequence and Structure* 5 (1978), and by Argos in *EMBO J.*, 8:779-785 (1989). For example, amino acids belonging to one of the following groups represent conservative changes: Group I: ala, pro, gly, gln, asn, ser, thr; Group II: cys, ser, tyr, thr; Group III: val, ile, leu, met, ala, phe; Group IV: lys, arg, his; Group V: phe, tyr, trp, his; and Group VI: asp, glu.

"Numbered in accordance with IL-2" means identifying a chosen amino acid with reference to the position at which that amino acid normally occurs in the mature sequence of wild type IL-2, for example R81 refers to the eighty-first amino acid, arginine, that occurs in SEQ ID NO:2. L80 refers to the eightieth amino acid, leucine, that occurs in SEQ ID NO:2. L85 refers to the eighty-fifth amino acid, leucine, that occurs in SEQ ID NO:2. I86 refers to the eighty-sixth amino acid, isoleucine, that occurs in SEQ ID NO:2. I92 refers to the ninety-second amino acid, isoleucine, that occurs in SEQ ID NO:2. F42 refers to the forty-second amino acid, phenylalanine, that occurs in SEQ ID NO:2. K43 refers to the forty-third amino acid, lysine, that occurs in SEQ ID NO:2.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

The term "cell types having the IL-2Rαβγ receptor" means the cells known to have this receptor type, i.e., T cells, activated T cells, B cells, activated monocytes, and activated NK cells. The term "cell types having the IL-2Rβγ receptor" means the cells known to have that receptor type, i.e., B cells, resting monocytes, and resting NK cells.

The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The terms "polypeptide," "protein" or "peptide" refer to any chain of amino acid residues, regardless of its length or post-translational modification (e.g., glycosylation or phosphorylation).

In the event the mutant IL-2 polypeptides of the disclosure are "substantially pure," they can be at least about 60% by weight (dry weight) the polypeptide of interest, for example, a polypeptide containing the mutant IL-2 amino acid sequence. For example, the polypeptide can be at least about 75%, about 80%, about 85%, about 90%, about 95% or about 99%, by weight, the polypeptide of interest. Purity can be measured by any appropriate standard method, for example, column chromatography, polyacrylamide gel electrophoresis, or HPLC analysis.

An "agonist" is a compound that interacts with a target to cause or promote an increase in the activation of the target.

A "partial agonist" is a compound that interacts with the same target as an agonist but does not produce as great a magnitude of a biochemical and/or physiological effect as the agonist, even by increasing the dosage of the partial agonist.

A "superagonist" (also referred to as a "superkine") is a type of agonist that is capable of producing a maximal response greater than the endogenous agonist for the target receptor, and thus has an efficacy of more than 100%.

"Operably linked" is intended to mean that the nucleotide sequence of interest (i.e., a sequence encoding an IL-2 mutein) is linked to the regulatory sequence(s) in a manner that allows for expression of the nucleotide sequence (e.g., in an in vitro transcription/translation system or in a host cell when the vector is introduced into the host cell). "Regulatory sequences" include promoters, enhancers, and other expression control elements (e.g., polyadenylation signals). See, for example, Goeddel (1990) in Gene Expression Technology: Methods in Enzymology 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression constructs of the invention can be introduced into host cells to thereby produce the human IL-2 muteins disclosed herein or to produce biologically active variants thereof.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein.

As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, particle gun, or electroporation.

As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

As used herein, the term "anti-PD-1 antibody" refers to any antibody that binds to PD-1, including inhibitory antibodies. An "anti-PD-1 inhibitor" refers to an inhibitor that binds to and inhibits PD-1. Such anti-PD-1 antibodies and/or inhibitors include but are not limited to nivolumab, BMS-936558, MDX-1106, ONO-4538, AMP224, CT-011, and MK-3475, among others.

As used herein, the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasm" are used to refer to malignancies of the various organ systems, including those affecting the lung, breast, thyroid, lymph glands and lymphoid tissue, reproductive systems, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus. Cancers generally can include prostate cancer, ovarian cancer, breast cancer, endometrial cancer, multiple myeloma, melanoma, lymphomas, lung cancers including small cell lung cancer, kidney cancer, colorectal cancer, pancreatic cancer, gastric cancer, and brain cancer.

The term "carcinoma" is art-recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma"

refers to a carcinoma derived from glandular tissue or in which the tumor cells form recognizable glandular structures.

As used herein, the term "hematopoietic neoplastic disorders" refers to diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CIVIL) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Stemberg disease.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease. A therapeutically effective amount can be an amount that reduces tumor number, tumor size, and/or increases survival.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terms "pharmaceutically acceptable" and "physiologically acceptable" mean a biologically acceptable formulation, gaseous, liquid or solid, or mixture thereof, suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering an IL-2 mutein to a subject. In particular, an IL-2 mutein comprising the substitutions L80F, R81D, L85V, I86V, and I92F is administered in combination with anti-PD-1 to a subject with cancer. In some embodiments, the IL-2 mutein administered further comprises a substitution at position F42A. In some embodiments, the IL-2 administered mutein further comprises a substitution at position K43N.

The phrase a "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, produces a desired effect (e.g., prophylactic or therapeutic effect). In some embodiments, the therapeutic effect is to reduce tumor number. In some embodiments, the therapeutic effect is to reduce tumor size. In some embodiments, the therapeutic effect is to increase survival.

In some embodiments, unit dosage forms may be within, for example, ampules and vials, including a liquid composition, or a composition in a freeze-dried or lyophilized state; a sterile liquid carrier, for example, can be added prior to administration or delivery in vivo. Individual unit dosage forms can be included in multi-dose kits or containers. IL-2 muteins in combination with anti-PD-1 antibodies, and pharmaceutical compositions thereof can be packaged in a single or multiple unit dosage form for ease of administration and uniformity of dosage.

A "therapeutically effective amount" will fall in a relatively broad range determinable through experimentation and/or clinical trials. For example, for in vivo injection, e.g., injection directly into the tissue or vasculature of a subject (for example, liver tissue or veins). Other effective dosages can be readily established by one of ordinary skill in the art through routine trials establishing dose response curves.

An "effective amount" or "sufficient amount" refers to an amount providing, in single or multiple doses, alone or in combination, with one or more other compositions (therapeutic agents such as a drug), treatments, protocols, or therapeutic regimens agents (including, for example, vaccine regimens), a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome. In some embodiments, the effective amount is an amount sufficient to reduce tumor number. In some embodiments, the effective amount is an amount sufficient to reduce tumor size. In some embodiments, the effective amount is an amount sufficient to increase survival.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for the described methods and uses, but the subject may not manifest the disease. Such subjects therefore include those screened positive for an insufficient amount or a deficiency in a functional gene product (protein), or producing an aberrant, partially functional or non-functional gene product (protein), leading to disease; and subjects screening positive for an aberrant, or defective (mutant) gene product (protein) leading to disease, even though such subjects do not manifest symptoms of the disease.

I. Detailed Description

Described herein IL-2 muteins comprising the substitutions L80F, R81D, L85V, I86V, and I92F, which have an increased binding capacity for IL-2Rβ receptor and that find use in combination treatments with anti-PD-1 antibodies. In some embodiments, the IL-2 mutein comprising L80F, R81D, L85V, I86V and I92F, numbered in accordance with wild-type human IL-2 (SEQ ID NO:2; wild-type hIL-2) is referred to as H9. Such IL-2 muteins find use, for example, when combined with anti-PD-1 antibodies for the treatment of cancer. Also provided are nucleic acids encoding such IL-2 muteins, methods of making such IL-2 muteins, pharmaceutical compositions that include such IL-2 muteins and methods of treatment using such IL-2 muteins.

A. IL-2 Muteins

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact the IL-2Rβ and/or the IL-2Rγ.

More specifically, a mutation (whether conservative or non-conservative, by way of addition(s) or deletion(s)) can be made at one or more of positions. For example, the mutation can be: I24V, P65H, Q74R, Q74 H, Q74N, Q74S, L80F, L80V, R81I, R81T, R81D, L85V, I86V, I89V, I92F, V93I. The sequences of exemplary IL-2 muteins are as follows: 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

In some embodiments, the substitutions in the IL-2 mutein comprise L80F, R81D, L85V, I86V, and I92F, numbered in accordance with wild-type human IL-2 of SEQ ID NO:2. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the substitutions in the IL-2 mutein comprise F42A, L80F, R81D, L85V, I86V, and I92F, numbered in accordance with wild-type human IL-2 of SEQ ID NO:2. In some embodiments, the substitutions in the IL-2 mutein comprise F42A, Y45A, L80F, R81D, L85V, I86V, and I92F, numbered in accordance with wild-type human IL-2 of SEQ ID NO:2. In some embodiments, the substitutions in the IL-2 mutein comprise F42A, E62A, L80F, R81D, L85V, I86V, and I92F, numbered in accordance with wild-type human IL-2 of SEQ ID NO:2. In some embodiments, the substitutions in the IL-2 mutein comprise F42A, Y45A, E62A, L80F, R81D, L85V, I86V, and I92F, numbered in accordance with wild-type human IL-2 of SEQ ID NO:2. In some embodiments, the substitutions in the IL-2 mutein comprise E62A, L80F, R81D, L85V, I86V, and I92F, numbered in accordance with wild-type human IL-2 of SEQ ID NO:2. In some embodiments, the substitutions in the IL-2 mutein comprise Y45A, E62A, L80F, R81D, L85V, I86V, and I92F, numbered in accordance with wild-type human IL-2 of SEQ ID NO:2. In some embodiments, the substitutions in the IL-2 mutein comprise Y45A and E62A, numbered in accordance with wild-type human IL-2 of SEQ ID NO:2.

In some embodiments, the substitutions in the IL-2 mutein that lead to increased and/or enhanced IL-2Rβ binding include L80F, R81D, L85V, I86V, and I92F, numbered in accordance with wild-type human IL-2 of SEQ ID NO:2. In some embodiments, an IL-2 mutein for use in the invention comprises L80F, R81D, L85V, I86V, and I92F and exhibits increased IL-2Rβ binding. In some embodiments, an IL-2 mutein for use in the invention further comprises a substitution at position F42A. In some embodiments, the IL-2 mutein for use in the invention further comprises a substitution at position K43N. In some embodiments, the mutein comprises substitutions L80F, R81D, L85V, I86V, and I92F, and one or more substitutions selected from the group consisting of F42A, Y45A, and E62A, all as compared to wild-type human IL-2 (SEQ ID NO:2).

In some embodiments, the amino acid substitutions increasing IL-2Rβ binding affinity include: L80F, R81D, L85V, I86V, and I92F. In some embodiments, the amino acid substitutions that increase IL-2Rβ binding affinity include: L80F, R81D, L85V, I86V, and I92F.

In some embodiments, the subject IL-2 mutein having a greater binding affinity for IL-2Rβ as compared to wild-type human IL-2, includes the amino acid substitutions L80F, R81D, L85V, I86V, and I92F. In some embodiments, the IL-2 mutein has the amino acid sequence:

```
(SEQ ID NO: 5; H9 as used in Example 1)
APTSSSTKKTQLQLEHLLLDLQMILNGINNYKNPKLTRMLTFKFYMP KKATELKHLQCLEEELKPLEEVLNLAQSKNFH<u>FD</u>PRD<u>VV</u>SNINV<u>F</u>VL

ELKGSETTFMCEYADETATIVEFLNRWITFCQSIISTLT.
```

In some embodiments, the IL-2 mutein has increased capabilities to stimulate one or more signaling pathways that are dependent on IL-2Rβ/IL-2Rγ$_c$ heterodimerization. In some embodiments, the subject IL-2 mutein has an enhanced capability to stimulate STAT5 phosphorylation in an IL-2Rβ+ cell as compared to wild-type human IL-2. In some embodiments, the IL-2 mutein stimulates STAT5 phosphorylation in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or more of the level that wild-type IL-2 stimulates STAT5 phosphorylation in the same cell. In some embodiments, the IL-2 mutein stimulates STAT5 phosphorylation in an IL-2Rβ+ cell at a level that is 105%, 110%, 115%, 120%, 125%, 130%, 135%, 140%, 145%, 150%, 155%, 160%, 165%, 170%, 175%, 180%, 185%, 190%, 195% or more as compared to the level that wild-type IL-2 stimulates STAT5 phosphorylation in the same cell. In some embodiments, the IL-2Rβ+ cell is a T cell. In particular embodiments, the T cell is a CD8+ T cell. In some embodiments, the CD8+ T cell is a freshly isolated CD8+ T cell. In other embodiments, the CD8+ T cell T cell is an activated CD8+ T cell. In other embodiments, the IL-2Rβ+ cell is a natural killer (NK) cell. In some embodiments, the IL-2 mutein comprises substitutions L80F, R81D, L85V, I86V, and I92F, as compared to wild-type human IL-2 (SEQ ID NO:2).

In some embodiments, the mutein has an enhanced capability to stimulate ERK1/ERK2 signaling in an IL-2Rβ+ cell as compared to wild-type human IL-2. In some embodiments, the IL-2 mutein stimulates pERK1/ERK2 signaling in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or more of the level that wild-type IL-2 stimulates pERK1/ERK2 signaling in the same cell. In some embodiments, the IL-2 mutein stimulates pERK1/ERK2 phosphorylation in an IL-2Rβ+ cell at a level that is 105%, 110%, 115%, 120%, 125%, 130%, 135%, 140%, 145%, 150%, 155%, 160%, 165%, 170%, 175%, 180%, 185%, 190%, 195% or more as compared to the level that wild-type IL-2 stimulates pERK1/ERK2 phosphorylation in the same cell. In some embodiments, the IL-2Rβ+ cell is a T cell. In particular embodiments, the T cell is a CD8+ T cell. In some embodiments, the CD8+ T cell is a freshly isolated CD8+ T cell. In other embodiments, the CD8+ T cell T cell is an activated CD8+ T cell. In other embodiments, the IL-2Rβ+ cell is a natural killer (NK) cell. In some embodiments, the IL-2 mutein comprises substitutions L80F, R81D, L85V, I86V, and I92F, as compared to wild-type human IL-2 (SEQ ID NO:2).

STAT5 and ERK1/2 signaling can be measured, for example, by phosphorylation of STAT5 and ERK1/2 using any suitable method known in the art. For example, STAT5 and ERK1/2 phosphorylation can be measured using antibodies specific for the phosphorylated version of these molecules in combination with flow cytometry analysis as described herein. In some embodiments, the mutein has an enhanced capability to stimulate PI 3-kinase signaling in a IL-2Rβ+ cell as compared to wild-type human IL-2. In some embodiments, the IL-2 mutein stimulates PI 3-kinase signaling in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 stimulates PI 3-kinase signaling in the same cell. In some embodiments, the IL-2 mutein stimulates PI 3-kinase signaling in an IL-2Rβ+ cell at a level that is 105%, 110%, 115%, 120%, 125%, 130%, 135%, 140%, 145%, 150%, 155%, 160%, 165%, 170%, 175%, 180%, 185%, 190%, 195% or more as compared to the level that wild-type IL-2 stimulates PI 3-kinase signaling phosphorylation in the same cell. In some embodiments, the IL-2Rβ+ cell is a T cell. In particular embodiments, the T cell is a CD8+ T cell. In some embodiments, the CD8+ T cell T cell is an activated CD8+ T cell. In other embodiments, the IL-2Rβ+ cell is a natural killer (NK) cell. In some embodiments, the IL-2 mutein comprises substitutions L80F, R81D, L85V, I86V, and I92F, as compared to wild-type human IL-2 (SEQ ID NO:2). PI3-kinase signaling can be measured using any suitable method known in the art. For example, PI 3-kinase signaling can be measured using antibodies that are specific for phospho-S6 ribosomal protein in conjunction with flow cytometry analysis as described herein.

In some embodiments the IL-2 mutein is a stimulator of IL-2 and/or IL-15 STAT5 phosphorylation in CD8+ T cells. In some embodiments, the mutein is a promoter of IL-2 and/or IL-15 induced proliferation of CD8+ T cells. In some embodiments, the mutein is a stimulator of IL-2 dependent, TCR-induced cell proliferation. In some embodiments, the IL-2 mutein comprises substitutions L80F, R81D, L85V, I86V, and I92F, as compared to wild-type human IL-2 (SEQ ID NO:2).

IL-2 promotes Th1, Th9, and Treg T cell differentiation and inhibits Th17 differentiation. Therefore, without being bound by any particular theory of operation, it is believed that IL-2 muteins that function as IL-2 superagonists are capable of promoting Th1, Th9, and/or Treg cell differentiation or inhibiting Th17 cell differentiation. In some embodiments, the IL-2 mutein is a promoter of IL-2 dependent Th1, Th9 and/or Treg differentiation. In some embodiments, the mutein is an inhibitor of Th17 differentiation. In some embodiments, the IL-2 mutein comprises substitutions L80F, R81D, L85V, I86V, and I92F, as compared to wild-type human IL-2 (SEQ ID NO:2).

In some embodiments, the IL-2 mutein signals less and/or independently of CD25 (for example, has reduced or ablated CD25 binding) as compared to wild-type human IL-2. In some embodiments the reduced and/or independent signaling with regard to CD25 allows for preferential activation of effector T-cells while limiting the stimulation of Tregs. In some embodiments the reduced and/or independent signaling with regard to CD25 allows for reduced toxicity. In some embodiments, the mutein comprises substitutions L80F, R81D, L85V, I86V, and I92F, and one or more substitutions selected from the group consisting of F42A, Y45A, and E62A, all as compared to wild-type human IL-2 (SEQ ID NO:2).

In some embodiments, the IL-2 mutein is capable of increasing and/or restoring responsiveness to anergic NK cells. In some embodiments, the IL-2 mutein is capable of increasing and/or restoring responsiveness to anergic NK cells in the tumor microenvironment. In some embodiments, the IL-2 mutein comprises substitutions L80F, R81D, L85V, I86V, and I92F, as compared to wild-type human IL-2 (SEQ ID NO:2).

In some embodiments the mutein is an inhibitor an inhibitor of IL-2 dependent activation of natural killer (NK) cells. IL-2 activation of NK cells can be measured by any suitable method known in the art, for example, by measuring IL-2 induced CD69 expression and/or cytotoxicity, as described herein.

In some embodiments, an increase in IL-2Rβ binding affinity is any binding affinity for IL-2Rβ that is greater than the wild-type human IL-2 binding affinity for IL-2Rβ. In some embodiments, the binding affinity is a 2-fold, 5-fold, 10-fold, 20-fold, 30-fold, 40-fold, 50-fold, 60-fold, 70-fold, 80-fold, 90-fold, 100-fold, 120-fold, 150-fold, 170-fold, 190-fold, 200-fold, 220-fold, 240-fold or more increase in binding affinity for IL-2Rβ as compared to the wild-type human IL-2 binding affinity for IL-2Rβ.

In some embodiments, an increase in binding capacity for IL-2Rβ is any binding capacity for IL-2Rβ that is greater than the wild-type human IL-2 binding capacity for IL-2Rβ. In some embodiments, the binding capacity is a 2-fold, 5-fold, 10-fold, 20-fold, 30-fold, 40-fold, 50-fold, 60-fold, 70-fold, 80-fold, 90-fold, 100-fold, 120-fold, 150-fold, 170-fold, 190-fold, 200-fold, 220-fold, 240-fold or more increase in binding capacity for IL-2Rβ as compared to the wild-type human IL-2 binding capacity for IL-2Rβ.

In some embodiments, the subject IL-2 mutein having a greater binding affinity for IL-2Rβ as compared to wild-type human IL-2 also exhibits reduced binding to CD25 and includes the amino acid substitutions F42A, L80F, R81D, L85V, I86V, and I92F. In some embodiments, the reduce binding affinity is about 220-fold, i.e., from about Kd of 6.6 nM for wild-type human IL-2 to about 1.4 μM for the mutein comprising F42A, L80F, R81D, L85V, I86V, and I92F. In some embodiments, the IL-2 mutein has the amino acid sequence:

```
(SEQ ID NO: 6; also referred to as H9-F42A)
APTSSSTKKTQLQLEHLLLDLQMILNGINNYKNPKLTRMLTAKFYMP

KKATELKHLQCLEEELKPLEEVLNLAQSKNFHFDPRDVVSNINVFVL

ELKGSETTFMCEYADETATIVEFLNRWITFCQSIISTLT.
```

In some embodiments, the subject IL-2 mutein having a greater binding affinity for IL-2Rβ as compared to wild-type human IL-2 also exhibits reduced binding to CD25 and includes the amino acid substitutions K43N, L80F, R81D, L85V, I86V, and I92F. In some embodiments, the reduce binding affinity is due to allowing for glycosylation at position 43 with the K43N substitution. By substituting lysine for asparagine (K43N), CD25 binding is reduced and/or ablated in the IL-2 mutein comprising the amino acid substitutions K43N, L80F, R81D, L85V, I86V, and I92F. In some embodiments, the IL-2 mutein has the amino acid sequence:

(SEQ ID NO: 7; also referred to as H9-K43N)
APTSSSTKKTQLQLEHLLLDLQMILNGINNYKNPKLTRMLTFNFYMP

KKATELKHLQCLEEELKPLEEVLNLAQSKNFHFDPRDVVSNINVFVL

ELKGSETTFMCEYADETATIVEFLNRWITFCQSIISTLT.

In some embodiments, a reduction in binding affinity for CD25 is any binding affinity for CD25 that is less than the wild-type human IL-2 binding affinity. In some embodiments, the binding affinity is a 10-fold, 20-fold, 30-fold, 40-fold, 50-fold, 60-fold, 70-fold, 80-fold, 90-fold, 100-fold, 120-fold, 150-fold, 170-fold, 190-fold, 200-fold, 220-fold, 240-fold or more decrease in binding affinity for CD25 as compared to the wild-type human IL-2 binding affinity for CD25.

In some embodiments, the subject IL-2 mutein having a greater binding affinity for IL-2Rβ and a reduced binding affinity for CD25 as compared to wild-type human IL-2 includes the amino acid substitutions F42A, Y45A L80F, R81D, L85V, I86V, and I92F. In some embodiments, the IL-2 mutein has the amino acid sequence:

(SEQ ID NO: 8; H9-F42A/Y45A; H9-FYAA)
APTSSSTKKTQLQLEHLLLDLQMILNGINNYKNPKLTRMLTAKFAMP

KKATELKHLQCLEEELKPLEEVLNLAQSKNFHFDPRDVVSNINVFVL

ELKGSETTFMCEYADETATIVEFLNRWITFCQSIISTLT.

In some embodiments, the subject IL-2 mutein having a greater binding affinity for IL-2Rβ and a reduced binding affinity for CD25 as compared to wild-type human IL-2 includes the amino acid substitutions F42A, E62A L80F, R81D, L85V, I86V, and I92F. In some embodiments, the IL-2 mutein has the amino acid sequence:

(SEQ ID NO: 9; H9-F42A/E62A; H9-FEAA)
APTSSSTKKTQLQLEHLLLDLQMILNGINNYKNPKLTRMLTAKFYMP

KKATELKHLQCLEEALKPLEEVLNLAQSKNFHFDPRDVVSNINVFVL

ELKGSETTFMCEYADETATIVEFLNRWITFCQSIISTLT.

In some embodiments, the subject IL-2 mutein having a greater binding affinity for IL-2Rβ and a reduced binding affinity for CD25 as compared to wild-type human IL-2 includes the amino acid substitutions F42A, Y45A, E62A, L80F, R81D, L85V, I86V, and I92F. In some embodiments, the IL-2 mutein has the amino acid sequence:

(SEQ ID NO: 10; H9-F42A/Y45A/E62A; H9-FYEAAA)
APTSSSTKKTQLQLEHLLLDLQMILNGINNYKNPKLTRMLTAKFAMP

KKATELKHLQCLEEALKPLEEVLNLAQSKNFHFDPRDVVSNINVFVL

ELKGSETTFMCEYADETATIVEFLNRWITFCQSIISTLT.

In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein sequence is 95% identical to any one of SEQ ID NO:2 or SEQ ID NO:6 through SEQ ID NO:10. In some embodiments, the IL-2 mutein sequence is 98% identical to any one of SEQ ID NO:2 or SEQ ID NO:6 through SEQ ID NO:10. In some embodiments, the IL-2 mutein sequence is 99% identical to any one of SEQ ID NO:2 or SEQ ID NO:6 through SEQ ID NO:10.

Further exemplary IL-2 sequences are provided in the table below.

TABLE 2

List of Exemplary IL-2 Muteins

| Amino Acid Sequences SEQ ID NO: (Information) | Amino acid sequence |
| --- | --- |
| SEQ ID NO: 6 (also referred to as H9-F42A) | APTSSSTKKTQLQLEHLLLDLQMILNGINNYKNPKLTRMLTA KFYMPKKATELKHLQCLEEELKPLEEVLNLAQSKNFHFDPRD VVSNINVFVLELKGSETTFMCEYADETATIVEFLNRWITFCQ SIISTLT( |
| (SEQ ID NO: 7 (also referred to as H9-K43N) | APTSSSTKKTQLQLEHLLLDLQMILNGINNYKNPKLTRMLTF NFYMPKKATELKHLQCLEEELKPLEEVLNLAQSKNFHFDPRD VVSNINVFVLELKGSETTFMCEYADETATIVEFLNRWITFCQ SIISTLT |
| SEQ ID NO: 8 (H9-F42A/Y45A; H9-FYAA) | APTSSSTKKTQLQLEHLLLDLQMILNGINNYKNPKLTRMLTA KFAMPKKATELKHLQCLEEELKPLEEVLNLAQSKNFHFDPRD VVSNINVFVLELKGSETTFMCEYADETATIVEFLNRWITFCQ SIISTLT |
| SEQ ID NO: 9) (H9-F42A/E62A; H9-FEAA) | APTSSSTKKTQLQLEHLLLDLQMILNGINNYKNPKLTRMLTA KFYMPKKATELKHLQCLEEALKPLEEVLNLAQSKNFHFDPRD VVSNINVFVLELKGSETTFMCEYADETATIVEFLNRWITFCQ SIISTLT |

TABLE 2-continued

List of Exemplary IL-2 Muteins

| Amino Acid Sequences SEQ ID NO: (Information) | Amino acid sequence |
|---|---|
| SEQ ID NO: 10; H9-F42A/Y45A/E62A; H9-FYEAAA). | APTSSSTKKTQLQLEHLLLDLQMILNGINNYKNPKLTRMLTA KFAMPKKATELKHLQCLEEALKPLEEVLNLAQSKNFHFDPRD VVSNINVFVLELKGSETTFMCEYADETATIVEFLNRWITFCQ SIISTLT |
| SEQ ID NO: 20 | APTSSSIKKTQLQLEHLLLDLQMILNGINNYKNPKLTRMLIF KFYMPKKATELKHLQCLEEELKPLEEVLNLARSKNFHLRPRD LISNINVIVLELKGSETTFMCEYADETATIVEFLNRWITFCQ SIISTLT |
| SEQ ID NO: 21 | APTSSSIKKTQLQLEHLLLDLQMILNGINNYKNPKLTRMLIF KFYMPKKATELKHLQCLEEELKPLEEVLNLARSKNFHLRPRD VISNINVIVLELKGSETTFMCEYADETATIVEFLNRWITFCQ SIISTLT |
| SEQ ID NO: 22 | APTSSSIKKTQLQLEHLLLDLQMILNGINNYKNPKLTRMLIF KFYMPKKATELKHLQCLEEELKPLEEVLNLARSKNFHLIPRD VISNINVIVLELKGSETTFMCEYADETATIVEFLNRWITFCQ SIISTLT |
| SEQ ID NO: 23 | APTSSSIKKTQLQLEHLLLDLQMILNGINNYKNPKLTRMLIF KFYMPKKATELKHLQCLEEELKPLEEVLNLAHSKNFHLTPRD VVSNINVFILELKGSETTFMCEYADETATIVEFLNRWITFCQ SIISTLT |
| SEQ ID NO: 24 | APTSSSIKKTQLQLEHLLLDLQMILNGINNYKNPKLTRMLIF KFYMPKKATELKHLQCLEEELKPLEEVLNLANSKNFHFDPRD VVSNVNVFVLELKGSETTFMCEYADETATIVEFLNRWITFCQ SIISTLT |
| SEQ ID NO: 25 | APTSSSIKKTQLQLEHLLLDLQMVLNGINNYKNPKLTRMLIF KFYMPKKATELKHLQCLEEELKPLEEVLNLASSKNFHFDPRD VVSNINVFVLELKGSETTFMCEYADETATIVEFLNRWITFCQ SIISTLT |
| SEQ ID NO: 26 | APTSSSIKKTQLQLEHLLLDLQMILNGINNYKNPKLTRMLIF KFYMPKKATELKHLQCLEEELKHLEEVLNLANSKNFHVTPRD VVSNINVFVLELKGSETTFMCEYADETATIVEFLNRWITFCQ SIISTLT |
| SEQ ID NO: 27 | APTSSSIKKTQLQLEHLLLDLQMILNGINNYKNPKLTRMLIF KFYMPKKATELKHLQCLEEELKPLEEVLNLAHSKNFHFDPRD VVSNINVFVLELKGSETTFMCEYADETATIVEFLNRWITFCQ SIISTLT |
| SEQ ID NO: 28 | APTSSSIKKTQLQLEHLLLDLQMILNGINNYKNPKLTRMLIF KFYMPKKATELKHLQCLEEELKPLEEVLNLASSKNFHFDPRD VVSNINVFVLELKGSETTFMCEYADETATIVEFLNRWITFCQ SIISTLT |
| SEQ ID NO: 29 | APTSSSIKKTQLQLEHLLLDLQMILNGINNYKNPKLTRMLIF KFYMPKKATELKHLQCLEEELKPLEEVLNLANSKNFHFDPRD VVSNINVFVLELKGSETTFMCEYADETATIVEFLNRWITFCQ SIISTLT |
| SEQ ID NO: 30 | APTSSSIKKTQLQLEHLLLDLQMILNGINNYKNPKLTRMLIF KFYMPKKATELKHLQCLEEELKPLEEVLNLASSKNFHLTPRD VISNINVFVLELKGSETTFMCEYADETATIVEFLNRWITFCQ SIISTLT |
| SEQ ID NO: 31 | APTSSSIKKTQLQLEHLLLDLQMILNGINNYKNPKLTRMLIF KFYMPKKATELKHLQCLEEELKPLEEVLNLAQSKNFHFDPRD VVSNINVFVLELKGSETTFMCEYADETATIVEFLNRWITFCQ SIISTLT |
| SEQ ID NO: 32 IL-2 agonist | H9D10 APTSSSTKKTQLQLEHLLLDLQMILNGINNYKNPKLTRMLTF KFYMPKKATELKHLQCLEEELKPLEEVLNLAHSKNFHFDPRD VVSNINVFVLELKGSETTFMCEYADETATIVEFLNRWITFCQ SIISTLT |

TABLE 2-continued

List of Exemplary IL-2 Muteins

Amino Acid Sequences
SEQ ID NO:
(Information)           Amino acid sequence

SEQ ID NO: 33
IL-2 agonist
H9E10
APTSSSTKKTQLQLEHLLLDLQMILNGINNYKNPKLTRMLTF
KFYMPKKATELKHLQCLEEELKPLEEVLNLASSKNFHFDPRD
VVSNINVFVLELKGSETTFMCEYADETATIVEFLNRWITFCQ
SIISTLT SEQ ID NO: 34
IL-2 agonist
H9G8
APTSSSTKKTQLQLEHLLLDLQMILNGINNYKNPKLTRMLTF
KFYMPKKATELKHLQCLEEELKPLEEVLNLANSKNFHFDPRD
VVSNINVFVLELKGSETTFMCEYADETATIVEFLNRWITFCQ
SIISTLT SEQ ID NO: 35
IL-2 agonist
H9B1
APTSSSTKKTQLQLEHLLLDLQMILNGINNYKNPKLTRMLTF
KFYMPKKATELKHLQCLEEELKPLEEVLNLANSKNFHFDPRD
VVSNVNVFVLELKGSETTFMCEYADETATIVEFLNRWITFCQ
SIISTLT B. IL-2 Mutein Fusion Proteins The IL-2 muteins can be prepared as fusion or chimeric polypeptides that include a subject IL-2 mutein and a heterologous polypeptide (i.e., a polypeptide that is not IL-2 or a mutant thereof) (see, e.g., U.S. Pat. No. 6,451,308). Exemplary heterologous polypeptides can increase the circulating half-life of the chimeric polypeptide in vivo, and may, therefore, further enhance the properties of the mutant IL-2 polypeptides. In various embodiments, the polypeptide that increases the circulating half-life may be a serum albumin, such as human serum albumin, PEG, PEG-derivatives, or the Fc region of the IgG subclass of antibodies that lacks the IgG heavy chain variable region. Exemplary Fc regions can include a mutation that inhibits complement fixation and Fc receptor binding, or it may be lytic, i.e., able to bind complement or to lyse cells via another mechanism, such as antibody-dependent complement lysis (ADCC; U.S. Ser. No. 08/355,502 filed Dec. 12, 1994).

Figure 2B:
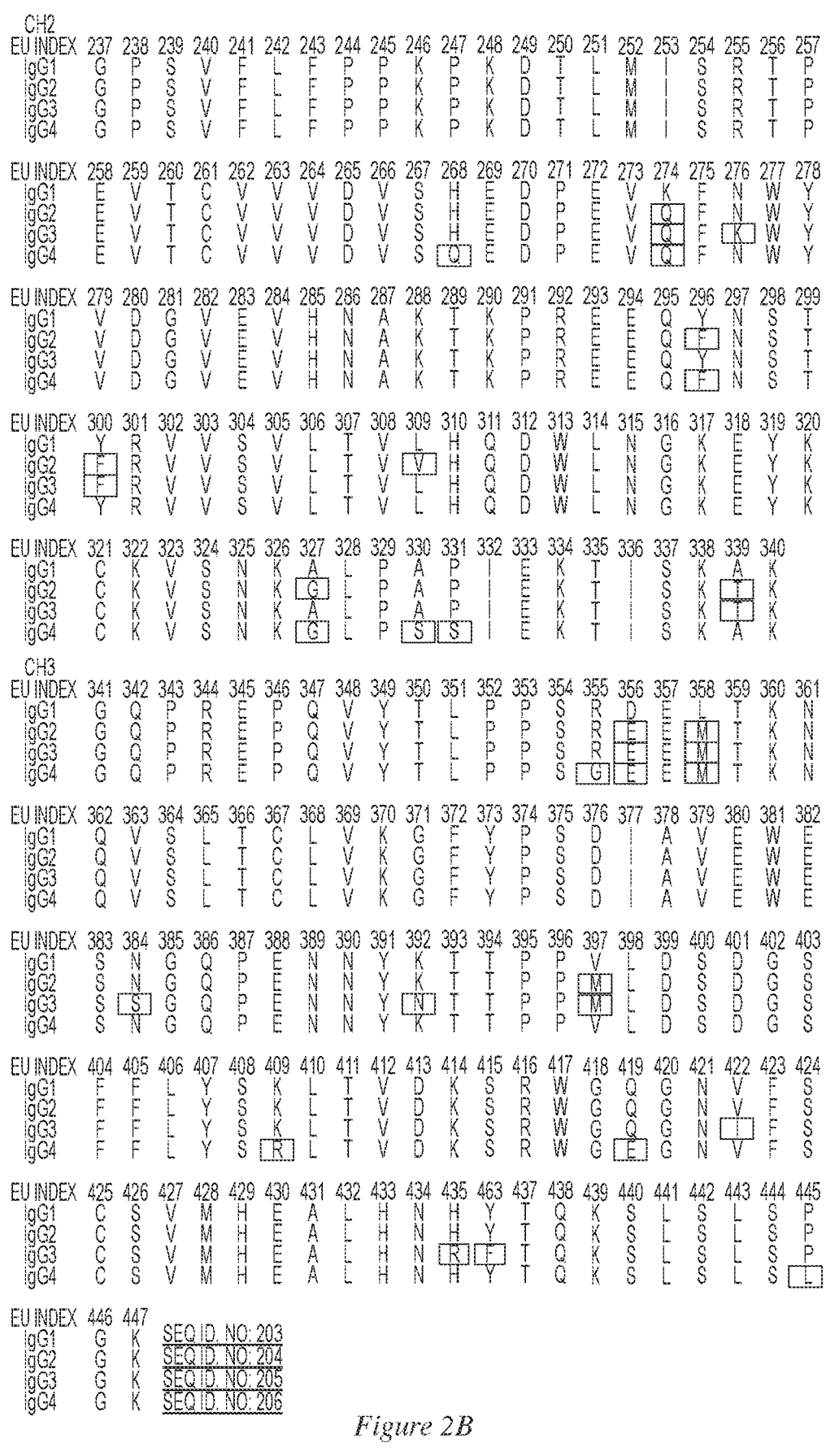

The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. In some embodiments, the IL-2 mutein fusion protein (e.g., an IL-2 mutein as described herein) includes an IgG1, IgG2, IgG3, or IgG4 Fc region (see, for example, sequences in FIG. 2A-2B). In some embodiments, the Fc region comprises the substitution N297A.

In some embodiments, the IL-2 mutein is linked directly or indirectly to the heterologous fusion polypeptide.

In some embodiments, the IL-2 mutein is linked directly to the Fc region. In some embodiments, the IL-2 mutein is linked to the Fc region via a linker peptide, such as GGGGS. In some embodiments, the linker is (GGGGS)n, wherein n is an integer between 1 and 10. In some embodiments, the linker is GGGGS. In some embodiments, the linker is GGGGSGGGGS (SEQ ID NO:16). In some embodiments, the linker is GGGGSGGGGSGGGGS (SEQ ID NO:17). In some embodiments, the linker is GGGGSGGGGSGGGGSGGGGS (SEQ ID NO:18). In some embodiments, the linker is GGGGSGGGGSGGGGSGGGGSGGGGS (SEQ ID NO:19).

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994).

In other embodiments, the chimeric polypeptide can include a subject IL-2 mutein and a polypeptide that functions as an antigenic tag, such as a FLAG sequence. FLAG sequences are recognized by biotinylated, highly specific, anti-FLAG antibodies, as described herein (see also Blanar et al., Science 256:1014, 1992; LeClair et al., Proc. Natl. Acad. Sci. USA 89:8145, 1992). In some embodiments, the chimeric polypeptide further comprises a C-terminal c-myc epitope tag.

In other embodiments, the chimeric polypeptide includes the mutant IL-2 polypeptide and a heterologous polypeptide that functions to enhance expression or direct cellular localization of the mutant IL-2 polypeptide, such as the Aga2p agglutinin subunit (see, e.g., Boder and Wittrup, Nature Biotechnol. 15:553-7, 1997).

In other embodiments, a chimeric polypeptide including a mutant IL-2 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the chimeric polypeptide comprises a fusion to an antibody or an antigen-binding portion thereof that disrupts the interaction between the PD-1 receptor and its ligand, PD-L1, and/or is an antibody to a component of the PD-1/PD-L1 signaling pathway. Antibodies known in the art which bind to PD-1 and disrupt the interaction between the PD-1 and its ligand, PD-L1, and stimulate an anti-tumor immune response, are suitable for use in the chimeric polypeptides disclosed herein. In some embodiments, the antibody or antigen-binding portion thereof binds specifically to PD-1. For example, antibodies that target PD-1 and which can find used in the present invention include, e.g., but are not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (cemiplimab, Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies include anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in the chimeric polypeptides disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, is suitable for use in the chimeric polypeptides disclosed herein. In some embodiments, the chimeric polypeptide comprises a fusion to an anti-PD-1 antibody. In some embodiments, the chimeric polypeptide comprises a fusion to an anti-PD-L1 antibody.

In some embodiments, the chimeric polypeptide comprises a fusion to an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the chimeric polypeptides disclosed herein. In some embodiments, the chimeric polypeptide comprises a fusion to an anti-CTLA-4 antibody.

In some embodiments, the chimeric polypeptide comprises a fusion to an antibody or an antigen-binding portion thereof that targets LAG-3 and disrupts its interaction with MHC class II molecules. An exemplary antibody that targets LAG-3 is IMP321 (Immutep), currently undergoing human trials. Other suitable antibodies that target LAG-3 are disclosed in U.S. Patent Application 2011/0150892, herein incorporated by reference. It will be understood by one of ordinary skill that any antibody which binds to LAG-3, disrupts its interaction with MHC class II molecules, and stimulates an anti-tumor immune response, is suitable for use in the chimeric polypeptides disclosed herein. In some embodiments, the chimeric polypeptide comprises a fusion to an anti-LAG-3 antibody.

In some embodiments, the chimeric polypeptide comprises a fusion to an antibody or an antigen-binding portion thereof that targets B7-H3 or B7-H4. The B7 family does not have any defined receptors but these ligands are upregulated on tumor cells or tumor-infiltrating cells. An exemplary antibody that targets B7-H3 is MGA271 (Macrogenics) is currently undergoing human trials. Other suitable antibodies that target B7 family members are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the chimeric polypeptides disclosed herein. In some embodiments, the chimeric polypeptide comprises a fusion to an anti-B7-H3 or B7-H4 antibody.

In some embodiments, the chimeric polypeptide comprises a fusion to an antibody or an antigen-binding portion thereof that targets TIM-3 and disrupts its interaction with galectin 9. Suitable antibodies that target TIM-3 are disclosed in U.S. Patent Application 2013/0022623, herein incorporated by reference. It will be understood by one of ordinary skill that any antibody which binds to TIM-3, disrupts its interaction with galectin 9, and stimulates an anti-tumor immune response, is suitable for use in the chimeric polypeptides disclosed herein. In some embodiments, the chimeric polypeptide comprises a fusion to an anti-TIM-3 antibody.

In some embodiments, the chimeric polypeptide comprises a fusion to an antibody or an antigen-binding portion thereof that targets 4-1BB/CD137 and disrupts its interaction with CD137L. It will be understood by one of ordinary skill that any antibody which binds to 4-1BB/CD137, disrupts its interaction with CD137L or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-4-1BB/CD137 antibody.

In some embodiments, the chimeric polypeptide comprises a fusion to an antibody or an antigen-binding portion thereof that targets GITR and disrupts its interaction with its ligand. It will be understood by one of ordinary skill that any antibody which binds to GITR, disrupts its interaction with GITRL or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-GITR antibody.

In some embodiments, the chimeric polypeptide comprises a fusion to an antibody or an antigen-binding portion thereof that targets OX40 and disrupts its interaction with its ligand. It will be understood by one of ordinary skill that any antibody which binds to OX40, disrupts its interaction with OX40L or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-OX40 antibody.

In some embodiments, the chimeric polypeptide comprises a fusion to an antibody or an antigen-binding portion thereof that targets CD40 and disrupts its interaction with its ligand. It will be understood by one of ordinary skill that any antibody which binds to CD40, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-CD40 antibody In some embodiments, the chimeric polypeptide comprises a fusion to an antibody or an antigen-binding portion thereof that targets ICOS and disrupts its interaction with its ligand. It will be understood by one of ordinary skill that any antibody which binds to ICOS, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-ICOS antibody.

In some embodiments, the chimeric polypeptide comprises a fusion to an antibody or an antigen-binding portion thereof that targets CD28 and disrupts its interaction with its ligand. It will be understood by one of ordinary skill that any antibody which binds to CD28, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-CD28 antibody.

In some embodiments, the chimeric polypeptide comprises a fusion to an antibody or an antigen-binding portion thereof that targets IFNα and disrupts its interaction with its ligand. It will be understood by one of ordinary skill that any antibody which binds to IFNα, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-IFNα antibody.

In some embodiments, the chimeric polypeptide comprises a fusion to a tumor antigen or polypeptide targeting a tumor antigen. Generally, tumor antigens allow for distinguishing the tumor cells from their normal cellular counterparts and can include, for example, tumor-specific antigens (TSA) as well as tumor-associated antigens (TAA). In some embodiments, a tumor antigen is a protooncogene and/or a tumor suppressor, as well as overexpressed or aberrantly expressed cellular proteins, tumor antigens produced by oncogenic viruses, oncofetal antigens, altered cell surface glycolipids and glycoproteins, and/or cell type-specific differentiation antigens. Such tumor antigens can include melanoma antigens, cancer-testis antigens, epithelial tumor antigens, cell cycle regulatory proteins, prostate specific antigens (including prostate carcinoma antigens, such as for example those disclosed in U.S. Pat. No. 5,538,866) lymphoma (U.S. Pat. Nos. 4,816,249; 5,068,177; and 5,227,159). Tumor antigens can include for example, but are not limited to, HMW mucins bound by 2G3 and 369F10, c-erbB-2 related tumor antigen (an approximately 42 kD or 55 kD glycoprotein), the approximately 40, 60, 100 and 200 kD antigens bound by 113F1, 9-O-acetyl GD3, p97, alphafetoprotein (AFP) (for example, for germ cell tumors and/or hepatocellular carcinoma), carcinoembryonic antigen (CEA) (for example, for bowel cancers occasional lung or breast cancer), CA-125 (for example, for ovarian cancer), MUC-1 (for example, for breast cancer), epithelial tumor antigen (ETA) (for example, for breast cancer), tyrosinase (for example, for malignant melanoma), melanoma-associated antigen (MAGE) (for example, for malignant melanoma), cancer/testis antigen 1 (CTAG1B), melanoma-associated antigen 1 (MAGEA1), abnormal Ras products, abnormal p53 products, overexpression of cyclins (including, for example, cyclin B1), mutation in fibronectin, post-translational alteration in the MUC1 glycoprotein, secreted tumor antigens (including, for example, gangliosides).

Other fusions can include fusions with pro-apoptotic payloads. Such exemplary sequences are provided in the table below. In some embodiments, and IL-2 mutein as described herein is fused to a pro-apoptotic payload, for example a BAD, BAX, BAK, BIK, and/or BIDsequence. In some embodiments, the pro-apoptotic payload is a Bcl-2 domain containing peptide and/or a subsequence of a BAD, BAX, BAK, BIK, and/or BID sequence. Exemplary pro-apoptotic fusions are provided below, in Table 3.

TABLE 3

List of Selected Pro-Apoptotic Fusion Partners

| SEQ ID NO: (Information) | Amino acid sequence |
|---|---|
| SEQ ID NO: 38 BAD amino acid sequence | MFQIPEFEPSEQEDSSSAERGLGPSPAGDG PSGSGKHHRQAPGLLWDASHQQEQPTSSSH HGGAGAVEIRSRHSAYPAGTEDDEGMGEEP SPFRGRSRAAPPNLWAAQRYGRELRRMSDE FVDSFKKGLPRPKSAGTATQMRQSSSWTRV FQSWWDRNLGRGSSAPSQ |
| SEQ ID NO: 39 >HsBAD_Q92934-1 (UniProtKB) | MFQIPEFEPSEQEDSSSAERGLGPSPAGDG PSGSGKHHRQAPGLLWDASHQQEQPTSSSH HGGAGAVEIRSRHSSYPAGTEDDEGMGEEP SPFRGRSRSAPPNLWAAQRYGRELRRMSDE FVDSFKKGLPRPKSAGTATQMRQSSSWTRV FQSWWDRNLGRGSSAPSQ |
| SEQ ID NO: 40 >HsBAX_Q07812-1 (UniProtKB) | MDGSGEQPRGGGPTSSEQIMKTGALLLQGF IQDRAGRMGGEAPELALDPVPQDASTKKLS ECLKRIGDELDSNMELQRMIAAVDTDSPRE VFFRVAADMFSDGNFNWGRVVALFYFASKL VLKALCTKVPELIRTIMGWTLDFLRERLLG WIQDQGGWDGLLSYFGTPTWQTVTIFVAGV LTASLTIWKKMG |
| SEQ ID NO: 41 >HsBAK1_Q16611-1 (UniProtKB) | MASGQGPGPPRQECGEPALPSASEEQVAQD TEEVFRSYVFYRHQQEQEAEGVAAPADPEM VTLPLQPSSTMGQVGRQLAIIGDDINRRYD SEFQTMLQHLQPTAENAYEYFTKIATSLFE SGINWGRVVALLGFGYRLALHVYQHGLTGF LGQVTRFVVDFMLHHCIARWIAQRGGWVAA LNLGNGPILNVLVVLGVVLLGQFVVRRFFK S |

TABLE 3-continued

List of Selected Pro-Apoptotic Fusion Partners

| SEQ ID NO: (Information) | Amino acid sequence |
|---|---|
| SEQ ID NO: 42 >HsBIK_Q13323-1 (UniProtKB) | MSEVRPLSRDILMETLLYEQLLEPPTMEVL GMTDSEEDLDPMEDFDSLECMEGSDALALR LACIGDEMDVSLRAPRLAQLSEVAMHSLGL AFIYDQTEDIRDVLRSFMDGFTTLKENIMR FWRSPNPGSWVSCEQVLLALLLLLALLLPL LSGGLHLLLK |
| SEQ ID NO: 43 >HsBID_P55957-1 (UniProtKB) | MDCEVNNGSSLRDECITNLLVEGFLQSCSD NSFRRELDALGHELPVLAPQWEGYDELQTD GNRSSHSRLGRIEADSESQEDIIRNIARHL AQVGDSMDRSIPPGLVNGLALQLRNTSRSE EDRNRDLATALEQLLQAYPRDMEKEKTMLV LALLLAKKVASHTPSLLRDVFHTTVNFINQ NLRTYVRSLARNGMD |

In some particular embodiments, an IL-2 antagonist can be fused to a pro-apoptotic payload for the treatment of cancer. An "antagonist" is a compound that opposes the actions of an agonist, e.g. by preventing, reducing, inhibiting, or neutralizing the activity of an agonist. An "antagonist" can also prevent, inhibit, or reduce constitutive activity of a target, e.g., a target receptor, even where there is no identified agonist. While typically IL-2 muteins with agonist or superagonist activity as compared to wild-type IL-2 are employed with the cancer treatment methods of the present invention, IL-2 muteins with antagonistic properties can be employed when such antagonists are fused to a pro-apoptotic payload. In some embodiments, the IL-2 antagonist comprises the following amino acid substitutions L18R, Q22E, Q126T, and S130R as compared to the wild-type IL-2 of SEQ ID NO:2. In some embodiments, the IL-2 antagonist comprises the following amino acid substitutions L18R, Q22E, L80F, R81D, L85V, I86V, and Q126T as compared to the wild-type IL-2 of SEQ ID NO:2. In some embodiments, the IL-2 antagonist comprises the following amino acid substitutions L18R, Q22E, L80F, R81D, L85V, I86V, Q126T, and S130R as compared to the wild-type IL-2 of SEQ ID NO:2. Exemplary antagonists that can be fuses with pro-apoptotic payloads, such as those provided above, are provided below in Table 4.

TABLE 4

IL-2 Antagonsits for Fusion with Pro-Apoptotic Payloads

| SEQ ID NO: (Information) | Amino acid sequence |
|---|---|
| SEQ ID NO: 36 IL-2 antagonist | APTSSSTKKTQLQLEHLRLDLEMILNGINNYKNPKLTRMLTFKFYM PKKATELKHLQCLEEELKPLEEVLNLAQSKNFHFDPR DVVSNINVFV LELKGSETTF MCEYADETATIVEFLNRWIT FCTSIISTLT |
| SEQ ID NO: 37 IL-2 VARIANT (antagonist) | APTSSSTKKTQLQLEHLRLDLEMILNGINNYKNPKLTRMLTFKFYM PKKATELKHLQCLEEELKPLEEVLNLAQSKNFHFDPRDVVSNINVF VLELKGSETTFMCEYADETATIVEFLNRWITFCTSIIRTLT |
| SEQ ID NO: 56 IL-2 extended half-life fusion (GS linker can be GGGGSGGGGSGGGGS as shown or anything other GS containingin linker) | H9RET-Fc APTSSSTKKTQLQLEHLRLDLEMILNGINNYKNPKLTRMLTFKFYM PKKATELKHLQCLEEELKPLEEVLNLAQSKNFHFDPRDVVSNINVF VLELKGSETTFMCEYADETATIVEFLNRWITFCTSIISTLTGGGGS GGGGSGGGGSDKTHTCPPCPAPELLGGPSVFLFPPKPKDTLMISRT PEVTCVVVDVSHEDPEVKFNWYVDGVEVHNAKTKPREEQYASTYRV VSVLTVLHQDWLNGKEYKCKVSNKALPAPIEKTISKAKGQPREPQV YTLPPSREEMTKNQVSLTCLVKGFYPSDIAVEWESNGQPENNYKTT PPVLDSDGSFFLYSKLTVDKSRWQQGNVFSCSVMHEALHNHYTQKS LSLSPGK* |
| SEQ ID NO: 57 IL-2 extended half-life fusion (GS linker can be GGGGSGGGGSGGGGS as shown or anything other GS containingin linker) | IL-2 VARIANT-Fc APTSSSTKKTQLQLEHLRLDLEMILNGINNYKNPKLTRMLTFKFYM PKKATELKHLQCLEEELKPLEEVLNLAQSKNFHFDPRDVVSNINVF VLELKGSETTFMCEYADETATIVEFLNRWITFCTSIIRTLTGGGGS GGGGSGGGGSDKTHTCPPCPAPELLGGPSVFLFPPKPKDTLMISRT PEVTCVVVDVSHEDPEVKFNWYVDGVEVHNAKTKPREEQYASTYRV VSVLTVLHQDWLNGKEYKCKVSNKALPAPIEKTISKAKGQPREPQV YTLPPSREEMTKNQVSLTCLVKGFYPSDIAVEWESNGQPENNYKTT PPVLDSDGSFFLYSKLTVDKSRWQQGNVFSCSVMHEALHNHYTQKS LSLSPGK* |
| SEQ ID NO: 58 IL-2 extended half-life fusion (GS linker can be GGGGSGGGGSGGGGS as shown or anything other GS containingin linker) | H9RETFYAA-Fc APTSSSTKKTQLQLEHLRLDLEMILNGINNYKNPKLTRMLTAKFAM PKKATELKHLQCLEEELKPLEEVLNLAQSKNFHFDPRDVVSNINVF VLELKGSETTFMCEYADETATIVEFLNRWITFCTSIISTLTGGGGS GGGGSGGGGSDKTHTCPPCPAPELLGGPSVFLFPPKPKDTLMISRT PEVTCVVVDVSHEDPEVKFNWYVDGVEVHNAKTKPREEQYASTYRV VSVLTVLHQDWLNGKEYKCKVSNKALPAPIEKTISKAKGQPREPQV YTLPPSREEMTKNQVSLTCLVKGFYPSDIAVEWESNGQPENNYKTT PPVLDSDGSFFLYSKLTVDKSRWQQGNVFSCSVMHEALHNHYTQKS LSLSPGK* |

TABLE 4-continued

IL-2 Antagonsits for Fusion with Pro-Apoptotic Payloads

| SEQ ID NO: (Information) | Amino acid sequence |
|---|---|
| SEQ ID NO: 59<br>IL-2 extended half-life fusion<br>(GS linker can be<br>GGGGSGGGGSGGGGS as shown<br>or any other GS containing<br>linker) | IL-2 VARIANTFYAA-Fc<br>APTSSSTKKTQLQLEHLRLDLEMILNGINNYKNPKLTRMLTAKFAM<br>PKKATELKHLQCLEEELKPLEEVLNLAQSKNFHFDPRDVVSNINVF<br>VLELKGSETTFMCEYADETATIVEFLNRWITFCTSIIRTLTGGGGS<br>GGGGSGGGGSDKTHTCPPCPAPELLGGPSVFLFPPKPKDTLMISRT<br>PEVTCVVVDVSHEDPEVKFNWYVDGVEVHNAKTKPREEQYASTYRV<br>VSVLTVLHQDWLNGKEYKCKVSNKALPAPIEKTISKAKGQPREPQV<br>YTLPPSREEMTKNQVSLTCLVKGFYPSDIAVEWESNGQPENNYKTT<br>PPVLDSDGSFFLYSKLTVDKSRWQQGNVFSCSVMHEALHNHYTQKS<br>LSLSPGK* |
| SEQ ID NO: 60<br>IL-2 extended half-life fusion<br>(GS linker can be<br>GGGGSGGGGSGGGGS as shown<br>or anyt other GS containing<br>linker) | H9RETFEAA-Fc<br>APTSSSTKKTQLQLEHLRLDLEMILNGINNYKNPKLTRMLTAKFYM<br>PKKATELKHLQCLEEALKPLEEVLNLAQSKNFHFDPRDVVSNINVF<br>VLELKGSETTFMCEYADETATIVEFLNRWITFCTSIISTLTGGGGS<br>GGGGSGGGGSDKTHTCPPCPAPELLGGPSVFLFPPKPKDTLMISRT<br>PEVTCVVVDVSHEDPEVKFNWYVDGVEVHNAKTKPREEQYASTYRV<br>VSVLTVLHQDWLNGKEYKCKVSNKALPAPIEKTISKAKGQPREPQV<br>YTLPPSREEMTKNQVSLTCLVKGFYPSDIAVEWESNGQPENNYKTT<br>PPVLDSDGSFFLYSKLTVDKSRWQQGNVFSCSVMHEALHNHYTQKS<br>LSLSPGK* |
| SEQ ID NO: 61<br>IL-2 extended half-life fusion<br>(GS linker can be<br>GGGGSGGGGSGGGGS as shown<br>or any other GS containing<br>linker) | IL-2 VARIANTFEAA-Fc<br>APTSSSTKKTQLQLEHLRLDLEMILNGINNYKNPKLTRMLTAKFYM<br>PKKATELKHLQCLEEALKPLEEVLNLAQSKNFHFDPRDVVSNINVF<br>VLELKGSETTFMCEYADETATIVEFLNRWITFCTSIIRTLTGGGGS<br>GGGGSGGGGSDKTHTCPPCPAPELLGGPSVFLFPPKPKDTLMISRT<br>PEVTCVVVDVSHEDPEVKFNWYVDGVEVHNAKTKPREEQYASTYRV<br>VSVLTVLHQDWLNGKEYKCKVSNKALPAPIEKTISKAKGQPREPQV<br>YTLPPSREEMTKNQVSLTCLVKGFYPSDIAVEWESNGQPENNYKTT<br>PPVLDSDGSFFLYSKLTVDKSRWQQGNVFSCSVMHEALHNHYTQKS<br>LSLSPGK* |

Other fusions can include fusions with anti-apoptotic payloads for use in prolonging activation of CD8 cells, NK cells and anergic NK cells as well, and such exemplary sequences are provided in the table below. Such prolong activation of T-cells can prove beneficial in cancer therapy treatment methods.

TABLE 4

List of Exemplary IL-2 Anti-Apoptotic Fusion Amino Acid Sequences

| SEQ ID NO: (Information) | Amino acid sequence |
|---|---|
| SEQ ID NO: 40 | H9-BclxL<br>APTSSSTKKTQLQLEHLLLDLQMILNGINNYKNPKLTRMLTFKFY<br>MPKKATELKHLQCLEEELKPLEEVLNLAQSKNFHFDPRDVVSNIN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWFLTGMTVAG<br>VVLLGSLFSRK* |
| SEQ ID NO: 41 | H9FYAA-BclxL<br>APTSSSTKKTQLQLEHLLLDLQMILNGINNYKNPKLTRMLTAKFA<br>MPKKATELKHLQCLEEELKPLEEVLNLAQSKNFHFDPRDVVSNIN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWFLTGMTVAG<br>VVLLGSLFSRK* |

TABLE 4-continued

List of Exemplary IL-2 Anti-Apoptotic
Fusion Amino Acid Sequences

| SEQ ID NO:<br>(Information) | Amino acid sequence |
|---|---|
| SEQ ID NO: 42 | H9FEAA-BclxL<br>APTSSSTKKTQLQLEHLLLDLQMILNGINNYKNPKLTRMLTAKFY<br>MPKKATELKHLQCLEEALKPLEEVLNLAQSKNFHFDPRDVVSNIN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWFLTGMTVAG<br>VVLLGSLFSRK* |
| SEQ ID NO: 43 | H9D10-BclxL<br>APTSSSTKKTQLQLEHLLLDLQMILNGINNYKNPKLTRMLTFKFY<br>MPKKATELKHLQCLEEELKPLEEVLNLAHSKNFHFDPRDVVSNIN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWFLTGMTVAG<br>VVLLGSLFSRK* |
| SEQ ID NO: 44 | H9E10-BclxL<br>APTSSSTKKTQLQLEHLLLDLQMILNGINNYKNPKLTRMLTFKFY<br>MPKKATELKHLQCLEEELKPLEEVLNLASSKNFHFDPRDVVSNIN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWFLTGMTVAG<br>VVLLGSLFSRK* |
| SEQ ID NO: 45 | H9G8-Bclxl<br>APTSSSTKKTQLQLEHLLLDLQMILNGINNYKNPKLTRMLTFKFY<br>MPKKATELKHLQCLEEELKPLEEVLNLANSKNFHFDPRDVVSNIN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWFLTGMTVAG<br>VVLLGSLFSRK* |
| SEQ ID NO: 46 | H9B1-BclxL<br>APTSSSTKKTQLQLEHLLLDLQMILNGINNYKNPKLTRMLTFKFY<br>MPKKATELKHLQCLEEELKPLEEVLNLANSKNFHFDPRDVVSNVN<br>VFVLELKGSETTFMCEYADETATIVEFLNRWITFCQSIISTLTGG<br>GGSMSQSNRELVVDFLSYKLSQKGYSWSQFSDVEENRTEAPEGTE<br>SEMETPSAINGNPSWHLADSPAVNGATGHSSSLDAREVIPMAAVK<br>QALREAGDEFELRYRRAFSDLTSQLHITPGTAYQSFEQVVNELFR<br>DGVNWGRIVAFFSFGGALCVESVDKEMQVLVSRIAAWMATYLNDH<br>LEPWIQENGGWDTFVELYGNNAAAESRKGQERFNRWELTGMTVAG<br>VVLLGSLFSRK* |

Other exemplary IL-2 fusions include those listed in the table below:

TABLE 5

List of Exemplary IL-2 Extended Half-Life Fusion Amino Acid Sequences

| SEQ ID NO: (Information) | Amino acid sequence |
| --- | --- |
| SEQ ID NO: 47<br>IL-2 extended half-life fusion | H9-Fc (H9 at N-terminal only shown)<br>APTSSSTKKTQLQLEHLLLDLQMILNGINNYKNPKLTRMLTFKFY<br>MPKKATELKHLQCLEEELKPLEEVLNLAQSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK* |
| SEQ ID NO: 48<br>IL-2 extended half-life fusion | H9-Fc ("Knob-in-hole" with H9 at N-terminus)<br>APTSSSTKKTQLQLEHLLLDLQMILNGINNYKNPKLTRMLTFKFY<br>MPKKATELKHLQCLEEELKPLEEVLNLAQSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK-[FC sequence] |
| SEQ ID NO: 49<br>IL-2 extended half-life fusion | H9-Fc ("Knob-in-hole" with H9 at C-terminus)<br>[FC sequence]-<br>APTSSSTKKTQLQLEHLLLDLQMILNGINNYKNPKLTRMLTFKFY<br>MPKKATELKHLQCLEEELKPLEEVLNLAQSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK* |
| SEQ ID NO: 50<br>IL-2 extended half-life fusion | H9FYAA-Fc<br>APTSSSTKKTQLQLEHLLLDLQMILNGINNYKNPKLTRMLTAKFA<br>MPKKATELKHLQCLEEELKPLEEVLNLAQSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK* |
| SEQ ID NO: 51<br>IL-2 extended half-life fusion<br>(GS linker can be GGGGSGGGGSGGGGS as shown or any other GS containing linker) | H9FEAA-Fc<br>APTSSSTKKTQLQLEHLLLDLQMILNGINNYKNPKLTRMLTAKFY<br>MPKKATELKHLQCLEEALKPLEEVLNLAQSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK* |
| SEQ ID NO: 52<br>IL-2 extended half-life fusion<br>(GS linker can be GGGGSGGGGSGGGGS as shown or any other GS containing linker) | H9D10-Fc<br>APTSSSTKKTQLQLEHLLLDLQMILNGINNYKNPKLTRMLTFKFY<br>MPKKATELKHLQCLEEELKPLEEVLNLAHSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK* |

TABLE 5-continued

List of Exemplary IL-2 Extended Half-Life
Fusion Amino Acid Sequences

| SEQ ID NO:<br>(Information) | Amino acid sequence |
|---|---|
| SEQ ID NO: 53<br>IL-2 extended half-life<br>fusion<br>(GS linker can be<br>GGGGSGGGGSGGGGS as shown<br>or any other GS<br>containing linker) | H9E10-Fc<br>APTSSSTKKTQLQLEHLLLDLQMILNGINNYKNPKLTRMLTFKFY<br>MPKKATELKHLQCLEEELKPLEEVLNLASSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK\* |
| SEQ ID NO: 54<br>IL-2 extended half-life<br>fusion<br>(GS linker can be<br>GGGGSGGGGSGGGGS as shown<br>or any other GS<br>containing linker) | H9G8-Fc<br>APTSSSTKKTQLQLEHLLLDLQMILNGINNYKNPKLTRMLTFKFY<br>MPKKATELKHLQCLEEELKPLEEVLNLANSKNFHFDPRDVVSNIN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK\* |
| SEQ ID NO: 55<br>IL-2 extended half-life<br>fusion<br>(GS linker can be<br>GGGGSGGGGSGGGGS as shown<br>or any other GS<br>containing linker) | H9B1-Fc<br>APTSSSTKKTQLQLEHLLLDLQMILNGINNYKNPKLTRMLTFKFY<br>MPKKATELKHLQCLEEELKPLEEVLNLANSKNFHFDPRDVVSNVN<br>VFVLELKGSETTFMCEYADETATIVEFLNRWITFCQSIISTLTGG<br>GGSGGGGSGGGGSDKTHTCPPCPAPELLGGPSVFLFPPKPKDTLM<br>ISRTPEVTCVVVDVSHEDPEVKFNWYVDGVEVHNAKTKPREEQYA<br>STYRVVSVLTVLHQDWLNGKEYKCKVSNKALPAPIEKTISKAKGQ<br>PREPQVYTLPPSREEMTKNQVSLTCLVKGFYPSDIAVEWESNGQP<br>ENNYKTTPPVLDSDGSFFLYSKLTVDKSRWQQGNVFSCSVMHEAL<br>HNHYTQKSLSLSPGK\* |
| SEQ ID NO: 62<br>(GS linker can be<br>GGGGSGGGGSGGGGS as shown<br>or any other GS<br>containing linker) | H9-Albumin (H9 at C-terminal shown)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTFKFY<br>MPKKATELKHLQCLEEELKPLEEVLNLAQSKNFHFDPRDVVSNIN<br>VEVLELKGSETTFMCEYADETATIVEFLNRWITFCQSIISTLT\* |
| SEQ ID NO: 63<br>(GS linker can be<br>GGGGSGGGGSGGGGS as shown<br>or any other GS<br>containing linker) | H9FYAA-Albumin (H9FYAA at C-terminal shown)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTAKFAMPKKA<br>TELKHLQCLEEELKPLEEVLNLAQSKNFHFDPRDVVSNINVFVLELKGSE<br>TTFMCEYADETATIVEFLNRWITFCQSIISTLT |

TABLE 5-continued

List of Exemplary IL-2 Extended Half-Life
Fusion Amino Acid Sequences

| SEQ ID NO:<br>(Information) | Amino acid sequence |
|---|---|
| SEQ ID NO: 64<br>(GS linker can be<br>GGGGSGGGGSGGGGS as shown<br>or any other GS<br>containing linker) | H9FEAA-Albumin (H9FEAA at C-terminal shown)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTAKFYMPKKA<br>TELKHLQCLEEALKPLEEVLNLAQSKNFHFDPRDVVSNINVFVLELKGSE<br>TTFMCEYADETATIVEFLNRWITFCQSIISTLT |
| SEQ ID NO: 65<br>(GS linker can be<br>GGGGSGGGGSGGGGS as shown<br>or any other GS<br>containing linker) | H9D10-Albumin (H9D10 shown at N-terminal)<br>APTSSSTKKTQLQLEHLLLDLQMILNGINNYKNPKLTRMLTFKFYMPKKA<br>TELKHLQCLEEELKPLEEVLNLAHSKNFHFDPRDVVSNINVFVLELKGSE<br>TTFMCEYADETATIVEFLNRWITFCQSIISTLTGGGGSGGGGSGGGGSDA<br>HKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECF<br>LQHKDDNPNLPRLVRPEVDVMCTAFHDNEETFLKKYLYEIARRHPYFYAP<br>ELLFFAKRYKAAFTECCQAADKAACLLPKLDELRDEGKASSAKQRLKCAS<br>LQKFGERAFKAWAVARLSQRFPKAEFAEVSKLVTDLTKVHTECCHGDLLE<br>CADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYK<br>FQNALLVRYTKKVPQVSTPTLVEVSRNLGKVGSKCCKHPEAKRMPCAEDY<br>LSVVLNQLCVLHEKTPVSDRVTKCCTESLVNRRPCFSALEVDETYVPKEF<br>NAETFTFHADICTLSEKERQIKKQTALVELVKHKPKATKEQLKAVMDDFA<br>AFVEKCCKADDKETCFAEEGKKLVAASQAALGL |
| SEQ ID NO: 66<br>(GS linker can be<br>GGGGSGGGGSGGGGS as shown<br>or any other GS<br>containing linker) | H9D10FEAA-Albumin<br>APTSSSTKKTQLQLEHLLLDLQMILNGINNYKNPKLTRMLTAKFYMPKKA<br>TELKHLQCLEEALKPLEEVLNLAHSKNFHFDPRDVVSNINVFVLELKGSE<br>TTFMCEYADETATIVEFLNRWITFCQSIISTLTGGGGSGGGGSGGGGSDA<br>HKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECF<br>LQHKDDNPNLPRLVRPEVDVMCTAFHDNEETFLKKYLYEIARRHPYFYAP<br>ELLFFAKRYKAAFTECCQAADKAACLLPKLDELRDEGKASSAKQRLKCAS<br>LQKFGERAFKAWAVARLSQRFPKAEFAEVSKLVTDLTKVHTECCHGDLLE<br>CADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYK<br>FQNALLVRYTKKVPQVSTPTLVEVSRNLGKVGSKCCKHPEAKRMPCAEDY<br>LSVVLNQLCVLHEKTPVSDRVTKCCTESLVNRRPCFSALEVDETYVPKEF<br>NAETFTFHADICTLSEKERQIKKQTALVELVKHKPKATKEQLKAVMDDFA<br>AFVEKCCKADDKETCFAEEGKKLVAASQAALGL |
| SEQ ID NO: 67<br>(GS linker can be<br>GGGGSGGGGSGGGGS as shown<br>or anything other GS<br>containingin linker) | H9E10-Albumin (H9E10 shown at N-terminal)<br>APTSSSTKKTQLQLEHLLLDLQMILNGINNYKNPKLTRMLTFKFYMPKKA<br>TELKHLQCLEEELKPLEEVLNLASSKNFHFDPRDVVSNINVFVLELKGSE<br>TTFMCEYADETATIVEFLNRWITFCQSIISTLTGGGGSGGGGSGGGGSDA<br>HKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECF<br>LQHKDDNPNLPRLVRPEVDVMCTAFHDNEETFLKKYLYEIARRHPYFYAP<br>ELLFFAKRYKAAFTECCQAADKAACLLPKLDELRDEGKASSAKQRLKCAS<br>LQKFGERAFKAWAVARLSQRFPKAEFAEVSKLVTDLTKVHTECCHGDLLE<br>CADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYK<br>FQNALLVRYTKKVPQVSTPTLVEVSRNLGKVGSKCCKHPEAKRMPCAEDY<br>LSVVLNQLCVLHEKTPVSDRVTKCCTESLVNRRPCFSALEVDETYVPKEF<br>NAETFTFHADICTLSEKERQIKKQTALVELVKHKPKATKEQLKAVMDDFA<br>AFVEKCCKADDKETCFAEEGKKLVAASQAALGL |

TABLE 5-continued

List of Exemplary IL-2 Extended Half-Life Fusion Amino Acid Sequences

| SEQ ID NO: (Information) | Amino acid sequence |
|---|---|
| SEQ ID NO: 68 (GS linker can be GGGGSGGGGSGGGGS as shown or anything other GS containingin linker) | H9G8-Albumin (H9G8 shown at N-terminal)<br>APTSSSTKKTQLQLEHLLLDLQMILNGINNYKNPKLTRMLTFKFYMPKKA<br>TELKHLQCLEEELKPLEEVLNLANSKNFHFDPRDVVSNINVFVLELKGSE<br>TTFMCEYADETATIVEFLNRWITFCQSIISTLTGGGGSGGGGSGGGGSDA<br>HKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECF<br>LQHKDDNPNLPRLVRPEVDVMCTAFHDNEETFLKKYLYEIARRHPYFYAP<br>ELLFFAKRYKAAFTECCQAADKAACLLPKLDELRDEGKASSAKQRLKCAS<br>LQKFGERAFKAWAVARLSQRFPKAEFAEVSKLVTDLTKVHTECCHGDLLE<br>CADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYK<br>FQNALLVRYTKKVPQVSTPTLVEVSRNLGKVGSKCCKHPEAKRMPCAEDY<br>LSVVLNQLCVLHEKTPVSDRVTKCCTESLVNRRPCFSALEVDETYVPKEF<br>NAETFTFHADICTLSEKERQIKKQTALVELVKHKPKATKEQLKAVMDDFA<br>AFVEKCCKADDKETCFAEEGKKLVAASQAALGL |
| SEQ ID NO: 69 (GS linker can be GGGGSGGGGSGGGGS as shown or anything other GS containingin linker) | H9B1-Albumin (H9B1 shown at N-terminal)<br>APTSSSTKKTQLQLEHLLLDLQMILNGINNYKNPKLTRMLTFKFYMPKKA<br>TELKHLQCLEEELKPLEEVLNLANSKNFHFDPRDVVSNVNVFVLELKGSE<br>TTFMCEYADETATIVEFLNRWITFCQSIISTLTGGGGSGGGGSGGGGSDA<br>HKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECF<br>LQHKDDNPNLPRLVRPEVDVMCTAFHDNEETFLKKYLYEIARRHPYFYAP<br>ELLFFAKRYKAAFTECCQAADKAACLLPKLDELRDEGKASSAKQRLKCAS<br>LQKFGERAFKAWAVARLSQRFPKAEFAEVSKLVTDLTKVHTECCHGDLLE<br>CADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYK<br>FQNALLVRYTKKVPQVSTPTLVEVSRNLGKVGSKCCKHPEAKRMPCAEDY<br>LSVVLNQLCVLHEKTPVSDRVTKCCTESLVNRRPCFSALEVDETYVPKEF<br>NAETFTFHADICTLSEKERQIKKQTALVELVKHKPKATKEQLKAVMDDFA<br>AFVEKCCKADDKETCFAEEGKKLVAASQAALGL |
| SEQ ID NO: 70 (GS linker can be GGGGSGGGGSGGGGS as shown or any other GS containing linker) | H9FEAA-Albumin (H9FEAA at N-terminal shown)<br><u>APTSSSTKKTQLQLEHLLLDLQMILNGINNYKNPKLTRMLTAKFYMPKKA</u><br><u>TELKHLQCLEEALKPLEEVLNLAQSKNFHFDPRDVVSNINVFVLELKGSE</u><br><u>TTFMCEYADETATIVEFLNRWITFCQSIISTLTGGGGSGGGGSGGGGS</u>DA<br>HKSEVAHRFKDLGEENFKALVLIAFAQYLQQCPFEDHVKLVNEVTEFAKT<br>CVADESAENCDKSLHTLFGDKLCTVATLRETYGEMADCCAKQEPERNECF<br>LQHKDDNPNLPRLVRPEVDVMCTAFHDNEETFLKKYLYEIARRHPYFYAP<br>ELLFFAKRYKAAFTECCQAADKAACLLPKLDELRDEGKASSAKQRLKCAS<br>LQKFGERAFKAWAVARLSQRFPKAEFAEVSKLVTDLTKVHTECCHGDLLE<br>CADDRADLAKYICENQDSISSKLKECCEKPLLEKSHCIAEVENDEMPADL<br>PSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYK<br>FQNALLVRYTKKVPQVSTPTLVEVSRNLGKVGSKCCKHPEAKRMPCAEDY<br>LSVVLNQLCVLHEKTPVSDRVTKCCTESLVNRRPCFSALEVDETYVPKEF<br>NAETFTFHADICTLSEKERQIKKQTALVELVKHKPKATKEQLKAVMDDFA<br>AFVEKCCKADDKETCFAEEGKKLVAASQAALGL |
| SEQ ID NO: 71 (GS linker can be GGGGSGGGGSGGGGS as shown or any other GS containing linker) | H9D10-Albumin (H9D10 shown at C-terminal)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTFKFYMPKKA<br>TELKHLQCLEEELKPLEEVLNLANSKNFHFDPRDVVSNINVFVLELKGSE<br>TTFMCEYADETATIVEFLNRWITFCQSIISTLT |

TABLE 5-continued

List of Exemplary IL-2 Extended Half-Life
Fusion Amino Acid Sequences

| SEQ ID NO:<br>(Information) | Amino acid sequence |
|---|---|
| SEQ ID NO: 72<br>(GS linker can be<br>GGGGSGGGGSGGGGS as shown<br>or any other GS<br>containing linker) | H9D10FEAA-Albumin (H9FEAA shown at C- terminal)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTAKFYMPKKA<br>TELKHLQCLEEALKPLEEVLNLAHSKNFHFDPRDVVSNINVFVLELKGSE<br>TTFMCEYADETATIVEFLNRWITFCQSIISTLT |
| SEQ ID NO: 73<br>(GS linker can be<br>GGGGSGGGGSGGGGS as shown<br>or anything other GS<br>containingin linker) | H9E10-Albumin (H9E10 shown at C-terminal)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTFKFYMPKKA<br>TELKHLQCLEEELKPLEEVLNLASSKNFHFDPRDVVSNINVFVLELKGSE<br>TTFMCEYADETATIVEFLNRWITFCQSIISTLT |
| SEQ ID NO: 74<br>(GS linker can be<br>GGGGSGGGGSGGGGS as shown<br>or anything other GS<br>containingin linker) | H9G8-Albumin (H9G8 shown at C-terminal)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTFKFYMPKKA<br>TELKHLQCLEEELKPLEEVLNLANSKNFHFDPRDVVSNINVFVLELKGSE<br>TTFMCEYADETATIVEFLNRWITFCQSIISTLT |
| SEQ ID NO: 75<br>(GS linker can be<br>GGGGSGGGGSGGGGS as shown<br>or anything other GS<br>containingin linker) | H9B1-Albumin (H9B1 shown at C-terminal)<br>DAHKSEVAHRFKDLGEENFKALVLIAFAQYLQQCPFEDHVKLVNEVTEFA<br>KTCVADESAENCDKSLHTLFGDKLCTVATLRETYGEMADCCAKQEPERNE<br>CFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKC<br>ASLQKFGERAFKAWAVARLSQRFPKAEFAEVSKLVTDLTKVHTECCHGDL<br>LECADDRADLAKYICENQDSISSKLKECCEKPLLEKSHCIAEVENDEMPA<br>DLPSLAADFVESKDVCKNYAEAKDVFLGMFLYEYARRHPDYSVVLLLRLA<br>KTYETTLEKCCAAADPHECYAKVFDEFKPLVEEPQNLIKQNCELFEQLGE<br>YKFQNALLVRYTKKVPQVSTPTLVEVSRNLGKVGSKCCKHPEAKRMPCAE<br>DYLSVVLNQLCVLHEKTPVSDRVTKCCTESLVNRRPCFSALEVDETYVPK<br>EFNAETFTFHADICTLSEKERQIKKQTALVELVKHKPKATKEQLKAVMDD<br>FAAFVEKCCKADDKETCFAEEGKKLVAASQAALGLGGGGSGGGGSGGGGS<br>APTSSSTKKTQLQLEHLLLDLQMILNGINNYKNPKLTRMLTFKFYMPKKA<br>TELKHLQCLEEELKPLEEVLNLANSKNFHFDPRDVVSNVNVFVLELKGSE<br>TTFMCEYADETATIVEFLNRWITFCQSIISTLT |

In some embodiments, the IL-2 mutein-Fc fusion comprises one of the following sequences:

TABLE 6

List of Amino Acid Sequences

| SEQ ID NO:<br>(Information) | Amino acid sequence |
|---|---|
| SEQ ID NO: 76<br>(also listed<br>herein as SEQ<br>ID NO: 11) | MYRMQLLSCIALSLALVTNSAPTSSSTKKTQLQLEHLLLDLQMILNGINNYKNPK<br>LTRMLTFKFYMPKKATELKHLQCLEE<br>ELKPLEEVLNLAQSKNFHLRPRDLISNINVIVLELKGSETTFMCEYADETATIVE<br>FLNRWITFCQSIISTLTGGGGSGGGG<br>SGGGGSDKTHTCPPCPAPELLGGPSVFLFPPKPKDTLMISRTPEVTCVVVDVSHE<br>DPEVKFNWYVDGVEVHNAKTKPREEQ<br>Y<u>A</u>STYRVVSVLTVLHQDWLNGKEYKCKVSNKALPAPIEKTISKAKGQPREPQVYT<br>LPPSREEMTKNQVSLTCLVKGFYPSD<br>IAVEWESNGQPENNYKTTPPVLDSDGSFFLYSKLTVDKSRWQQGNVFSCSVMHEA<br>LHNHYTQKSLSLSPGK* |
| SEQ ID NO: 77<br>(also listed<br>herein as SEQ<br>ID NO: 12) | MYRMQLLSCIALSLALVTNSAPTSSSTKKTQLQLEHLLLDLQMILNGINNYKNPK<br>LTRMLTFKFYMPKKATELKHLQCLEE<br>ELKPLEEVLNLAQSKNFHFDPRDVVSNINVFVLELKGSETTFMCEYADETATIVE<br>FLNRWITFCQSIISTLTGGGGSGGGG<br>SGGGGSDKTHTCPPCPAPELLGGPSVFLFPPKPKDTLMISRTPEVTCVVVDVSHE<br>DPEVKFNWYVDGVEVHNAKTKPREEQ<br>Y<u>A</u>STYRVVSVLTVLHQDWLNGKEYKCKVSNKALPAPIEKTISKAKGQPREPQVYT<br>LPPSREEMTKNQVSLTCLVKGFYPSD<br>IAVEWESNGQPENNYKTTPPVLDSDGSFFLYSKLTVDKSRWQQGNVFSCSVMHEA<br>LHNHYTQKSLSLSPGK* |
| SEQ ID NO: 78<br>(also listed<br>herein as SEQ<br>ID NO: 13) | MYRMQLLSCIALSLALVTNSAPTSSSTKKTQLQLEHLLLDLQMILNGINNYKNPK<br>LTRMLTAKFAMPKKATELKHLQCLEE<br>ELKPLEEVLNLAQSKNFHFDPRDVVSNINVFVLELKGSETTFMCEYADETATIVE<br>FLNRWITFCQSIISTLTGGGGSGGGG<br>SGGGGSDKTHTCPPCPAPELLGGPSVFLFPPKPKDTLMISRTPEVTCVVVDVSHE<br>DPEVKFNWYVDGVEVHNAKTKPREEQ<br>Y<u>A</u>STYRVVSVLTVLHQDWLNGKEYKCKVSNKALPAPIEKTISKAKGQPREPQVYT<br>LPPSREEMTKNQVSLTCLVKGFYPSD<br>IAVEWESNGQPENNYKTTPPVLDSDGSFFLYSKLTVDKSRWQQGNVFSCSVMHEA<br>LHNHYTQKSLSLSPGK* |
| SEQ ID NO: 79<br>(also listed<br>herein as SEQ<br>ID NO: 14) | MYRMQLLSCIALSLALVTNSAPTSSSTKKTQLQLEHLLLDLQMILNGINNYKNPK<br>LTRMLTAKFYMPKKATELKHLQCLEE<br>ALKPLEEVLNLAQSKNFHFDPRDVVSNINVFVLELKGSETTFMCEYADETATIVE<br>FLNRWITFCQSIISTLTGGGGSGGGG<br>SGGGGSDKTHTCPPCPAPELLGGPSVFLFPPKPKDTLMISRTPEVTCVVVDVSHE<br>DPEVKFNWYVDGVEVHNAKTKPREEQ<br>Y<u>A</u>STYRVVSVLTVLHQDWLNGKEYKCKVSNKALPAPIEKTISKAKGQPREPQVYT<br>LPPSREEMTKNQVSLTCLVKGFYPSD<br>IAVEWESNGQPENNYKTTPPVLDSDGSFFLYSKLTVDKSRWQQGNVFSCSVMHEA<br>LHNHYTQKSLSLSPGK* |
| SEQ ID NO: 80<br>(also listed<br>herein as SEQ<br>ID NO: 15) | MYRMQLLSCIALSLALVTNSAPTSSSTKKTQLQLEHLLLDLQMILNGINNYKNPK<br>LTRMLTAKFAMPKKATELKHLQCLEE<br>ALKPLEEVLNLAQSKNFHFDPRDVVSNINVFVLELKGSETTFMCEYADETATIVE<br>FLNRWITFCQSIISTLTGGGGSGGGG<br>SGGGGSDKTHTCPPCPAPELLGGPSVFLFPPKPKDTLMISRTPEVTCVVVDVSHE<br>DPEVKFNWYVDGVEVHNAKTKPREEQ<br>Y<u>A</u>STYRVVSVLTVLHQDWLNGKEYKCKVSNKALPAPIEKTISKAKGQPREPQVYT<br>LPPSREEMTKNQVSLTCLVKGFYPSD<br>IAVEWESNGQPENNYKTTPPVLDSDGSFFLYSKLTVDKSRWQQGNVFSCSVMHEA<br>LHNHYTQKSLSLSPGK* |

In some embodiments, the IL-2 mutein sequence is 90% identical to any one of SEQ ID NO:12 through SEQ ID NO:15 and/or SEQ ID NO:20 through SEQ ID NO:80 (for example, any of the IL-2 sequences provided herein). In some embodiments, the IL-2 mutein sequence is 95% identical to any one of SEQ ID NO:12 through SEQ ID NO:15 and/or SEQ ID NO:20 through SEQ ID NO:80 (for example, any of the IL-2 sequences provided herein). In some embodiments, the IL-2 mutein sequence is 98% identical to any one of SEQ ID NO:12 through SEQ ID NO:15 and/or SEQ ID NO:20 through SEQ ID NO:80 (for example, any of the IL-2 sequences provided herein). In some embodiments, the IL-2 mutein sequence is 99% identical to any one of SEQ ID NO:12 through SEQ ID NO:15 and/or SEQ ID NO:20 through SEQ ID NO:80 (for example, any of the IL-2 sequences provided herein).

C. IL-4, IL-13 IL-10, IL-12, IL15, and IL-18 for Fusion with IL-2

In some embodiments, an IL-2 mutein can be fused to an IL-4 mutein as described herein. In some embodiments, an IL-2 mutein can be fused to an IL-13 mutein as described herein. In some embodiments, an IL-2 mutein can be fused to an IL-10. In some embodiments, an IL-2 mutein can be fused to an IL-12. In some embodiments, an IL-2 mutein can be fused to an IL-15. In some embodiments, an IL-2 mutein can be fused to an IL-18. In some embodiments, such fusions function to specifically target cancer cells and/or cancer stem cells and reduce or inhibit cancer stem cell growth, as well as targeting the immunosuppressive cells in the tumor microenvironment (TME).

Any IL-13 sequence or variant thereof can be used in a fusion with an IL-2 mutein as described herein. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. Exemplary IL-13 polypeptide sequences are provided in SEQ ID NO:81-SEQ ID NO:128, as well as the table below. In some embodiments, the IL-13 polypeptide sequence is as provided in any one of SEQ ID NO:81-SEQ ID NO:128. In some embodiments, the IL-13 polypeptide sequence is SEQ ID NO:81. In some embodiments, the IL-13 polypeptide sequence is SEQ ID NO:82. In some embodiments, the IL-13 polypeptide sequence is SEQ ID NO:83. In some embodiments, the IL-13 polypeptide sequence is SEQ ID NO:84. In some embodiments, the IL-13 polypeptide sequence is SEQ ID NO:85. In some embodiments, the IL-13 polypeptide sequence is SEQ ID NO:86. In some embodiments, the IL-13 polypeptide sequence is SEQ ID NO:87. In some embodiments, the IL-13 polypeptide sequence is SEQ ID NO:88. In some embodiments, the IL-13 polypeptide sequence is SEQ ID NO:89. In some embodiments, the IL-13 polypeptide sequence is SEQ ID NO:90. In some embodiments, the IL-13 polypeptide sequence is SEQ ID NO:91. In some embodiments, the IL-13 polypeptide sequence is SEQ ID NO:92. In some embodiments, the IL-13 polypeptide sequence is SEQ ID NO:93. In some embodiments, the IL-13 polypeptide sequence is SEQ ID NO:94. In some embodiments, the polypeptide sequence is SEQ ID NO:95. In some embodiments, the IL-13 polypeptide sequence is SEQ ID NO:96. In some embodiments, the IL-13 polypeptide sequence is SEQ ID NO:97. In some embodiments, the IL-13 polypeptide sequence is SEQ ID NO:98. In some embodiments, the IL-13 polypeptide sequence is SEQ ID NO:99. In some embodiments, the polypeptide sequence is SEQ ID NO:100. In some embodiments, the IL-13 polypeptide sequence is SEQ ID NO:101. In some embodiments, the IL-13 polypeptide sequence is SEQ ID NO:102. In some embodiments, the IL-13 polypeptide sequence is SEQ ID NO:103. In some embodiments, the IL-13 polypeptide sequence is SEQ ID NO:104. In some embodiments, the IL-13 polypeptide sequence is SEQ ID NO:105. In some embodiments, the IL-13 polypeptide sequence is SEQ ID NO:106. In some embodiments, the IL-13 polypeptide sequence is SEQ ID NO:107. In some embodiments, the IL-13 polypeptide sequence is SEQ ID NO:108. In some embodiments, the IL-13 polypeptide sequence is SEQ ID NO:109. In some embodiments, the IL-13 polypeptide sequence is SEQ ID NO:110. In some embodiments, the polypeptide sequence is SEQ ID NO:111. In some embodiments, the IL-13 polypeptide sequence is SEQ ID NO:112. In some embodiments, the IL-13 polypeptide sequence is SEQ ID NO:113. In some embodiments, the IL-13 polypeptide sequence is SEQ ID NO:114. In some embodiments, the IL-13 polypeptide sequence is SEQ ID NO:115. In some embodiments, the IL-13 polypeptide sequence is SEQ ID NO:116. In some embodiments, the IL-13 polypeptide sequence is SEQ ID NO:117. In some embodiments, the IL-13 polypeptide sequence is SEQ ID NO:118. In some embodiments, the IL-13 polypeptide sequence is SEQ ID NO:119. In some embodiments, the IL-13 polypeptide sequence is SEQ ID NO:120. In some embodiments, the IL-13 polypeptide sequence is SEQ ID NO:121. In some embodiments, the IL-13 polypeptide sequence is SEQ ID NO:122. In some embodiments, the IL-13 polypeptide sequence is SEQ ID NO:123. In some embodiments, the IL-13 polypeptide sequence is SEQ ID NO:124. In some embodiments, the IL-13 polypeptide sequence is SEQ ID NO:125. In some embodiments, the IL-13 polypeptide sequence is SEQ ID NO:126. In some embodiments, the IL-13 polypeptide sequence is SEQ ID NO:127. In some embodiments, the IL-13 polypeptide sequence is SEQ ID NO:128. IL-13 In some embodiments, the IL-13 polypeptide sequence is 90% identical to any one of SEQ ID NO:81 through SEQ ID NO:128. In some embodiments, the IL-13 polypeptide sequence is 95% identical to any one of SEQ ID NO:81 through SEQ ID NO:128. In some embodiments, the IL-13 polypeptide sequence is 98% identical to any one of SEQ ID NO:81 through SEQ ID NO:128. In some embodiments, the IL-13 polypeptide sequence is 99% identical to any one of SEQ ID NO:81 through SEQ ID NO:128.

In some embodiments, any one of SEQ ID NO:81-SEQ ID NO:128 are linked to an IL-2 or IL-2 mutein as described herein. In some embodiments, SEQ ID NO:81 is linked to an IL-2 or IL-2 mutein as described herein. In some embodiments, SEQ ID NO:82 is linked to an IL-2 or IL-2 mutein as described herein. In some embodiments, SEQ ID NO:83 is linked to an IL-2 or IL-2 mutein as described herein. In some embodiments, SEQ ID NO:84 is linked to an IL-2 or IL-2 mutein as described herein. In some embodiments, SEQ ID NO:85 is linked to an IL-2 or IL-2 mutein as described herein. In some embodiments, SEQ ID NO:86 is linked to an IL-2 or IL-2 mutein as described herein. In some embodiments, SEQ ID NO:87 is linked to an IL-2 or IL-2 mutein as described herein. In some embodiments, SEQ ID NO:88 is linked to an IL-2 or IL-2 mutein as described herein. In some embodiments, SEQ ID NO:89 is linked to an IL-2 or IL-2 mutein as described herein. In some embodiments, SEQ ID NO:90 is linked to an IL-2 or IL-2 mutein as described herein. In some embodiments, SEQ ID NO:91 is linked to an IL-2 or IL-2 mutein as described herein. In some embodiments, SEQ ID NO:92 is linked to an IL-2 or IL-2 mutein as described herein. In some embodiments, SEQ ID NO:93 is linked to an IL-2 or IL-2 mutein as described herein. In some embodiments, SEQ ID NO:94 is linked to an IL-2 or IL-2 mutein as described herein. In some embodiments, SEQ ID NO:94 is linked to an IL-2 or IL-2 mutein as described herein. In some embodiments, SEQ ID NO:96 is linked to an IL-2 or IL-2 mutein as described herein. In some embodiments, SEQ ID NO:97 is linked to an IL-2 or IL-2 mutein as described herein. In some embodiments, SEQ ID NO:98 is linked to an IL-2 or IL-2 mutein as described herein. In some embodiments, SEQ ID NO:99 is linked to an IL-2 or IL-2 mutein as described herein. In some embodiments, SEQ ID NO:100 is linked to an IL-2 or IL-2 mutein as described herein. In some embodiments, SEQ ID NO:101 is linked to an IL-2 or IL-2 mutein as described herein. In some embodiments, SEQ ID NO:102 is linked to an IL-2 or IL-2 mutein as described herein. In some embodiments, SEQ ID NO:103 is linked to an IL-2 or IL-2 mutein as described herein. In some embodiments, SEQ ID NO:104 is linked to an IL-2 or IL-2 mutein as described herein. In some embodiments, SEQ ID NO:105 is linked to an IL-2 or IL-2 mutein as described herein. In some embodiments, SEQ ID NO:106 is linked to an IL-2 or IL-2 mutein as described herein. In some embodiments, SEQ ID NO:107 is linked to an IL-2 or IL-2 mutein as described herein. In some embodiments, SEQ ID NO:108 is linked to an IL-2 or IL-2 mutein as described herein. In some embodiments, SEQ ID NO:109 is linked to an IL-2 or IL-2 mutein as described herein. In some embodiments, SEQ ID NO:110 is linked to an IL-2 or IL-2 mutein as described herein. In some embodiments, SEQ ID NO:111 is linked to an IL-2 or IL-2 mutein as described herein. In some embodiments, SEQ ID NO:112 is linked to an IL-2 or IL-2 mutein as described herein. In some embodiments, SEQ ID NO:113 is linked to an IL-2 or IL-2 mutein as described herein. In some embodiments, SEQ ID NO:114 is linked to an IL-2 or IL-2 mutein as described herein. In some embodiments, SEQ ID NO:115 is linked to an IL-2 or IL-2 mutein as described herein. In some embodiments, SEQ ID NO:116 is linked to an IL-2 or IL-2 mutein as described herein. In some embodiments, SEQ ID NO:117 is linked to an IL-2 or IL-2 mutein as described herein. In some embodiments, SEQ ID NO:118 is linked to an IL-2 or IL-2 mutein as described herein. In some embodiments, SEQ ID NO:119 is linked to an IL-2 or IL-2 mutein as described herein. In some embodiments, SEQ ID NO:120 is linked to an IL-2 or IL-2 mutein as described herein. In some embodiments, SEQ ID NO:121 is linked to an IL-2 or IL-2 mutein as described herein. In some embodiments, SEQ ID NO:122 is linked to an IL-2 or IL-2 mutein as described herein. In some embodiments, SEQ ID NO:123 is linked to an IL-2 or IL-2 mutein as described herein. In some embodiments, SEQ ID NO:124 is linked to an IL-2 or IL-2 mutein as described herein. In some embodiments, SEQ ID NO:125 is linked to an IL-2 or IL-2 mutein as described herein. In some embodiments, SEQ ID NO:126 is linked to an IL-2 or IL-2 mutein as described herein. In some embodiments, SEQ ID NO:127 is linked to an IL-2 or IL-2 mutein as described herein. In some embodiments, SEQ ID NO:128 is linked to an IL-2 or IL-2 mutein as described herein. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

In some embodiments an IL-13 peptide of the invention comprises one or more of the amino acids substitutions: (1) L10F, L10I, L10V, L10A, L10D, L10T, L10H; (2) R11S, R11N, R11H, R11L, R11I; (3) I14L, I14F, I14V, I14M; (4) V18L, V18F, V18I; (5) E12A, (6) R65D, (7) R86K, R86T, R86M; (8) D87E, D87K, D87R, D87G, D87S; (9) T88I, T88K, T88R; (10) K89R, K89T, K89M; (11) L101 F, L101I, L101Y, L101H, L101N; (12) K104R, K104T, K104M; (13) K105T, K105A, K105R, K105E; (14) F107L, F107I, F107V, F107M; and (15) R108K, R108T, R108M, which substitutions cause an altered affinity for one or both of IL-13Rα1 and IL-13Rα2. In other embodiments, modified residues are at two or more, three or more, four or more, five or more, and not more than 14 amino acids within the combined set of contact residues defined above. As described in International Patent Publication WO 2013/112871, the disclosure of which is incorporated by reference herein in its entirety. In some embodiments, amino acid substitutions include without limitation those provided in FIG. 4.

Sets of modifications may include the following specific changes: (1) L10H; L10A; (2) R11L; (4) V18I; (7) R86M; R86K; R86T; (8) D87K; D87G; (9) T88R, T88S; T88K; (10) K89R; (11) L101N; (12) K104R; (13) K105A; K105E; (14) R108K. In some embodiments, the modification includes any one of the recited specific changes. In some embodiments, the modification includes L10H. In some embodiments, the modification includes L10A. In some embodiments, the modification includes R11L. In some embodiments, the modification includes V18I. In some embodiments, the modification includes R86M. In some embodiments, the modification includes R86K. In some embodiments, the modification includes R86T. In some embodiments, the modification includes D87K. In some embodiments, the modification includes D87G. In some embodiments, the modification includes T88R. In some embodiments, the modification includes T88S. In some embodiments, the modification includes T88K. In some embodiments, the modification includes K89R. In some embodiments, the modification includes L101N. In some embodiments, the modification includes K104R. In some embodiments, the modification includes K105A. In some embodiments, the modification includes K105E. In some embodiments, the modification includes R108K. In some embodiments, the polypeptide comprising the one or more modifications is linked to an IL-2 or IL-2 mutein as described herein. In some embodiments, amino acid substitutions include without limitation those provided in FIG. 4. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

Specific sets of modifications that provide for greater selectivity in binding to IL-13Rα2 versus IL-13Rα1 relative to a native IL-13 sequence may include, without limitation:

[L10D, R11I, V18I, R86K, D87K, k89R, R108K] (for example, C2, e.g. SEQ ID NO:31 or SEQ ID NO:49)

[L10A, R86T, D87G, T88K, K89R, L101N, K104R, K105A, R108K] (for example, C3, e.g. SEQ ID NO:32 or SEQ ID NO:50)

[L10V, K89R, L101N, K105E, R108T] (for example, C4, e.g. SEQ ID NO:33 or SEQ ID NO:31)

[R11S, I14M, T88S, L101N, K105A, R108K] (for example, C7, e.g. SEQ ID NO:34 or SEQ ID NO:52)

[L10H, R11L, V18I, R86K, D87E, K89R, L101N, K105T, R108K] (C9, e.g. SEQ ID NO:53)

[L10H, R86T, D87G, T88R, R108K] (C11 e.g. SEQ ID NO:38 or SEQ ID NO:55)

[L10A, V18F, R86K, D87K, K89R, L101I, K104R, R108K] (D7, e.g. SEQ ID NO:40 or SEQ ID NO:57)

[L10T/D; R11I; V18I; R86K; D87K/G; T88S; K89R; L101Y; K104R; K105T; R108K]

[L10A/V; R86T; D87G; T88K; K89R; L101N; K104R; K105A/E; R108K/T]

In some embodiments, the set of modifications comprises L10V, K89R, L101N, K105E, R108T. In some embodiments, the set of modifications comprises R11S, I14M, T88S, L101N, K105A, and R108K (C7, e.g. SEQ ID NO:35 or SEQ ID NO:52). In some embodiments, the set of modifications comprises L10H, R11L, V18I, R86K, D87E, K89R, L101N, K105T, and R108K (C9, e.g. SEQ ID NO:36 or SEQ ID NO:53). In some embodiments, the set of modifications comprises L10H, R86T, D87G, T88R, and R108K (C11 e.g. SEQ ID NO:38 or SEQ ID NO:55). In some embodiments, the set of modifications comprises L10A, V18F, R86K, D87K, K89R, L101I, K104R, and R108K (D7, e.g. SEQ ID NO:40 or SEQ ID NO:57). In some embodiments, the set of modifications comprises L10T/D, R11I, V18I, R86K, D87K/G, T88S, K89R, L101Y, K104R, K105T, and R108K. In some embodiments, the set of modifications comprises L10T, R11I, V18I, R86K, D87K, T88S, K89R, L101Y, K104R, K105T, and R108K. In some embodiments, the set of modifications comprises L10T, R11I, V18I, R86K, D87G, T88S, K89R, L101Y, K104R, K105T, and R108K. In some embodiments, the set of modifications comprises L10D, R11I, V18I, R86K, D87K, T88S, K89R, L101Y, K104R, K105T, and R108K. In some embodiments, the set of modifications comprises L10D, R11I, V18I, R86K, D87G, T88S, K89R, L101Y, K104R, K105T, R108K. In some embodiments, the set of modifications comprises L10A/V, R86T, D87G, T88K, K89R, L101N, K104R, K105A/E, and R108K/T. In some embodiments, the set of modifications comprises L10A, R86T, D87G, T88K, K89R, L101N, K104R, K105A, and R108K. In some embodiments, the set of modifications comprises L10A, R86T, D87G, T88K, K89R, L101N, K104R, K105E, and R108K. In some embodiments, the set of modifications comprises L10A, R86T, D87G, T88K, K89R, L101N, K104R, K105A, and R108T. In some embodiments, the set of modifications comprises L10A, R86T, D87G, T88K, K89R, L101N, K104R, K105E, and R108T. In some embodiments, the set of modifications comprises L10V, R86T, D87G, T88K, K89R, L101N, K104R, K105A, and R108K. In some embodiments, the set of modifications comprises L10V, R86T, D87G, T88K, K89R, L101N, K104R, K105E, and R108K. In some embodiments, the set of modifications comprises L10V, R86T, D87G, T88K, K89R, L101N, K104R, K105A, an dR108T. In some embodiments, the set of modifications comprises L10V, R86T, D87G, T88K, K89R, L101N, K104R, K105E, and R108T. In some embodiments, the amino acid sequence is 90% identical. In some embodiments, the amino acid sequence is 95% identical. In some embodiments, the amino acid sequence is 98% identical. In some embodiments, the amino acid sequence is 99% identical. In some embodiments, the polypeptide comprising the one or more modifications is linked to an IL-2 or IL-2 mutein as described herein. In some embodiments, amino acid substitutions include without limitation those provided in FIG. 4. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

Specific sets of modifications that provide for greater selectivity in binding to IL-13Rα1 v IL-13Rα2 relative to a native IL-13 sequence may include, without limitation:

[L10V, V18I, D87S, D88S, L101F, K104R, K105T]
[R11S, V18I, R86K, D87G, T88S, K89M, L101Y, K104R, K105T]
[L10V, V18I, D87S, T88S, L101F, K104R, K105T]
[L10V/I; D87S; T88S; K89R; L101H/F; K104R; K105T]
[L10I; V18I; R86T; D87G; T88S; K89R; L101Y/H; K104R; K105A]
[L10V; V18I; D87S; T88S; L101F; K104R; K105T]
[V18I, R86T, D87G, T88S, L101Y, K104R, K105A]
[R11I, V18I, R86K, D87G, T88S, L101H, K104R, K105A, F107M] which substitutions are optionally combined with the substitutions [E12A/G/S, R65D/E].

In some embodiments, the set of modifications comprises L10V, V18I, D87S, T88S, L101F, K104R, and K105T. In some embodiments, the set of modifications comprises R11S, V18I, R86K, D87G, T88S, K89M, L101Y, K104R, and K105T. In some embodiments, the set of modifications comprises L10V, V18I, D87S, T88S, L101F, K104R, and K105T. In some embodiments, the set of modifications comprises L10V/I, D87S, T88S, K89R, L101H/F, K104R, and K105T. In some embodiments, the set of modifications comprises L10I, V18I, R86T, D87G, T88S, K89R, L101Y/H, K104R, and K105A. In some embodiments, the set of modifications comprises L10V, V18I, D87S, T88S, L101F, K104R, and K105T. In some embodiments, the set of modifications comprises V18I, R86T, D87G, T88S, L101Y, K104R, and K105A. In some embodiments, the set of modifications comprises R11I, V18I, R86K, D87G, T88S, L101H, K104R, and K105A, and F107M. In some embodiments, the set of modifications comprises L10V, V18I, D87S, D88S, L101F, K104R, K105T, E12A/G/S, and R65D/E. In some embodiments, the set of modifications comprises R11S, V18I, R86K, D87G, T88S, K89M, L101Y, K104R, K105T, E12A/G/S, and R65D/E. In some embodiments, the set of modifications comprises L10V, V18I, D87S, T88S, L101F, K104R, K105T, E12A/G/S, and R65D/E. In some embodiments, the set of modifications comprises L10V/I, D87S, T88S, K89R, L101H/F, K104R, K105T, E12A/G/S, and R65D/E. In some embodiments, the set of modifications comprises L10I, V18I, R86T, D87G, T88S, K89R, L101Y/H, K104R, K105A, E12A/G/S, and R65D/E. In some embodiments, the set of modifications comprises L10V, V18I, D87S, T88S, L101F, K104R, K105T, E12A/G/S, and R65D/E. In some embodiments, the set of modifications comprises V18I, R86T, D87G, T88S, L101Y, K104R, K105A, E12A/G/S, and R65D/E. In some embodiments, the set of modifications comprises R11I, V18I, R86K, D87G, T88S, L101H, K104R, K105A, F107M, E12A/G/S, and R65D/E. In some embodiments, the set of modifications comprises L10V, V18I, D87S, D88S, L101F, K104R, K105T, E12A, and R65D/E. In some embodiments, the set of modifications comprises R11S, V18I, R86K, D87G, T88S, K89M, L101Y, K104R, K105T, E12A, and R65D/E. In some embodiments, the set of modifications comprises L10V, V18I, D87S, T88S, L101F, K104R, K105T, E12A, and R65D/E. In some embodiments, the set of modifications comprises L10V/I, D87S, T88S, K89R, L101H/F, K104R, K105T, E12A, and R65D/E. In some embodiments, the set of modifications comprises L10I, V18I, R86T, D87G, T88S, K89R, L101Y/H, K104R, K105A, E12A, and R65D/E. In some embodiments, the set of modifications comprises L10V, V18I, D87S, T88S, L101F, K104R, K105T, E12A, and R65D/E. In some embodiments, the set of modifications comprises V18I, R86T, D87G, T88S, L101Y, K104R, K105A, E12A, and R65D/E. In some embodiments, the set of modifications comprises R11I, V18I, R86K, D87G, T88S, L101H, K104R, K105A, F107M, E12A, and R65D/E. In some embodiments, the set of modifications comprises L10V, V18I, D87S, D88S, L101F, K104R, K105T, E12G, and R65D/E. In some embodiments, the set of modifications comprises R11S, V18I, R86K, D87G, T88S, K89M, L101Y, K104R, K105T, E12G, and R65D/E. In some embodiments, the set of modifications comprises L10V, V18I, D87S, T88S, L101F, K104R, K105T, E12A/G/S, and R65D/E. In some embodiments, the set of modifications comprises L10V/I, D87S, T88S, K89R, L101H/F, K104R, K105T, E12G, and R65D/E. In some embodiments, the set of modifications comprises L10I, V18I, R86T, D87G, T88S, K89R, L101Y/H, K104R, K105A, E12G, and R65D/E. In some embodiments, the set of modifications comprises L10V, V18I, D87S, T88S, L101F, K104R, K105T, E12G, and R65D/E. In some embodiments, the set of modifications comprises V18I, R86T, D87G, T88S, L101Y, K104R, K105A, E12G, and R65D/E. In some embodiments, the set of modifications comprises R11I, V18I, R86K, D87G, T88S, L101H, K104R, K105A, F107M, E12G, and R65D/E. In some embodiments, the set of modifications comprises L10V, V18I, D87S, D88S, L101F, K104R, K105T, E12S, and R65D/E. In some embodiments, the set of modifications comprises R11S, V18I, R86K, D87G, T88S, K89M, L101Y, K104R, K105T, E12A/G/S, and R65D/E. In some embodiments, the set of modifications comprises L10V, V18I, D87S, T88S, L101F, K104R, K105T, E12S, and R65D/E. In some embodiments, the set of modifications comprises L10V/I, D87S, T88S, K89R, L101H/F, K104R, K105T, E12S, and R65D/E. In some embodiments, the set of modifications comprises L10I, V18I, R86T, D87G, T88S, K89R, L101Y/H, K104R, K105A, E12S, and R65D/E. In some embodiments, the set of modifications comprises L10V, V18I, D87S, T88S, L101F, K104R, K105T, E12S, and R65D/E. In some embodiments, the set of modifications comprises V18I, R86T, D87G, T88S, L101Y, K104R, K105A, E12S, and R65D/E. In some embodiments, the set of modifications comprises R11I, V18I, R86K, D87G, T88S, L101H, K104R, K105A, F107M, E12S, and R65D/E. In some embodiments, the set of modifications comprises L10V, V18I, D87S, D88S, L101F, K104R, K105T, E12A, and R65D. In some embodiments, the set of modifications comprises R11S, V18I, R86K, D87G, T88S, K89M, L101Y, K104R, K105T, E12A, and R65E. In some embodiments, the set of modifications comprises L10V, V18I, D87S, T88S, L101F, K104R, K105T, E12A, and R65D. In some embodiments, the set of modifications comprises L10V/I, D87S, T88S, K89R, L101H/F, K104R, K105T, E12A, and R65D. In some embodiments, the set of modifications comprises L10I, V18I, R86T, D87G, T88S, K89R, L101Y/H, K104R, K105A, E12A, and R65D. In some embodiments, the set of modifications comprises L10V, V18I, D87S, T88S, L101F, K104R, K105T, E12A, and R65D. In some embodiments, the set of modifications comprises V18I, R86T, D87G, T88S, L101Y, K104R, K105A, E12A, and R65D. In some embodiments, the set of modifications comprises R11I, V18I, R86K, D87G, T88S, L101H, K104R, K105A, F107M, E12A, and R65D. In some embodiments, the set of modifications comprises L10V, V18I, D87S, D88S, L101F, K104R, K105T, E12G, and R65D. In some embodiments, the set of modifications comprises R11S, V18I, R86K, D87G, T88S, K89M, L101Y, K104R, K105T, E12G, and R65D. In some embodiments, the set of modifications comprises L10V, V18I, D87S, T88S, L101F, K104R, K105T, E12A/G/S, and R65D. In some embodiments, the set of modifications comprises L10V/I, D87S, T88S, K89R, L101H/F, K104R, K105T, E12G, and R65D. In some embodiments, the set of modifications comprises L10I, V18I, R86T, D87G, T88S, K89R, L101Y/H, K104R, K105A, E12G, and R65D. In some embodiments, the set of modifications comprises L10V, V18I, D87S, T88S, L101F, K104R, K105T, E12G, and R65D. In some embodiments, the set of modifications comprises V18I, R86T, D87G, T88S, L101Y, K104R, K105A, E12G, and R65D. In some embodiments, the set of modifications comprises R11I, V18I, R86K, D87G, T88S, L101H, K104R, K105A, F107M, E12G, and R65D. In some embodiments, the set of modifications comprises L10V, V18I, D87S, D88S, L101F, K104R, K105T, E12S, and R65D. In some embodiments, the set of modifications comprises R11S, V18I, R86K, D87G, T88S, K89M, L101Y, K104R, K105T, E12S, and R65D. In some embodiments, the set of modifications comprises L10V, V18I, D87S, T88S, L101F, K104R, K105T, E12S, and R65D. In some embodiments, the set of modifications comprises L10V/I, D87S, T88S, K89R, L101H/F, K104R, K105T, E12S, and R65D. In some embodiments, the set of modifications comprises L10I, V18I, R86T, D87G, T88S, K89R, L101Y/H, K104R, K105A, E12S, and R65D. In some embodiments, the set of modifications comprises L10V, V18I, D87S, T88S, L101F, K104R, K105T, E12S, and R65D. In some embodiments, the set of modifications comprises V18I, R86T, D87G, T88S, L101Y, K104R, K105A, E12S, and R65D. In some embodiments, the set of modifications comprises R11I, V18I, R86K, D87G, T88S, L101H, K104R, K105A, F107M, E12S, and R65D. In some embodiments, the set of modifications comprises L10V, V18I, D87S, D88S, L101F, K104R, K105T, E12A, and R65E. In some embodiments, the set of modifications comprises R11S, V18I, R86K, D87G, T88S, K89M, L101Y, K104R, K105T, E12A, and R65E. In some embodiments, the set of modifications comprises L10V, V18I, D87S, T88S, L101F, K104R, K105T, E12A, and R65E. In some embodiments, the set of modifications comprises L10V/I, D87S, T88S, K89R, L101H/F, K104R, K105T, E12A, and R65E. In some embodiments, the set of modifications comprises L10I, V18I, R86T, D87G, T88S, K89R, L101Y/H, K104R, K105A, E12A, and R65E. In some embodiments, the set of modifications comprises L10V, V18I, D87S, T88S, L101F, K104R, K105T, E12A, and R65E. In some embodiments, the set of modifications comprises V18I, R86T, D87G, T88S, L101Y, K104R, K105A, E12A, and R65E. In some embodiments, the set of modifications comprises R11I, V18I, R86K, D87G, T88S, L101H, K104R, K105A, F107M, E12A, and R65E. In some embodiments, the set of modifications comprises L10V, V18I, D87S, D88S, L101F, K104R, K105T, E12G, and R65E. In some embodiments, the set of modifications comprises R11S, V18I, R86K, D87G, T88S, K89M, L101Y, K104R, K105T, E12G, and R65E. In some embodiments, the set of modifications comprises L10V, V18I, D87S, T88S, L101F, K104R, K105T, E12A/G/S, and R65E. In some embodiments, the set of modifications comprises L10V/I, D87S, T88S, K89R, L101H/F, K104R, K105T, E12G, and R65E. In some embodiments, the set of modifications comprises L10I, V18I, R86T, D87G, T88S, K89R, L101Y/H, K104R, K105A, E12G, and R65E. In some embodiments, the set of modifications comprises L10V, V18I, D87S, T88S, L101F, K104R, K105T, E12G, and R65E. In some embodiments, the set of modifications comprises V18I, R86T, D87G, T88S, L101Y, K104R, K105A, E12G, and R65E. In some embodiments, the set of modifications comprises R11I, V18I, R86K, D87G, T88S, L101H, K104R, K105A, F107M, E12G, and R65E. In some embodiments, the set of modifications comprises L10V, V18I, D87S, D88S, L101F, K104R, K105T, E12S, and R65E. In some embodiments, the set of modifications comprises R11S, V18I, R86K, D87G, T88S, K89M, L101Y, K104R, K105T, E12A/G/S, and R65E. In some embodiments, the set of modifications comprises L10V, V18I, D87S, T88S, L101F, K104R, K105T, E12S, and R65E. In some embodiments, the set of modifications comprises L10V/I, D87S, T88S, K89R, L101H/F, K104R, K105T, E12S, and R65E. In some embodiments, the set of modifications comprises L10I, V18I, R86T, D87G, T88S, K89R, L101Y/H, K104R, K105A, E12S, and R65E. In some embodiments, the set of modifications comprises L10V, V18I, D87S, T88S, L101F, K104R, K105T, E12S, and R65E. In some embodiments, the set of modifications comprises V18I, R86T, D87G, T88S, L101Y, K104R, K105A, E12S, and R65E. In some embodiments, the set of modifications comprises R11I, V18I, R86K, D87G, T88S, L101H, K104R, K105A, F107M, E12S, and R65E. In some embodiments, the set of modifications comprises L10V, E12A, V18I, R65D, D87S, T88S, L101F, K104R, and K105T (see, for example, IL-13dn; SEQ ID NO:38). In some embodiments, the amino acid sequence is 90% identical. In some embodiments, the amino acid sequence is 95% identical. In some embodiments, the amino acid sequence is 98% identical. In some embodiments, the amino acid sequence is 99% identical. In some embodiments, the polypeptide comprising the one or more modifications is linked to an IL-2 or IL-2 mutein as described herein. In some embodiments, amino acid substitutions include without limitation those provided in FIG. 4. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

Table of IL-13 sequences is provided below.

TABLE 7

List of IL-13 Amino Acid Sequences

| SEQ ID NO: (Information) | Amino acid sequence |
|---|---|
| SEQ ID NO: 81 (IL-13 wildtype) | PGPVPPSTALRELIEELVNITQNQKAPLCNGSMVW SINLTAGMYCAALESLINVSGCSAIEKTQRMLSGF CPHKVSAGQFSSLHVRDTKIEVAQFVKDLLLHLKK LFREGQFN |
| SEQ ID NO: 82 | PGPVPPSTAVRALIEELINITQNQKAPLCNGSMVW SINRTAGMYCAALESLINVSGCSAIEKTQDMLSGF CPHKVSAGQFSSLHVRSSKIEVAQFVKDLLFHLRT LFREGQFN |
| SEQ ID NO: 83 | PGPVPPSTAIRELIEELINITQNQKAPLCNGSMVW SINLTAGMYCAALESLINVSGCSAIEKTQRMLSGF CPHKVSAGQFSSLHVRGSKIEVAQFVKDLLHHLRA LFREGQFN |
| SEQ ID NO: 84 | PGPVPPSTAVRELIEELINITQNQKAPLCNGSMVW SINRTAGMYCAALESLINVSGCSAIEKTQRMLSGF CPHKVSAGQFSSLHVRSSKIEVAQFVKDLLFHLRT LFREGQFN |
| SEQ ID NO: 85 | PGPVPPSTALIELIEELINITQNQKAPLCNGSMVW SINLTAGIYCAALESLINVSGCSAIEKTQRMLSGF CPHKVSAGQFSSLHVKGSKIEVAQFVKDLLHHLRA LMREGQFN |
| SEQ ID NO: 86 | PGPVPPSTAIRELIEELLNITQNQKAPLCNGSMVW SINLTAGMYCAALESLINVSGCSAIEKTQRMLSGF CPHKVSAGQFSSLHVMKSKIEVAQFVKDLLHHLRA LFREGQFN |
| SEQ ID NO: 87 | PGPVPPSTAIRELIEELINITQNQKAPLCNGSMVW SINLTAGMYCAALESLINVSGCSAIEKTQRMLSGF CPHKVSAGQFSSLHVRSSRIEVAQFVKDLLHHLRT LFREGQFN |
| SEQ ID NO: 88 | PGPVPPSTALRELIEELINITQNEKAPLCNGSMVW SINLTAGIYCAALESLINVSGCSAIEKTQRMLSGF CPHKVSAGQFSSLHVTGSKIEVAQFVKDLLYHLRA LFREGQFN |
| SEQ ID NO: 89 | PGPVPPSTALSELIEELINITQNQKAPLCNGSMVW SINPTAGMYCAALESLINVSGCSAIEKTQRMLSGF CPHKVAAGQFSSLHDKGSMIEVAQFVKDLLYHLRT LFREGQFN |
| SEQ ID NO: 90 | PGPVPPSTATRELIEELINITQNQKAPLCNGSMVW SINLTADMYCAALESLINVSGCSAIEKTQRMLSGF CPHKVSVGQFSSLHVRGSKIEVAQFVKDLLYHLRT LFREGQFN |
| SEQ ID NO: 91 | PGPVPPSTADIELIAELINITQNQKAPLCNGSMVW SINLTADMYCAALESLINVSGCSAIEKTQRMLSGF CPHKVSAGQFSSLHVKKTRIEVAQFVKDLLLHLKK LFKEGQFN |
| SEQ ID NO: 92 | PGPVPPSTAARELIEELVNITQNQKAPLCNGSMVW SINLTAGMYCAALESLINVSGCSAIEKTQRMLSGF CPHKVSAGQLSSLHVTGKRIEVAQFVKDLLNHLRA LFKEGQFN |
| SEQ ID NO: 93 | PGPVPPSTAVRELIEELVNITQNQKAPLCNGSMVW SINLTAGMYCAALESLINVSGCSAIEKTQRMLSGF CPHKVSAGQFSSLHVRDTRIEVAQFVKDLLNHLKE LFTEGQFN |

TABLE 7-continued

List of IL-13 Amino Acid Sequences

| SEQ ID NO: (Information) | Amino acid sequence |
| --- | --- |
| SEQ ID NO: 94 | PGPVPPSTALSELMEELVNITQNQKAPLCNGSMVW SINLTAGMYCAALESLINVSGCSAIEKTQRMLSGF CPHKVSAGQFSSLHVRDSKIEVAQFVKDLLNHLKA LFKEGQFN |
| SEQ ID NO: 95 | GPVPPSTAFRELIEELVNITQNQKAPLCNGSMVWS INLTAGMYCAALESLINVSGCSAIEKTQRMLSGFC PHKVSPGQFSSLHVTNSRIEVAQFVKDLLNHLKAL FKEGQYN |
| SEQ ID NO: 96 | GPVPPSTAHLELIEELINITQNQKAPLCNGSMVWS INLTAGMYCAALESLINVSGCSAIEKTQRMLSGFC PHKVSAGQFSSLHVKETRIEVAQFVKDLLNHLKTL FKEGQFN |
| SEQ ID NO: 97 | PGPVPPSTAHLELIEELINITQNQKAPLCNGSMVW SINPTAGMYCAALESLINVSGCSAIEKTQRMLSGF CPHKVSAGQFSSLHVMDTRIEVAQFVKDLLLHLKK LFKEGQFN |
| SEQ ID NO: 98 | PGPVPPSTAHRELIEELVNITQNQKAPLCNGSMVW SINLTAGMYCAALESLINVSGCSAIEKTQRMLSGF CPHKVSAGQFSSLHVTGRKIEVAQFVKDLLLHLKK LFKEGQFN |
| SEQ ID NO: 99 | PGPVPPSTAHRELIEELVNITQNQKAPLCNGSMVW RINRTAGMYCAALESLINVSGCSAIEKTQRMLSGF CPHKVSAGQFSSLHVMDSRIEVAQFVKDLLNHLRA LFKEGQFN |
| SEQ ID NO: 100 | PGPVPPSTAARELIEELFNITQNQKAPLCNGSMVW SINLTAGMYCAALESLINVSGCSAIEKTKRMLSGF CPHKVSAGQFPSLHVKKTRIEVAQFVKDLLIHLRK LFKEGQFN |
| SEQ ID NO: 101 (Exemplary sequence comprising R11I, V18I, R86K, D87G, T88S, L101H, K104R, K105A, F107M, referred to herein as A5) | PGPVPPSTALIELIEELINITQNQKAPLCNGSMVWS INLTAGMYCAALESLINVSGCSAIEKTQRMLSGFCP HKVSAGQFSSLHVKGSKIEVAQFVKDLLHHLRALMR EGQFN |
| SEQ ID NO: 102 (Exemplary sequence comprising L10I, V18L, R86M, D87K, T88S, L101H, K104R, K105A, referred to herein as A6) | PGPVPPSTAIRELIEELLNITQNQKAPLCNGSMVWS INLTAGMYCAALESLINVSGCSAIEKTQRMLSGFCP HKVSAGQFSSLHVMKSKIEVAQFVKDLLHHLRALFR EGQFN |
| SEQ ID NO: 103 (Exemplary sequence comprising L10I, V18I, D87G, T88S, L101H, K104R, K105A, referred to herein as A7) | PGPVPPSTAIRELIEELINITQNQKAPLCNGSMVWS INLTAGMYCAALESLINVSGCSAIEKTQRMLSGFCP HKVSAGQFSSLHVRGSKIEVAQFVKDLLHHLRALFR EGQFN |
| SEQ ID NO: 104 (Exemplary sequence comprising L10I, V18I, D87S, T88S, K89R, L101H, K104R, K105T; referred to herein as A8) | PGPVPPSTAIRELIEELINITQNQKAPLCNGSMVWS INLTAGMYCAALESLINVSGCSAIEKTQRMLSGFCP HKVSAGQFSSLHVRSSRIEVAQFVKDLLHHLRTLFR EGQFN |
| SEQ ID NO: 105 (Exemplary sequence comprising L10V, V18I, D87S, T88S, L101F, K104R, K105T, referred to herein as A11 variant 1) | PGPVPPSTAVRELIEELINITQNQKAPLCNGSMVWS INLTAGMYCAALESLINVSGCSAIEKTQRMLSGFCP HKVSAGQFSSLHVRSSKIEVAQFVKDLLFHLRTLFR EGQFN |
| SEQ ID NO: 105 (Exemplary sequence comprising L10V, V18I, D87S, T88S, L101F, K104R, K105T, referred to herein as A11 variant 2) | PGPVPPSTAVRELIEELINITQNQKAPLCNGSMVWS INRTAGMYCAALESLINVSGCSAIEKTQRMLSGFCP HKVSAGQFSSLHVRSSKIEVAQFVKDLLFHLRTLFR EGQFN |

TABLE 7-continued

List of IL-13 Amino Acid Sequences

| SEQ ID NO:<br>(Information) | Amino acid sequence |
|---|---|
| SEQ ID NO: 106<br>(Exemplary sequence comprising V18I, R86T, D87G, T88S, L101Y, K104R, K105A, referred to herein as B2) | PGPVPPSTALRELIEELINITQNQKAPLCNGSMVWS<br>INLTAGMYCAALESLINVSGCSAIEKTQRMLSGFCP<br>HKVSAGQFSSLHVIGSKIEVAQFVKDLLYHLRALFR<br>EGQFN |
| SEQ ID NO: 107<br>(Exemplary sequence comprising R11S, V18I, R86K, D87G, T88S, K89M, L101Y, K104R, K105T, referred to herein as B4) | PGPVPPSTALSELIEELINITQNQKAPLCNGSMVW<br>SINLTAGMYCAALESLINVSGCSAIEKTQRMLSGF<br>CPHKVSAGQFSSLHVKGSMIEVAQFVKDLLYHLRT<br>LFREGQFN |
| SEQ ID NO: 108<br>(Exemplary sequence comprising L10T, V18I, D87G, T88S, K89K, L10Y1, K104R, K105T, referred to herein as B6) | PGPVPPSTATRELIEELINITQNQKAPLCNGSMVW<br>SINLTAGMYCAALESLINVSGCSAIEKTQRMLSGF<br>CPHKVSAGQFSSLHVRGSKIEVAQFVKDLLYHLRT<br>LFREGQFN |
| SEQ ID NO: 109<br>(Exemplary sequence comprising L10D, R11I, V18I, R86K, D87K, K89R, R108K, referred to herein as C2) | PGPVPPSTADIELIEELINITQNQKAPLCNGSMVW<br>SINLTAGMYCAALESLINVSGCSAIEKTQRMLSGF<br>CPHKVSAGQFSSLHVKKTRIEVAQFVKDLLLHLKK<br>LFKEGQFN |
| SEQ ID NO: 110<br>(Exemplary sequence comprising L10A, R86T, D87G, T88K, K89R, L101N, K104R, K105A, R108K, referred to herein as C3) | PGPVPPSTAARELIEELVNITQNQKAPLCNGSMVW<br>SINLTAGMYCAALESLINVSGCSAIEKTQRMLSGF<br>CPHKVSAGQFSSLHVTGKRIEVAQFVKDLLNHLRA<br>LFKEGQFN |
| SEQ ID NO: 111<br>(Exemplary sequence comprising L10V, K89R, L101N, K105E, R108T, referred to herein as C4) | PGPVPPSTAVRELIEELVNITQNQKAPLCNGSMVW<br>SINLTAGMYCAALESLINVSGCSAIEKTQRMLSGF<br>CPHKVSAGQFSSLHVRDTRIEVAQFVKDLLNHLKE<br>LFTEGQFN |
| SEQ ID NO: 112<br>(Exemplary sequence comprising R11S, I14M, T88S, L101N, K105A, R108K, referred to herein as C7) | PGPVPPSTALSELMEELVNITQNQKAPLCNGSMVW<br>SINLTAGMYCAALESLINVSGCSAIEKTQRMLSGF<br>CPHKVSAGQFSSLHVRDSKIEVAQFVKDLLNHLKA<br>LFKEGQFN |
| SEQ ID NO: 113<br>(Exemplary sequence comprising L10H, R11L, V18I, R86K, D87E, K89R, L101N, K105T, R108K, refered to herein as C9) | PGPVPPSTAHLELIEELINITQNQKAPLCNGSMVW<br>SINLTAGMYCAALESLINVSGCSAIEKTQRMLSGF<br>CPHKVSAGQFSSLHVKETRIEVAQFVKDLLNHLKT<br>LFKEGQFN |
| SEQ ID NO: 114<br>(Exemplary sequence comprising L10H, R11L, V18I, R86M, K89R, R108K, referred to herein as C10) | PGPVPPSTAHLELIEELINITQNQKAPLCNGSMVW<br>SINLTAGMYCAALESLINVSGCSAIEKTQRMLSGF<br>CPHKVSAGQFSSLHVMDTRIEVAQFVKDLLLHLKK<br>LFKEGQFN |
| SEQ ID NO: 115<br>(Exemplary sequence comprising L10H, R86T, D87G, T88R, R108K, referred to herein as C11) | PGPVPPSTAHRELIEELVNITQNQKAPLCNGSMVW<br>SINLTAGMYCAALESLINVSGCSAIEKTQRMLSGF<br>CPHKVSAGQFSSLHVTGRKIEVAQFVKDLLLHLKK<br>LFKEGQFN |
| SEQ ID NO: 116<br>(Exemplary sequence comprising L10H, R86M, T88S, K89R, L101N, K104R, K105A, R108K, referred to herein as C12) | PGPVPPSTAHRELIEELVNITQNQKAPLCNGSMVW<br>SINLTAGMYCAALESLINVSGCSAIEKTQRMLSGF<br>CPHKVSAGQFSSLHVMDSRIEVAQFVKDLLNHLRA<br>LFKEGQFN |
| SEQ ID NO: 117<br>(Exemplary sequence comprising L10A, V18F, R86F, D87F, K89R, L101I, K104R, R108K, referred to herein as D7) | PGPVPPSTAARELIEELFNITQNQKAPLCNGSMVW<br>SINLTAGMYCAALESLINVSGCSAIEKTQRMLSGF<br>CPHKVSAGQFSSLHVKKTRIEVAQFVKDLLIHLRK<br>LFKEGQFN |

TABLE 7-continued

List of IL-13 Amino Acid Sequences

| SEQ ID NO: (Information) | Amino acid sequence |
|---|---|
| SEQ ID NO: 118 (Exemplary sequence comprising L10V, E12A, V18I, R65D, D87S, T88S, L101F, K104R, K105T, referred to herein as IL-13dn) | PGPVPPSTAVRALIEELINITQNQKAPLCNGSMVW SINLTAGMYCAALESLINVSGCSAIEKTQDMLSGF CPHKVSAGQFSSLHVRSSKIEVAQFVKDLLFHLRT LFREGQFN |
| SEQ ID NO: 119 signal peptide | MHPLLNPLLLALGLMALLLTTVIALTCLGGFASPG PVPPSTAHRELIEELVNITQNQKAPLCNGSMVWSI NLTAGMYCAALESLINVSGCSAIEKTQRMLSGFCP HKVSAGQFSSLHVTGRKIEVAQFVKDLLLHLKKLF KEGQFN |
| SEQ ID NO: 120 (Exemplary sequence comprising L10V, E12A, V18I, R65D, D87S, T88S, L101F, K104R, K105T, referred to herein as IL-13DN variant 1) | PGPVPPSTAVRALIEELINITQNQKAPLCNGSMVW SINRTAGMYCAALESLINVSGCSAIEKTQDMLSGF CPHKVSAGQFSSLHVRSSKIEVAQFVKDLLFHLRT LFREGQFN |
| SEQ ID NO: 121 (Exemplary sequence comprising L10V, E12A, V18I, R65D, D87S, T88S, L101F, K104R, K105T, referred to herein as IL-13DN variant 2) | PGPVPPSTAVRALIEELINITQNQKAPLCNGSMVW SINLTAGMYCAALESLINVSGCSAIEKTQDMLSGF CPHKVSAGQFSSLHVRSSKIEVAQFVKDLLFHLRT LFREGQFN |
| SEQ ID NO: 122 wild-type IL-13 including an additional methionine at the N-terminus | MPGPVPPSTALRELIEELVNITQNQKAPLCNGSMV WSINLTAGMYCAALESLINVSGCSAIEKTQRMLSG FCPHKVSAGQFSSLHVRDTKIEVAQFVKDLLLHLK KLFREGQFN |
| SEQ ID NO: 123 circularly permuted IL-13 | MYCAALESLINVSGCSAIEKTQRMLSGFCPHKVSA GQFSSLHVRDTKIEVAQFVKDLLLHLKKLFREGQF NGGSGPGPVPPSTALRELIEELVNITQNQKAPLCN GSMVWSINLTAG |
| SEQ ID NO: 124 Circularly permuted IL-13 | MYCAALESLINVSGCSAIEKTQRMLSGFCPHKVSA GQFSSLHVRDTKIEVAQFVKDLLLHLKKLFREGQF NGGSGMPGPVPPSTALRELIEELVNITQNQKAPLC NGSMVWSINLTAG |
| SEQ ID NO: 125 circularly permuted IL-13 "A11" variant | MYCAALESLINVSGCSAIEKTQRMLSGFCPHKVSA GQFSSLHVRSSKIEVAQFVKDLLFHLRTLFREGQF NGGSGPGPVPPSTAVRELIEELINITQNQKAPLCN GSMVWSINRTAG |
| SEQ ID NO: 126 circularly permuted IL-13 | MYCAALESLINVSGCSAIEKTQRMLSGFCPHKVSA GQFSSLHVRSSKIEVAQFVKDLLFHLRTLFREGQF NGGSGMPGPVPPSTAVRELIEELINITQNQKAPLC NGSMVWSINRTAG |
| SEQ ID NO: 127 circularly permuted IL-13 "DN" variant | MYCAALESLINVSGCSAIEKTQDMLSGFCPHKVSA GQFSSLHVRSSKIEVAQFVKDLLFHLRTLFREGQF NGGSGPGPVPPSTAVRALIEELINITQNQKAPLCN GSMVWSINLTAG |
| SEQ ID NO: 128 circular permuted IL-13 | MYCAALESLINVSGCSAIEKTQDMLSGFCPHKVSA GQFSSLHVRSSKIEVAQFVKDLLFHLRTLFREGQF NGGSGMPGPVPPSTAVRALIEELINITQNQKAPLC NGSMVWSINLTAG |

Any IL-4 sequence or variant thereof can be used in a fusion with an IL-2 mutein or variant, including those as described herein. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. Exemplary polypeptide sequences are provided in SEQ ID NO:130-SEQ ID NO:135, including any of those provided herein. In some embodiments, the IL-4 polypeptide sequence is as provided in any one of SEQ ID NO:130 through SEQ ID NO:135. In some embodiments, the IL-4 polypeptide sequence is SEQ ID NO:130. In some embodiments, the IL-4 polypeptide sequence is SEQ ID NO:131. In some embodiments, the IL-4 polypeptide sequence is SEQ ID NO:132. In some embodiments, the IL-4 polypeptide sequence is SEQ ID NO:133. In some embodiments, the IL-4 polypeptide sequence is SEQ ID NO:134. In some embodiments, the IL-4 polypeptide sequence is SEQ ID NO:135. In some embodiments, the IL-4 polypeptide sequence is 98% identical to any one of SEQ ID NO:130 through SEQ ID NO:135. In some embodiments, the IL-4 polypeptide sequence is 99% identical to any one of SEQ ID NO:130 through SEQ ID NO:135. In some embodiments, any one of SEQ ID NO:130-SEQ ID NO:135 are linked to an IL-2 or IL-2 mutein as described herein. In some embodiments, SEQ ID NO:130 is linked to an IL-2 or IL-2 mutein as described herein. In some embodiments, SEQ ID NO:131 is linked to an IL-2 or IL-2 mutein as described herein. In some embodiments, SEQ ID NO:132 is linked to an IL-2 or IL-2 mutein as described herein. In some embodiments, SEQ ID NO:133 is linked to an IL-2 or IL-2 mutein as described herein. In some embodiments, SEQ ID NO:134 is linked to an IL-2 or IL-2 mutein as described herein. In some embodiments, SEQ ID NO:135 is linked to an IL-2 or IL-2 mutein as described herein. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

Table of IL-4 sequences is provided below.

In some embodiments, an IL-2 mutein can be fused to an IL-10, IL-12, IL-15, and/or IL-18 sequence. In some embodiments, such fusions function to specifically target the fusion construct to NK cells and/or CD8+ cells. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, SEQ ID NO:136 is linked to an IL-2 or IL-2 mutein as described herein. In some embodiments, SEQ ID NO:137 is linked to an IL-2 or IL-2 mutein as described herein. In some embodiments, SEQ ID NO:138 is linked to an IL-2 or IL-2 mutein as described herein. In some embodiments, SEQ ID NO:139 is linked to an IL-2 or IL-2 mutein as described herein. In some embodiments, SEQ ID NO:140 is linked to an IL-2 or IL-2 mutein as described herein. In some embodiments, SEQ ID NO:141 is linked to an IL-2 or IL-2 mutein as described herein. In some embodiments, the IL-2 mutein can be fused to an IL-IL-10, IL-12, IL-15, and/or IL-18 sequence as provided in the table below, in SEQ ID NOs: 136-141.

TABLE 8

List of IL-4 Amino Acid Sequences

| SEQ ID NO: (Information) | Amino acid sequence |
|---|---|
| SEQ ID NO: 129 (IL-4 wildtype with signal peptide) | MGLTSQLLPPLFFLLACAGNFVHGHKCDITLQEII KTLNSLTEQKTLCTELTVTDIFAASKNTTEKETFC RAATVLRQFYSHHEKDTRCLGATAQQFHRHKQLIR FLKRLDRNLWGLAGLNSCPVKEANQSTLENFLERL KTIMREKYSKCSS |
| SEQ ID NO: 130 IL-4 including an additional methionine at the N-terminus" starting | MHKCDITLQEIIKTLNSLTEQKTLCTELTVTDIFA ASKDTTEKETFCRAATVLRQFYSHHEKDTRCLGAT AQQFHRHKQLIRFLKRLDRNLWGLAGLNSCPVKEA NQSTLENFLERLKTIMREKYSKCSS |
| SEQ ID NO: 131 KFR | KCDITLQEIIKTLNSLTEQKTLCTELTVTDIFAAS KNTTEKETFCRAATVLRQFYSHHEKDTRCLGATAQ QFHRHKQLIRFLKRLDRNLWGLAGLNSCPVKEANQ STLENFLERLKTIMKEKFRKCSS |
| SEQ ID NO: 132 RGA | MDTTEKETFCRAATVLRQFYSHHEKDTRCLGATAQ QFHRHKQLIRFLKRLDRNLWGLAGLNSCPVKEANQ STLENFLERLRVIMQSKWFKCGAGGNGGHKCDITL QEIIKTLNSLTEQKTLCTELTVTDIFAAS |
| SEQ ID NO: 133 cirularly permuted wild-type IL-4 | MDTTEKETFCRAATVLRQFYSHHEKDTRCLGATAQ QFHRHKQLIRFLKRLDRNLWGLAGLNSCPVKEANQ STLENFLERLKTIMREKYSKCSSGGNGGHKCDITL QEIIKTLNSLTEQKTLCTELTVTDIFAAS |
| SEQ ID NO: 134 circularly permuted "KFR" IL-4 variant | MDTTEKETFCRAATVLRQFYSHHEKDTRCLGATAQ QFHRHKQLIRFLKRLDRNLWGLAGLNSCPVKEANQ STLENFLERLKTIMKEKFRKCSSGGNGGHKCDITL QEIIKTLNSLTEQKTLCTELTVTDIFAASRQFYSH HEKDTRCLGATAQQFHRHKQLIRFLKRLDRNLWGL AGLNSCPVKEANQSTLENFLERLRVIMQSKWFKCG AGGNGGHKCDITLQEIIKTLNSLTEQKTLCTELTV TDIFAAS |
| SEQ ID NO: 135 circularly permuted "KF" IL-4 variant | MDTTEKETFCRAATVLRQFYSHHEKDTRCLGATAQ QFHRHKQLIRFLKRLDRNLWGLAGLNSCPVKEANQ STLENFLERLKTIMKEKFKCSSGGNGGHKCDITLQ EIIKTLNSLTEQKTLCTELTVTDIFAAS |

TABLE 9

Exemplary IL-10, IL-12, IL-15, and/or IL-18 Sequences

| SEQ ID NO: | Amino Acid Sequence |
|---|---|
| SEQ ID NO: 136 IL-10 (Uniprot sp\|P22301\|) | MHSSALLCCLVLLTGVRASPGQGTQ SENSCTHFPGNLPNMLRDLRDAFSR VKTFFQMKDQLDNLLLKESLLEDFK GYLGCQALSEMIQFYLEEVMPQAEN QDPDIKAHVNSLGENLKTLRLRLRR CHRFLPCENKSKAVEQVKNAFNKLQ EKGIYKAMSEFDIFINYIEAYMTMK IRN |
| SEQ ID NO: 137 IL-12A (Uniprot sp\|P29459\|) | MCPARSLLLVATLVLLDHLSLARNL PVATPDPGMFPCLHHSQNLLRAVSN MLQKARQTLEFYPCTSEEIDHEDIT KDKTSTVEACLPLELTKNESCLNSR ETSFITNGSCLASRKTSFMMALCLS SIYEDLKMYQVEFKTMNAKLLMDPK RQIFLDQNMLAVIDELMQALNFNSE TVPQKSSLEEPDFYKTKIKLCILLH AFRIRAVIIDRVMSYLNAS |
| SEQ ID NO: 138 IL-12B (Uniprot sp\|P29460\|) | MCHQQLVISWFSLVFLASPLVAIWE LKKDVYVVELDWYPDAPGEMVVLTC DTPEEDGITWTLDQSSEVLGSGKTL TIQVKEFGDAGQYTCHKGGEVLSHS LLLLHKKEDGIWSTDILKDQKEPKN KTFLRCEAKNYSGRETCWWLITIST DLIFSVKSSRGSSDPQGVTCGAATL SAERVRGDNKEYEYSVECQEDSACP AAEESLPIEVMVDAVHKLKYENYTS SFFIRDIIKPDPPKNLQLKPLKNSR QVEVSWEYPDTWSTPHSYFSLTFCV QVQGKSKREKKDRVFTDKTSATVIC RKNASISVRAQDRYYSSSWSEWASV PCS |
| SEQ ID NO: 139 IL-15 (Uniprot sp\|P40933\|) | MRISKPHLRSISIQCYLCLLLNSHF LTEAGIHVFILGCFSAGLPKTEANW VNVISDLKKIEDLIQSMHIDATLYT ESDVHPSCKVTAMKCELLELQVISL ESGDASIHDTVENLIILANNSLSSN GNVTESGCKECEELEEKNIKEFLQS FVHIVQMFINTS |

TABLE 9-continued

Exemplary IL-10, IL-12, IL-15, and/or IL-18 Sequences

| SEQ ID NO: | Amino Acid Sequence |
|---|---|
| SEQ ID NO: 140<br>IL-18<br>(Uniprot<br>sp\|Q14116\|) | MAAEPVEDNCINEVAMKFIDNTLYF<br>IAEDDENLESDYFGKLESKLSVIRN<br>LNDQVLFIDQGNRPLFEDMTDSDCR<br>DNAPRTIFIISMYKDSQPRGMAVTI<br>SVKCEKISTLSCENKIISFKEMNPP<br>DNIKDTKSDIIFFQRSVPGHDNKMQ<br>FESSSYEGYFLACEKERDLFKLILK<br>KEDELGDRSIMFTVQNED |
| SEQ ID NO: 141<br>IL-18<br>(mature) | YFGKLESKLSVIRNLNDQVLFIDQG<br>NRPLFEDMTDSDCRDNAPRTIFIIS<br>MYKDSQPRGMAVTISVKCEKISTLS<br>CENKIISFKEMNPPDNIKDTKSDII<br>FFQRSVPGHDNKMQFESSSYEGYFL<br>ACEKERDLFKLILKKEDELGDRSIM<br>FTVQNED |

The sequences of exemplary IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

In some embodiments, the cytokine-cytokine fusion is one of those included in the table below.

TABLE 10

List of Exemplary IL-2 Fusion Amino Acid Sequences

| SEQ ID NO:<br>(Information) | Amino acid sequence |
|---|---|
| SEQ ID NO: 142<br>IL-13 variant-<br>H9 (linker in<br>bold and<br>underlined) | PGPVPPSTAVRALIEELINTTQNQKAPLCNGSMVWSINRTAGMY<br>CAALESLINVSGCSAIEKTQDMLSGFCPHKVSAGQFSSLHVRSS<br>KIEVAQFVKDLLFHLRTLFREGQFNGGGGSGGGGSGGGGSAPTS<br>SSTKKTQLQLEHLLLDLQMILNGINNYKNPKLTRMLTFKFYMPK<br>KATELKHLQCLEEELKPLEEVLNLAQSKNEHFDPRDVVSNINVF<br>VLELKGSETTFMCEYADETATIVEFLNRWITFCQSIISTLT |
| SEQ ID NO: 143<br>IL-13 variant-<br>H9 (linker in<br>bold and<br>underlined) | PGPVPPSTAHRELIEELVNITQNQKAPLCNGSMVWSINLTAGMY<br>CAALESLINVSGCSAIEKTQRMLSGFCPHKVSAGQFSSLHVTGR<br>KIEVAQFVKDLLLHLKKLFKEGQFNGGGGSGGGGSGGGGSAPTS<br>SSTKKTQLQLEHLLLDLQMILNGINNYKNPKLTRMLTFKFYMPK<br>KATELKHLQCLEEELKPLEEVLNLAQSKNEHFDPRDVVSNINVF<br>VLELKGSETTFMCEYADETATIVEFLNRWITFCQSIISTLT |
| SEQ ID NO: 144<br>H9-IL-12<br>(linker in<br>bold and<br>underlined) | APTSSSTKKTQLQLEHLLLDLQMILNGINNYKNPKLTRMLTFKF<br>YMPKKATELKHLQCLEEELKPLEEVLNLAQSKNFHFDPRDVVSN<br>INVFVLELKGSETTFMCEYADETATIVEFLNRWITFCQSIISTL<br>TGGGGSGGGGSGGGGSRNLPVATPDPGMFPCLHHSQNLLRAVSN<br>MLQKARQTLEFYPCTSEEIDHEDITKDKTSTVEACLPLELTKNE<br>SCLNSRETSFITNGSCLASRKTSFMMALCLSSIYEDLKMYQVEF<br>KTMNAKLLMDPKRQIFLDQNMLAVIDELMQALNFNSETVPQKSS<br>LEEPDFYKTKIKLCILLHAFRIRAVTIDRVMSYLNASIWELKKD<br>VYVVELDWYPDAPGEMVVLTCDTPEEDGITWTLDQSSEVLGSGK<br>TLTIQVKEFGDAGQYTCHKGGEVLSHSLLLLHKKEDGIWSTDIL<br>KDQKEPKNKTFLRCEAKNYSGRFTCWWLTTISTDLTFSVKSSRG<br>SSDPQGVTCGAATLSAERVRGDNKEYEYSVECQEDSACPAAEES<br>LPIEVMVDAVHKLKYENYTSSFFIRDIIKPDPPKNLQLKPLKNS<br>RQVEVSWEYPDTWSTPHSYFSLTFCVQVQGKSKREKKDRVFTDK<br>TSATVICRKNASISVRAQDRYYSSSWSEWASVPCS |
| SEQ ID NO: 145<br>H9-IL18<br>(linker in<br>bold and<br>underlined) | APTSSSTKKTQLQLEHLLLDLQMILNGINNYKNPKLTRMLTFKF<br>YMPKKATELKHLQCLEEELKPLEEVLNLAQSKNFHFDPRDVVSN<br>INVFVLELKGSETTFMCEYADETATIVEFLNRWITFCQSIISTL<br>TGGGGSGGGGSGGGGSYFGKLESKLSVIRNLNDQVLFIDQGNRP<br>LFEDMTDSDCRDNAPRTIFIISMYKDSQPRGMAVTISVKCEKIS<br>TLSCENKIISFKEMNPPDNIKDTKSDIIFFQRSVPGHDNKMQFE<br>SSSYEGYFLACEKERDLFKLILKKEDELGDRSIMFTVQNED |

D. Recombinant Expression of IL-2 Muteins, Expression Vectors and Host Cells In various embodiments, polypeptides used in the practice of the instant invention are synthetic, or are produced by expression of a recombinant nucleic acid molecule. In the event the polypeptide is a chimera (e.g., a fusion protein containing at least a mutant IL-2 polypeptide and a heterologous polypeptide), it can be encoded by a hybrid nucleic acid molecule containing one sequence that encodes all or part of the IL-2 mutein, and a second sequence that encodes all or part of the heterologous polypeptide. For example, subject IL-2 muteins described herein may be fused to a hexa-histidine tag to facilitate purification of bacterially expressed protein, or to a hemagglutinin tag to facilitate purification of protein expressed in eukaryotic cells.

Methods for constructing a DNA sequence encoding the IL-2 muteins and expressing those sequences in a suitably transformed host include, but are not limited to, using a PCR-assisted mutagenesis technique. Mutations that consist of deletions or additions of amino acid residues to an IL-2 polypeptide can also be made with standard recombinant techniques. In the event of a deletion or addition, the nucleic acid molecule encoding IL-2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

The complete amino acid sequence can be used to construct a back-translated gene. A DNA oligomer containing a nucleotide sequence coding for IL-2 mutein can be synthesized. For example, several small oligonucleotides coding for portions of the desired polypeptide can be synthesized and then ligated. The individual oligonucleotides typically contain 5' or 3' overhangs for complementary assembly.

In addition to generating mutant polypeptides via expression of nucleic acid molecules that have been altered by recombinant molecular biological techniques, subject IL-2 muteins can be chemically synthesized. Chemically synthesized polypeptides are routinely generated by those of skill in the art.

Once assembled (by synthesis, site-directed mutagenesis or another method), the DNA sequences encoding an IL-2 mutein will be inserted into an expression vector and operatively linked to an expression control sequence appropriate for expression of the IL-2 mutein in the desired transformed host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The DNA sequence encoding the IL-2 mutein, whether prepared by site directed mutagenesis, chemical synthesis or other methods, can also include DNA sequences that encode a signal sequence. Such signal sequence, if present, should be one recognized by the cell chosen for expression of the IL-2 mutein. It can be prokaryotic, eukaryotic or a combination of the two. It can also be the signal sequence of native IL-2. The inclusion of a signal sequence depends on whether it is desired to secrete the IL-2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

E. Oncolytic Viruses Targeting Moieties

In some examples, the IL-2 muteins described herein can be employed to target an oncolytic virus (e.g., see Allen et al., Mol. Ther. 16:1556-64, 2008). In some examples, oncolytic virus can be used to target an IL-2 mutein to a tumor or TME. Numerous viruses can be employed as the oncolytic virus, including adenoviruses as well as self-replicating alphavirus, as well as oncolyctic vaccinia viruses (see, for example WO2013038066, incorporated herein by reference in its entirety; in particular FIG. 17). Other oncolytic viruses can include Seneca Valley Virus, Newcastle disease Virus (also referred to as Newcastle virus), Maraba virus, vesicular stomatitis virus (VSV), Herpes virus (including HSV-1), Measles virus, poliovirus, reovirus, coxsackie virus, a lentivirus, a morbillivirus, an influenza virus, Sinbis virus, myxoma virus and/or retrovirus (see, for example, Twumasi-Boateng, et al., "Oncolytic viruses as engineering platforms for combination immunotherapy", Nature Reviews Cancer, 2018), and Kaufman et al., Cancer Immunotherapy, 14:642-662 (2015), all of which are incorporated by reference herein their entireties). In some embodiments, the oncolytic virus includes but is not limited to an adenovirus, a self-replicating alphavirus, a vaccinia virus, a Seneca Valley Virus, a Newcastle disease Virus, a Maraba virus, vesicular stomatitis virus (VSV), a Herpes virus (including HSV-1 and HSV-2), a measles virus, a poliovirus, a reovirus, a coxsackie virus, a lentivirus, a morbillivirus, an influenza virus, Sinbis virus, myxoma virus and/or a retrovirus. The IL-2 superkines (H9 and IL-2 variants as described herein) also can be used to direct T cells/OVs to the TME. An IL-2 variant (such as H9) can boost effector T cells and NK cells while IL-2 variant can suppress T reg activity. Other oncolytic viruses include can include, for example, oncoVex/T-VEC, which involves the intratumoral injection of replication-conditional herpes simplex virus which preferentially infects cancer cells. The virus, which is also engineered to express GM-CSF, is able to replicate inside a cancer cell causing its lysis, releasing new viruses and an array of tumor antigens, and secreting GM-CSF in the process. Such oncolytic virus vaccines enhance DCs function in the tumor microenvironment to stimulate anti-tumor immune responses. These oncolytic viruses can be used to target or deliver the IL-2 muteins described herein to the tumor. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, the substitutions in the IL-2 mutein comprise L80F, R81D, L85V, I86V, and I92F, numbered in accordance with wild-type human IL-2 of SEQ ID NO:2. In some embodiments, the oncolytic virus comprises a transgene capable of expressing an IL-2 mutein as described herein. In some embodiments, the oncolytic virus comprises a transgene capable of expressing an IL-2 mutein comprising the following amino acid substitutions L80F, R81D, L85V, I86V, and I92F, numbered in accordance with wild-type human IL-2 of SEQ ID NO:2. In some embodiments, the oncolytic virus comprises a nucleic acid encoding an IL-2 mutein comprising the following amino acid substitutions L80F, R81D, L85V, I86V, and I92F, numbered in accordance with wild-type human IL-2 of SEQ ID NO:2. In some embodiments, the oncolytic virus comprises a transgene that is expressed as a therapeutic payload. In some embodiments, the therapeutic payload is an 11-2 as described herein. In some embodiments, the therapeutic payload is IL-2 mutein comprising the following amino acid substitutions L80F, R81D, L85V, I86V, and I92F, numbered in accordance with wild-type human IL-2 of SEQ ID NO:2.

In some embodiments, the oncolytic virus is an oncolytic vaccinia virus. In some embodiments, the oncolytic vaccinia virus vector is characterized in that the virus particle is of the type intracellular mature virus (IMV), intracellular enveloped virus (IEV), cell-associated enveloped virus (CEV), or extracellular enveloped virus (EEV). In some embodiments, the oncolytic vaccinia virus particle is of the type EEV or IMV. In some embodiments, the oncolytic vaccinia virus particle is of the type EEV.

Generally, construction of oncolytic vaccinia virus recombinants and cells and pharmaceutical compositions comprising said vectors which preferentially replicate in tumor cells and express at least one transgene (for example, and IL-2 muteina as described herein) to facilitate antitumor efficacy and apoptosis induction and to modulate host immune responses in a subject. According to the present invention, oncolytic adenoviruses and oncolytic vaccinia viruses can be combined with IL-2 expression or targeting moieties as described herein in order to target the oncolytic vaccinia virus or the oncolytic adenovirus and/or express the IL-2 mutein. Oncolysis releases tumor antigens and provides costimulatory danger signals. However, arming the virus can improve efficacy further. For example, CD40 ligand (CD40L, CD154) is known to induce apoptosis of tumor cells and it also triggers several immune mechanisms. One of these is a T-helper type 1 (Th1) response that leads to activation of cytotoxic T-cells and reduction of immune suppression. The present invention provides for oncolytic viruses that express the IL-2 muteins of the present invention. In some embodiments, the present invention provides for oncolytic viruses that are targeted (for example, "armed") with the IL-2 targeting moieties of the present invention.

In some embodiments, the oncolytic virus is a modified vaccinia virus vector, a virus particle, a host cell, a pharmaceutical composition and a kit comprising vaccinia virus genome wherein the thymidine kinase gene is inactivated by either a substitution in the thymidine kinase (TK) gene and/or an open reading frame ablating deletion of at least one nucleotide providing a partially deleted thymidine kinase gene, the vaccinia growth factor gene is deleted, and the modified vaccinia virus vector comprises at least one nucleic acid sequence encoding a non-viral protein (e.g., an IL-2 mutein as described herein which is capable of being expressed). In another aspect is provided the modified vaccinia virus vector, the virus particle, the pharmaceutical composition or the kit can be used for cancer therapy, for eliciting immune response in a subject, for use in a method of inhibiting malignant cell proliferation in a mammal, for use in a therapy or prophylaxis of cancer, for detecting the presence of the modified vaccinia virus in a subject, and as an in situ cancer vaccine, optionally in combination with adenovirus. In some embodiments, the invention provides method of producing a modified vaccinia virus comprising vaccinia virus genome wherein the thymidine kinase gene is inactivated by a substitution in the thymidine kinase (TK) gene and/or an open reading frame ablating deletion of at least one nucleotide providing a partially deleted thymidine kinase gene, the vaccinia growth factor gene is deleted, and the modified vaccinia virus vector comprises at least one nucleic acid sequence encoding a non-viral protein (e.g., an IL-2 mutein as described herein), comprising the steps of providing producer cells capable of sustaining production of vaccinia virus particles and carrying the modified vaccinia vector; culturing the producer cells in conditions suitable for virus replication and production; and harvesting the virus particles.

In some embodiments, the present invention provides methods of administering an oncolytic virus "armed" with or including an nucleic acid encoding an IL-2 mutein as described herein, wherein said IL-2 mutein is expressed at the tumor location or is expressed systemically in the subject. In some embodiments, the present invention also provides methods of administering an oncolytic virus "armed" or targeted with an IL-2 mutein as described herein. The routes of administration vary, naturally, with the location and nature of the tumor, and include, e.g., intradermal, transdermal, parenteral, intravenous, intramuscular, intranasal, subcutaneous, regional (e.g., in the proximity of a tumor, particularly with the vasculature or adjacent vasculature of a tumor), percutaneous, intratracheal, intraperitoneal, intraarterial, intravesical, intratumoral, inhalation, perfusion, lavage, and oral administration. Compositions are formulated relative to the particular administration route.

1. Oncolytic Vaccinia Virus

Vaccinia virus is a member of the Orthopoxvirus genus of the Poxviridae. It has large double-stranded DNA genome (~200 kb, ~200 genes) and a complex morphogenic pathway produces distinct forms of infectious virions from each infected cell. Viral particles contain lipid membranes(s) around a core. Virus core contains viral structural proteins, tightly compacted viral DNA genome, and transcriptional enzymes. Dimensions of vaccinia virus are ~360×270×250 nm, and weight of ~5-10 fg. Genes are tightly packed with little non-coding DNA and open-reading frames (ORFs) lack introns. Three classes of genes (early, intermediate, late) exists. Early genes (~100 genes; immediate and delayed) code for proteins mainly related to immune modulation and virus DNA replication. Intermediate genes code for regulatory proteins which are required for the expression of late genes (e.g. transcription factors) and late genes code for proteins required to make virus particles and enzymes that are packaged within new virions to initiate the next round of infection. Vaccinia virus replicates in the cell cytoplasm.

Different strains of vaccinia viruses have been identified (as an example: Copenhagen, modified virus Ankara (MVA), Lister, Tian Tan, Wyeth (=New York City Board of Health), Western Reserve (WR)). The genome of WR vaccinia has been sequenced (Accession number AY243312). In some embodiments, the oncolytic vaccinia virus is a Copenhagen, modified virus Ankara (MVA), Lister, Tian Tan, Wyeth, or Western Reserve (WR) vaccinia virus.

Different forms of viral particles have different roles in the virus life cycle Several forms of viral particles exist: intracellular mature virus (IMV), intracellular enveloped virus (IEV), cell-associated enveloped virus (CEV), extracellular enveloped virus (EEV). EEV particles have an extra membrane derived from the trans-Golgi network. This outer membrane has two important roles: a) it protects the internal IMV from immune aggression and, b) it mediates the binding of the virus onto the cell surface.

CEVs and EEVs help virus to evade host antibody and complement by being wrapped in a host-derived membrane. IMV and EEV particles have several differences in their biological properties and they play different roles in the virus life cycle. EEV and IMV bind to different (unknown) receptors (1) and they enter cells by different mechanisms. EEV particles enter the cell via endocytosis and the process is pH sensitive. After internalization, the outer membrane of EEV is ruptured within an acidified endosome and the exposed IMV is fused with the endosomal membrane and the virus core is released into the cytoplasm. IMV, on the other hand, enters the cell by fusion of cell membrane and virus membrane and this process is pH-independent. In addition to this, CEV induces the formation of actin tails from the cell surface that drive virions towards uninfected neighboring cells.

Furthermore, EEV is resistant to neutralization by antibodies (NAb) and complement toxicity, while IMV is not. Therefore, EEV mediates long range dissemination in vitro and in vivo. Comet-inhibition test has become one way of measuring EEV-specific antibodies since even if free EEV cannot be neutralized by EEV NAb, the release of EEV from infected cells is blocked by EEV NAb and comet shaped plaques cannot be seen. EEV has higher specific infectivity in comparison to IMV particles (lower particle/pfu ratio) which makes EEV an interesting candidate for therapeutic use. However, the outer membrane of EEV is an extremely fragile structure and EEV particles need to be handled with caution which makes it difficult to obtain EEV particles in quantities required for therapeutic applications. EEV outer membrane is ruptured in low pH (pH ~6). Once EEV outer membrane is ruptured, the virus particles inside the envelope retain full infectivity as an IMV.

Some host-cell derived proteins co-localize with EEV preparations, but not with IMV, and the amount of cell-derived proteins is dependent on the host cell line and the virus strain. For instance, WR EEV contains more cell-derived proteins in comparison to VV IHD-J strain. Host cell derived proteins can modify biological effects of EEV particles. As an example, incorporation of the host membrane protein CD55 in the surface of EEV makes it resistance to complement toxicity. In the present invention it is shown that human A549 cell derived proteins in the surface of EEV particles may target virus towards human cancer cells. Similar phenomenon has been demonstrated in the study with human immunodeficiency virus type 1, where host-derived ICAM-1 glycoproteins increased viral infectivity. IEV membrane contains at least 9 proteins, two of those not existing in CEV/EEV. F12L and A36R proteins are involved in IEV transport to the cell surface where they are left behind and are not part of CEV/EEV (9, 11). 7 proteins are common in (IEV)/CEV/EEV: F13L, A33R, A34R, A56R, BSR, E2, (K2L). For Western Reserve strain of vaccinia virus, a maximum of 1% of virus particles are normally EEV and released into the culture supernatant before oncolysis of the producer cell. 50-fold more EEV particles are released from International Health Department (IHD)-J strain of vaccinia. IHD has not been studied for use in cancer therapy of humans however. The IHD-W phenotype was attributed largely to a point mutation within the A34R EEV lectin-like protein. Also, deletion of A34R increases the number of EEVs released. EEV particles can be first detected on cell surface 6 hours post-infection (as CEV) and 5 hours later in the supernatant (IHD-J strain). Infection with a low multiplicity of infection (MOI) results in higher rate of EEV in comparison to high viral dose. The balance between CEV and EEV is influenced by the host cell and strain of virus.

Vaccinia has been used for eradication of smallpox and later, as an expression vector for foreign genes and as a live recombinant vaccine for infectious diseases and cancer. Vaccinia virus is the most widely used pox virus in humans and therefore safety data for human use is extensive. During worldwide smallpox vaccination programs, hundreds of thousands humans have been vaccinated safety with modified vaccinia virus strains and only very rare severe adverse events have been reported. Those are generalized vaccinia (systemic spread of vaccinia in the body), erythema multiforme (toxic/allergic reaction), eczema vaccinatum (widespread infection of the skin), progressive vaccinia (tissue destruction), and postvaccinia! encephalitis.

All together 44 melanoma patients have been treated in early clinical trials with wild type vaccinia virus in 1960s-1990s and the overall objective response rate of injected tumors was 50%. Also some beneficial immunological responses were seen (36). Wild type vaccinia virus has been used also for treatment of bladder cancer, lung and kidney cancer, and myeloma and only mild adverse events were seen. JX-594, an oncolytic Wyeth strain vaccinia virus coding for GM-CSF, has been successfully evaluated in three phase I studies and preliminary results from randomized phase II trial has been presented in the scientific meeting.

Vaccinia virus is appealing for cancer gene therapy due to several characteristics. It has natural tropism towards cancer cells and the selectivity can be significantly enhanced by deleting some of the viral genes. The present invention relates to the use of double deleted vaccinia virus (vvdd) in which two viral genes, viral thymidine kinase (TK) and vaccinia growth factor (VGF), are at least partially deleted. TK and VGF genes are needed for virus to replicate in normal but not in cancer cells. The partial TK deletion may be engineered in the TK region conferring activity.

TK deleted vaccinia viruses are dependent on cellular nucleotide pool present in dividing cells for DNA synthesis and replication. IN some embodiments, the TK deletion limits virus replication significantly in resting cells allowing efficient virus replication to occur only in actively dividing cells (e.g., cancer cells). VGF is secreted from infected cells and has a paracrine priming effect on surrounding cells by acting as a mitogen. Replication of VGF deleted vaccinia viruses is highly attenuated in resting (non-cancer) cells. The effects of TK and VGF deletions have been shown to be synergistic.

2. Oncolytic Adenovirus

Generally, adenovirus is a 36 kb, linear, double-stranded DNA virus (Grunhaus and Horwitz, 1992). The term "adenovirus" or "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV 9_hu14, avian AAV, bovine AAV, canine AAV, equine AAV, primate AAV, non-primate AAV, and ovine AAV. "Primate AAV" refers to AAV capable of infecting primates, "non-primate AAV" refers to AAV capable of infecting non-primate mammals, "bovine AAV" refers to AAV capable of infecting bovine mammals, etc.

Adenoviral infection of host cells results in adenoviral DNA being maintained episomally, which reduces the potential genotoxicity associated with integrating vectors. Also, adenoviruses are structurally stable, and no genome rearrangement has been detected after extensive amplification. Adenovirus can infect, virtually all epithelial cells regardless of their cell cycle stage. (See, for example, US200601.47420, incorporated by reference herein in its entirety) Moreover, the Ela and E4 regions of adenovirus are essential for an efficient and productive infection of human cells. The Ela gene is the first viral gene to be transcribed in a productive infection, and its transcription is not dependent on the action of any other viral gene products. However, the transcription of the remaining early viral genes requires Ela gene expression. The Ela promoter, in addition to regulating the expression of the Ela gene, also integrates signals for packaging of the viral genome as well as sites required for the initiation of viral DNA replication. See, Schmid, S. I., and Hearing, P. in Current Topics in Microbiology and Immunology, vol. 199: pages 67-80 (1995).

In some embodiments, the oncolytic virus is an oncolytic adenovirus. It has been established that naturally occurring viruses can be engineered to produce an oncolytic effect in tumor cells (Wildner, 2001; Jacotat, 1967; Kim, 2001; Geoerger et al., 2002; Yan et al., 2003; Vile et al., 2002, each of which is incorporated herein by reference). In the case of adenoviruses, specific deletions within their adenoviral genome can attenuate their ability to replicate within normal quiescent cells, while they retain the ability to replicate in tumor cells. One such conditionally replicating adenovirus, Δ24, has been described by Fueyo et al. (2000), see also U.S. Patent Application No. 20030138405, each of which are incorporated herein by reference. The Δ24 adenovirus is derived from adenovirus type 5 (Ad-5) and contains a 24-base-pair deletion within the CR2 portion of the E1A gene. See, for example WO2001036650A2 (incorporated by reference herein in it's entirety.

Oncolytic adenoviruses include conditionally replicating adenoviruses (CRADs), such as Delta 24, which have several properties that make them candidates for use as biotherapeutic agents. One such property is the ability to replicate in a permissive cell or tissue, which amplifies the original input dose of the oncolytic virus and helps the agent spread to adjacent tumor cells providing a direct antitumor effect.

In some embodiments, the oncolytic component of Delta 24 with a transgene expression approach to produce an armed Delta 24. Armed Delta 24 adenoviruses may be used for producing or enhancing bystander effects within a tumor and/or producing or enhancing detection/imaging of an oncolytic adenovirus in a patient, or tumor associated tissue and/or cell. In some embodiments, the combination of oncolytic adenovirus with various transgene strategies (e.g., expression of and IL2 mutein) will improve the therapeutic potential, including for example, potential against a variety of refractory tumors, as well as provide for improved imaging capabilities. In certain embodiments, an oncolytic adenovirus may be administered with a replication defective adenovirus, another oncolytic virus, a replication competent adenovirus, and/or a wildtype adenovirus. Each of which may be adminstered concurrently, before or after the other adenoviruses.

In some embodiments, an E1a adenoviral vectors involves the replacement of the basic adenovirus Ela promoter, including the CAAT box, TATA box and start site for transcription initiation, with a basic promoter that exhibits tumor specificity, and preferably is E2F responsive, and more preferably is the human E2F-1 promoter. Thus, this virus will be repressed in cells that lack molecules, or such molecules are non functional, that activate transcription from the E2F responsive promoter. Normal non dividing, or quiescent cells, fall in this class, as the transcription factor, E2F, is bound to pRb, or retinoblastoma protein, thus making E2F unavailable to bind to and activate the E2F responsive promoter. In contrast, cells that contain free E2F should support E2F based transcription. An example of such cells are neoplastic cells that lack pRb function, allowing for a productive viral infection to occur. In some embodiments, an Ela adenoviral vector is targeted use an IL-2 moiety as described herein.

Retention of the enhancer sequences, packaging signals, and DNA replication start sites which lie in the Ela promoter will ensure that the adenovirus infection proceeds to wild type levels in the neoplastic cells that lack pRb function. In essence, the modified Ela promoter confers tumor specific transcriptional activation resulting in substantial tumor specific killing, yet provides for enhanced safety in normal cells.

In some embodiments, an Ela adenoviral vector is prepared by substituting the endogenous Ela promoter with the E2F responsive promoter, the elements upstream of nucleotide 375 in the adenoviral 5 genome are kept intact. The nucleotide numbering is as described by See, Schmid, S. I., and Hearing, P. Current Topics in Microbiology and Immunology, vol. 199: pages 67-80 (1995). This includes all of the seven A repeat motifs identified for packaging of the viral genome. Sequences from nucleotide 375 to nucleotide 536 are deleted by a BsaAI to BsrBI restriction start site, while still retaining 23 base pairs upstream of the translational initiation codon for the E1A protein. An E2F responsive promoter, preferably human E2F-1 is substituted for the deleted endogenous Ela promoter sequences using known materials and methods. The E2F-1 promoter may be isolated as described in Example 1.

The E4 region has been implicated in many of the events that occur late in adenoviral infection, and is required for efficient viral DNA replication, late mRNA accumulation and protein synthesis, splicing, and the shutoff of host cell protein synthesis. Adenoviruses that are deficient for most of the E4 transcription unit are severely replication defective and, in general, must be propagated in E4 complementing cell lines to achieve high titers. The E4 promoter is positioned near the right end of the viral genome and governs the transcription of multiple open reading frames (ORF). A number of regulatory elements have been characterized in this promoter that are critical for mediating maximal transcriptional activity. In addition to these sequences, the E4 promoter region contains regulatory sequences that are required for viral DNA replication. A depiction of the E4 promoter and the position of these regulatory sequences can be seen in FIGS. 2 and 3 of U.S. Pat. No. 7,001,596, incorporated by reference herein in its entirety.

In some embodiments, the adenoviral vector that has the E4 basic promoter substituted with one that has been demonstrated to show tumor specificity, preferably an E2F responsive promoter, and more preferably the human E2F-1 promoter. The reasons for preferring an E2F responsive promoter to drive E4 expression are the same as were discussed above in the context of an Ela adenoviral vector having the Ela promoter substituted with an E2F responsive promoter. The tumor suppressor function of pRb correlates with its ability to repress E2F-responsive promoters such as the E2F-1 promoter (Adams, P. D., and W. G. Kaelin, Jr. 1995, Cancer Biol. 6:99-108; Sellers, W. R., and W. G. Kaelin. 1996, published erratum appears in Biochim Biophys Acta 1996 Dec. 9; 1288(3):E-1, Biochim Biophys Acta. 1288:M1-5. Sellers, W. R., J. W. Rodgers, and W. G. Kaelin, Jr. 1995, Proc Natl Acad Sci USA. 92:11544-8.) The human E2F-1 promoter has been extensively characterized and shown to be responsive to the pRb signaling pathway, including pRb/p107, E2F-1/-2/-3, and G1 cyclin/cdk complexes, and E1A (Johnson, D. G., K. Ohtani, and J. R. Nevins. 1994, Genes Dev. 8:1514-25; Neuman, E., E. K. Flemington, W. R. Sellers, and W. G. Kaelin, Jr. 1995. Mol Cell Biol. 15:4660; Neuman, E., W. R. Sellers, J. A. McNeil, J. B. Lawrence, and W. G. Kaelin, Jr. 1996, Gene. 173:163-9.) Most, if not all, of this regulation has been attributed to the presence of multiple E2F sites present within the E2F-1 promoter. Hence, a virus carrying this (these) modification(s) would be expected to be attenuated in normal cells that contain an intact (wild type) pRb pathway, yet exhibit a normal infection/replication profile in cells that are deficient for pRb's repressive function. In order to maintain the normal infection/replication profile of this mutant virus we have retained the inverted terminal repeat (ITR) at the distal end of the E4 promoter as this contains all of the regulatory elements that are required for viral DNA replication (Hatfield, L. and P. Hearing. 1993, J. Virol. 67:3931-9; Rawlins, D. R., P. J. Rosenfeld, R. J. Wides, M. D. Challberg, and T. J. Kelly, Jr. 1984, Cell. 37:309-19; Rosenfeld, P. J., E. A. O'Neill, R. J. Wides, and T. J. Kelly. 1987, Mol Cell Biol. 7:875-86; Wides, R. J., M. D. Challberg, D. R. Rawlins, and T. J. Kelly. 1987, Mol Cell Biol. 7:864-74). This facilitates attaining wild type levels of virus in pRb pathway deficient tumor cells infected with this virus.

In some embodiments, the E4 promoter is positioned near the right end of the viral genome and it governs the transcription of multiple open reading frames (ORFs) (Freyer, G. A., Y. Katoh, and R. J. Roberts. 1984, Nucleic Acids Res. 12:3503-19; Tigges, M. A., and H. J. Raskas. 1984. Splice junctions in adenovirus 2 early region 4 mRNAs: multiple splice sites produce 18 to 24 RNAs. J. Virol. 50:106-17; Virtanen, A. P. Gilardi, A. Naslund, J. M. LeMoullec, U. Pettersson, and M. Perricaudet. 1984, J. Virol. 51:822-31.) A number of regulatory elements have been characterized in this promoter that mediate transcriptional activity (Berk, A. J. 1986, Annu Rev Genet. 20:45-79; Gilardi, P., and M. Perricaudet. 1986, Nucleic Acids Res. 14:9035-49; Gilardi, P., and M. Perricaudet. 1984, Nucleic Acids Res. 12:7877-88; Hanaka, S., T. Nishigaki, P. A. Sharp, and H. Handa. 1987, Mol Cell Biol. 7:2578-87; Jones, C., and K. A. Lee. 1991, Mol Cell Biol. 11:4297-305; Lee, K. A., and M. R. Green. 1987, Embo J. 6:1345-53.) In addition to these sequences, the E4 promoter region contains elements that are involved in viral DNA replication (Hatfield, L., and P. Hearing. 1993, J Virol. 67:3931-9; Rawlins, D. R., P. J. Rosenfeld, R. J. Wides, M. D. Challberg, and T. J. Kelly, Jr. 1984, Cell. 37:309-19; Rosenfeld, P. J., E. A. O'Neill, R. J. Wides, and T. J. Kelly. 1987, Mol Cell Biol. 7:875-86; Wides, R. J., M. D. Challberg, D. R. Rawlins, and T. J. Kelly. 1987, Mol Cell Biol. 7:864-74.) A depiction of the E4 promoter and the position of these regulatory sequences can be seen in FIGS. 1 and 2. See, also, Jones, C., and K. A. Lee. Mol Cell Biol. 11:4297-305 (1991). With these considerations in mind, an E4 promoter shuttle was designed by creating two novel restriction endonuclease sites: a XhoI site at nucleotide 35,576 and a SpeI site at nucleotide 35,815 (see FIG. 3). Digestion with both XhoI and SpeI removes nucleotides from 35,581 to 35,817. This effectively eliminates bases −208 to +29 relative to the E4 transcriptional start site, including all of the sequences that have been shown to have maximal influence on E4 transcription. In particular, this encompasses the two inverted repeats of E4F binding sites that have been demonstrated to have the most significant effect on promoter activation. However, all three Sp1 binding sites, two of the five ATF binding sites, and both of the NF1 and NFIII/Oct-1 binding sites that are critical for viral DNA replication are retained.

In some embodiments, the E2F responsive promoter is the human E2F-1 promoter. Key regulatory elements in the E2F-1 promoter that mediate the response to the pRb pathway have been mapped both in vitro and in vivo (Johnson, D. G., K. Ohtani, and J. R. Nevins. 1994, Genes Dev. 8:1514-25; Neuman, E., E. K. Flemington, W. R. Sellers, and W. G. Kaelin, Jr. 1995, Mol Cell Biol. 15:4660; Parr, M. J., Y. Manome, T. Tanaka, P. Wen, D. W. Kufe, W. G. Kaelin, Jr., and H. A. Fine. 1997, Nat Med. 3:1145-9.) Thus, we isolated the human E2F-1 promoter fragment from base pairs −218 to +51, relative to the transcriptional start site, by PCR with primers that incorporated a SpeI and XhoI site into them. This creates the same sites present within the E4 promoter shuttle and allows for direct substitution of the E4 promoter with the E2F-1 promoter.

F. Nucleic Acid Molecules Encoding Mutant IL-2

In some embodiments the subject IL-2 mutein, either alone or as a part of a chimeric polypeptide, such as those described above, can be obtained by expression of a nucleic acid molecule. Just as IL-2 muteins can be described in terms of their identity with wild-type IL-2 polypeptides, the nucleic acid molecules encoding them will necessarily have a certain identity with those that encode wild-type IL-2. For example, the nucleic acid molecule encoding a subject IL-2 mutein can be at least 50%, at least 65%, preferably at least 75%, more preferably at least 85%, and most preferably at least 95% (e.g., 99%) identical to the nucleic acid encoding wild-type IL-2 (e.g., SEQ ID NO:2).

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding a mutant IL-2) is incorporated into a vector (e.g., a plasmid or viral vector) or into the genome of a heterologous cell (or the genome of a homologous cell, at a position other than the natural chromosomal location).

As described above, the subject IL-2 mutein may exist as a part of a chimeric polypeptide. In addition to, or in place of, the heterologous polypeptides described above, a subject nucleic acid molecule can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). One of skill in the art will be aware of additional useful reagents, for example, of additional sequences that can serve the function of a marker or reporter.

The subject nucleic acid molecules can be obtained by introducing a mutation into IL-2-encoding DNA obtained from any biological cell, such as the cell of a mammal. Thus, the subject nucleic acids (and the polypeptides they encode) can be those of a mouse, rat, guinea pig, cow, sheep, horse, pig, rabbit, monkey, baboon, dog, or cat. In one embodiment, the nucleic acid molecules will be those of a human.

G. Chimerica Antigen Receptors (CARS)

Targeted immunotherapy has emerged as promising field of research in the treatment of malignancies and has received a great deal of interest in recent years. Indeed, cures have been reported of lymphoma patients with engineered or genetically modified T cells targeting CD19 malignant cells. This has increased the focus towards antigens present on cancer cells as targets for gene- and immunotherapy. These CARS can be used to target or deliver the IL-2 muteins described herein to the tumor, or even allow for systemic IL-2 mutein expression. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, the substitutions in the IL-2 mutein comprise L80F, R81D, L85V, I86V, and I92F, numbered in accordance with wild-type human IL-2 of SEQ ID NO:2.

Genetic manipulation of autologous or allogeneic T cells or NK cells to specifically target a particular tumor antigen provides a strategy to bypass the failure of cytotoxic immune response induction by most tumor cells. In some embodiments, these genetically manipulated T-cells or NK cells can be used to target the IL-2 muteins described herein to the the tumor, for example, so that the IL-2 mutein is expressed at the tumor location. These technologies are based on the genetic modification of human immune cells, where the cells may be extracted from a patient or donor by leukapheresis. Specific cells, usually T-cells, are purified and engineered to express a receptor targeting a cancer antigen of interest. Engineering may utilize transduction by retroviral, lentiviral, transposon, mRNA electroporation, and the like. The immune cells may be expanded to the desired dose, and introduced into a patient. The engineered cells can specifically kill cancer cells through cell-mediated toxicity (cytotoxic T-cells) and/or eliciting an immune response to the cancer cell by immune recognition of tumor, cytokine release and immune cell recruitment.

For example, the application of chimeric antigen receptors (CAR) for immunogene therapy of malignant tumors is a promising strategy in which an antibody or ligand binding domain is fused with the zeta signaling chain of the T cell receptor. The resulting CAR immune cells are redirected by the neospecificity to attack tumors expressing the surface antigen or receptors recognized by the gene-modified T cell receptors and provide cellular therapy that attacks the tumor through normal host immune response in a highly regulated fashion. These cells are free to circulate throughout the brain and systemic circulation, making the need for colocalization and bioavailability less of a problem.

A number of generations of CAR immune cells have been developed. CARs are created by the fusion of a tumour-specific scFv antibody or other extracellular ligand binding domain to either the TCR-associated CD3ζ signalling domain or another intracellular signalling domains from co-stimulatory protein receptors. This structure allows CARs to have the tumor specificity of the B cell antigen receptor, and to activate T cells through the T cell antigen receptor independently of MHC binding. The first-generation CAR contained one intracellular signalling domain, typically with the CD3ζ signalling domain to allow for TCR signalling. Second-generation CARs have two intracellular signalling domains: a co-stimulatory domain comprising either a CD28 or a 4-1BB signalling domain, coupled with a CD3ζ signalling domain. This arrangement enables T-cell activation and proliferation upon antigen recognition by the scFv region of the CAR. The third-generation CARs have two co-stimulatory domains and a CD3ζ signalling domain. The first co-stimulatory domain is either a CD28 or a 4-1BB domain, with the second co-stimulatory domain consisting of either a CD28, a 4-1BB or a OX40 domain. Fourth-generation "armoured CAR T cells" combine a second-generation CAR with the addition of various genes, including cytokine and co-stimulatory ligands, to enhance the tumoricidal effect of the CAR T cells. See, for example, Batlevi et al. (2016) Nature Reviews Clinical Oncology 13:25-40. See also, U.S. Pat. No. 7,741,465 and International Patent Publication No. WO2014127261; all of which are incorporated by reference herein in their entireties.

Alternative approaches to T cell targeting include T cell antigen couplers, as described in International application WO2015/117229, entitled "Trifunctional T cell antigen Coupler and Methods and Uses thereof", herein specifically incorporated by reference. The T cell antigen coupler system comprises three linked domains: a target-specific polypeptide ligand; a ligand that binds a protein associated with the TCR complex, for example an scFv binding to CD3 (TCR, T-cell receptor) to stimulate T cell activation; and a T cell receptor signaling domain, for example a CD4 transmembrane and intracellular domain to amplify T cell activation. By stimulating T cell activation through the TCR, TACs were engineered to work with the T cell's essential molecular machinery.

Antibody coupled T cell receptors are another approach to T cell targeting. ACTRs are a hybrid approach to CARs and the established monoclonal antibody oncology therapeutics. ACTRs are composed of a typical CAR construct that can bind the heavy chain of an antibody through a high-affinity variant of the Fc receptor CD16. ACTR-T cells can target tumours by binding a ligand targeted to a specific cancer antigen. T cell activation is performed by the CAR module.

Bispecific T cell exchangers (BiTEs) are bispecific antibodies that can bind the TCR of T cells and target tumour cells through two modules: a cancer targeting ligand; and a CD3-binding scFv domain that bridges T cells to the tumor.

Targeted therapies have been developed against IL13Rα2, including bacterial toxins conjugated to IL13, nanoparticles, oncolytic virus, as well as immunotherapies using monoclonal antibodies, IL13Rα2-pulsed dendritic cells, and IL13Rα2-targeted chimeric antigen receptors (see Kahlon et al. (2004) *Cancer Research.* 64(24):9160-9166; Kong et al. (2012) *Clinical Cancer Research.* 18(21):5949-5960; Thaci et al. (2014) *Neuro-Oncology*; and clinical trials NCT02208362, NCT00730613 and NCT01082926). In some embodiments, these targeted therapies can be used to deliver the IL-2 muteins to the tumor.

Biologicals that provide for selective alteration of IL-13 activity are of interest for a number of therapeutic purposes, including the treatment of certain cancers with by engineering of T cell specificities. The present invention addresses this issue.

Methods and compositions are provided for enhancing anti-tumor immune effector cells, e.g. T cells, NK cells, etc. with targeted compositions, including without limitation chimeric antigen receptors (CARs); T cell antigen couplers (TACs); antibody coupled T cell receptors (ACTRs); and bispecific T cell exchangers (BiTEs), where an IL-13 or IL-4 superkine provides the target-specific ligand. In further embodiments, the immune effector cell expresses an IL-2 mutein.

Immune cell targeting or expression constructs comprising IL-2 superkine sequences are provided and can include any IL-2 sequence as described herein. Superkines are useful for targeting immune cells to cells, e.g. tumor cells, expressing the at least one receptor. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, the substitutions in the IL-2 mutein comprise L80F, R81D, L85V, I86V, and I92F, numbered in accordance with wild-type human IL-2 of SEQ ID NO:2.

The IL-2 superkine or mutein component of the construct may be at least about 50 amino acids in length, at least about 75, at least about 100, at least about 110, at least about 115 amino acids in length, up to the full-length of the wild-type protein at the transmembrane domain, i.e. about 116 amino acids in length. For example, the superkine or mutein may be fused to the hinge, transmembrane or signaling domains of a CAR. Exemplary polypeptide sequences are provided Included as superkines or muteins are amino acid and nucleic acid coding sequences that are 90%, 95%, 98% or 99% identical to these sequences, longer sequences that comprise those sequences but also include additional nucleotides at the 3' or 5' end, for example any number of additional nucleotides or codons, such as 3, 6, 9, 12 or more nucleotides, or up to about 12, 20, 50 or 100 additional nucleotides, and any sequence that encodes the same amino acid sequence as these nucleic acids due to the degeneracy of the genetic code. In particular, sequences that are codon optimized (CO) for expression by the desired host are contemplated as part of the invention. In some embodiments, the amino acid sequence is 90% identical. In some embodiments, the amino acid sequence is 95% identical. In some embodiments, the amino acid sequence is 98% identical. In some embodiments, the amino acid sequence is 99% identical. In some embodiments, the polypeptide is linked to an IL-2 superkine immune cell targeting or expression construct. In some embodiments, an IL-2 superkine immune cell targeting or expression construct comprises one or more signaling domains derived from CD3-ζ CD28, DAP10, OX-40, ICOS and CD137. In some embodiments, an IL-2 superkine immune cell targeting or expression construct or expression comprises one or more signaling domains derived from CD3-ζ. In some embodiments, an IL-2 superkine immune cell targeting or expression construct comprises one or more signaling domains derived from CD28. In some embodiments, an IL-2 superkine immune cell targeting or expression construct comprises one or more signaling domains derived from DAP10. In some embodiments, an IL-2 superkine immune cell targeting or expression construct comprises one or more signaling domains derived from OX-40. In some embodiments, an IL-2 superkine immune cell targeting or expression construct comprises one or more signaling domains derived from CD137. In some embodiments, an IL-2 superkine immune cell targeting or expression construct comprises an IL-2 variant/IL-2 superkine including those provided herein. In some embodiments, an IL-2superkine immune cell targeting or expression construct comprises an IL-2 variant/IL-2 superkine including those provided in SEQ ID NO:2 through SEQ ID NO:38.

1. NK Cells

In some embodiments the immune cells are natural killer (NK) cells. NK cells recognize infected or transformed cells through multiple cell surface receptors including NKG2D, CD16, and natural cytotoxicity receptors (NCRs) such as NKp44, NKp46, and NKp30. These receptors activate signaling adapter proteins such as DAP10, DAP12, and CD3ζ which contain immuno-tyrosine activation motifs (ITAMs) that initiate the release of cytolytic granules containing perforin and granzymes, as well as mediate production and release of cytokines and chemokines such as IFN-γ and TNF-α. Importantly, NK cell-mediated cytotoxicity does not rely on the presentation of self HLA. Therefore, NK cells hold significant clinical interest as a cell-based therapy for cancer because of their ability to be used in an allogeneic setting and potentially provide an off-the-shelf cellular product.

Natural killer cells provide an alternative to the use of T cells for adoptive immunotherapy since they do not require HLA matching, so can be used as allogeneic effector cells. Clinical trials of adoptively transferred allogeneic NK cells demonstrate these cells can survive in patients for several weeks to months. Additionally, expression of CARs in NK cells allow these cells to more effectively kill solid tumors that are often resistant to NK cell-mediated activity compared to hematologic malignancies (especially acute myelogenous leukemia) that are typically more NK cell-sensitive. CARs useful in NK cell targeting include, for example, first generation CAR constructs that contain CD3ζ as the sole signaling domain. Second and third generation CARs are also useful in NK cells. In some embodiments the ectodomain of NKG2D, an NK cell activation receptor, is linked directly to CD3ζ.

NK cells for modification include cell lines, or peripheral blood NK cells, which can be isolated from donors through simple blood draws or by apheresis if larger numbers of cells are needed. Activated PB-NK cells express a wider range of activating receptors, such as CD16, NKp44, and NKp46 as well as KIRs, which play an important role in NK cell licensing. In addition, PB-NK cells can be given without irradiating the cells so have the ability to expand in vivo. Another source of NK cells suitable for CAR expression are NK cells derived from human pluripotent stem cells—both induced pluripotent stem cells (iPSCs) or human embryonic stem cells (hESCs). These NK cells display a similar phenotype to PB-NK cells, and hESC/iPSC-NK cells can be grown on a clinical scale.

2. Chimerica Antigen Receptors (CARs)

In addition to the superkine sequence, CARs contain the signaling domain for CD3ζ and the signaling domains of one or more costimulatory receptors that further promote the recycling, survival and/or expansion of immune cells expressing the CARs. The signaling domains of the costimulatory receptors are the intracellular portions of each receptor protein that generate the activating signal in the cell. Examples are amino acids 180-220 of the native CD28 molecule and amino acids 214-255 of the native 4-1BB molecule.

Examples of suitable hinge and transmembrane regions to link the superkine to the signaling region may include without limitation the constant (Fc) regions of immunoglobins, human CD8a, and artificial linkers that serve to move the targeting moiety away from the cell surface for improved access to and binding on target cells. Examples of suitable transmembrane domains include the transmembrane domains of the leukocyte CD markers, preferably that of CD4 or CD28. Examples of intracellular receptor signaling domains include the T cell antigen receptor complex, preferably the zeta chain of CD3, however any transmembrane region sufficient to anchor the CAR in the membrane can be used. Persons of skill are aware of numerous transmembrane regions and the structural elements (such as lipophilic amino acid regions) that produce transmembrane domains in numerous membrane proteins and therefore can substitute any convenient sequence. T cell costimulatory signaling receptors suitable for improving the function and activity of CAR-expressing cells include, but are not limited to, CD28, CD137, and OX-40.

Signaling via CD28 is required for IL2 production and proliferation, but does not play a primary role in sustaining T cell function and activity. CD137 (a tumor necrosis factor-receptor family member expressed following CD28 activation) and OX-40 are involved in driving long-term survival of T cells, and accumulation of T cells. The ligands for these receptors typically are expressed on professional antigen presenting cells such as dendritic cells and activated macrophages, but not on tumor cells. Expressing a CAR that incorporates CD28 and/or 4-1BB signaling domains in CD4$^+$ T cells enhances the activity and anti-tumor potency of those cells compared to those expressing a CAR that contains only the CD3t signaling domain, which constructs may be referred to as second or third generation CARs.

Included as CAR constructs of interest are tandem CARs, e.g. see Hegde et al. (2016) J. Clin. Invest 126(8):3036-3052, herein specifically incorporated by reference. In such constructs a binding moiety for a tumor specific antigen is combined in tandem with an IL-13 superkine. The binding moiety may be, for example, an scFv specific for a tumor cell antigen, including without limitation HER-2, EGFR, CD20, etc. as known in the art.

In various embodiments, the antigen binding domain binds to an antigen on a target cell, e.g., a cancer cell. The antigen binding domain can bind an antigen, such as but not limited to a tumor target antigen. In some case, the antigen binding domain binds one or more antigens. Exemplary antigen binding domains can bind to an antigen including, but not limited to, D19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAca Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Rα2 or CD213A2); Mesothelin; Interleukin 11 receptor alpha (IL-11Rα); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp 100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDG1cp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART 1); Rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); androgen receptor; Cyclin B 1; v-myc avian myelocytomatosis viral oncogene neuroblastoma derived homolog (MYCN); Ras Homolog Family Member C (RhoC); Tyrosinase-related protein 2 (TRP-2); cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the antigen binding domain comprises a monoclonal antibody, a polyclonal antibody, a synthetic antibody, a human antibody, a humanized antibody, a non-human antibody, a nanobody, a single-chain variable fragment (scFv), F(ab')2, Fab', Fab, Fv, and the like. The antigen binding domain can be linked to the transmembrane domain of the CAR. In some embodiments, a nucleic acid encoding the antigen binding domain is operably linked to a nucleic acid encoding a transmembrane domain of the CAR.

In some embodiments, the transmembrane domain can be derived from a membrane-bound or transmembrane protein. In certain embodiments, the transmembrane domain comprises one or more, e.g., 1, 2, 3, 4, 5, 6, 7, 8 or more amino acid modifications (e.g., substitutions, insertions, and deletions) compared to the wild-type amino acid sequence of the transmembrane domain of the membrane-bound or transmembrane protein. Non-limiting examples of a transmembrane domain of a CAR include at least the transmembrane region(s) of the alpha, beta or zeta chain of the T-cell receptor, CD28, CD3 epsilon (CD3), CD45, CD4, CD5, CD8, CD9, CD16, CD22, CD33, CD37, CD64, CD80, CD86, CD134, CD137, CD154, or an erythropoietin receptor. In some embodiments, the transmembrane domain includes a human immunoglobulin (Ig) hinge region, e.g., an IgG4Fc hinge. In other embodiments, the transmembrane domain is a recombinant or synthetic domain comprising hydrophobic amino acid residues (e.g., leucine and valine). In some cases, the transmembrane domain includes a phenylalanine, tryptophan and valine at one or both ends of the domain.

The transmembrane domain links the antigen binding domain to the intracellular signaling domain of the CAR. In some embodiments, the nucleic acid encoding the antigen binding domain is operably linked to the nucleic acid encoding the transmembrane domain that is operably linked to the nucleic acid encoding the intracellular signaling domain.

In some embodiments, the intracellular signaling domain of a CAR comprises a signal activation or signal transduction domain. As such, an intracellular signaling domain includes any portion of an intracellular signaling domain of a protein sufficient to transduce or transmit a signal, e.g., an activation signal or to mediate a cellular response within a cell. Non-limiting examples include TCR, CD2, CD3 zeta, CD3 gamma, CD3 delta, CD3 epsilon, CD7, CD27, CD86, common FcR gamma, FcR beta, CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, any derivative, variant, or fragment thereof. In certain embodiments, the intracellular signaling domain comprises an intracellular domain of a co-stimulatory molecule such as from CD3, CD27, CD28, CD127, ICOS, 4-1BB (CD137), PD-1, T cell receptor (TCR), any derivative thereof, or any variant thereof. In some embodiments, the intracellular signaling domain of the CAR is selected from the group consisting of a MEW class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

3. BiTES

Bi-specific T-cell engagers (BiTEs) are fusion proteins comprising an IL-13 superkine fused to an antibody variable region that specifically binds to CD3. In some embodiments the antibody variable region in a single-chain variable fragments (scFvs). THe superkine may be fused to the variable region through a linker. An Fc region is optionally provided.

4. TACs

A TAC construct comprises an IL-2 superkine fused to a ligand that binds a protein associated with the TCR complex; fused to a T cell receptor signaling domain polypeptide. The domains may be separated by linkers. The protein associated with the TCR complex may be CD3. The ligand that binds a protein associated with the TCR complex may be a single chain antibody. The ligand that binds a protein associated with the TCR complex may be UCHT1, or a variant thereof. The T cell receptor signaling domain polypeptide may comprise a cytosolic domain and a transmembrane domain. The cytosolic domain may be a CD4 cytosolic domain and the transmembrane domain is a CD4 transmembrane domain.

5. ACTRs

ACTRs are a hybrid approach to CARs and the established monoclonal antibody oncology therapeutics. ACTRs are composed of a typical CAR construct that can bind the heavy chain of an antibody through a high-affinity variant of the Fc receptor CD16. A superkine is fused to a moiety recognized by the CAR, which may include, without limitation, an Fc region of an antibody with high affinity for CD16.

An immune cell targeting or expression construct coding sequence can be produced by any means known in the art, including recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region may be inserted into an expression vector and used to transform a suitable expression host cell line, e.g. a population of allogeneic or autologous T lymphocytes, allogeneic or autologous NK cells, including primary cultures, cell lines, iPSC derived cells, etc. The methods can be used on cells in vitro (e.g., in a cell-free system), in culture, e.g. in vitro or ex vivo. For example, IL-2 superkine CAR-expressing cells can be cultured and expanded in vitro in culture medium.

An non-IL-2 superkine immune cell targeting or expression construct can also be used specifically direct immune cells to target specific tumor cells. Anti-tumor effector cells, e.g. $CD4^+$ or $CD8^+$ effector T cells, are generated to be re-directed to recognize such tumor cells by introducing into the T cells an superkine immune cell targeting or expression construct comprising one or more signaling domains derived from CD3-ζ, CD28, DAP10, OX-40, ICOS and CD137. In some embodiments, the cells can further comprise a transgene capable of expressing an IL-2 mutein as described herein. An IL-2 superkine immune cell targeting or expression construct can specifically direct immune cells to target IL-2R expressing cell, including tumor cells. Anti-tumor effector cells, e.g. $CD4^+$ or $CD8^+$ effector T cells, are generated to be re-directed to recognize such tumor cells by introducing into the T cells an IL-2 superkine immune cell targeting or expression construct comprising one or more signaling domains derived from CD3-ζ, CD28, DAP10, OX-40, ICOS and CD137.

The IL-2 superkine immune cell targeting or expression construct is infected or transfected into human immune cells, e.g. using a non-viral plasmid vector and electroporation methods; a viral vector and infection methods, etc. as known in the art. A CAR comprising co-stimulatory signaling domains may enhance the duration and/or retention of anti-tumor activity in a manner that can significantly improve the clinical efficacy of adoptive therapy protocols. $CD4^+$ and $CD8^+$ T cell effector functions, and NK cell functions can be triggered via these receptors, therefore these cell types are contemplated for use with the invention. $CD8^+$ T cells expressing the IL13 superkine CARs of this invention may be used to lyse target cells and to produce IL-2 in the presence of target cells, among the other functions of these cells. Expression of the appropriate costimulatory CAR in either or both $CD4^+$ and $CD8^+$ T cells is used to provide the most effective population of cells for adoptive immunotherapy, consisting therefore of either or both professional helper and killer T cells that exhibit enhanced and/or long term viability and anti-tumor activity. In some embodiments, an IL-2 superkine immune cell targeting or expression construct comprises an IL-2 variant/IL-2 superkine including those provided in FIG. 2. In some embodiments, an IL-2 superkine immune cell targeting or expression construct comprises an IL-2 variant/IL-2 superkine including any of those provided herein.

Polypeptides of the present invention can be further modified, e.g., joined to a wide variety of other oligopeptides or proteins for a variety of purposes. For example, post-translationally modified, for example by prenylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes.

Methods which are well known to those skilled in the art can be used to construct T cell targeting construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

According to the present invention, immune cell targeting or expression construct vectors and immune cell targeting or expression construct modified cells can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent, e.g., another anti-tumor agent.

Therapeutic entities of the present invention are often administered as pharmaceutical compositions comprising an active therapeutic agent and another pharmaceutically acceptable excipient. Such formulations can include one or more non-toxic pharmaceutically acceptable carriers, diluents, excipients and/or adjuvants. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The maximum tolerated dose (MTD) of CAR immune cells may be determined during clinical trial development, for example at up to about $10^4$ T cells/kg of body weight, up to about $10^5$ cells/kg of body weight, up to about $10^6$ cells/kg of body weight, up to about $5 \times 10^6$ cells/kg of body weight, up to about $10^7$ cells/kg of body weight, up to about $5 \times 10^7$ cells/kg of body weight, or more, as empirically determined. In some embodiments, the maximum tolerated dose (MTD) of CAR immune cells is up to about $10^4$ T cells/kg of body weight. In some embodiments, the maximum tolerated dose (MTD) of CAR immune cells is up to about $10^5$ T cells/kg of body weight. In some embodiments, the maximum tolerated dose (MTD) of CAR immune cells is up to about $10^6$ T cells/kg of body weight. In some embodiments, the maximum tolerated dose (MTD) of CAR immune cells is up to about $10^7$ T cells/kg of body weight. In some embodiments, the maximum tolerated dose (MTD) of CAR immune cells is up to about $5 \times 10^6$ T cells/kg of body weight. In some embodiments, the maximum tolerated dose (MTD) of CAR immune cells is up to about $5 \times 10^7$ T cells/kg of body weight.

Toxicity of the cells described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

After a dose escalation phase, patients in the expansion cohort are treated with immune cells at the MTD. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient.

In prophylactic applications, e.g. to maintain remission in a patient, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Examples of additional therapeutic agents that can be coadministered and/or coformulated with an immune cell targeting or expression construct include: anti-proliferative, or cytoreductive therapy, which is used therapeutically to eliminate tumor cells and other undesirable cells in a host, and includes the use of therapies such as delivery of ionizing radiation, and administration of chemotherapeutic agents. Chemotherapeutic agents are well-known in the art and are used at conventional doses and regimens, or at reduced dosages or regimens, including for example, topoisomerase inhibitors such as anthracyclines, including the compounds daunorubicin, adriamycin (doxorubicin), epirubicin, idarubicin, anamycin, MEN 10755, and the like. Other topoisomerase inhibitors include the podophyllotoxin analogues etoposide and teniposide, and the anthracenediones, mitoxantrone and amsacrine. Other anti-proliferative agent interferes with microtubule assembly, e.g. the family of vinca alkaloids. Examples of vinca alkaloids include vinblastine, vincristine; vinorelbine (NAVELBINE); vindesine; vindoline; vincamine; etc. DNA-damaging agent include nucleotide analogs, alkylating agents, etc. Alkylating agents include nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Nucleotide analogs include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other chemotherapeutic agents of interest include metal complexes, e.g. cisplatin (cis-DDP), carboplatin, oxaliplatin, etc.; ureas, e.g. hydroxyurea; and hydrazines, e.g. N-methylhydrazine.

For example, ionizing radiation (IR) is used to treat about 60% of cancer patients, by depositing energy that injures or destroys cells in the area being treated, and for the purposes of the present invention may be delivered at conventional doses and regimens, or at reduced doses. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area. A suitable dose of ionizing radiation may range from at least about 2 Gy to not more than about 10 Gy, usually about 5 Gy. A suitable dose of ultraviolet radiation may range from at least about 5 J/m² to not more than about 50 J/m², usually about 10 J/m². The sample may be collected from at least about 4 and not more than about 72 hours following ultraviolet radiation, usually around about 4 hours.

Treatment may also be combined with immunoregulatory modulating agents, including an agent that agonizes an immune costimulatory molecule, e.g. CD40, OX40, etc.; and/or (iii) an agent that antagonizes an immune inhibitory molecule, e.g. CTLA-4, PD-1, PD-L1, etc. The active agents are administered within a period of time to produce an additive or synergistic effect on depletion of cancer cells in the host. Methods of administration include, without limitation, systemic administration, intra-tumoral administration, etc.

In some embodiments, an individual cancer is selected for treatment with a combination therapy because the cancer is a cancer type that is responsive to a checkpoint inhibitor, e.g. a PD-1 antagonist, a PD-L1 antagonist, a CTLA4 antagonist, a TIM-3 antagonist, a BTLA antagonist, a VISTA antagonist, a LAG3 antagonist; etc. In some embodiments, such an immunoregulatory agent is a CTLA-4, PD1 or PDL1 antagonist, e.g. avelumab, nivolumab, pembrolizumab, ipilimumab, and the like. In some such embodiments the cancer is, without limitation, melanoma or small cell lung cancer. In some such embodiments, the cancer is a type that has a high neoantigen, or mutagenesis, burden (see Vogelstein et al. (2013) Science 339(6127):1546-1558, herein specifically incorporated by reference).

In some embodiments, an individual cancer is selected for treatment with a combination therapy of the present invention because the cancer is a cancer type that is responsive to an immune response agonist, e.g. a CD28 agonist, an OX40 agonist; a GITR agonist, a CD137 agonist, a CD27 agonist, an HVEM agonist, etc. In some embodiments, such an immunoregulatory agent is an OX40, CD137, or GITR agonist e.g. tremelimumab, and the like. In some such embodiments the cancer is, without limitation, melanoma or small cell lung cancer. In some such embodiments, the cancer is a type that has a high neoantigen, or mutagenesis, burden.

In some embodiments, the combination therapy includes an antibody known in the art which binds to PD-1 and disrupt the interaction between the PD-1 and its ligand, PD-L1, and stimulate an anti-tumor immune response. In some embodiments, the antibody or antigen-binding portion thereof binds specifically to PD-1. For example, antibodies that target PD-1 and which can find used in the present invention include, e.g., but are not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies include anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in the combination treatment methods disclosed herein. For example, antibodies that target PD-L1 and are in clinical trials, include BMS-936559 (Bristol-Myers Squibb) and PDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, is suitable for use in the combination treatment methods.

In some embodiments, the combination therapy includes an antibody known in the art which binds CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the combination treatment methods. In some embodiments, the combination therapy includes an antibody known in the art which binds LAG-3 and disrupts its interaction with MHC class II molecules. An exemplary antibody that targets LAG-3 is IMP321 (Immutep), currently undergoing human trials. Other suitable antibodies that target LAG-3 are disclosed in U.S. Patent Application 2011/0150892, herein incorporated by reference. It will be understood by one of ordinary skill that any antibody which binds to LAG-3, disrupts its interaction with MEW class II molecules, and stimulates an anti-tumor immune response, is suitable for use in the combination treatment methods.

In some embodiments, the combination therapy includes an antibody known in the art which binds TIM-3 and disrupts its interaction with galectin 9. Suitable antibodies that target TIM-3 are disclosed in U.S. Patent Application 2013/0022623, herein incorporated by reference. It will be understood by one of ordinary skill that any antibody which binds to TIM-3, disrupts its interaction with galectin 9, and stimulates an anti-tumor immune response, is suitable for use in the combination treatment methods.

In some embodiments, the combination therapy includes an antibody known in the art which binds 4-1BB/CD137 and disrupts its interaction with CD137L. It will be understood by one of ordinary skill that any antibody which binds to 4-1BB/CD137, disrupts its interaction with CD137L or another ligand, and stimulates an anti-tumor immune response or an immune stimulatory response that results in anti-tumor activity overall, is suitable for use in the combination treatment methods.

In some embodiments, the combination therapy includes an antibody known in the art which binds GITR and disrupts its interaction with its ligand. It will be understood by one of ordinary skill that any antibody which binds to GITR, disrupts its interaction with GITRL or another ligand, and stimulates an anti-tumor immune response or an immune stimulatory response that results in anti-tumor activity overall, is suitable for use in the combination treatment methods.

In some embodiments, the combination therapy includes an antibody known in the art which binds OX40 and disrupts its interaction with its ligand. It will be understood by one of ordinary skill that any antibody which binds to OX40, disrupts its interaction with OX40L or another ligand, and stimulates an anti-tumor immune response or an immune stimulatory response that results in anti-tumor activity overall, is suitable for use in the combination treatment methods.

In some embodiments, the combination therapy includes an antibody known in the art which binds CD40 and disrupts its interaction with its ligand. It will be understood by one of ordinary skill that any antibody which binds to CD40, disrupts its interaction with its ligand, and stimulates an anti-tumor immune response or an immune stimulatory response that results in anti-tumor activity overall, is suitable for use in the combination treatment methods.

In some embodiments, the combination therapy includes an antibody known in the art which binds ICOS and disrupts its interaction with its ligand. It will be understood by one of ordinary skill that any antibody which binds to ICOS, disrupts its interaction with its ligand, and stimulates an anti-tumor immune response or an immune stimulatory response that results in anti-tumor activity overall, is suitable for use in the combination treatment methods.

In some embodiments, the combination therapy includes an antibody known in the art which binds CD28 and disrupts its interaction with its ligand. It will be understood by one of ordinary skill that any antibody which binds to CD28, disrupts its interaction with its ligand, and stimulates an anti-tumor immune response or an immune stimulatory response that results in anti-tumor activity overall, is suitable for use in the combination treatment methods.

In some embodiments, the combination therapy includes an antibody known in the art which binds IFNα and disrupts its interaction with its ligand. It will be understood by one of ordinary skill that any antibody which binds to IFNα, disrupts its interaction with its ligand, and stimulates an anti-tumor immune response or an immune stimulatory response that results in anti-tumor activity overall, is suitable for use in the combination treatment methods.

An "anti-cancer therapeutic" is a compound, composition, or treatment (e.g., surgery) that prevents or delays the growth and/or metastasis of cancer cells. Such anti-cancer therapeutics include, but are not limited to, surgery (e.g., removal of all or part of a tumor), chemotherapeutic drug treatment, radiation, gene therapy, hormonal manipulation, immunotherapy (e.g., therapeutic antibodies and cancer vaccines) and antisense or RNAi oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C, Avastin, Herceptin®, flurouracil, and temozolamide and the like. The compounds are also suitable for use with standard combination therapies employing two or more chemotherapeutic agents. It is to be understood that anti-cancer therapeutics includes novel compounds or treatments developed in the future.

The pharmaceutical compositions and/or formulations described above include one or more therapeutic entities in an amount effective to achieve the intended purpose. Thus the term "therapeutically effective dose" refers to the amount of the therapeutic entities that ameliorates the symptoms of cancer. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Also within the scope of the invention are kits comprising the compositions of the invention and instructions for use. The kit may further contain a least one additional reagent, e.g. a chemotherapeutic drug, anti-tumor antibody, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention. In some embodiments, the kit comprises an IL-2 superkine immune cell targeting or expression construct comprising an IL-2 variant/IL-2 superkine as described herein. In some embodiments, the kit comprises an IL-2 superkine immune cell targeting or expression construct comprising an IL-2 variant/IL-2 superkine including those provided herein. In some embodiments, an IL-2 superkine immune cell targeting or expression construct comprises an IL-2 variant/IL-2 superkine including those provided herein.

6. Exemplary Immune Cell Targeting or Expression Construct Embodiments

An immune cell targeting or expression construct comprising: an interleukin-2 receptor β (IL-2Rβ) binding protein, wherein the equilibrium dissociation constant for the IL-2Rβ of said binding protein is less than that of wild-type human IL-2 (hIL-2); linked to an immune cell targeting or expression construct.

In some embodiments, the immune cell targeting or expression construct exhibits a cyotoxic effect on a T-cell, for example a CD8+ T-cell or a CD4+ T-cell.

In some embodiments, the construct is a chimeric antigen receptor (CAR) and wherein the IL-2 superkine is fused to a transmembrane domain; linked to an intracellular signaling region.

In some embodiments, the intracellular signaling region comprises a CD3 signaling domain.

In some embodiments, the intracellular signaling region comprises one or more of a CD28 signaling domain, a CD137 signaling domain, an OX-40 signaling domain, an ICOS signaling domain, a DAP10 signaling domain.

In some embodiments, the construct is a T cell antigen coupler (TAC), wherein the IL-2 superkine is fused to a ligand that binds a protein associated with the TCR complex; fused to a T cell receptor signaling domain polypeptide.

In some embodiments, the protein associated with the TCR complex is CD3.

In some embodiments, the T cell receptor signaling domain polypeptide comprises CD4 cytosolic domain and CD4 transmembrane domain.

In some embodiments, the construct is an antibody coupled T cell receptors (ACTR), comprising a chimeric antigen receptor component that binds to the IL-2 superkine at a high affinity.

In some embodiments, the CAR component comprises CD16, and the IL-2 superkine is fused to an Fc sequence.

In some embodiments, the construct is a bispecific T cell exchanger (BiTE) comprising an IL-2 superkine fused to a variable region of an antibody that binds to a component of a T cell receptor.

In some embodiments, the BiTE component of a T cell receptor is CD3.

In some embodiments, the IL-2Rβ binding protein comprises the following amino acid substitutions: L80F, R81D, L85V, I86V, and I92F, numbered in accordance with wild-type hIL-2.

In some embodiments, the a nucleic acid encoding and IL-2 described herein is provided. In some embodiments, the vector comprising the nucleic acid is provided.

In some embodiments, a T cell comprising a construct according to any of the above is provided. In some embodiments, an NK cell comprising a construct according to any of the above is provided. In some embodiments, the T cell is a CD4$^+$ T cell. In some embodiments, the T cell is a CD8$^+$ T cell.

Also provide are an isolated population of immune cells described above. Also provided are pharmaceutical formulations comprising the immune cell population described above.

H. Expression of Mutant IL-2 Gene Products

The nucleic acid molecules described above can be contained within a vector that is capable of directing their expression in, for example, a cell that has been transduced with the vector. Accordingly, in addition to the subject IL-2 muteins, expression vectors containing a nucleic acid molecule encoding a subject IL-2 mutein and cells transfected with these vectors are among the preferred embodiments.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the IL-2 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction of a Modular Dihydrafolate Reductase cDNA Gene: Analysis of Signals Utilized for Efficient Expression", Mol. Cell. Biol., 2, pp. 1304-19 (1982)) or glutamine synthetase ("GS") amplification (see, e.g., U.S. Pat. No. 5,122,464 and European published application 338,841).

In some embodiments, the human IL-2 muteins of the present disclosure will be expressed from vectors, preferably expression vectors. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are included also.

Exemplary recombinant expression vectors can include one or more regulatory sequences, selected on the basis of the host cells to be used for expression, operably linked to the nucleic acid sequence to be expressed.

The expression constructs or vectors can be designed for expression of an IL-2 mutein or variant thereof in prokaryotic or eukaryotic host cells.

Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

Expression of proteins in prokaryotes is most often carried out in *Escherichia coli* with vectors containing constitutive or inducible promoters. Strategies to maximize recombinant protein expression in *E. coli* can be found, for example, in Gottesman (1990) in Gene Expression Technology: Methods in Enzymology 185 (Academic Press, San Diego, Calif.), pp. 119-128 and Wada et al. (1992) Nucleic Acids Res. 20:2111-2118. Processes for growing, harvesting, disrupting, or extracting the IL-2 mutein or variant thereof from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

In some embodiments the recombinant IL-2 muteins or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerenvisiae* include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) Molecular Cloning: A Laboratory Manual ($2^{nd}$ ed., Cold Spring Harbor Laboratory Press, Plainview, N.Y.). See, Goeddel (1990) in Gene Expression Technology: Methods in Enzymology 185 (Academic Press, San Diego, Calif.).

The sequences encoding the human IL-2 muteins of the present disclosure can be optimized for expression in the host cell of interest. The G-C content of the sequence can be adjusted to levels average for a given cellular host, as calculated by reference to known genes expressed in the host cell. Methods for codon optimization are well known in the art. Codons within the IL-2 mutein coding sequence can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example, the expression vector pBacPAK9 from Clontech, Palo Alto, Calif.) for use in insect cells.

In some embodiments nucleic acid inserts, which encode the subject IL-2 muteins in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject IL-2 mutein, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Useful expression vectors for eukaryotic hosts, include, for example, vectors with expression control sequences from SV40, bovine papilloma virus, adenovirus and cytomegalovirus. Useful expression vectors for bacterial hosts include known bacterial plasmids, such as plasmids from *E. coli*, including col El, pCRl, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941 and pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685-98 (1986).

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a subject IL-2 mutein disclosed herein are also features of the invention. A cell of the invention is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the invention.

The precise components of the expression system are not critical. For example, an IL-2 mutein can be produced in a prokaryotic host, such as the bacterium *E. coli*, or in a eukaryotic host, such as an insect cell (e.g., an Sf21 cell), or mammalian cells (e.g., CHO, HEK293, COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

In some embodiments, IL-2 muteins obtained will be glycosylated or unglycosylated depending on the host organism used to produce the mutein. If bacteria are chosen as the host then the IL-2 mutein produced will be unglycosylated. Eukaryotic cells, on the other hand, will glycosylate the IL-2 muteins, although perhaps not in the same way as native-IL-2 is glycosylated. The IL-2 mutein produced by the transformed host can be purified according to any suitable method. Various methods are known for purifying IL-2. See, e.g. Current Protocols in Protein Science, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. IL-2 muteins can be isolated from inclusion bodies generated in *E. coli*, or from conditioned medium from either mammalian or yeast cultures producing a given mutein using cation exchange, gel filtration, and/or reverse phase liquid chromatography.

Another exemplary method of constructing a DNA sequence encoding the IL-2 muteins is by chemical synthesis. This includes direct synthesis of a peptide by chemical means of the protein sequence encoding for an IL-2 mutein exhibiting the properties described. This method can incorporate both natural and unnatural amino acids at positions that affect the interactions of IL-2 with the IL-2Rα, the IL-2Rβ and/or the IL-2Rγ. Alternatively a gene which encodes the desired IL-2 mutein can be synthesized by chemical means using an oligonucleotide synthesizer. Such oligonucleotides are designed based on the amino acid sequence of the desired IL-2 mutein, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 mutein, there will be many DNA degenerate sequences that will code for that IL-2 mutein. For example, it will be appreciated that in addition to the preferred DNA sequence for mutein H9, there will be many degenerate DNA sequences that code for the IL-2 mutein shown. These degenerate DNA sequences are considered within the scope of this disclosure. Therefore, "degenerate variants thereof" in the context of this invention means all DNA sequences that code for and thereby enable expression of a particular mutein.

The biological activity of the IL-2 muteins can be assayed by any suitable method known in the art. Such assays include PHA-blast proliferation and NK cell proliferation.

I. Anti-PD-1 Antibodies and Combinations

Anti-PD-1 antibodies for use according to the invention and methods described herein include but are not limited to nivolumab, BMS-936558, MDX-1106, ONO-4538, AMP224, CT-011, and MK-3475 (pembrolizumab), cemiplimab (REGN2810), SHR-1210 (CTR20160175 and CTR20170090), SHR-1210 (CTR20170299 and CTR20170322), JS-001 (CTR20160274), IBI308 (CTR20160735), BGB-A317 (CTR20160872) and/or a PD-1 antibody as recited in U.S. Patent Publication No. 2017/0081409. There are two approved anti-PD-1 antibodies, pembrolizumab (Keytruda®; MK-3475-033) and nivolumab (Opdivo®; CheckMate078) and many more in development which can be used in combination described herein. Exemplary anti-PD-1 antibody sequences are shown in FIG. 7 and any of these can be used with the combination methods with the IL-2 muteins as described herein.

In some embodiments, the IL-2 mutein comprising substitutions L80F, R81D, L85V, I86V, and I92F, numbered in accordance with human wild-type IL-2 (SEQ ID NO:2) is used in combination with an anti-PD-1 antibody or inhibitor. In some embodiments, the IL-2 mutein comprising substitutions L80F, R81D, L85V, I86V, and I92F, numbered in accordance with human wild-type IL-2 (SEQ ID NO:2) is used in combination with nivolumab. In some embodiments, the IL-2 mutein comprising substitutions L80F, R81D, L85V, I86V, and I92F, numbered in accordance with human wild-type IL-2 (SEQ ID NO:2) is used in combination with pembrolizumab. In some embodiments, the IL-2 mutein comprising substitutions L80F, R81D, L85V, I86V, and I92F, numbered in accordance with human wild-type IL-2 (SEQ ID NO:2) is used in combination with cemiplimab. In some embodiments, the IL-2 mutein comprising substitutions L80F, R81D, L85V, I86V, and I92F, numbered in accordance with human wild-type IL-2 (SEQ ID NO:2) is used in combination BMS-936558. In some embodiments, the IL-2 mutein comprising substitutions L80F, R81D, L85V, I86V, and I92F, numbered in accordance with human wild-type IL-2 (SEQ ID NO:2) is used in combination MDX-1106. In some embodiments, the IL-2 mutein comprising substitutions L80F, R81D, L85V, I86V, and I92F, numbered in accordance with human wild-type IL-2 (SEQ ID NO:2) is used in combination ONO-4538. In some embodiments, the IL-2 mutein comprising substitutions L80F, R81D, L85V, I86V, and I92F, numbered in accordance with human wild-type IL-2 (SEQ ID NO:2) is used in combination AMP224. In some embodiments, the IL-2 mutein comprising substitutions L80F, R81D, L85V, I86V, and I92F, numbered in accordance with human wild-type IL-2 (SEQ ID NO:2) is used in combination CT-011. In some embodiments, the IL-2 mutein comprising substitutions L80F, R81D, L85V, I86V, and I92F, numbered in accordance with human wild-type IL-2 (SEQ ID NO:2) is used in combination MK-3475. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2.

In some embodiments, the IL-2 mutein comprising substitutions L80F, R81D, L85V, I86V, and I92F, numbered in accordance with human wild-type IL-2 (SEQ ID NO:2) is used in combination with any of the referenced antibodies. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, the IL-2 mutein used in combination with an anti-PD-1 antibody is a fusion mutein as described herein. In some embodiments, the IL-2 mutein used in combination with an anti-PD-1 antibody is a fusion mutein as described herein.

J. Anti-PD-L1 Antibodies and Combinations

In some embodiments, any of the IL-2 muteins described herein can be used in combination with an anti-PD-1 antibody. There are three approved anti-PD-L1 antibodies, atezolizumab (TECENTRIQ®; MPDL3280A), avelumab (BAVENCIO®; MSB001071 8C), and Durvalumab (MEDI4736), as well as other anti-PD-L1 antibodies in development. Numerous anti-PD-L1 antibodies are available and many more in development which can be used in combination with the IL-2 muteins as described herein. In some embodiments, the PD-L1 antibody is one described in U.S. Patent Publication No. 2017/0281764 as well as International Patent Publication No. WO 2013/079174 (avelumab) and WO 2010/077634 (or U.S. Patent Application No. 20160222117 or U.S. Pat. No. 8,217,149; atezolizumab). In some embodiments, the PD-L1 antibody comprises a heavy chain sequence of SEQ ID NO:34 and a light chain sequence of SEQ ID NO:36 (from US 2017/281764). In some embodiments, the PD-L1 antibody is atezolizumab (TECENTRIQ®; MPDL3280A; IMpower110). In some embodiments, the PD-L1 antibody is avelumab (BAVENCIO®; MSB001071 8C). In some embodiments, the PD-L1 antibody is durvalumab (MEDI4736). In some embodiments, the PD-L1 antibody includes, for example, Atezolizumab (IMpower133), BMS-936559/MDX-1105, and/or RG-7446/MPDL3280A, and/or YW243.55.570, as well as any of the exemplary anti-PD-L1 antibodies provided herein in FIG. 8. In some embodiments, the IL-2 mutein comprising substitutions L80F, R81D, L85V, I86V, and I92F, numbered in accordance with human wild-type IL-2 (SEQ ID NO:2) is used in combination with any of the referenced antibodies. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, the IL-2 mutein used in combination with an anti-PD-L1 antibody is a fusion mutein as described herein. In some embodiments, the IL-2 mutein used in combination with an anti-PD-L1 antibody is a fusion mutein as described herein.

K. Other Immunotherapy Combinations

Other antibodies and/or immunotherapies for use according to the methods of the present invention include but are not limited to, anti-CTLA4 mAbs, such as ipilimumab, tremelimumab; anti-PD-L1 antagonistic antibodies such as BMS-936559/MDX-1105, MEDI4736, RG-7446/MPDL3280A; anti-LAG-3 such as IMP-321; agonistic antibodies targeting immunostimulatory proteins, including anti-CD40 mAbs such as CP-870,893, lucatumumab, dacetuzumab; anti-CD137 mAbs (anti-4-1-BB antibodies) such as BMS-663513 urelumab (anti-4-1BB antibody; see, for example, U.S. Pat. Nos. 7,288,638 and 8,962,804, incorporated by reference herein in their entireties); lirilumab (anti-KIR mAB; IPH2102/BMS-986015; blocks NK cell inhibitory receptors) and PF-05082566 (utomilumab; see, for example, U.S. Pat. Nos. 8,821,867; 8,337,850; and 9,468,678, as well as International Patent Application Publication No. WO 2012/032433, incorporated by reference herein in their entireties); anti-OX40 mAbs (see, for example, WO 2006/029879 or WO 2010/096418, incorporated by reference herein in their entireties); anti-GITR mAbs such as TRX518 (see, for example, U.S. Pat. No. 7,812,135, incorporated by reference herein in its entirety); anti-CD27 mAbs, such as varlilumab CDX-1127 (see, for example, WO 2016/145085 and U.S. Patent Publication Nos. US 2011/0274685 and US 2012/0213771, incorporated by reference herein in their entireties) anti-ICOS mAbs (for example, MEDI-570, JTX-2011, and anti-TIM-3 antibodies (see, for example, WO 2013/006490 or U.S. Patent Publication No US 2016/0257758, incorporated by reference herein in their entireties). In some embodiments, the IL-2 mutein comprising substitutions L80F, R81D, L85V, I86V, and I92F, numbered in accordance with human wild-type IL-2 (SEQ ID NO:2) is used in combination with any of the referenced antibodies. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

Other antibodies can also include monoclonal antibodies to prostate cancer, ovarian cancer, breast cancer, endometrial cancer, multiple myeloma, melanoma, lymphomas, lung cancers including small cell lung cancer, kidney cancer, colorectal cancer, pancreatic cancer, gastric cancer, brain cancer (see, generally www.clinicaltrials.gov). In some embodiments, the IL-2 mutein comprising substitutions L80F, R81D, L85V, I86V, and I92F, numbered in accordance with human wild-type IL-2 (SEQ ID NO:2) is used in combination with any of the referenced antibodies. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16.

Antibodies can also include antibodies for antibody-dependent cell-mediated cytotoxicity (ADCC). In some embodiments, the IL-2 mutein comprising substitutions L80F, R81D, L85V, I86V, and I92F, numbered in accordance with human wild-type IL-2 (SEQ ID NO:2) is used in combination with an antibody for antibody-dependent cell-mediated cytotoxicity (ADCC). In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2.

L. Methods of Treatment

In some embodiments, subject IL-2 muteins, and/or nucleic acids expressing them, can be administered to a subject to treat a disorder associated with abnormal apoptosis or a differentiative process (e.g., cellular proliferative disorders or cellular differentiative disorders, such as cancer, by, for example, producing an active or passive immunity). In the treatment of such diseases, the disclosed IL-2 muteins may possess advantageous properties, such as reduced vascular leak syndrome. In some embodiments, the IL-2 mutein is any IL-2 mutein or variant disclosed herein. In some embodiments, the IL-2 mutein sequence is 90% identical to any one of SEQ ID NO:2 or SEQ ID NO:6 through SEQ ID NO:10 or SEQ ID NO:16. In some embodiments, the IL-2 mutein incudes any one of 5-1 SEQ ID NO:5; 5-2 SEQ ID NO:6; 6-6 SEQ ID NO:7; A2 SEQ ID NO:8; B1 SEQ ID NO:9; B11 SEQ ID NO:10; C5 SEQ ID NO:11; D10 SEQ ID NO:12; E10 SEQ ID NO:13; G8 SEQ ID NO:14; H4 SEQ ID NO:15; and H9 SEQ ID NO:16. In some embodiments, the substitutions in the IL-2 mutein comprise L80F, R81D, L85V, I86V, and I92F, numbered in accordance with wild-type human IL-2 of SEQ ID NO:2. In some embodiments, the IL-2 mutein is a fusion protein. In some embodiments, the IL-2 mutein is associated with and/or expressed by a CAR-T construct. In some embodiments, the IL-2 mutein is expressed by and/or associated with an oncolytic virus.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate cancer, ovarian cancer, breast cancer, endometrial cancer, multiple myeloma, melanoma, lymphomas, lung cancers including small cell lung cancer, kidney cancer, liver cancer, colon cancer, colorectal cancer, pancreatic cancer, gastric cancer, and brain cancer.

The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues.

Additional examples of proliferative disorders include hematopoietic neoplastic disorders.

Alternatively, or in addition to methods of direct administration to patients, in some embodiments, mutant IL-2 polypeptides can be used in ex vivo methods. For example, cells (e.g., peripheral blood lymphocytes or purified populations of lymphocytes isolated from a patient and placed or maintained in culture) can be cultured in vitro in culture medium and the contacting step can be affected by adding the IL-2 mutant to the culture medium. The culture step can include further steps in which the cells are stimulated or treated with other agents, e.g., to stimulate proliferation, or to expand a population of cells that is reactive to an antigen of interest (e.g., a cancer antigen or a viral antigen). The cells are then administered to the patient after they have been treated.

Anti-PD-1 antibodies for use in combination with the IL-2 muteins disclosed herein for the treatment methods include but are not limited to nivolumab, BMS-936558, MDX-1106, ONO-4538, AMP224, CT-011, and MK-3475.

In some embodiments, the IL-2 mutein comprising substitutions L80F, R81D, L85V, I86V, and I92F, numbered in accordance with human wild-type IL-2 (SEQ ID NO:2) is used in combination with an anti-PD-1 antibody or inhibitor for the treatment of cancer. In some embodiments, the IL-2 mutein comprising substitutions L80F, R81D, L85V, I86V, and I92F, numbered in accordance with human wild-type IL-2 (SEQ ID NO:2) is used in combination with nivolumab for the treatment of cancer. In some embodiments, the IL-2 mutein comprising substitutions L80F, R81D, L85V, I86V, and I92F, numbered in accordance with human wild-type IL-2 (SEQ ID NO:2) is used in combination BMS-936558 for the treatment of cancer. In some embodiments, the IL-2 mutein comprising substitutions L80F, R81D, L85V, I86V, and I92F, numbered in accordance with human wild-type IL-2 (SEQ ID NO:2) is used in combination MDX-1106 for the treatment of cancer. In some embodiments, the IL-2 mutein comprising substitutions L80F, R81D, L85V, I86V, and I92F, numbered in accordance with human wild-type IL-2 (SEQ ID NO:2) is used in combination ONO-4538 for the treatment of cancer. In some embodiments, the IL-2 mutein comprising substitutions L80F, R81D, L85V, I86V, and I92F, numbered in accordance with human wild-type IL-2 (SEQ ID NO:2) is used in combination AMP224 for the treatment of cancer. In some embodiments, the IL-2 mutein comprising substitutions L80F, R81D, L85V, I86V, and I92F, numbered in accordance with human wild-type IL-2 (SEQ ID NO:2) is used in combination CT-011 for the treatment of cancer. In some embodiments, the IL-2 mutein comprising substitutions L80F, R81D, L85V, I86V, and I92F, numbered in accordance with human wild-type IL-2 (SEQ ID NO:2) is used in combination MK-3475 for the treatment of cancer. In some embodiments, the IL-2 mutein further comprises F42A substitution, wherein numbering is in accordance with the wild-type human IL-2 of SEQ ID NO:2. In some embodiments, the IL-2 mutein further comprises K43N substitution, wherein numbering is in accordance with the wild-type human IL-2 of SEQ ID NO:2. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2.

In some embodiments, the IL-2 mutein comprising substitutions L80F, R81D, L85V, I86V, and I92F, numbered in accordance with human wild-type IL-2 (SEQ ID NO:2) is used in combination with an antibody and/or immunotherapy including but not limited to, anti-CTLA4 mAbs, such as ipilimumab, tremelimumab; anti-PD-L1 antagonistic antibodies such as BMS-936559/MDX-1105, MEDI4736, RG-7446/MPDL3280A; anti-LAG-3 such as IMP-321; agonistic antibodies targeting immunostimulatory proteins, including anti-CD40 mAbs such as CP-870,893, lucatumumab, dacetuzumab; anti-CD137 mAbs (anti-4-1-BB antibodies) such as BMS-663513 urelumab (anti-4-1BB antibody; see, for example, U.S. Pat. Nos. 7,288,638 and 8,962,804, incorporated by reference herein in their entireties); lirilumab (anti-KIR mAB; IPH2102/BMS-986015; blocks NK cell inhibitory receptors) and PF-05082566 (utomilumab; see, for example, U.S. Pat. Nos. 8,821,867; 8,337,850; and 9,468,678, as well as International Patent Application Publication No. WO 2012/032433, incorporated by reference herein in their entireties); anti-OX40 mAbs (see, for example, WO 2006/029879 or WO 2010/096418, incorporated by reference herein in their entireties); anti-GITR mAbs such as TRX518 (see, for example, U.S. Pat. No. 7,812,135, incorporated by reference herein in its entirety); anti-CD27 mAbs, such as varlilumab CDX-1127 (see, for example, WO 2016/145085 and U.S. Patent Publication Nos. US 2011/274685 and US 2012/0213771, incorporated by reference herein in their entireties) anti-ICOS mAbs (for example, MEDI-570, JTX-2011, and anti-TIM-3 antibodies (see, for example, WO 2013/006490 or U.S. Patent Publication No US 2016/0257758, incorporated by reference herein in their entireties) for the treatment of cancer.

In some embodiments, the IL-2 mutein comprising substitutions L80F, R81D, L85V, I86V, and I92F, numbered in accordance with human wild-type IL-2 (SEQ ID NO:2) is used in combination with another antibody which can include monoclonal antibodies to prostate cancer, ovarian cancer, breast cancer, endometrial cancer, multiple myeloma, melanoma, lymphomas, lung cancers including small cell lung cancer, kidney cancer, colorectal cancer, pancreatic cancer, gastric cancer, brain cancer (see, generally www.clinicaltrials.gov), for the treatment of cancer.

In some embodiments, the IL-2 mutein comprising substitutions L80F, R81D, L85V, I86V, and I92F, numbered in accordance with human wild-type IL-2 (SEQ ID NO:2) is used in combination with antibodies for antibody-dependent cell-mediated cytotoxicity (ADCC) for the treatment of cancer.

M. Pharmaceutical Compositions and Methods of Administration

In some embodiments, subject IL-2 muteins and nucleic acids can be incorporated into compositions, including pharmaceutical compositions. Such compositions typically include the polypeptide or nucleic acid molecule and a pharmaceutically acceptable carrier. Such compositions can also comprise anti-PD-1 antibodies. In some embodiments, the composition comprises an IL-2 mutein that is a fusion protein and/or is associated with a CAR-T construct and/or expressed by or associated with an oncolytic virus.

The anti-PD-1 antibodies and IL-2 muteins can be administered as a co-composition, simultaneously as two separate compositions, and/or sequentially as two separate compositions. In some embodiments, the anti-PD-1 antibody or inhibitor and IL-2 mutein are administered together as a single co-composition (i.e., co-formulated). In some embodiments, the anti-PD-1 antibody or inhibitor and IL-2 mutein are administered simultaneously as two separate compositions (i.e., separate formulations). In some embodiments, the anti-PD-1 antibody or inhibitor and IL-2 mutein are administered sequentially as separate compositions (i.e., separate formulations). In some embodiments, when the anti-PD-1 antibody or inhibitor and IL-2 mutein are administered sequentially as separate compositions, the anti-PD-1 antibody or inhibitor is administered before the IL-2 mutein. In some embodiments, when the anti-PD-1 antibody or inhibitor and IL-2 mutein are administered sequentially as separate compositions, the IL-2 mutein is administered before the anti-PD-1 antibody or inhibitor. In some embodiments, the anti-PD-1 antibodies include but are not limited to nivolumab, BMS-936558, MDX-1106, ONO-4538, AMP224, CT-011, and MK-3475. In some embodiments, the IL-2 mutein is the IL-2 mutein comprising substitutions L80F, R81D, L85V, I86V, and I92F, numbered in accordance with human wild-type IL-2 (SEQ ID NO:2). In some embodiments, the IL-2 mutein further comprises F42A substitution, wherein numbering is in accordance with the wild-type human IL-2 of SEQ ID NO:2. In some embodiments, the IL-2 mutein further comprises K43N substitution, wherein numbering is in accordance with the wild-type human IL-2 of SEQ ID NO:2. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2.

The other immunotherapy agents as described and IL-2 muteins can be administered as a co-composition, simultaneously as two separate compositions, and/or sequentially as two separate compositions. In some embodiments, the other immunotherapy agents and IL-2 mutein are administered together as a single co-composition (i.e., co-formulated). In some embodiments, the other immunotherapy agents and IL-2 mutein are administered simultaneously as two separate compositions (i.e., separate formulations). In some embodiments, the other immunotherapy agents and IL-2 mutein are administered sequentially as separate compositions (i.e., separate formulations). In some embodiments, when the other immunotherapy agents and IL-2 mutein are administered sequentially as separate compositions, the anti-PD-1 antibody or inhibitor is administered before the IL-2 mutein. In some embodiments, when other immunotherapy agents and IL-2 mutein are administered sequentially as separate compositions, the IL-2 mutein is administered before other immunotherapy agents. In some embodiments, the IL-2 mutein is the IL-2 mutein comprising substitutions L80F, R81D, L85V, I86V, and I92F, numbered in accordance with human wild-type IL-2 (SEQ ID NO:2). In some embodiments, the IL-2 mutein further comprises F42A substitution, wherein numbering is in accordance with the wild-type human IL-2 of SEQ ID NO:2. In some embodiments, the IL-2 mutein further comprises K43N substitution, wherein numbering is in accordance with the wild-type human IL-2 of SEQ ID NO:2. In some embodiments, the IL-2 mutein further comprises F42A substitution, wherein numbering is in accordance with the wild-type human IL-2 of SEQ ID NO:2. In some embodiments, the IL-2 mutein further comprises Y45A substitution, wherein numbering is in accordance with the wild-type human IL-2 of SEQ ID NO:2. In some embodiments, the IL-2 mutein further comprises E62A substitution, wherein numbering is in accordance with the wild-type human IL-2 of SEQ ID NO:2.

A pharmaceutical composition is formulated to be compatible with its intended route of administration. The anti-PD-1 antibodies and/or mutant IL-2 polypeptides of the invention may be given orally, but it is more likely that they will be administered through a parenteral route, including for example intravenous administration. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, anti-PD-1 antibodies and/or IL-2 muteins, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the anti-PD-1 antibodies and/or IL-2 muteins or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, compounds (anti-PD-1 antibodies and/or mutant IL-2 polypeptides or nucleic acids) can also be prepared in the form of suppositories (e.g., with conventional suppository bases such as cocoa butter and other glycerides) or retention enemas for rectal delivery.

In some embodiments, compounds (subject IL-2 muteins or nucleic acids) can also be administered by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996).

In one embodiment, the anti-PD-1 antibodies and/or IL-2 muteins or nucleic acids are prepared with carriers that will protect the anti-PD-1 antibodies and/or mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such anti-PD-1 antibodies, IL-2 muteins, or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a subject IL-2 mutein (i.e., an effective dosage) and/or the anti-PD-1 antibody or inhibitor depends on the polypeptide or antibody selected. In some embodiments, single dose amounts of the IL-2 mutein can be in the range of approximately 0.001 mg/kg to 0.1 mg/kg of patient body weight can be administered. In some embodiments, single dose amounts of the anti-PD-1 antibody or inhibitor can be in the range of approximately 1 mg/kg to 20 mg/kg, or about 5 mg/kg to about 15 mg/kg, or about 10 mg/kg of patient body weight can be administered. In some embodiments, doses of the anti-PD-1 antibody or inhibitor and/or the IL-2 mutein of about 0.005 mg/kg, 0.01 mg/kg, 0.025 mg/kg, 0.05 mg/kg, 0.1 mg/kg, 0.25 mg/kg, 0.5 mg/kg, 1.0 mg/kg, 5.0 mg/kg, 10.0 mg/kg may be administered. In some embodiments, 600,000 IU/kg is administered (IU can be determined by a lymphocyte proliferation bioassay and is expressed in International Units (IU) as established by the World Health Organization 1$^{st}$ International Standard for Interleukin-2 (human)). The dosage may be similar to, but is expected to be less than, that prescribed for PROLEUKIN®. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the subject IL-2 muteins can include a single treatment or, can include a series of treatments. In one embodiment, the compositions are administered every 8 hours for five days, followed by a rest period of 2 to 14 days, e.g., 9 days, followed by an additional five days of administration every 8 hours. In some embodiments, administration is 3 doses administered every 4 days.

The pharmaceutical compositions can be included in a container, pack, or dispenser together with instructions for administration.

The following examples are provided to describe certain embodiments of the invention provided herein and are not to be construed to as limiting.

EXAMPLES

Example 1: 119 Synergizes with Anti-PD-1 Immunotherapy in Mouse MC38 Colon Cancer Model This example provides data showing that combination therapy produces robust responses in a dose-dependent fashion.

Table 11 below shows the substitution matrix for the H9 IL-2 mutein used in this example.

TABLE 11

H9 substitution matrix

| | residue # | | | | | | | $K_d$ |
|---|---|---|---|---|---|---|---|---|
| | 74 | 80 | 81 | 85 | 86 | 89 | 92 | 93 | (nM) |
| wt IL-2 | Q | L | R | L | I | I | I | V | 280 |
| H9 | | F | D | V | V | | F | | 1.3 |

An anti-PD-1 antibody was administered at 10 mg/kg intravenously with 3 doses administered every 4 days (10 mg/kg IV q4dx3). H9 (IL-2 mutein having the amino acid substitutions L80F, R81D, L85V, I86V, and I92F, wherein numbering is in accordance with the wild-type human IL-2 of SEQ ID NO:2) was administered at the indicated dosage of 5 µg q.d. or 25 µg q.d. (µg/mouse), according to the same dosing regimen. MC38 colon cancer model mice were then monitored for up to 40 days post-tumor implant. The combination of anti-PD-1 antibody plus H9 resulted in an increase in the number of cured mice at both the low and high dose, with a substantial increase at the 25 ug q.d, dose of H9.

As provided in the data in FIG. 1, H9 and anti-PD-1 produce limited efficacy alone. However, the combination treatment is sufficient to cure most mice at a well-tolerated H9 dose. Increased efficacy of the combination did not result in new or increased toxicities.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method of treating cancer comprising administering a combination treatment comprising:
   (i) an anti-PD-1 antibody or inhibitor or an anti-PD-L1 antibody or inhibitor or an anti-CTLA-4 antibody or inhibitor, and
   (ii) an IL-2 mutein comprising the following amino acid substitutions L80F, R81D, L85V, I86V, and I92F, wherein numbering is in accordance with the wild-type human IL-2 of SEQ ID NO:2, and wherein said IL-2 mutein comprises SEQ ID NO:9.

2. The method of claim 1, wherein said anti-PD-1 antibody or inhibitor is selected from the group consisting of nivolumab, BMS-936558, MDX-1106, ONO-4538, AMP224, CT-011, pembrolizumab, cemiplimab, SHR-1210, SHR-1210, JS-001, IBI308, and BGB-A317.

3. The method of claim 1, wherein said anti-PD-L1 antibody or inhibitor is selected from the group consisting of atezolizumab, avelumab, and Durvalumab.

4. The method of claim 1, wherein said IL-2 mutein is a fusion protein.

5. The method of claim 4, wherein said fusion protein comprises said IL-2 mutein linked to an Fc antibody fragment.

6. The method of claim 5, wherein said Fc antibody fragment is a human Fc antibody fragment.

7. The method of claim 5, wherein said Fc antibody fragment comprises a N297A substitution.

8. The method of claim 4, wherein said fusion protein comprises said IL-2 mutein linked to an albumin.

9. The method of claim 1, wherein said cancer is selected from the group consisting of prostate cancer, ovarian cancer, breast cancer, endometrial cancer, multiple myeloma, melanoma, lymphomas, lung cancers including small cell lung cancer, kidney cancer, liver cancer, colon cancer, colorectal cancer, pancreatic cancer, gastric cancer, and brain cancer.

10. The method of claim 9, wherein said cancer is colon cancer.

11. The method of claim 10, wherein said IL-2 mutein is fused to said anti-PD-1 antibody or inhibitor, said anti-PD-L1 antibody or inhibitor, or said anti-CTLA-4 antibody or inhibitor.

12. The method of claim 11, wherein said IL-2 mutein is fused to said anti-PD-1 antibody.

13. The method of claim 1, wherein said anti-CTLA-4 antibody or inhibitor is selected from the group consisting of ipilumumab and tremelimumab.

14. The method of claim 1, wherein said IL-2 mutein is fused to said anti-PD-1 antibody or inhibitor, said anti-PD-L1 antibody or inhibitor, or said anti-CTLA-4 antibody or inhibitor.

15. The method of claim 14, wherein said IL-2 mutein is fused to said anti-PD-1 antibody.

* * * * *

SEQUENCE LISTING

<160> NUMBER OF SEQ ID NOS: 206

<210> SEQ ID NO 1
<211> LENGTH: 153
<212> TYPE: PRT
<213> ORGANISM: Artificial Sequence
<220> FEATURE:
<223> OTHER INFORMATION: Human IL-2

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Artificial Sequence
<220> FEATURE:
<223> OTHER INFORMATION: Mature human IL-2

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 3
<211> LENGTH: 169
<212> TYPE: PRT
<213> ORGANISM: Artificial Sequence
<220> FEATURE:
<223> OTHER INFORMATION: Mus Musculus

<400> SEQUENCE: 3

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Thr Ala
            20                  25                  30

Glu Ala Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 4
<211> LENGTH: 149
<212> TYPE: PRT
<213> ORGANISM: Artificial Sequence
<220> FEATURE:
<223> OTHER INFORMATION: Mature Murine IL-2

<400> SEQUENCE: 4

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
130                 135                 140

Ser Thr Ser Pro Gln
145

<210> SEQ ID NO 5
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 6
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

```
<210> SEQ ID NO 7
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Asn Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 8
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 9
<211> LENGTH: 133
<212> TYPE: PRT
<213> ORGANISM: Artificial Sequence
<220> FEATURE:
```

<223> OTHER INFORMATION: IL-2 Mutein

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 10
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 11
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 11

Met Tyr Arg Met Gln Leu Leu Ser Cys Ile Ala Leu Ser Leu Ala Leu

```
1               5                   10                  15
Val Thr Asn Ser Ala Pro Thr Ser Ser Thr Lys Lys Thr Gln Leu
            20                  25                  30

Gln Leu Glu His Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
            195                 200                 205

Cys Val Val Val Asp Val Ser His Glu Asp Pro Glu Val Lys Phe Asn
210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
            275                 280                 285

Gly Gln Pro Arg Glu Pro Gln Val Tyr Thr Leu Pro Pro Ser Arg Glu
            290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
            355                 360                 365

Asn Val Phe Ser Cys Ser Val Met His Glu Ala Leu His Asn His Tyr
370                 375                 380

Thr Gln Lys Ser Leu Ser Leu Ser Pro Gly Lys
385                 390                 395

<210> SEQ ID NO 12
<211> LENGTH: 395
<212> TYPE: PRT
<213> ORGANISM: Artificial Sequence
```

<220> FEATURE:
<223> OTHER INFORMATION: IL-2 Mutein

<400> SEQUENCE: 12

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Phe Asp Pro Arg Asp Val Val Ser Asn Ile Asn Val Phe
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
    210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
        275                 280                 285

Gly Gln Pro Arg Glu Pro Gln Val Tyr Thr Leu Pro Pro Ser Arg Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
    370                 375                 380

Thr Gln Lys Ser Leu Ser Leu Ser Pro Gly Lys
385                 390                 395
```

<210> SEQ ID NO 13
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 13

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
50                  55                  60

Ala Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Phe Asp Pro Arg Asp Val Val Ser Asn Ile Asn Val Phe
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Gly Ser Gly Gly
145                 150                 155                 160

Gly Gly Ser Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
        275                 280                 285

Gly Gln Pro Arg Glu Pro Gln Val Tyr Thr Leu Pro Pro Ser Arg Glu
290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365
```

Asn Val Phe Ser Cys Ser Val Met His Glu Ala Leu His Asn His Tyr
            370                 375                 380

Thr Gln Lys Ser Leu Ser Leu Ser Pro Gly Lys
385                 390                 395

<210> SEQ ID NO 14
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 14

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Ala Leu Lys Pro Leu Glu Glu Val Leu Asn Leu Ala Gln Ser Lys
                85                  90                  95

Asn Phe His Phe Asp Pro Arg Asp Val Val Ser Asn Ile Asn Val Phe
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Ser Gly Gly
145                 150                 155                 160

Gly Gly Ser Gly Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
            195                 200                 205

Cys Val Val Val Asp Val Ser His Glu Asp Pro Glu Val Lys Phe Asn
    210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
            275                 280                 285

Gly Gln Pro Arg Glu Pro Gln Val Tyr Thr Leu Pro Pro Ser Arg Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

```
Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
            355                 360                 365

Asn Val Phe Ser Cys Ser Val Met His Glu Ala Leu His Asn His Tyr
            370                 375                 380

Thr Gln Lys Ser Leu Ser Leu Ser Pro Gly Lys
385                 390                 395

<210> SEQ ID NO 15
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 15

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Ala Lys Phe
50                  55                  60

Ala Met Pro Lys Lys Ala Thr Glu Leu Lys His Leu Gln Cys Leu Glu
65                  70                  75                  80

Glu Ala Leu Lys Pro Leu Glu Glu Val Leu Asn Leu Ala Gln Ser Lys
                85                  90                  95

Asn Phe His Phe Asp Pro Arg Asp Val Val Ser Asn Ile Asn Val Phe
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
            195                 200                 205

Cys Val Val Val Asp Val Ser His Glu Asp Pro Glu Val Lys Phe Asn
            210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
            275                 280                 285

Gly Gln Pro Arg Glu Pro Gln Val Tyr Thr Leu Pro Pro Ser Arg Glu
            290                 295                 300
```

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
            325                 330                 335

Asn Asn Tyr Lys Thr Thr Pro Pro Val Leu Asp Ser Asp Gly Ser Phe
        340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
370                 375                 380

Thr Gln Lys Ser Leu Ser Leu Ser Pro Gly Lys
385                 390                 395

<210> SEQ ID NO 16
<211> LENGTH: 10
<212> TYPE: PRT
<213> ORGANISM: Artificial Sequence
<220> FEATURE:
<223> OTHER INFORMATION: Linker Peptide

<400> SEQUENCE: 16

Gly Gly Gly Gly Ser Gly Gly Gly Gly Ser
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Linker Peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: Linker Peptide

<400> SEQUENCE: 18

Gly Gly Gly Gly Ser Gly Gly Gly Ser Gly Gly Gly Gly Ser Gly
1               5                   10                  15

Gly Gly Gly Ser
            20

<210> SEQ ID NO 19
<211> LENGTH: 20
<212> TYPE: PRT
<213> ORGANISM: Artificial Sequence
<220> FEATURE:
<223> OTHER INFORMATION: Linker Peptide

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20

<211> LENGTH: 133
<212> TYPE: PRT
<213> ORGANISM: Artificial Sequence
<220> FEATURE:
<223> OTHER INFORMATION: IL-2 Mutein

<400> SEQUENCE: 20

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Arg Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130
```

<210> SEQ ID NO 21
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 21

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Arg Ser Lys Asn Phe His Leu
65                  70                  75                  80
Arg Pro Arg Asp Val Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130
```

<210> SEQ ID NO 22
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Ile Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 23
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 23

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Leu
65                  70                  75                  80

Thr Pro Arg Asp Val Val Ser Asn Ile Asn Val Phe Ile Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 24
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 24

Ala Pro Thr Ser Ser Ser Thr Lys Lys Thr Gln Leu Gln Leu Glu His
1               5                   10                  15

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Asn Ser Lys Asn Phe His Phe
 65                  70                  75                  80

Asp Pro Arg Asp Val Val Ser Asn Val Asn Val Phe Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 25
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 25

Ala Pro Thr Ser Ser Ser Thr Lys Lys Thr Gln Leu Gln Leu Glu His
 1               5                  10                  15

Leu Leu Leu Asp Leu Gln Met Val Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Ser Ser Lys Asn Phe His Phe
 65                  70                  75                  80

Asp Pro Arg Asp Val Val Ser Asn Ile Asn Val Phe Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 26
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 26

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
```

-continued

```
                 35                  40                  45
Lys Ala Thr Glu Leu Lys His Leu Gln Cys Leu Glu Glu Glu Leu Lys
 50                  55                  60
His Leu Glu Glu Val Leu Asn Leu Ala Asn Ser Lys Asn Phe His Val
 65                  70                  75                  80
Thr Pro Arg Asp Val Val Ser Asn Ile Asn Val Phe Val Leu Glu Leu
                 85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
                130

<210> SEQ ID NO 27
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 27

Ala Pro Thr Ser Ser Ser Thr Lys Lys Thr Gln Leu Gln Leu Glu His
  1               5                  10                  15
Leu Leu Leu Asp Leu Gln Met Ile Leu Asn Gly Ile Asn Asn Tyr Lys
                 20                  25                  30
Asn Pro Lys Leu Thr Arg Met Leu Thr Phe Lys Phe Tyr Met Pro Lys
                 35                  40                  45
Lys Ala Thr Glu Leu Lys His Leu Gln Cys Leu Glu Glu Glu Leu Lys
 50                  55                  60
Pro Leu Glu Glu Val Leu Asn Leu Ala His Ser Lys Asn Phe His Phe
 65                  70                  75                  80
Asp Pro Arg Asp Val Val Ser Asn Ile Asn Val Phe Val Leu Glu Leu
                 85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
                130

<210> SEQ ID NO 28
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 28

Ala Pro Thr Ser Ser Ser Thr Lys Lys Thr Gln Leu Gln Leu Glu His
  1               5                  10                  15
Leu Leu Leu Asp Leu Gln Met Ile Leu Asn Gly Ile Asn Asn Tyr Lys
                 20                  25                  30
Asn Pro Lys Leu Thr Arg Met Leu Thr Phe Lys Phe Tyr Met Pro Lys
                 35                  40                  45
Lys Ala Thr Glu Leu Lys His Leu Gln Cys Leu Glu Glu Glu Leu Lys
 50                  55                  60
```

```
Pro Leu Glu Glu Val Leu Asn Leu Ala Ser Ser Lys Asn Phe His Phe
 65                  70                  75                  80

Asp Pro Arg Asp Val Val Ser Asn Ile Asn Val Phe Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 29
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 29

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Asn Ser Lys Asn Phe His Phe
 65                  70                  75                  80

Asp Pro Arg Asp Val Val Ser Asn Ile Asn Val Phe Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 30
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 30

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Ser Ser Lys Asn Phe His Leu
 65                  70                  75                  80

Thr Pro Arg Asp Val Ile Ser Asn Ile Asn Val Phe Val Leu Glu Leu
                 85                  90                  95
```

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 31
<211> LENGTH: 133
<212> TYPE: PRT
<213> ORGANISM: Artificial Sequence
<220> FEATURE:
<223> OTHER INFORMATION: IL-2 Mutein

<400> SEQUENCE: 31

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 32
<211> LENGTH: 133
<212> TYPE: PRT
<213> ORGANISM: Artificial Sequence
<220> FEATURE:
<223> OTHER INFORMATION: H9D10

<400> SEQUENCE: 32

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile

```
            115                 120                 125

Ile Ser Thr Leu Thr
        130

<210> SEQ ID NO 33
<211> LENGTH: 133
<212> TYPE: PRT
<213> ORGANISM: Artificial Sequence
<220> FEATURE:
<223> OTHER INFORMATION: H9E10

<400> SEQUENCE: 33

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 34
<211> LENGTH: 133
<212> TYPE: PRT
<213> ORGANISM: Artificial Sequence
<220> FEATURE:
<223> OTHER INFORMATION: H9G8

<400> SEQUENCE: 34

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130
```

```
<210> SEQ ID NO 35
<211> LENGTH: 133
<212> TYPE: PRT
<213> ORGANISM: Artificial Sequence
<220> FEATURE:
<223> OTHER INFORMATION: H9B1

<400> SEQUENCE: 35

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 36
<211> LENGTH: 133
<212> TYPE: PRT
<213> ORGANISM: Artificial Sequence
<220> FEATURE:
<223> OTHER INFORMATION: IL-2 Antagonist

<400> SEQUENCE: 36

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr
        130

<210> SEQ ID NO 37
<211> LENGTH: 133
<212> TYPE: PRT
<213> ORGANISM: Artificial Sequence
```

```
<220> FEATURE:
<223> OTHER INFORMATION: IL-2 Antagonist

<400> SEQUENCE: 37

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Arg Thr Leu Thr
        130

<210> SEQ ID NO 38
<211> LENGTH: 168
<212> TYPE: PRT
<213> ORGANISM: Artificial Sequence
<220> FEATURE:
<223> OTHER INFORMATION: BAD amino acid sequence

<400> SEQUENCE: 38

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ala Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ala Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 39
<211> LENGTH: 168
<212> TYPE: PRT
```

<213> ORGANISM: Artificial Sequence
<220> FEATURE:
<223> OTHER INFORMATION: >HsBAD_Q92934-1(UniProtKB)

<400> SEQUENCE: 39

```
Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165
```

<210> SEQ ID NO 40
<211> LENGTH: 371
<212> TYPE: PRT
<213> ORGANISM: Artificial Sequence
<220> FEATURE:
<223> OTHER INFORMATION: H9-BclxL

<400> SEQUENCE: 40

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Met Ser Gln Ser Asn Arg
    130                 135                 140

Glu Leu Val Val Asp Phe Leu Ser Tyr Lys Leu Ser Gln Lys Gly Tyr
145                 150                 155                 160
```

Ser Trp Ser Gln Phe Ser Asp Val Glu Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
            195                 200                 205

His Ser Ser Ser Leu Asp Ala Arg Glu Val Ile Pro Met Ala Ala Val
    210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
            260                 265                 270

Val Asn Trp Gly Arg Ile Val Ala Phe Phe Ser Phe Gly Gly Ala Leu
            275                 280                 285

Cys Val Glu Ser Val Asp Lys Glu Met Gln Val Leu Val Ser Arg Ile
    290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
            340                 345                 350

Leu Thr Gly Met Thr Val Ala Gly Val Val Leu Leu Gly Ser Leu Phe
            355                 360                 365

Ser Arg Lys
    370

<210> SEQ ID NO 41
<211> LENGTH: 371
<212> TYPE: PRT
<213> ORGANISM: Artificial Sequence
<220> FEATURE:
<223> OTHER INFORMATION: H9FYAA-BclxL

<400> SEQUENCE: 41

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Met Ser Gln Ser Asn Arg
130                 135                 140

-continued

```
Glu Leu Val Val Asp Phe Leu Ser Tyr Lys Leu Ser Gln Lys Gly Tyr
145                 150                 155                 160

Ser Trp Ser Gln Phe Ser Asp Val Glu Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
        195                 200                 205

His Ser Ser Ser Leu Asp Ala Arg Glu Val Ile Pro Met Ala Ala Val
    210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
            260                 265                 270

Val Asn Trp Gly Arg Ile Val Ala Phe Phe Ser Phe Gly Gly Ala Leu
        275                 280                 285

Cys Val Glu Ser Val Asp Lys Glu Met Gln Val Leu Val Ser Arg Ile
    290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
            340                 345                 350

Leu Thr Gly Met Thr Val Ala Gly Val Val Leu Leu Gly Ser Leu Phe
        355                 360                 365

Ser Arg Lys
    370

<210> SEQ ID NO 42
<211> LENGTH: 371
<212> TYPE: PRT
<213> ORGANISM: Artificial Sequence
<220> FEATURE:
<223> OTHER INFORMATION: H9FEAA-BclxL

<400> SEQUENCE: 42

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

Ile Ser Thr Leu Thr Gly Gly Gly Ser Met Ser Gln Ser Asn Arg
    130                 135                 140

Glu Leu Val Val Asp Phe Leu Ser Tyr Lys Leu Ser Gln Lys Gly Tyr
145                 150                 155                 160

Ser Trp Ser Gln Phe Ser Asp Val Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
                195                 200                 205

His Ser Ser Ser Leu Asp Ala Arg Glu Val Ile Pro Met Ala Ala Val
    210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
                260                 265                 270

Val Asn Trp Gly Arg Ile Val Ala Phe Phe Ser Phe Gly Gly Ala Leu
    275                 280                 285

Cys Val Glu Ser Val Asp Lys Glu Met Gln Val Leu Val Ser Arg Ile
    290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
                340                 345                 350

Leu Thr Gly Met Thr Val Ala Gly Val Val Leu Leu Gly Ser Leu Phe
                355                 360                 365

Ser Arg Lys
    370

<210> SEQ ID NO 43
<211> LENGTH: 371
<212> TYPE: PRT
<213> ORGANISM: Artificial Sequence
<220> FEATURE:
<223> OTHER INFORMATION: H9D10-BclxL

<400> SEQUENCE: 43

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Cys Gln Ser Ile
            115                 120                 125

Ile Ser Thr Leu Thr Gly Gly Gly Ser Met Ser Gln Ser Asn Arg
    130                 135                 140

Glu Leu Val Val Asp Phe Leu Ser Tyr Lys Leu Ser Gln Lys Gly Tyr
145                 150                 155                 160

Ser Trp Ser Gln Phe Ser Asp Val Glu Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
                195                 200                 205

His Ser Ser Ser Leu Asp Ala Arg Glu Val Ile Pro Met Ala Ala Val
    210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
            260                 265                 270

Val Asn Trp Gly Arg Ile Val Ala Phe Phe Ser Phe Gly Gly Ala Leu
    275                 280                 285

Cys Val Glu Ser Val Asp Lys Glu Met Gln Val Leu Val Ser Arg Ile
290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
            340                 345                 350

Leu Thr Gly Met Thr Val Ala Gly Val Val Leu Leu Gly Ser Leu Phe
                355                 360                 365

Ser Arg Lys
    370

<210> SEQ ID NO 44
<211> LENGTH: 371
<212> TYPE: PRT
<213> ORGANISM: Artificial Sequence
<220> FEATURE:
<223> OTHER INFORMATION: H9E10-BclxL

<400> SEQUENCE: 44

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Met Ser Gln Ser Asn Arg
    130                 135                 140

Glu Leu Val Val Asp Phe Leu Ser Tyr Lys Leu Ser Gln Lys Gly Tyr
145                 150                 155                 160

Ser Trp Ser Gln Phe Ser Asp Val Glu Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
                195                 200                 205

His Ser Ser Ser Leu Asp Ala Arg Glu Val Ile Pro Met Ala Ala Val
    210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
            260                 265                 270

Val Asn Trp Gly Arg Ile Val Ala Phe Phe Ser Phe Gly Gly Ala Leu
                275                 280                 285

Cys Val Glu Ser Val Asp Lys Glu Met Gln Val Leu Val Ser Arg Ile
290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
            340                 345                 350

Leu Thr Gly Met Thr Val Ala Gly Val Val Leu Leu Gly Ser Leu Phe
                355                 360                 365

Ser Arg Lys
    370

<210> SEQ ID NO 45
<211> LENGTH: 371
<212> TYPE: PRT
<213> ORGANISM: Artificial Sequence
<220> FEATURE:
<223> OTHER INFORMATION: H9G8-Bclxl

<400> SEQUENCE: 45

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Asn Ser Lys Asn Phe His Phe
65                  70                  75                  80
```

```
Asp Pro Arg Asp Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Met Ser Gln Ser Asn Arg
    130                 135                 140

Glu Leu Val Val Asp Phe Leu Ser Tyr Lys Leu Ser Gln Lys Gly Tyr
145                 150                 155                 160

Ser Trp Ser Gln Phe Ser Asp Val Glu Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
        195                 200                 205

His Ser Ser Ser Leu Asp Ala Arg Glu Val Ile Pro Met Ala Ala Val
    210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
            260                 265                 270

Val Asn Trp Gly Arg Ile Val Ala Phe Phe Ser Phe Gly Gly Ala Leu
        275                 280                 285

Cys Val Glu Ser Val Asp Lys Glu Met Gln Val Leu Val Ser Arg Ile
    290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
            340                 345                 350

Leu Thr Gly Met Thr Val Ala Gly Val Val Leu Leu Gly Ser Leu Phe
        355                 360                 365

Ser Arg Lys
    370

<210> SEQ ID NO 46
<211> LENGTH: 371
<212> TYPE: PRT
<213> ORGANISM: Artificial Sequence
<220> FEATURE:
<223> OTHER INFORMATION: H9B1-BclxL

<400> SEQUENCE: 46

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

-continued

```
Pro Leu Glu Glu Val Leu Asn Leu Ala Asn Ser Lys Asn Phe His Phe
 65                  70                  75                  80

Asp Pro Arg Asp Val Val Ser Asn Val Asn Val Phe Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Met Ser Gln Ser Asn Arg
130                 135                 140

Glu Leu Val Val Asp Phe Leu Ser Tyr Lys Leu Ser Gln Lys Gly Tyr
145                 150                 155                 160

Ser Trp Ser Gln Phe Ser Asp Val Glu Glu Asn Arg Thr Glu Ala Pro
                165                 170                 175

Glu Gly Thr Glu Ser Glu Met Glu Thr Pro Ser Ala Ile Asn Gly Asn
            180                 185                 190

Pro Ser Trp His Leu Ala Asp Ser Pro Ala Val Asn Gly Ala Thr Gly
        195                 200                 205

His Ser Ser Ser Leu Asp Ala Arg Glu Val Ile Pro Met Ala Ala Val
210                 215                 220

Lys Gln Ala Leu Arg Glu Ala Gly Asp Glu Phe Glu Leu Arg Tyr Arg
225                 230                 235                 240

Arg Ala Phe Ser Asp Leu Thr Ser Gln Leu His Ile Thr Pro Gly Thr
                245                 250                 255

Ala Tyr Gln Ser Phe Glu Gln Val Val Asn Glu Leu Phe Arg Asp Gly
            260                 265                 270

Val Asn Trp Gly Arg Ile Val Ala Phe Phe Ser Phe Gly Gly Ala Leu
        275                 280                 285

Cys Val Glu Ser Val Asp Lys Glu Met Gln Val Leu Val Ser Arg Ile
290                 295                 300

Ala Ala Trp Met Ala Thr Tyr Leu Asn Asp His Leu Glu Pro Trp Ile
305                 310                 315                 320

Gln Glu Asn Gly Gly Trp Asp Thr Phe Val Glu Leu Tyr Gly Asn Asn
                325                 330                 335

Ala Ala Ala Glu Ser Arg Lys Gly Gln Glu Arg Phe Asn Arg Trp Phe
            340                 345                 350

Leu Thr Gly Met Thr Val Ala Gly Val Val Leu Leu Gly Ser Leu Phe
        355                 360                 365

Ser Arg Lys
370

<210> SEQ ID NO 47
<211> LENGTH: 375
<212> TYPE: PRT
<213> ORGANISM: Artificial Sequence
<220> FEATURE:
<223> OTHER INFORMATION: H9-Fc

<400> SEQUENCE: 47

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45
```

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 48
<211> LENGTH: 375
<212> TYPE: PRT
<213> ORGANISM: Artificial Sequence
<220> FEATURE:
<223> OTHER INFORMATION: H9-Fc

<400> SEQUENCE: 48

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Phe
 65                  70                  75                  80

Asp Pro Arg Asp Val Ser Asn Ile Asn Val Phe Leu Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 49
<211> LENGTH: 375
<212> TYPE: PRT
<213> ORGANISM: Artificial Sequence
<220> FEATURE:
<223> OTHER INFORMATION: H9-Fc

<400> SEQUENCE: 49

Ala Pro Thr Ser Ser Ser Thr Lys Lys Thr Gln Leu Gln Leu Glu His
1               5                   10                  15

```
Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Phe
 65                  70                  75                  80

Asp Pro Arg Asp Val Val Ser Asn Ile Asn Val Phe Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
        130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
        370                 375

<210> SEQ ID NO 50
<211> LENGTH: 375
<212> TYPE: PRT
<213> ORGANISM: Artificial Sequence
<220> FEATURE:
<223> OTHER INFORMATION: H9FYAA-Fc

<400> SEQUENCE: 50
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Gly Gly Gly Gly Ser Gly
130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
            195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
            275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys
370                 375

<210> SEQ ID NO 51
<211> LENGTH: 375
<212> TYPE: PRT
<213> ORGANISM: Artificial Sequence
<220> FEATURE:
<223> OTHER INFORMATION: H9FEAA-Fc
```

<400> SEQUENCE: 51

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Ala Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Gly Ser Gly
130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
            195                 200                 205

Gly Val Glu Val His Asn Ala Lys Thr Lys Pro Arg Glu Glu Gln Tyr
            210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
            275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys
            370                 375
```

<210> SEQ ID NO 52
<211> LENGTH: 375
<212> TYPE: PRT

<213> ORGANISM: Artificial Sequence
<220> FEATURE:
<223> OTHER INFORMATION: H9D10-Fc

<400> SEQUENCE: 52

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala His Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Gly Ser Gly Gly Gly Gly Ser Gly
    130                 135                 140
Gly Gly Gly Ser Asp Lys Thr His Thr Cys Pro Pro Cys Pro Ala Pro
145                 150                 155                 160
Glu Leu Leu Gly Gly Pro Ser Val Phe Leu Phe Pro Pro Lys Pro Lys
                165                 170                 175
Asp Thr Leu Met Ile Ser Arg Thr Pro Glu Val Thr Cys Val Val Val
            180                 185                 190
Asp Val Ser His Glu Asp Pro Glu Val Lys Phe Asn Trp Tyr Val Asp
        195                 200                 205
Gly Val Glu Val His Asn Ala Lys Thr Lys Pro Arg Glu Glu Gln Tyr
    210                 215                 220
Ala Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
            260                 265                 270
Glu Pro Gln Val Tyr Thr Leu Pro Pro Ser Arg Glu Glu Met Thr Lys
        275                 280                 285
Asn Gln Val Ser Leu Thr Cys Leu Val Lys Gly Phe Tyr Pro Ser Asp
    290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
            340                 345                 350
Cys Ser Val Met His Glu Ala Leu His Asn His Tyr Thr Gln Lys Ser
        355                 360                 365
Leu Ser Leu Ser Pro Gly Lys
    370                 375
```

```
<210> SEQ ID NO 53
<211> LENGTH: 375
<212> TYPE: PRT
<213> ORGANISM: Artificial Sequence
<220> FEATURE:
<223> OTHER INFORMATION: H9E10-Fc

<400> SEQUENCE: 53
```

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Gly Ser Gly
130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
370                 375

370            375

<210> SEQ ID NO 54
<211> LENGTH: 375
<212> TYPE: PRT
<213> ORGANISM: Artificial Sequence
<220> FEATURE:
<223> OTHER INFORMATION: H9G8-Fc

<400> SEQUENCE: 54

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
```

```
            355                 360                 365
Leu Ser Leu Ser Pro Gly Lys
    370                 375

<210> SEQ ID NO 55
<211> LENGTH: 375
<212> TYPE: PRT
<213> ORGANISM: Artificial Sequence
<220> FEATURE:
<223> OTHER INFORMATION: H9B1-Fc

<400> SEQUENCE: 55

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
```

```
                340             345             350
Cys Ser Val Met His Glu Ala Leu His Asn His Tyr Thr Gln Lys Ser
        355                 360                 365
Leu Ser Leu Ser Pro Gly Lys
    370                 375

<210> SEQ ID NO 56
<211> LENGTH: 375
<212> TYPE: PRT
<213> ORGANISM: Artificial Sequence
<220> FEATURE:
<223> OTHER INFORMATION: H9RET-Fc

<400> SEQUENCE: 56

Ala Pro Thr Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Ser Thr Leu Thr Gly Gly Gly Ser Gly Gly Gly Ser Gly
        130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
```

```
                    325                 330                 335
Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys
    370                 375

<210> SEQ ID NO 57
<211> LENGTH: 375
<212> TYPE: PRT
<213> ORGANISM: Artificial Sequence
<220> FEATURE:
<223> OTHER INFORMATION: IL-2 VARIANT-Fc

<400> SEQUENCE: 57

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Arg Thr Leu Thr Gly Gly Gly Ser Gly Gly Gly Ser Gly
    130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
```

```
                305                 310                 315                 320
Thr Thr Pro Pro Val Leu Asp Ser Asp Gly Ser Phe Phe Leu Tyr Ser
                        325                 330                 335

Lys Leu Thr Val Asp Lys Ser Arg Trp Gln Gln Gly Asn Val Phe Ser
                        340                 345                 350

Cys Ser Val Met His Glu Ala Leu His Asn His Tyr Thr Gln Lys Ser
                        355                 360                 365

Leu Ser Leu Ser Pro Gly Lys
                        370                 375

<210> SEQ ID NO 58
<211> LENGTH: 375
<212> TYPE: PRT
<213> ORGANISM: Artificial Sequence
<220> FEATURE:
<223> OTHER INFORMATION: H9RETFYAA-Fc

<400> SEQUENCE: 58

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
                20                  25                  30

Asn Pro Lys Leu Thr Arg Met Leu Thr Ala Lys Phe Ala Met Pro Lys
                35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Thr Ser Ile
                115                 120                 125

Ile Ser Thr Leu Thr Gly Gly Gly Gly Ser Gly Gly Gly Ser Gly
130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
                180                 185                 190

Asp Val Ser His Glu Asp Pro Glu Val Lys Phe Asn Trp Tyr Val Asp
                195                 200                 205

Gly Val Glu Val His Asn Ala Lys Thr Lys Pro Arg Glu Glu Gln Tyr
        210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
                260                 265                 270

Glu Pro Gln Val Tyr Thr Leu Pro Pro Ser Arg Glu Glu Met Thr Lys
                275                 280                 285

Asn Gln Val Ser Leu Thr Cys Leu Val Lys Gly Phe Tyr Pro Ser Asp
```

```
                    290                 295                 300
Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                    325                 330                 335

Lys Leu Thr Val Asp Lys Ser Arg Trp Gln Gln Gly Asn Val Phe Ser
                    340                 345                 350

Cys Ser Val Met His Glu Ala Leu His Asn His Tyr Thr Gln Lys Ser
                355                 360                 365

Leu Ser Leu Ser Pro Gly Lys
            370             375

<210> SEQ ID NO 59
<211> LENGTH: 375
<212> TYPE: PRT
<213> ORGANISM: Artificial Sequence
<220> FEATURE:
<223> OTHER INFORMATION: IL-2 VARIANTFYAA-Fc

<400> SEQUENCE: 59

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
                20                  25                  30

Asn Pro Lys Leu Thr Arg Met Leu Thr Ala Lys Phe Ala Met Pro Lys
                35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Thr Ser Ile
                115                 120                 125

Ile Arg Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
                180                 185                 190

Asp Val Ser His Glu Asp Pro Glu Val Lys Phe Asn Trp Tyr Val Asp
                195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
                260                 265                 270

Glu Pro Gln Val Tyr Thr Leu Pro Pro Ser Arg Glu Glu Met Thr Lys
```

```
                275                 280                 285
Asn Gln Val Ser Leu Thr Cys Leu Val Lys Gly Phe Tyr Pro Ser Asp
            290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
            340                 345                 350
Cys Ser Val Met His Glu Ala Leu His Asn His Tyr Thr Gln Lys Ser
                355                 360                 365
Leu Ser Leu Ser Pro Gly Lys
            370                 375

<210> SEQ ID NO 60
<211> LENGTH: 375
<212> TYPE: PRT
<213> ORGANISM: Artificial Sequence
<220> FEATURE:
<223> OTHER INFORMATION: H9RETFEAA-Fc

<400> SEQUENCE: 60

Ala Pro Thr Ser Ser Ser Thr Lys Lys Thr Gln Leu Gln Leu Glu His
1               5                   10                  15
Leu Arg Leu Asp Leu Glu Met Ile Leu Asn Gly Ile Asn Asn Tyr Lys
                20                  25                  30
Asn Pro Lys Leu Thr Arg Met Leu Thr Ala Lys Phe Tyr Met Pro Lys
            35                  40                  45
Lys Ala Thr Glu Leu Lys His Leu Gln Cys Leu Glu Glu Ala Leu Lys
        50                  55                  60
Pro Leu Glu Glu Val Leu Asn Leu Ala Gln Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Thr Ser Ile
        115                 120                 125
Ile Ser Thr Leu Thr Gly Gly Gly Ser Gly Gly Gly Ser Gly
130                 135                 140
Gly Gly Gly Ser Asp Lys Thr His Thr Cys Pro Pro Cys Pro Ala Pro
145                 150                 155                 160
Glu Leu Leu Gly Gly Pro Ser Val Phe Leu Phe Pro Pro Lys Pro Lys
                165                 170                 175
Asp Thr Leu Met Ile Ser Arg Thr Pro Glu Val Thr Cys Val Val Val
            180                 185                 190
Asp Val Ser His Glu Asp Pro Glu Val Lys Phe Asn Trp Tyr Val Asp
        195                 200                 205
Gly Val Glu Val His Asn Ala Lys Thr Lys Pro Arg Glu Glu Gln Tyr
    210                 215                 220
Ala Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
```

```
                260                 265                 270
Glu Pro Gln Val Tyr Thr Leu Pro Pro Ser Arg Glu Glu Met Thr Lys
                275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                    325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys
        370                 375

<210> SEQ ID NO 61
<211> LENGTH: 375
<212> TYPE: PRT
<213> ORGANISM: Artificial Sequence
<220> FEATURE:
<223> OTHER INFORMATION: IL-2 VARIANTFEAA-Fc

<400> SEQUENCE: 61

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Thr Ser Ile
        115                 120                 125

Ile Arg Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
```

```
                    245                 250                 255
Pro Ala Pro Ile Glu Lys Thr Ile Ser Lys Ala Lys Gly Gln Pro Arg
                260                 265                 270

Glu Pro Gln Val Tyr Thr Leu Pro Pro Ser Arg Glu Glu Met Thr Lys
            275                 280                 285

Asn Gln Val Ser Leu Thr Cys Leu Val Lys Gly Phe Tyr Pro Ser Asp
        290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
        370                 375

<210> SEQ ID NO 62
<211> LENGTH: 733
<212> TYPE: PRT
<213> ORGANISM: Artificial Sequence
<220> FEATURE:
<223> OTHER INFORMATION: H9-Albumin

<400> SEQUENCE: 62

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
```

```
            225                 230                 235                 240
Val His Thr Glu Cys Cys His Gly Asp Leu Leu Glu Cys Ala Asp Asp
                    245                 250                 255
Arg Ala Asp Leu Ala Lys Tyr Ile Cys Glu Asn Gln Asp Ser Ile Ser
                    260                 265                 270
Ser Lys Leu Lys Glu Cys Cys Glu Lys Pro Leu Leu Glu Lys Ser His
                    275                 280                 285
Cys Ile Ala Glu Val Glu Asn Asp Glu Met Pro Ala Asp Leu Pro Ser
                    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                    325                 330                 335
Arg His Pro Asp Tyr Ser Val Val Leu Leu Leu Arg Leu Ala Lys Thr
                    340                 345                 350
Tyr Glu Thr Thr Leu Glu Lys Cys Cys Ala Ala Ala Asp Pro His Glu
                    355                 360                 365
Cys Tyr Ala Lys Val Phe Asp Glu Phe Lys Pro Leu Val Glu Glu Pro
                    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                    405                 410                 415
Gln Val Ser Thr Pro Thr Leu Val Glu Val Ser Arg Asn Leu Gly Lys
                    420                 425                 430
Val Gly Ser Lys Cys Cys Lys His Pro Glu Ala Lys Arg Met Pro Cys
                    435                 440                 445
Ala Glu Asp Tyr Leu Ser Val Val Leu Asn Gln Leu Cys Val Leu His
                    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                    485                 490                 495
Tyr Val Pro Lys Glu Phe Asn Ala Glu Thr Phe Thr Phe His Ala Asp
                    500                 505                 510
Ile Cys Thr Leu Ser Glu Lys Glu Arg Gln Ile Lys Lys Gln Thr Ala
                    515                 520                 525
Leu Val Glu Leu Val Lys His Lys Pro Lys Ala Thr Lys Glu Gln Leu
                    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Gly Lys Lys Leu Val
                    565                 570                 575
Ala Ala Ser Gln Ala Ala Leu Gly Leu Gly Gly Gly Ser Gly Gly
                    580                 585                 590
Gly Gly Ser Gly Gly Gly Ser Ala Pro Thr Ser Ser Ser Thr Lys
                    595                 600                 605
Lys Thr Gln Leu Gln Leu Glu His Leu Leu Asp Leu Gln Met Ile
                    610                 615                 620
Leu Asn Gly Ile Asn Asn Tyr Lys Asn Pro Lys Leu Thr Arg Met Leu
625                 630                 635                 640
Thr Phe Lys Phe Tyr Met Pro Lys Lys Ala Thr Glu Leu Lys His Leu
                    645                 650                 655
```

```
Gln Cys Leu Glu Glu Leu Lys Pro Leu Glu Val Leu Asn Leu
            660                 665                 670

Ala Gln Ser Lys Asn Phe His Phe Asp Pro Arg Asp Val Ser Asn
        675                 680                 685

Ile Asn Val Phe Val Leu Glu Leu Lys Gly Ser Glu Thr Thr Phe Met
690                 695                 700

Cys Glu Tyr Ala Asp Glu Thr Ala Thr Ile Val Glu Phe Leu Asn Arg
705                 710                 715                 720

Trp Ile Thr Phe Cys Gln Ser Ile Ile Ser Thr Leu Thr
                725                 730
```

<210> SEQ ID NO 63
<211> LENGTH: 733
<212> TYPE: PRT
<213> ORGANISM: Artificial Sequence
<220> FEATURE:
<223> OTHER INFORMATION: H9FYAA-Albumin

<400> SEQUENCE: 63

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

```
Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
                580                 585                 590

Gly Gly Ser Gly Gly Gly Ser Ala Pro Thr Ser Ser Ser Thr Lys
            595                 600                 605

Lys Thr Gln Leu Gln Leu Glu His Leu Leu Leu Asp Leu Gln Met Ile
610                 615                 620

Leu Asn Gly Ile Asn Asn Tyr Lys Asn Pro Lys Leu Thr Arg Met Leu
625                 630                 635                 640

Thr Ala Lys Phe Ala Met Pro Lys Lys Ala Thr Glu Leu Lys His Leu
                645                 650                 655

Gln Cys Leu Glu Glu Glu Leu Lys Pro Leu Glu Glu Val Leu Asn Leu
            660                 665                 670

Ala Gln Ser Lys Asn Phe His Phe Asp Pro Arg Asp Val Val Ser Asn
            675                 680                 685

Ile Asn Val Phe Val Leu Glu Leu Lys Gly Ser Glu Thr Thr Phe Met
690                 695                 700
```

```
Cys Glu Tyr Ala Asp Glu Thr Ala Thr Ile Val Glu Phe Leu Asn Arg
705                 710                 715                 720

Trp Ile Thr Phe Cys Gln Ser Ile Ile Ser Thr Leu Thr
                725                 730

<210> SEQ ID NO 64
<211> LENGTH: 733
<212> TYPE: PRT
<213> ORGANISM: Artificial Sequence
<220> FEATURE:
<223> OTHER INFORMATION: H9FEAA-Albumin

<400> SEQUENCE: 64

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335
```

```
Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
            580                 585                 590

Gly Gly Ser Gly Gly Gly Gly Ser Ala Pro Thr Ser Ser Ser Thr Lys
        595                 600                 605

Lys Thr Gln Leu Gln Leu Glu His Leu Leu Leu Asp Leu Gln Met Ile
    610                 615                 620

Leu Asn Gly Ile Asn Asn Tyr Lys Asn Pro Lys Leu Thr Arg Met Leu
625                 630                 635                 640

Thr Ala Lys Phe Tyr Met Pro Lys Lys Ala Thr Glu Leu Lys His Leu
                645                 650                 655

Gln Cys Leu Glu Glu Ala Leu Lys Pro Leu Glu Glu Val Leu Asn Leu
            660                 665                 670

Ala Gln Ser Lys Asn Phe His Phe Asp Pro Arg Asp Val Val Ser Asn
        675                 680                 685

Ile Asn Val Phe Val Leu Glu Leu Lys Gly Ser Glu Thr Thr Phe Met
    690                 695                 700

Cys Glu Tyr Ala Asp Glu Thr Ala Thr Ile Val Glu Phe Leu Asn Arg
705                 710                 715                 720

Trp Ile Thr Phe Cys Gln Ser Ile Ile Ser Thr Leu Thr
                725                 730

<210> SEQ ID NO 65
<211> LENGTH: 733
<212> TYPE: PRT
```

<213> ORGANISM: Artificial Sequence
<220> FEATURE:
<223> OTHER INFORMATION: H9D10-Albumin

<400> SEQUENCE: 65

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Asp Ala His Lys Ser Glu Val Ala His Arg Phe Lys
145                 150                 155                 160

Asp Leu Gly Glu Glu Asn Phe Lys Ala Leu Val Leu Ile Ala Phe Ala
                165                 170                 175

Gln Tyr Leu Gln Gln Cys Pro Phe Glu Asp His Val Lys Leu Val Asn
            180                 185                 190

Glu Val Thr Glu Phe Ala Lys Thr Cys Val Ala Asp Glu Ser Ala Glu
        195                 200                 205

Asn Cys Asp Lys Ser Leu His Thr Leu Phe Gly Asp Lys Leu Cys Thr
    210                 215                 220

Val Ala Thr Leu Arg Glu Thr Tyr Gly Glu Met Ala Asp Cys Cys Ala
225                 230                 235                 240

Lys Gln Glu Pro Glu Arg Asn Glu Cys Phe Leu Gln His Lys Asp Asp
                245                 250                 255

Asn Pro Asn Leu Pro Arg Leu Val Arg Pro Glu Val Asp Val Met Cys
            260                 265                 270

Thr Ala Phe His Asp Asn Glu Glu Thr Phe Leu Lys Lys Tyr Leu Tyr
        275                 280                 285

Glu Ile Ala Arg Arg His Pro Tyr Phe Tyr Ala Pro Glu Leu Leu Phe
    290                 295                 300

Phe Ala Lys Arg Tyr Lys Ala Ala Phe Thr Glu Cys Cys Gln Ala Ala
305                 310                 315                 320

Asp Lys Ala Ala Cys Leu Leu Pro Lys Leu Asp Glu Leu Arg Asp Glu
                325                 330                 335

Gly Lys Ala Ser Ser Ala Lys Gln Arg Leu Lys Cys Ala Ser Leu Gln
            340                 345                 350

Lys Phe Gly Glu Arg Ala Phe Lys Ala Trp Ala Val Ala Arg Leu Ser
        355                 360                 365

Gln Arg Phe Pro Lys Ala Glu Phe Ala Glu Val Ser Lys Leu Val Thr
    370                 375                 380

Asp Leu Thr Lys Val His Thr Glu Cys Cys His Gly Asp Leu Leu Glu
```

```
                385                 390                 395                 400
Cys Ala Asp Asp Arg Ala Asp Leu Ala Lys Tyr Ile Cys Glu Asn Gln
                405                 410                 415
Asp Ser Ile Ser Ser Lys Leu Lys Glu Cys Cys Glu Lys Pro Leu Leu
            420                 425                 430
Glu Lys Ser His Cys Ile Ala Glu Val Glu Asn Asp Glu Met Pro Ala
        435                 440                 445
Asp Leu Pro Ser Leu Ala Ala Asp Phe Val Glu Ser Lys Asp Val Cys
    450                 455                 460
Lys Asn Tyr Ala Glu Ala Lys Asp Val Phe Leu Gly Met Phe Leu Tyr
465                 470                 475                 480
Glu Tyr Ala Arg Arg His Pro Asp Tyr Ser Val Val Leu Leu Leu Arg
                485                 490                 495
Leu Ala Lys Thr Tyr Glu Thr Thr Leu Glu Lys Cys Cys Ala Ala Ala
            500                 505                 510
Asp Pro His Glu Cys Tyr Ala Lys Val Phe Asp Glu Phe Lys Pro Leu
        515                 520                 525
Val Glu Glu Pro Gln Asn Leu Ile Lys Gln Asn Cys Glu Leu Phe Glu
    530                 535                 540
Gln Leu Gly Glu Tyr Lys Phe Gln Asn Ala Leu Leu Val Arg Tyr Thr
545                 550                 555                 560
Lys Lys Val Pro Gln Val Ser Thr Pro Thr Leu Val Glu Val Ser Arg
                565                 570                 575
Asn Leu Gly Lys Val Gly Ser Lys Cys Cys Lys His Pro Glu Ala Lys
            580                 585                 590
Arg Met Pro Cys Ala Glu Asp Tyr Leu Ser Val Val Leu Asn Gln Leu
        595                 600                 605
Cys Val Leu His Glu Lys Thr Pro Val Ser Asp Arg Val Thr Lys Cys
    610                 615                 620
Cys Thr Glu Ser Leu Val Asn Arg Arg Pro Cys Phe Ser Ala Leu Glu
625                 630                 635                 640
Val Asp Glu Thr Tyr Val Pro Lys Glu Phe Asn Ala Glu Thr Phe Thr
                645                 650                 655
Phe His Ala Asp Ile Cys Thr Leu Ser Glu Lys Glu Arg Gln Ile Lys
            660                 665                 670
Lys Gln Thr Ala Leu Val Glu Leu Val Lys His Lys Pro Lys Ala Thr
        675                 680                 685
Lys Glu Gln Leu Lys Ala Val Met Asp Asp Phe Ala Ala Phe Val Glu
    690                 695                 700
Lys Cys Cys Lys Ala Asp Asp Lys Glu Thr Cys Phe Ala Glu Glu Gly
705                 710                 715                 720
Lys Lys Leu Val Ala Ala Ser Gln Ala Ala Leu Gly Leu
                725                 730
```

<210> SEQ ID NO 66
<211> LENGTH: 733
<212> TYPE: PRT
<213> ORGANISM: Artificial Sequence
<220> FEATURE:
<223> OTHER INFORMATION: H9D10FEAA-Albumin

<400> SEQUENCE: 66

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

-continued

```
                20                  25                  30
Asn Pro Lys Leu Thr Arg Met Leu Thr Ala Lys Phe Tyr Met Pro Lys
             35                  40                  45
Lys Ala Thr Glu Leu Lys His Leu Gln Cys Leu Glu Glu Ala Leu Lys
         50                  55                  60
Pro Leu Glu Glu Val Leu Asn Leu Ala His Ser Lys Asn Phe His Phe
 65                  70                  75                  80
Asp Pro Arg Asp Val Val Ser Asn Ile Asn Val Phe Val Leu Glu Leu
                         85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
            115                 120                 125
Ile Ser Thr Leu Thr Gly Gly Gly Ser Gly Gly Gly Gly Ser Gly
        130                 135                 140
Gly Gly Gly Ser Asp Ala His Lys Ser Glu Val Ala His Arg Phe Lys
145                 150                 155                 160
Asp Leu Gly Glu Glu Asn Phe Lys Ala Leu Val Leu Ile Ala Phe Ala
                    165                 170                 175
Gln Tyr Leu Gln Gln Cys Pro Phe Glu Asp His Val Lys Leu Val Asn
                180                 185                 190
Glu Val Thr Glu Phe Ala Lys Thr Cys Val Ala Asp Glu Ser Ala Glu
            195                 200                 205
Asn Cys Asp Lys Ser Leu His Thr Leu Phe Gly Asp Lys Leu Cys Thr
        210                 215                 220
Val Ala Thr Leu Arg Glu Thr Tyr Gly Glu Met Ala Asp Cys Cys Ala
225                 230                 235                 240
Lys Gln Glu Pro Glu Arg Asn Glu Cys Phe Leu Gln His Lys Asp Asp
                    245                 250                 255
Asn Pro Asn Leu Pro Arg Leu Val Arg Pro Glu Val Asp Val Met Cys
                260                 265                 270
Thr Ala Phe His Asp Asn Glu Glu Thr Phe Leu Lys Lys Tyr Leu Tyr
            275                 280                 285
Glu Ile Ala Arg Arg His Pro Tyr Phe Tyr Ala Pro Glu Leu Leu Phe
        290                 295                 300
Phe Ala Lys Arg Tyr Lys Ala Ala Phe Thr Glu Cys Cys Gln Ala Ala
305                 310                 315                 320
Asp Lys Ala Ala Cys Leu Leu Pro Lys Leu Asp Glu Leu Arg Asp Glu
                    325                 330                 335
Gly Lys Ala Ser Ser Ala Lys Gln Arg Leu Lys Cys Ala Ser Leu Gln
                340                 345                 350
Lys Phe Gly Glu Arg Ala Phe Lys Ala Trp Ala Val Ala Arg Leu Ser
            355                 360                 365
Gln Arg Phe Pro Lys Ala Glu Phe Ala Glu Val Ser Lys Leu Val Thr
        370                 375                 380
Asp Leu Thr Lys Val His Thr Glu Cys Cys His Gly Asp Leu Leu Glu
385                 390                 395                 400
Cys Ala Asp Asp Arg Ala Asp Leu Ala Lys Tyr Ile Cys Glu Asn Gln
                    405                 410                 415
Asp Ser Ile Ser Ser Lys Leu Lys Glu Cys Cys Glu Lys Pro Leu Leu
                420                 425                 430
Glu Lys Ser His Cys Ile Ala Glu Val Glu Asn Asp Glu Met Pro Ala
            435                 440                 445
```

```
Asp Leu Pro Ser Leu Ala Ala Asp Phe Val Glu Ser Lys Asp Val Cys
    450                 455                 460

Lys Asn Tyr Ala Glu Ala Lys Asp Val Phe Leu Gly Met Phe Leu Tyr
465                 470                 475                 480

Glu Tyr Ala Arg Arg His Pro Asp Tyr Ser Val Val Leu Leu Leu Arg
                485                 490                 495

Leu Ala Lys Thr Tyr Glu Thr Thr Leu Glu Lys Cys Cys Ala Ala Ala
            500                 505                 510

Asp Pro His Glu Cys Tyr Ala Lys Val Phe Asp Glu Phe Lys Pro Leu
        515                 520                 525

Val Glu Glu Pro Gln Asn Leu Ile Lys Gln Asn Cys Glu Leu Phe Glu
530                 535                 540

Gln Leu Gly Glu Tyr Lys Phe Gln Asn Ala Leu Leu Val Arg Tyr Thr
545                 550                 555                 560

Lys Lys Val Pro Gln Val Ser Thr Pro Thr Leu Val Glu Val Ser Arg
                565                 570                 575

Asn Leu Gly Lys Val Gly Ser Lys Cys Cys Lys His Pro Glu Ala Lys
            580                 585                 590

Arg Met Pro Cys Ala Glu Asp Tyr Leu Ser Val Val Leu Asn Gln Leu
        595                 600                 605

Cys Val Leu His Glu Lys Thr Pro Val Ser Asp Arg Val Thr Lys Cys
610                 615                 620

Cys Thr Glu Ser Leu Val Asn Arg Arg Pro Cys Phe Ser Ala Leu Glu
625                 630                 635                 640

Val Asp Glu Thr Tyr Val Pro Lys Glu Phe Asn Ala Glu Thr Phe Thr
                645                 650                 655

Phe His Ala Asp Ile Cys Thr Leu Ser Glu Lys Glu Arg Gln Ile Lys
            660                 665                 670

Lys Gln Thr Ala Leu Val Glu Leu Val Lys His Lys Pro Lys Ala Thr
        675                 680                 685

Lys Glu Gln Leu Lys Ala Val Met Asp Asp Phe Ala Ala Phe Val Glu
690                 695                 700

Lys Cys Cys Lys Ala Asp Asp Lys Glu Thr Cys Phe Ala Glu Glu Gly
705                 710                 715                 720

Lys Lys Leu Val Ala Ala Ser Gln Ala Ala Leu Gly Leu
                725                 730

<210> SEQ ID NO 67
<211> LENGTH: 733
<212> TYPE: PRT
<213> ORGANISM: Artificial Sequence
<220> FEATURE:
<223> OTHER INFORMATION: H9E10-Albumin

<400> SEQUENCE: 67

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Phe
65                  70                  75                  80
```

```
Asp Pro Arg Asp Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Ser Asp Ala His Lys Ser Glu Val Ala His Arg Phe Lys
145             150                 155                 160

Asp Leu Gly Glu Glu Asn Phe Lys Ala Leu Val Leu Ile Ala Phe Ala
            165                 170                 175

Gln Tyr Leu Gln Gln Cys Pro Phe Glu Asp His Val Lys Leu Val Asn
        180                 185                 190

Glu Val Thr Glu Phe Ala Lys Thr Cys Val Ala Asp Glu Ser Ala Glu
    195                 200                 205

Asn Cys Asp Lys Ser Leu His Thr Leu Phe Gly Asp Lys Leu Cys Thr
210             215                 220

Val Ala Thr Leu Arg Glu Thr Tyr Gly Glu Met Ala Asp Cys Cys Ala
225             230                 235                 240

Lys Gln Glu Pro Glu Arg Asn Glu Cys Phe Leu Gln His Lys Asp Asp
            245                 250                 255

Asn Pro Asn Leu Pro Arg Leu Val Arg Pro Glu Val Asp Val Met Cys
        260                 265                 270

Thr Ala Phe His Asp Asn Glu Glu Thr Phe Leu Lys Lys Tyr Leu Tyr
    275                 280                 285

Glu Ile Ala Arg Arg His Pro Tyr Phe Tyr Ala Pro Glu Leu Leu Phe
290             295                 300

Phe Ala Lys Arg Tyr Lys Ala Ala Phe Thr Glu Cys Cys Gln Ala Ala
305             310                 315                 320

Asp Lys Ala Ala Cys Leu Leu Pro Lys Leu Asp Glu Leu Arg Asp Glu
            325                 330                 335

Gly Lys Ala Ser Ser Ala Lys Gln Arg Leu Lys Cys Ala Ser Leu Gln
        340                 345                 350

Lys Phe Gly Glu Arg Ala Phe Lys Ala Trp Ala Val Ala Arg Leu Ser
    355                 360                 365

Gln Arg Phe Pro Lys Ala Glu Phe Ala Glu Val Ser Lys Leu Val Thr
370             375                 380

Asp Leu Thr Lys Val His Thr Glu Cys Cys His Gly Asp Leu Leu Glu
385             390                 395                 400

Cys Ala Asp Asp Arg Ala Asp Leu Ala Lys Tyr Ile Cys Glu Asn Gln
            405                 410                 415

Asp Ser Ile Ser Ser Lys Leu Lys Glu Cys Cys Glu Lys Pro Leu Leu
        420                 425                 430

Glu Lys Ser His Cys Ile Ala Glu Val Glu Asn Asp Glu Met Pro Ala
    435                 440                 445

Asp Leu Pro Ser Leu Ala Ala Asp Phe Val Glu Ser Lys Asp Val Cys
450             455                 460

Lys Asn Tyr Ala Glu Ala Lys Asp Val Phe Leu Gly Met Phe Leu Tyr
465             470                 475                 480

Glu Tyr Ala Arg Arg His Pro Asp Tyr Ser Val Val Leu Leu Leu Arg
            485                 490                 495
```

```
Leu Ala Lys Thr Tyr Glu Thr Thr Leu Glu Lys Cys Cys Ala Ala Ala
                500                 505                 510

Asp Pro His Glu Cys Tyr Ala Lys Val Phe Asp Glu Phe Lys Pro Leu
            515                 520                 525

Val Glu Glu Pro Gln Asn Leu Ile Lys Gln Asn Cys Glu Leu Phe Glu
        530                 535                 540

Gln Leu Gly Glu Tyr Lys Phe Gln Asn Ala Leu Leu Val Arg Tyr Thr
545                 550                 555                 560

Lys Lys Val Pro Gln Val Ser Thr Pro Thr Leu Val Glu Val Ser Arg
                565                 570                 575

Asn Leu Gly Lys Val Gly Ser Lys Cys Cys Lys His Pro Glu Ala Lys
            580                 585                 590

Arg Met Pro Cys Ala Glu Asp Tyr Leu Ser Val Val Leu Asn Gln Leu
        595                 600                 605

Cys Val Leu His Glu Lys Thr Pro Val Ser Asp Arg Val Thr Lys Cys
610                 615                 620

Cys Thr Glu Ser Leu Val Asn Arg Arg Pro Cys Phe Ser Ala Leu Glu
625                 630                 635                 640

Val Asp Glu Thr Tyr Val Pro Lys Glu Phe Asn Ala Glu Thr Phe Thr
                645                 650                 655

Phe His Ala Asp Ile Cys Thr Leu Ser Glu Lys Glu Arg Gln Ile Lys
            660                 665                 670

Lys Gln Thr Ala Leu Val Glu Leu Val Lys His Lys Pro Lys Ala Thr
        675                 680                 685

Lys Glu Gln Leu Lys Ala Val Met Asp Asp Phe Ala Ala Phe Val Glu
    690                 695                 700

Lys Cys Cys Lys Ala Asp Asp Lys Glu Thr Cys Phe Ala Glu Glu Gly
705                 710                 715                 720

Lys Lys Leu Val Ala Ala Ser Gln Ala Ala Leu Gly Leu
                725                 730

<210> SEQ ID NO 68
<211> LENGTH: 733
<212> TYPE: PRT
<213> ORGANISM: Artificial Sequence
<220> FEATURE:
<223> OTHER INFORMATION: H9G8-Albumin

<400> SEQUENCE: 68

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125
```

-continued

```
Ile Ser Thr Leu Thr Gly Gly Gly Ser Gly Gly Gly Ser Gly
    130                 135             140

Gly Gly Gly Ser Asp Ala His Lys Ser Glu Val Ala His Arg Phe Lys
145             150                 155                 160

Asp Leu Gly Glu Glu Asn Phe Lys Ala Leu Val Leu Ile Ala Phe Ala
                165                 170                 175

Gln Tyr Leu Gln Gln Cys Pro Phe Glu Asp His Val Lys Leu Val Asn
        180                 185                 190

Glu Val Thr Glu Phe Ala Lys Thr Cys Val Ala Asp Glu Ser Ala Glu
        195                 200                 205

Asn Cys Asp Lys Ser Leu His Thr Leu Phe Gly Asp Lys Leu Cys Thr
210                 215                 220

Val Ala Thr Leu Arg Glu Thr Tyr Gly Glu Met Ala Asp Cys Cys Ala
225                 230                 235                 240

Lys Gln Glu Pro Glu Arg Asn Glu Cys Phe Leu Gln His Lys Asp Asp
                245                 250                 255

Asn Pro Asn Leu Pro Arg Leu Val Arg Pro Glu Val Asp Val Met Cys
            260                 265                 270

Thr Ala Phe His Asp Asn Glu Glu Thr Phe Leu Lys Lys Tyr Leu Tyr
        275                 280                 285

Glu Ile Ala Arg Arg His Pro Tyr Phe Tyr Ala Pro Glu Leu Leu Phe
290                 295                 300

Phe Ala Lys Arg Tyr Lys Ala Ala Phe Thr Glu Cys Cys Gln Ala Ala
305                 310                 315                 320

Asp Lys Ala Ala Cys Leu Leu Pro Lys Leu Asp Glu Leu Arg Asp Glu
                325                 330                 335

Gly Lys Ala Ser Ser Ala Lys Gln Arg Leu Lys Cys Ala Ser Leu Gln
            340                 345                 350

Lys Phe Gly Glu Arg Ala Phe Lys Ala Trp Ala Val Ala Arg Leu Ser
        355                 360                 365

Gln Arg Phe Pro Lys Ala Glu Phe Ala Glu Val Ser Lys Leu Val Thr
        370                 375                 380

Asp Leu Thr Lys Val His Thr Glu Cys Cys His Gly Asp Leu Leu Glu
385                 390                 395                 400

Cys Ala Asp Asp Arg Ala Asp Leu Ala Lys Tyr Ile Cys Glu Asn Gln
                405                 410                 415

Asp Ser Ile Ser Ser Lys Leu Lys Glu Cys Cys Glu Lys Pro Leu Leu
            420                 425                 430

Glu Lys Ser His Cys Ile Ala Glu Val Glu Asn Asp Glu Met Pro Ala
        435                 440                 445

Asp Leu Pro Ser Leu Ala Ala Asp Phe Val Glu Ser Lys Asp Val Cys
450                 455                 460

Lys Asn Tyr Ala Glu Ala Lys Asp Val Phe Leu Gly Met Phe Leu Tyr
465                 470                 475                 480

Glu Tyr Ala Arg Arg His Pro Asp Tyr Ser Val Val Leu Leu Leu Arg
                485                 490                 495

Leu Ala Lys Thr Tyr Glu Thr Thr Leu Glu Lys Cys Cys Ala Ala Ala
            500                 505                 510

Asp Pro His Glu Cys Tyr Ala Lys Val Phe Asp Glu Phe Lys Pro Leu
        515                 520                 525

Val Glu Glu Pro Gln Asn Leu Ile Lys Gln Asn Cys Glu Leu Phe Glu
        530                 535                 540

Gln Leu Gly Glu Tyr Lys Phe Gln Asn Ala Leu Leu Val Arg Tyr Thr
```

```
                545                 550                 555                 560
Lys Lys Val Pro Gln Val Ser Thr Pro Thr Leu Val Glu Val Ser Arg
                    565                 570                 575

Asn Leu Gly Lys Val Gly Ser Lys Cys Cys Lys His Pro Glu Ala Lys
                580                 585                 590

Arg Met Pro Cys Ala Glu Asp Tyr Leu Ser Val Val Leu Asn Gln Leu
            595                 600                 605

Cys Val Leu His Glu Lys Thr Pro Val Ser Asp Arg Val Thr Lys Cys
        610                 615                 620

Cys Thr Glu Ser Leu Val Asn Arg Arg Pro Cys Phe Ser Ala Leu Glu
625                 630                 635                 640

Val Asp Glu Thr Tyr Val Pro Lys Glu Phe Asn Ala Glu Thr Phe Thr
                    645                 650                 655

Phe His Ala Asp Ile Cys Thr Leu Ser Glu Lys Glu Arg Gln Ile Lys
                660                 665                 670

Lys Gln Thr Ala Leu Val Glu Leu Val Lys His Lys Pro Lys Ala Thr
            675                 680                 685

Lys Glu Gln Leu Lys Ala Val Met Asp Asp Phe Ala Ala Phe Val Glu
        690                 695                 700

Lys Cys Cys Lys Ala Asp Asp Lys Glu Thr Cys Phe Ala Glu Glu Gly
705                 710                 715                 720

Lys Lys Leu Val Ala Ala Ser Gln Ala Ala Leu Gly Leu
                    725                 730

<210> SEQ ID NO 69
<211> LENGTH: 733
<212> TYPE: PRT
<213> ORGANISM: Artificial Sequence
<220> FEATURE:
<223> OTHER INFORMATION: H9B1-Albumin

<400> SEQUENCE: 69

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
        130                 135                 140

Gly Gly Gly Ser Asp Ala His Lys Ser Glu Val Ala His Arg Phe Lys
145                 150                 155                 160

Asp Leu Gly Glu Glu Asn Phe Lys Ala Leu Val Leu Ile Ala Phe Ala
                165                 170                 175

Gln Tyr Leu Gln Gln Cys Pro Phe Glu Asp His Val Lys Leu Val Asn
```

-continued

```
            180                 185                 190
Glu Val Thr Glu Phe Ala Lys Thr Cys Val Ala Asp Glu Ser Ala Glu
            195                 200                 205

Asn Cys Asp Lys Ser Leu His Thr Leu Phe Gly Asp Lys Leu Cys Thr
            210                 215                 220

Val Ala Thr Leu Arg Glu Thr Tyr Gly Glu Met Ala Asp Cys Cys Ala
225                 230                 235                 240

Lys Gln Glu Pro Glu Arg Asn Glu Cys Phe Leu Gln His Lys Asp Asp
                245                 250                 255

Asn Pro Asn Leu Pro Arg Leu Val Arg Pro Glu Val Asp Val Met Cys
            260                 265                 270

Thr Ala Phe His Asp Asn Glu Glu Thr Phe Leu Lys Lys Tyr Leu Tyr
            275                 280                 285

Glu Ile Ala Arg Arg His Pro Tyr Phe Tyr Ala Pro Glu Leu Leu Phe
            290                 295                 300

Phe Ala Lys Arg Tyr Lys Ala Ala Phe Thr Glu Cys Cys Gln Ala Ala
305                 310                 315                 320

Asp Lys Ala Ala Cys Leu Leu Pro Lys Leu Asp Glu Leu Arg Asp Glu
                325                 330                 335

Gly Lys Ala Ser Ser Ala Lys Gln Arg Leu Lys Cys Ala Ser Leu Gln
            340                 345                 350

Lys Phe Gly Glu Arg Ala Phe Lys Ala Trp Ala Val Ala Arg Leu Ser
            355                 360                 365

Gln Arg Phe Pro Lys Ala Glu Phe Ala Glu Val Ser Lys Leu Val Thr
            370                 375                 380

Asp Leu Thr Lys Val His Thr Glu Cys Cys His Gly Asp Leu Leu Glu
385                 390                 395                 400

Cys Ala Asp Asp Arg Ala Asp Leu Ala Lys Tyr Ile Cys Glu Asn Gln
                405                 410                 415

Asp Ser Ile Ser Ser Lys Leu Lys Glu Cys Cys Glu Lys Pro Leu Leu
            420                 425                 430

Glu Lys Ser His Cys Ile Ala Glu Val Glu Asn Asp Glu Met Pro Ala
            435                 440                 445

Asp Leu Pro Ser Leu Ala Ala Asp Phe Val Glu Ser Lys Asp Val Cys
            450                 455                 460

Lys Asn Tyr Ala Glu Ala Lys Asp Val Phe Leu Gly Met Phe Leu Tyr
465                 470                 475                 480

Glu Tyr Ala Arg Arg His Pro Asp Tyr Ser Val Val Leu Leu Leu Arg
                485                 490                 495

Leu Ala Lys Thr Tyr Glu Thr Thr Leu Glu Lys Cys Cys Ala Ala Ala
            500                 505                 510

Asp Pro His Glu Cys Tyr Ala Lys Val Phe Asp Glu Phe Lys Pro Leu
            515                 520                 525

Val Glu Glu Pro Gln Asn Leu Ile Lys Gln Asn Cys Glu Leu Phe Glu
            530                 535                 540

Gln Leu Gly Glu Tyr Lys Phe Gln Asn Ala Leu Leu Val Arg Tyr Thr
545                 550                 555                 560

Lys Lys Val Pro Gln Val Ser Thr Pro Thr Leu Val Glu Val Ser Arg
                565                 570                 575

Asn Leu Gly Lys Val Gly Ser Lys Cys Cys Lys His Pro Glu Ala Lys
            580                 585                 590

Arg Met Pro Cys Ala Glu Asp Tyr Leu Ser Val Val Leu Asn Gln Leu
            595                 600                 605
```

```
Cys Val Leu His Glu Lys Thr Pro Val Ser Asp Arg Val Thr Lys Cys
        610                 615                 620
Cys Thr Glu Ser Leu Val Asn Arg Arg Pro Cys Phe Ser Ala Leu Glu
625                 630                 635                 640
Val Asp Glu Thr Tyr Val Pro Lys Glu Phe Asn Ala Glu Thr Phe Thr
            645                 650                 655
Phe His Ala Asp Ile Cys Thr Leu Ser Glu Lys Glu Arg Gln Ile Lys
            660                 665                 670
Lys Gln Thr Ala Leu Val Glu Leu Val Lys His Lys Pro Lys Ala Thr
        675                 680                 685
Lys Glu Gln Leu Lys Ala Val Met Asp Asp Phe Ala Ala Phe Val Glu
690                 695                 700
Lys Cys Cys Lys Ala Asp Asp Lys Glu Thr Cys Phe Ala Glu Glu Gly
705                 710                 715                 720
Lys Lys Leu Val Ala Ala Ser Gln Ala Ala Leu Gly Leu
                725                 730
```

<210> SEQ ID NO 70
<211> LENGTH: 733
<212> TYPE: PRT
<213> ORGANISM: Artificial Sequence
<220> FEATURE:
<223> OTHER INFORMATION: H9FEAA-Albumin

<400> SEQUENCE: 70

```
Ala Pro Thr Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Ala Lys Phe Tyr Met Pro Lys
            35                  40                  45
Lys Ala Thr Glu Leu Lys His Leu Gln Cys Leu Glu Glu Ala Leu Lys
        50                  55                  60
Pro Leu Glu Glu Val Leu Asn Leu Ala Gln Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Ser Gly Gly Gly Gly Ser Gly
130                 135                 140
Gly Gly Gly Ser Asp Ala His Lys Ser Glu Val Ala His Arg Phe Lys
145                 150                 155                 160
Asp Leu Gly Glu Glu Asn Phe Lys Ala Leu Val Leu Ile Ala Phe Ala
                165                 170                 175
Gln Tyr Leu Gln Gln Cys Pro Phe Glu Asp His Val Lys Leu Val Asn
            180                 185                 190
Glu Val Thr Glu Phe Ala Lys Thr Cys Val Ala Asp Glu Ser Ala Glu
        195                 200                 205
Asn Cys Asp Lys Ser Leu His Thr Leu Phe Gly Asp Lys Leu Cys Thr
210                 215                 220
Val Ala Thr Leu Arg Glu Thr Tyr Gly Glu Met Ala Asp Cys Cys Ala
225                 230                 235                 240
```

```
Lys Gln Glu Pro Glu Arg Asn Glu Cys Phe Leu Gln His Lys Asp Asp
                245                 250                 255

Asn Pro Asn Leu Pro Arg Leu Val Arg Pro Glu Val Asp Val Met Cys
            260                 265                 270

Thr Ala Phe His Asp Asn Glu Glu Thr Phe Leu Lys Lys Tyr Leu Tyr
        275                 280                 285

Glu Ile Ala Arg Arg His Pro Tyr Phe Tyr Ala Pro Glu Leu Leu Phe
    290                 295                 300

Phe Ala Lys Arg Tyr Lys Ala Ala Phe Thr Glu Cys Cys Gln Ala Ala
305                 310                 315                 320

Asp Lys Ala Ala Cys Leu Leu Pro Lys Leu Asp Glu Leu Arg Asp Glu
                325                 330                 335

Gly Lys Ala Ser Ser Ala Lys Gln Arg Leu Lys Cys Ala Ser Leu Gln
            340                 345                 350

Lys Phe Gly Glu Arg Ala Phe Lys Ala Trp Ala Val Ala Arg Leu Ser
        355                 360                 365

Gln Arg Phe Pro Lys Ala Glu Phe Ala Glu Val Ser Lys Leu Val Thr
    370                 375                 380

Asp Leu Thr Lys Val His Thr Glu Cys Cys His Gly Asp Leu Leu Glu
385                 390                 395                 400

Cys Ala Asp Asp Arg Ala Asp Leu Ala Lys Tyr Ile Cys Glu Asn Gln
                405                 410                 415

Asp Ser Ile Ser Ser Lys Leu Lys Glu Cys Cys Glu Lys Pro Leu Leu
            420                 425                 430

Glu Lys Ser His Cys Ile Ala Glu Val Glu Asn Asp Glu Met Pro Ala
        435                 440                 445

Asp Leu Pro Ser Leu Ala Ala Asp Phe Val Glu Ser Lys Asp Val Cys
    450                 455                 460

Lys Asn Tyr Ala Glu Ala Lys Asp Val Phe Leu Gly Met Phe Leu Tyr
465                 470                 475                 480

Glu Tyr Ala Arg Arg His Pro Asp Tyr Ser Val Val Leu Leu Leu Arg
                485                 490                 495

Leu Ala Lys Thr Tyr Glu Thr Thr Leu Glu Lys Cys Cys Ala Ala Ala
            500                 505                 510

Asp Pro His Glu Cys Tyr Ala Lys Val Phe Asp Glu Phe Lys Pro Leu
        515                 520                 525

Val Glu Glu Pro Gln Asn Leu Ile Lys Gln Asn Cys Glu Leu Phe Glu
    530                 535                 540

Gln Leu Gly Glu Tyr Lys Phe Gln Asn Ala Leu Leu Val Arg Tyr Thr
545                 550                 555                 560

Lys Lys Val Pro Gln Val Ser Thr Pro Thr Leu Val Glu Val Ser Arg
                565                 570                 575

Asn Leu Gly Lys Val Gly Ser Lys Cys Cys Lys His Pro Glu Ala Lys
            580                 585                 590

Arg Met Pro Cys Ala Glu Asp Tyr Leu Ser Val Val Leu Asn Gln Leu
        595                 600                 605

Cys Val Leu His Glu Lys Thr Pro Val Ser Asp Arg Val Thr Lys Cys
    610                 615                 620

Cys Thr Glu Ser Leu Val Asn Arg Arg Pro Cys Phe Ser Ala Leu Glu
625                 630                 635                 640

Val Asp Glu Thr Tyr Val Pro Lys Glu Phe Asn Ala Glu Thr Phe Thr
                645                 650                 655
```

```
Phe His Ala Asp Ile Cys Thr Leu Ser Glu Lys Glu Arg Gln Ile Lys
            660                 665                 670

Lys Gln Thr Ala Leu Val Glu Leu Val Lys His Lys Pro Lys Ala Thr
        675                 680                 685

Lys Glu Gln Leu Lys Ala Val Met Asp Asp Phe Ala Ala Phe Val Glu
    690                 695                 700

Lys Cys Cys Lys Ala Asp Asp Lys Glu Thr Cys Phe Ala Glu Glu Gly
705                 710                 715                 720

Lys Lys Leu Val Ala Ala Ser Gln Ala Ala Leu Gly Leu
                725                 730

<210> SEQ ID NO 71
<211> LENGTH: 733
<212> TYPE: PRT
<213> ORGANISM: Artificial Sequence
<220> FEATURE:
<223> OTHER INFORMATION: H9D10-Albumin

<400> SEQUENCE: 71

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

```
Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
                580                 585                 590

Gly Gly Ser Gly Gly Gly Ser Ala Pro Thr Ser Ser Ser Thr Lys
            595                 600                 605

Lys Thr Gln Leu Gln Leu Glu His Leu Leu Leu Asp Leu Gln Met Ile
    610                 615                 620

Leu Asn Gly Ile Asn Asn Tyr Lys Asn Pro Lys Leu Thr Arg Met Leu
625                 630                 635                 640

Thr Phe Lys Phe Tyr Met Pro Lys Lys Ala Thr Glu Leu Lys His Leu
                645                 650                 655

Gln Cys Leu Glu Glu Glu Leu Lys Pro Leu Glu Glu Val Leu Asn Leu
    660                 665                 670

Ala His Ser Lys Asn Phe His Phe Asp Pro Arg Asp Val Val Ser Asn
                675                 680                 685

Ile Asn Val Phe Val Leu Glu Leu Lys Gly Ser Glu Thr Thr Phe Met
    690                 695                 700

Cys Glu Tyr Ala Asp Glu Thr Ala Thr Ile Val Glu Phe Leu Asn Arg
```

```
                  705                 710                 715                 720

Trp Ile Thr Phe Cys Gln Ser Ile Ile Ser Thr Leu Thr
                  725                 730

<210> SEQ ID NO 72
<211> LENGTH: 733
<212> TYPE: PRT
<213> ORGANISM: Artificial Sequence
<220> FEATURE:
<223> OTHER INFORMATION: H9D10FEAA-Albumin

<400> SEQUENCE: 72

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
```

```
                    340                 345                 350
Tyr Glu Thr Thr Leu Glu Lys Cys Cys Ala Ala Asp Pro His Glu
                355                 360                 365
Cys Tyr Ala Lys Val Phe Asp Glu Phe Lys Pro Leu Val Glu Pro
            370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Gly Ser Gly Gly
            580                 585                 590
Gly Gly Ser Gly Gly Gly Gly Ser Ala Pro Thr Ser Ser Ser Thr Lys
595                 600                 605
Lys Thr Gln Leu Gln Leu Glu His Leu Leu Leu Asp Leu Gln Met Ile
    610                 615                 620
Leu Asn Gly Ile Asn Asn Tyr Lys Asn Pro Lys Leu Thr Arg Met Leu
625                 630                 635                 640
Thr Ala Lys Phe Tyr Met Pro Lys Lys Ala Thr Glu Leu Lys His Leu
                645                 650                 655
Gln Cys Leu Glu Glu Ala Leu Lys Pro Leu Glu Glu Val Leu Asn Leu
            660                 665                 670
Ala His Ser Lys Asn Phe His Phe Asp Pro Arg Asp Val Val Ser Asn
            675                 680                 685
Ile Asn Val Phe Val Leu Glu Leu Lys Gly Ser Glu Thr Thr Phe Met
            690                 695                 700
Cys Glu Tyr Ala Asp Glu Thr Ala Thr Ile Val Glu Phe Leu Asn Arg
705                 710                 715                 720
Trp Ile Thr Phe Cys Gln Ser Ile Ile Ser Thr Leu Thr
                725                 730

<210> SEQ ID NO 73
<211> LENGTH: 733
<212> TYPE: PRT
<213> ORGANISM: Artificial Sequence
```

<220> FEATURE:
<223> OTHER INFORMATION: H9E10-Albumin

<400> SEQUENCE: 73

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly Gly
            580                 585                 590

Gly Gly Ser Gly Gly Gly Gly Ser Ala Pro Thr Ser Ser Ser Thr Lys
        595                 600                 605

Lys Thr Gln Leu Gln Leu Glu His Leu Leu Leu Asp Leu Gln Met Ile
    610                 615                 620

Leu Asn Gly Ile Asn Asn Tyr Lys Asn Pro Lys Leu Thr Arg Met Leu
625                 630                 635                 640

Thr Phe Lys Phe Tyr Met Pro Lys Lys Ala Thr Glu Leu Lys His Leu
                645                 650                 655

Gln Cys Leu Glu Glu Glu Leu Lys Pro Leu Glu Glu Val Leu Asn Leu
            660                 665                 670

Ala Ser Ser Lys Asn Phe His Phe Asp Pro Arg Asp Val Val Ser Asn
        675                 680                 685

Ile Asn Val Phe Val Leu Glu Leu Lys Gly Ser Glu Thr Thr Phe Met
    690                 695                 700

Cys Glu Tyr Ala Asp Glu Thr Ala Thr Ile Val Glu Phe Leu Asn Arg
705                 710                 715                 720

Trp Ile Thr Phe Cys Gln Ser Ile Ile Ser Thr Leu Thr
                725                 730

<210> SEQ ID NO 74
<211> LENGTH: 733
<212> TYPE: PRT
<213> ORGANISM: Artificial Sequence
<220> FEATURE:
<223> OTHER INFORMATION: H9G8-Albumin

<400> SEQUENCE: 74

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

-continued

```
Gln Cys Pro Phe Glu Asp His Val Lys Leu Val Asn Glu Val Thr Glu
         35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                 165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                 245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                 325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                 405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
```

```
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Gly Ser Gly Gly
            580                 585                 590
Gly Gly Ser Gly Gly Gly Gly Ser Ala Pro Thr Ser Ser Ser Thr Lys
        595                 600                 605
Lys Thr Gln Leu Gln Leu Glu His Leu Leu Leu Asp Leu Gln Met Ile
    610                 615                 620
Leu Asn Gly Ile Asn Asn Tyr Lys Asn Pro Lys Leu Thr Arg Met Leu
625                 630                 635                 640
Thr Phe Lys Phe Tyr Met Pro Lys Lys Ala Thr Glu Leu Lys His Leu
                645                 650                 655
Gln Cys Leu Glu Glu Glu Leu Lys Pro Leu Glu Glu Val Leu Asn Leu
            660                 665                 670
Ala Asn Ser Lys Asn Phe His Phe Asp Pro Arg Asp Val Val Ser Asn
        675                 680                 685
Ile Asn Val Phe Val Leu Glu Leu Lys Gly Ser Glu Thr Thr Phe Met
    690                 695                 700
Cys Glu Tyr Ala Asp Glu Thr Ala Thr Ile Val Glu Phe Leu Asn Arg
705                 710                 715                 720
Trp Ile Thr Phe Cys Gln Ser Ile Ile Ser Thr Leu Thr
                725                 730

<210> SEQ ID NO 75
<211> LENGTH: 733
<212> TYPE: PRT
<213> ORGANISM: Artificial Sequence
<220> FEATURE:
<223> OTHER INFORMATION: H9B1-Albumin

<400> SEQUENCE: 75

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
```

-continued

```
Arg Glu Thr Tyr Gly Glu Met Ala Asp Cys Cys Ala Lys Gln Pro
             85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
```

-continued

```
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
        530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Gly Ser Gly Gly
            580                 585                 590
Gly Gly Ser Gly Gly Gly Gly Ser Ala Pro Thr Ser Ser Ser Thr Lys
        595                 600                 605
Lys Thr Gln Leu Gln Leu Glu His Leu Leu Leu Asp Leu Gln Met Ile
        610                 615                 620
Leu Asn Gly Ile Asn Asn Tyr Lys Asn Pro Lys Leu Thr Arg Met Leu
625                 630                 635                 640
Thr Phe Lys Phe Tyr Met Pro Lys Lys Ala Thr Glu Leu Lys His Leu
                645                 650                 655
Gln Cys Leu Glu Glu Glu Leu Lys Pro Leu Glu Glu Val Leu Asn Leu
            660                 665                 670
Ala Asn Ser Lys Asn Phe His Phe Asp Pro Arg Asp Val Val Ser Asn
        675                 680                 685
Val Asn Val Phe Val Leu Glu Leu Lys Gly Ser Glu Thr Thr Phe Met
        690                 695                 700
Cys Glu Tyr Ala Asp Glu Thr Ala Thr Ile Val Glu Phe Leu Asn Arg
705                 710                 715                 720
Trp Ile Thr Phe Cys Gln Ser Ile Ile Ser Thr Leu Thr
                725                 730
```

<210> SEQ ID NO 76
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 76

```
Met Tyr Arg Met Gln Leu Leu Ser Cys Ile Ala Leu Ser Leu Ala Leu
1               5                   10                  15
Val Thr Asn Ser Ala Pro Thr Ser Ser Ser Thr Lys Lys Thr Gln Leu
            20                  25                  30
Gln Leu Glu His Leu Leu Leu Asp Leu Gln Met Ile Leu Asn Gly Ile
        35                  40                  45
Asn Asn Tyr Lys Asn Pro Lys Leu Thr Arg Met Leu Thr Phe Lys Phe
    50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
                85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
        115                 120                 125
Asp Glu Thr Ala Thr Ile Val Glu Phe Leu Asn Arg Trp Ile Thr Phe
```

```
                    130                 135                 140
Cys Gln Ser Ile Ile Ser Thr Leu Thr Gly Gly Gly Ser Gly Gly
145                 150                 155                 160

Gly Gly Ser Gly Gly Gly Ser Asp Lys Thr His Thr Cys Pro Pro
                    165                 170                 175

Cys Pro Ala Pro Glu Leu Leu Gly Gly Pro Ser Val Phe Leu Phe Pro
                180                 185                 190

Pro Lys Pro Lys Asp Thr Leu Met Ile Ser Arg Thr Pro Glu Val Thr
                195                 200                 205

Cys Val Val Val Asp Val Ser His Glu Asp Pro Glu Val Lys Phe Asn
                210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
                260                 265                 270

Asn Lys Ala Leu Pro Ala Pro Ile Glu Lys Thr Ile Ser Lys Ala Lys
                275                 280                 285

Gly Gln Pro Arg Glu Pro Gln Val Tyr Thr Leu Pro Pro Ser Arg Glu
                290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
                340                 345                 350

Phe Leu Tyr Ser Lys Leu Thr Val Asp Lys Ser Arg Trp Gln Gln Gly
                355                 360                 365

Asn Val Phe Ser Cys Ser Val Met His Glu Ala Leu His Asn His Tyr
                370                 375                 380

Thr Gln Lys Ser Leu Ser Leu Ser Pro Gly Lys
385                 390                 395

<210> SEQ ID NO 77
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 77

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Phe Asp Pro Arg Asp Val Val Ser Asn Ile Asn Val Phe
```

Val Leu Glu Leu Lys Gly Ser Glu Thr Thr Phe Met Cys Glu Tyr Ala
100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Gly Gly Gly Ser Gly Gly
130                 135                 140

Cys Gln Ser Ile Ile Ser Thr Leu Thr Gly Gly Gly Ser Gly Gly
145                 150                 155                 160

Gly Gly Ser Gly Gly Gly Ser Asp Lys Thr His Thr Cys Pro Pro
            165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
            245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
            275                 280                 285

Gly Gln Pro Arg Glu Pro Gln Val Tyr Thr Leu Pro Pro Ser Arg Glu
        290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
            370                 375                 380

Thr Gln Lys Ser Leu Ser Leu Ser Pro Gly Lys
385                 390                 395

<210> SEQ ID NO 78
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 78

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Ala Met Pro Lys Lys Ala Thr Glu Leu Lys His Leu Gln Cys Leu Glu 65                  70                  75                  80
Glu Glu Leu Lys Pro Leu Glu Glu Val Leu Asn Leu Ala Gln Ser Lys
                85                  90                  95

Asn Phe His Phe Asp Pro Arg Asp Val Val Ser Asn Ile Asn Val Phe
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr Gly Gly Gly Ser Gly Gly
145                 150                 155                 160

Gly Gly Ser Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
        210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
        275                 280                 285

Gly Gln Pro Arg Glu Pro Gln Val Tyr Thr Leu Pro Pro Ser Arg Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
    370                 375                 380

Thr Gln Lys Ser Leu Ser Leu Ser Pro Gly Lys
385                 390                 395

<210> SEQ ID NO 79
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 79

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile

```
                 35                  40                  45
Asn Asn Tyr Lys Asn Pro Lys Leu Thr Arg Met Leu Thr Ala Lys Phe
             50                  55                  60

Tyr Met Pro Lys Lys Ala Thr Glu Leu Lys His Leu Gln Cys Leu Glu
 65                  70                  75                  80

Glu Ala Leu Lys Pro Leu Glu Glu Val Leu Asn Leu Ala Gln Ser Lys
                 85                  90                  95

Asn Phe His Phe Asp Pro Arg Asp Val Ser Asn Ile Asn Val Phe
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr Gly Gly Gly Ser Gly Gly
145                 150                 155                 160

Gly Gly Ser Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
            195                 200                 205

Cys Val Val Val Asp Val Ser His Glu Asp Pro Glu Val Lys Phe Asn
210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
            275                 280                 285

Gly Gln Pro Arg Glu Pro Gln Val Tyr Thr Leu Pro Pro Ser Arg Glu
            290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
            355                 360                 365

Asn Val Phe Ser Cys Ser Val Met His Glu Ala Leu His Asn His Tyr
            370                 375                 380

Thr Gln Lys Ser Leu Ser Leu Ser Pro Gly Lys
385                 390                 395

<210> SEQ ID NO 80
<211> LENGTH: 395
<212> TYPE: PRT
<213> ORGANISM: Artificial Sequence
<220> FEATURE:
<223> OTHER INFORMATION: IL-2 Mutein

<400> SEQUENCE: 80

Met Tyr Arg Met Gln Leu Leu Ser Cys Ile Ala Leu Ser Leu Ala Leu
```

```
            1               5                   10                  15
Val Thr Asn Ser Ala Pro Thr Ser Ser Ser Thr Lys Lys Thr Gln Leu
                    20                  25                  30

Gln Leu Glu His Leu Leu Asp Leu Gln Met Ile Leu Asn Gly Ile
                35                  40                  45

Asn Asn Tyr Lys Asn Pro Lys Leu Thr Arg Met Leu Thr Ala Lys Phe
            50                  55                  60

Ala Met Pro Lys Lys Ala Thr Glu Leu Lys His Leu Gln Cys Leu Glu
65                  70                  75                  80

Glu Ala Leu Lys Pro Leu Glu Glu Val Leu Asn Leu Ala Gln Ser Lys
                    85                  90                  95

Asn Phe His Phe Asp Pro Arg Asp Val Val Ser Asn Ile Asn Val Phe
                100                 105                 110

Val Leu Glu Leu Lys Gly Ser Glu Thr Thr Phe Met Cys Glu Tyr Ala
                115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Asp Lys Thr His Thr Cys Pro Pro
                165                 170                 175

Cys Pro Ala Pro Glu Leu Leu Gly Gly Pro Ser Val Phe Leu Phe Pro
                180                 185                 190

Pro Lys Pro Lys Asp Thr Leu Met Ile Ser Arg Thr Pro Glu Val Thr
                195                 200                 205

Cys Val Val Val Asp Val Ser His Glu Asp Pro Glu Val Lys Phe Asn
210                 215                 220

Trp Tyr Val Asp Gly Val Glu Val His Asn Ala Lys Thr Lys Pro Arg
225                 230                 235                 240

Glu Glu Gln Tyr Ala Ser Thr Tyr Arg Val Val Ser Val Leu Thr Val
                245                 250                 255

Leu His Gln Asp Trp Leu Asn Gly Lys Glu Tyr Lys Cys Lys Val Ser
                260                 265                 270

Asn Lys Ala Leu Pro Ala Pro Ile Glu Lys Thr Ile Ser Lys Ala Lys
                275                 280                 285

Gly Gln Pro Arg Glu Pro Gln Val Tyr Thr Leu Pro Pro Ser Arg Glu
                290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
                340                 345                 350

Phe Leu Tyr Ser Lys Leu Thr Val Asp Lys Ser Arg Trp Gln Gln Gly
                355                 360                 365

Asn Val Phe Ser Cys Ser Val Met His Glu Ala Leu His Asn His Tyr
                370                 375                 380

Thr Gln Lys Ser Leu Ser Leu Ser Pro Gly Lys
385                 390                 395

<210> SEQ ID NO 81
<211> LENGTH: 113
<212> TYPE: PRT
<213> ORGANISM: Artificial Sequence
```

<220> FEATURE:
<223> OTHER INFORMATION: IL-13 Cytokine

<400> SEQUENCE: 81

```
Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Gln Phe
            100                 105                 110

Asn
```

<210> SEQ ID NO 82
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 82

```
Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn
```

<210> SEQ ID NO 83
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 83

```
Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45
```

```
Glu Ser Leu Ile Asn Val Ser Gly Cys Ser Ala Ile Glu Lys Thr Gln
            50                  55                  60

Arg Met Leu Ser Gly Phe Cys Pro His Lys Val Ser Ala Gly Gln Phe
 65                  70                  75                  80

Ser Ser Leu His Val Arg Gly Ser Lys Ile Glu Val Ala Gln Phe Val
                85                  90                  95

Lys Asp Leu Leu His His Leu Arg Ala Leu Phe Arg Glu Gly Gln Phe
                100                 105                 110

Asn

<210> SEQ ID NO 84
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 84

Pro Gly Pro Val Pro Pro Ser Thr Ala Val Arg Glu Leu Ile Glu Glu
 1               5                  10                  15

Leu Ile Asn Ile Thr Gln Asn Gln Lys Ala Pro Leu Cys Asn Gly Ser
                20                  25                  30

Met Val Trp Ser Ile Asn Arg Thr Ala Gly Met Tyr Cys Ala Ala Leu
            35                  40                  45

Glu Ser Leu Ile Asn Val Ser Gly Cys Ser Ala Ile Glu Lys Thr Gln
            50                  55                  60

Arg Met Leu Ser Gly Phe Cys Pro His Lys Val Ser Ala Gly Gln Phe
 65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
                100                 105                 110

Asn

<210> SEQ ID NO 85
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 85

Pro Gly Pro Val Pro Pro Ser Thr Ala Leu Ile Glu Leu Ile Glu Glu
 1               5                  10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Ile Tyr Cys Ala Ala Leu
            35                  40                  45

Glu Ser Leu Ile Asn Val Ser Gly Cys Ser Ala Ile Glu Lys Thr Gln
            50                  55                  60

Arg Met Leu Ser Gly Phe Cys Pro His Lys Val Ser Ala Gly Gln Phe
 65                  70                  75                  80

Ser Ser Leu His Val Lys Gly Ser Lys Ile Glu Val Ala Gln Phe Val
                85                  90                  95

Lys Asp Leu Leu His His Leu Arg Ala Leu Met Arg Glu Gly Gln Phe
                100                 105                 110
```

Asn

<210> SEQ ID NO 86
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 86

```
Pro Gly Pro Val Pro Pro Ser Thr Ala Ile Arg Glu Leu Ile Glu Glu
1               5                   10                  15

Leu Leu Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Lys Ser Lys Ile Glu Val Ala Gln Phe Val
                85                  90                  95

Lys Asp Leu Leu His His Leu Arg Ala Leu Phe Arg Glu Gly Gln Phe
                100                 105                 110

Asn
```

<210> SEQ ID NO 87
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 87

```
Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Ser Arg Ile Glu Val Ala Gln Phe Val
                85                  90                  95

Lys Asp Leu Leu His His Leu Arg Thr Leu Phe Arg Glu Gly Gln Phe
                100                 105                 110

Asn
```

<210> SEQ ID NO 88
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 88

```
Pro Gly Pro Val Pro Pro Ser Thr Ala Leu Arg Glu Leu Ile Glu Glu
```

```
                1               5                  10                 15
            Leu Ile Asn Ile Thr Gln Asn Glu Lys Ala Pro Leu Cys Asn Gly Ser
                            20                 25                 30

Met Val Trp Ser Ile Asn Leu Thr Ala Gly Ile Tyr Cys Ala Ala Leu
                            35                 40                 45

Glu Ser Leu Ile Asn Val Ser Gly Cys Ser Ala Ile Glu Lys Thr Gln
                            50                 55                 60

Arg Met Leu Ser Gly Phe Cys Pro His Lys Val Ser Ala Gly Gln Phe
             65                 70                 75                 80

Ser Ser Leu His Val Thr Gly Ser Lys Ile Glu Val Ala Gln Phe Val
                                85                 90                 95

Lys Asp Leu Leu Tyr His Leu Arg Ala Leu Phe Arg Glu Gly Gln Phe
                               100                105                110

Asn
```

<210> SEQ ID NO 89
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 89

```
            Pro Gly Pro Val Pro Ser Thr Ala Leu Ser Glu Leu Ile Glu Glu
            1               5                  10                 15

Leu Ile Asn Ile Thr Gln Asn Gln Lys Ala Pro Leu Cys Asn Gly Ser
                            20                 25                 30

Met Val Trp Ser Ile Asn Pro Thr Ala Gly Met Tyr Cys Ala Ala Leu
                            35                 40                 45

Glu Ser Leu Ile Asn Val Ser Gly Cys Ser Ala Ile Glu Lys Thr Gln
                            50                 55                 60

Arg Met Leu Ser Gly Phe Cys Pro His Lys Val Ala Ala Gly Gln Phe
             65                 70                 75                 80

Ser Ser Leu His Asp Lys Gly Ser Met Ile Glu Val Ala Gln Phe Val
                                85                 90                 95

Lys Asp Leu Leu Tyr His Leu Arg Thr Leu Phe Arg Glu Gly Gln Phe
                               100                105                110

Asn
```

<210> SEQ ID NO 90
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 90

```
            Pro Gly Pro Val Pro Ser Thr Ala Thr Arg Glu Leu Ile Glu Glu
            1               5                  10                 15

Leu Ile Asn Ile Thr Gln Asn Gln Lys Ala Pro Leu Cys Asn Gly Ser
                            20                 25                 30

Met Val Trp Ser Ile Asn Leu Thr Ala Asp Met Tyr Cys Ala Ala Leu
                            35                 40                 45

Glu Ser Leu Ile Asn Val Ser Gly Cys Ser Ala Ile Glu Lys Thr Gln
                            50                 55                 60

Arg Met Leu Ser Gly Phe Cys Pro His Lys Val Ser Val Gly Gln Phe
             65                 70                 75                 80
```

```
Ser Ser Leu His Val Arg Gly Ser Lys Ile Glu Val Ala Gln Phe Val
                85                  90                  95

Lys Asp Leu Leu Tyr His Leu Arg Thr Leu Phe Arg Glu Gly Gln Phe
                100                 105                 110

Asn
```

<210> SEQ ID NO 91
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 91

```
Pro Gly Pro Val Pro Ser Thr Ala Asp Ile Glu Leu Ile Ala Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Asp Met Tyr Cys Ala Ala Leu
                35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
                85                  90                  95

Lys Asp Leu Leu Leu His Leu Lys Lys Leu Phe Lys Glu Gly Gln Phe
                100                 105                 110

Asn
```

<210> SEQ ID NO 92
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 92

```
Pro Gly Pro Val Pro Ser Thr Ala Ala Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
                35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Leu
65                  70                  75                  80

Ser Ser Leu His Val Thr Gly Lys Arg Ile Glu Val Ala Gln Phe Val
                85                  90                  95

Lys Asp Leu Leu Asn His Leu Arg Ala Leu Phe Lys Glu Gly Gln Phe
                100                 105                 110

Asn
```

<210> SEQ ID NO 93
<211> LENGTH: 113
<212> TYPE: PRT

<213> ORGANISM: Artificial Sequence
<220> FEATURE:
<223> OTHER INFORMATION: IL-13 Cytokine

<400> SEQUENCE: 93

```
Pro Gly Pro Val Pro Pro Ser Thr Ala Val Arg Glu Leu Ile Glu Glu
1               5                   10                  15
Leu Val Asn Ile Thr Gln Asn Gln Lys Ala Pro Leu Cys Asn Gly Ser
            20                  25                  30
Met Val Trp Ser Ile Asn Leu Thr Ala Gly Met Tyr Cys Ala Ala Leu
        35                  40                  45
Glu Ser Leu Ile Asn Val Ser Gly Cys Ser Ala Ile Glu Lys Thr Gln
    50                  55                  60
Arg Met Leu Ser Gly Phe Cys Pro His Lys Val Ser Ala Gly Gln Phe
65                  70                  75                  80
Ser Ser Leu His Val Arg Asp Thr Arg Ile Glu Val Ala Gln Phe Val
                85                  90                  95
Lys Asp Leu Leu Asn His Leu Lys Glu Leu Phe Thr Glu Gly Gln Phe
            100                 105                 110
Asn
```

<210> SEQ ID NO 94
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 94

```
Pro Gly Pro Val Pro Pro Ser Thr Ala Leu Ser Glu Leu Met Glu Glu
1               5                   10                  15
Leu Val Asn Ile Thr Gln Asn Gln Lys Ala Pro Leu Cys Asn Gly Ser
            20                  25                  30
Met Val Trp Ser Ile Asn Leu Thr Ala Gly Met Tyr Cys Ala Ala Leu
        35                  40                  45
Glu Ser Leu Ile Asn Val Ser Gly Cys Ser Ala Ile Glu Lys Thr Gln
    50                  55                  60
Arg Met Leu Ser Gly Phe Cys Pro His Lys Val Ser Ala Gly Gln Phe
65                  70                  75                  80
Ser Ser Leu His Val Arg Asp Ser Lys Ile Glu Val Ala Gln Phe Val
                85                  90                  95
Lys Asp Leu Leu Asn His Leu Lys Ala Leu Phe Lys Glu Gly Gln Phe
            100                 105                 110
Asn
```

<210> SEQ ID NO 95
<211> LENGTH: 112
<212> TYPE: PRT
<213> ORGANISM: Artificial Sequence
<220> FEATURE:
<223> OTHER INFORMATION: IL-13 Cytokine

<400> SEQUENCE: 95

```
Gly Pro Val Pro Pro Ser Thr Ala Phe Arg Glu Leu Ile Glu Glu Leu
1               5                   10                  15
Val Asn Ile Thr Gln Asn Gln Lys Ala Pro Leu Cys Asn Gly Ser Met
            20                  25                  30
Val Trp Ser Ile Asn Leu Thr Ala Gly Met Tyr Cys Ala Ala Leu Glu
```

```
            35                  40                  45
Ser Leu Ile Asn Val Ser Gly Cys Ser Ala Ile Glu Lys Thr Gln Arg
 50                  55                  60

Met Leu Ser Gly Phe Cys Pro His Lys Val Ser Pro Gly Gln Phe Ser
65                  70                  75                  80

Ser Leu His Val Thr Asn Ser Arg Ile Glu Val Ala Gln Phe Val Lys
                85                  90                  95

Asp Leu Leu Asn His Leu Lys Ala Leu Phe Lys Glu Gly Gln Tyr Asn
            100                 105                 110
```

<210> SEQ ID NO 96
<211> LENGTH: 112
<212> TYPE: PRT
<213> ORGANISM: Artificial Sequence
<220> FEATURE:
<223> OTHER INFORMATION: IL-13 Cytokine

<400> SEQUENCE: 96

```
Gly Pro Val Pro Pro Ser Thr Ala His Leu Glu Leu Ile Glu Glu Leu
1               5                   10                  15

Ile Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
 50                  55                  60

Met Leu Ser Gly Phe Cys Pro His Lys Val Ser Ala Gly Gln Phe Ser
65                  70                  75                  80

Ser Leu His Val Lys Glu Thr Arg Ile Glu Val Ala Gln Phe Val Lys
                85                  90                  95

Asp Leu Leu Asn His Leu Lys Thr Leu Phe Lys Glu Gly Gln Phe Asn
            100                 105                 110
```

<210> SEQ ID NO 97
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 97

```
Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Pro Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
65                  70                  75                  80

Ser Ser Leu His Val Met Asp Thr Arg Ile Glu Val Ala Gln Phe Val
                85                  90                  95

Lys Asp Leu Leu Leu His Leu Lys Lys Leu Phe Lys Glu Gly Gln Phe
            100                 105                 110

Asn
```

```
<210> SEQ ID NO 98
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 98

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 99
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 99

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Arg Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Ser Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn

<210> SEQ ID NO 100
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 100

Pro Gly Pro Val Pro Pro Ser Thr Ala Ala Arg Glu Leu Ile Glu Glu
1               5                   10                  15

Leu Phe Asn Ile Thr Gln Asn Gln Lys Ala Pro Leu Cys Asn Gly Ser
```

```
            20                  25                  30
Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Lys
        50                  55                  60

Arg Met Leu Ser Gly Phe Cys Pro His Lys Val Ser Ala Gly Gln Phe
65                  70                  75                  80

Pro Ser Leu His Val Lys Lys Thr Arg Ile Glu Val Ala Gln Phe Val
                85                  90                  95

Lys Asp Leu Leu Ile His Leu Arg Lys Leu Phe Lys Glu Gly Gln Phe
                100                 105                 110

Asn
```

<210> SEQ ID NO 101
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 101

```
Pro Gly Pro Val Pro Ser Thr Ala Leu Ile Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Lys Gly Ser Lys Ile Glu Val Ala Gln Phe Val
                85                  90                  95

Lys Asp Leu Leu His His Leu Arg Ala Leu Met Arg Glu Gly Gln Phe
                100                 105                 110

Asn
```

<210> SEQ ID NO 102
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 102

```
Pro Gly Pro Val Pro Ser Thr Ala Ile Arg Glu Leu Ile Glu Glu
1               5                   10                  15

Leu Leu Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Met Lys Ser Lys Ile Glu Val Ala Gln Phe Val
                85                  90                  95
```

Lys Asp Leu Leu His His Leu Arg Ala Leu Phe Arg Glu Gly Gln Phe
                100                 105                 110

Asn

<210> SEQ ID NO 103
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 103

Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Gly Ser Lys Ile Glu Val Ala Gln Phe Val
                85                  90                  95

Lys Asp Leu Leu His His Leu Arg Ala Leu Phe Arg Glu Gly Gln Phe
                100                 105                 110

Asn

<210> SEQ ID NO 104
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 104

Pro Gly Pro Val Pro Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Ser Arg Ile Glu Val Ala Gln Phe Val
                85                  90                  95

Lys Asp Leu Leu His His Leu Arg Thr Leu Phe Arg Glu Gly Gln Phe
                100                 105                 110

Asn

<210> SEQ ID NO 105
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 105

```
Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
                100                 105                 110

Asn
```

<210> SEQ ID NO 106
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 106

```
Pro Gly Pro Val Pro Pro Ser Thr Ala Leu Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Ser Lys Ile Glu Val Ala Gln Phe Val
                85                  90                  95

Lys Asp Leu Leu Tyr His Leu Arg Ala Leu Phe Arg Glu Gly Gln Phe
                100                 105                 110

Asn
```

<210> SEQ ID NO 107
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 107

```
Pro Gly Pro Val Pro Pro Ser Thr Ala Leu Ser Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
```

```
                    50                  55                  60
Arg Met Leu Ser Gly Phe Cys Pro His Lys Val Ser Ala Gly Gln Phe
 65                  70                  75                  80

Ser Ser Leu His Val Lys Gly Ser Met Ile Glu Val Ala Gln Phe Val
                 85                  90                  95

Lys Asp Leu Leu Tyr His Leu Arg Thr Leu Phe Arg Glu Gly Gln Phe
                100                 105                 110

Asn
```

<210> SEQ ID NO 108
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 108

```
Pro Gly Pro Val Pro Ser Thr Ala Thr Arg Glu Leu Ile Glu Glu
  1               5                  10                  15

Leu Ile Asn Ile Thr Gln Asn Gln Lys Ala Pro Leu Cys Asn Gly Ser
                 20                  25                  30

Met Val Trp Ser Ile Asn Leu Thr Ala Gly Met Tyr Cys Ala Ala Leu
                 35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Arg Gly Ser Lys Ile Glu Val Ala Gln Phe Val
                 85                  90                  95

Lys Asp Leu Leu Tyr His Leu Arg Thr Leu Phe Arg Glu Gly Gln Phe
                100                 105                 110

Asn
```

<210> SEQ ID NO 109
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 109

```
Pro Gly Pro Val Pro Ser Thr Ala Asp Ile Glu Leu Ile Glu Glu
  1               5                  10                  15

Leu Ile Asn Ile Thr Gln Asn Gln Lys Ala Pro Leu Cys Asn Gly Ser
                 20                  25                  30

Met Val Trp Ser Ile Asn Leu Thr Ala Gly Met Tyr Cys Ala Ala Leu
                 35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Lys Lys Thr Arg Ile Glu Val Ala Gln Phe Val
                 85                  90                  95

Lys Asp Leu Leu Leu His Leu Lys Lys Leu Phe Lys Glu Gly Gln Phe
                100                 105                 110

Asn
```

<210> SEQ ID NO 110
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 110

```
Pro Gly Pro Val Pro Pro Ser Thr Ala Ala Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Lys Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn
```

<210> SEQ ID NO 111
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 111

```
Pro Gly Pro Val Pro Pro Ser Thr Ala Val Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Arg Ile Glu Val Ala Gln Phe Val
                85                  90                  95

Lys Asp Leu Leu Asn His Leu Lys Glu Leu Phe Thr Glu Gly Gln Phe
            100                 105                 110

Asn
```

<210> SEQ ID NO 112
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 112

```
Pro Gly Pro Val Pro Pro Ser Thr Ala Leu Ser Glu Leu Met Glu Glu
1               5                   10                  15
```

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Arg Asp Ser Lys Ile Glu Val Ala Gln Phe Val
            85                  90                  95

Lys Asp Leu Leu Asn His Leu Lys Ala Leu Phe Lys Glu Gly Gln Phe
            100                 105                 110

Asn

<210> SEQ ID NO 113
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 113

Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Lys Glu Thr Arg Ile Glu Val Ala Gln Phe Val
            85                  90                  95

Lys Asp Leu Leu Asn His Leu Lys Thr Leu Phe Lys Glu Gly Gln Phe
            100                 105                 110

Asn

<210> SEQ ID NO 114
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 114

Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Met Asp Thr Arg Ile Glu Val Ala Gln Phe Val 85                  90                  95

Lys Asp Leu Leu Leu His Leu Lys Lys Leu Phe Lys Glu Gly Gln Phe
            100                 105                 110

Asn

<210> SEQ ID NO 115
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 115

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn

<210> SEQ ID NO 116
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 116

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Ser Arg Ile Glu Val Ala Gln Phe Val
                85                  90                  95

Lys Asp Leu Leu Asn His Leu Arg Ala Leu Phe Lys Glu Gly Gln Phe
            100                 105                 110

Asn

<210> SEQ ID NO 117
<211> LENGTH: 113
<212> TYPE: PRT
<213> ORGANISM: Artificial Sequence
<220> FEATURE:

<223> OTHER INFORMATION: IL-13 Cytokine

<400> SEQUENCE: 117

Pro Gly Pro Val Pro Pro Ser Thr Ala Ala Arg Glu Leu Ile Glu Glu
1               5                   10                  15

Leu Phe Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
                85                  90                  95

Lys Asp Leu Leu Ile His Leu Arg Lys Leu Phe Lys Glu Gly Gln Phe
                100                 105                 110

Asn

<210> SEQ ID NO 118
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 118

Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
                100                 105                 110

Asn

<210> SEQ ID NO 119
<211> LENGTH: 146
<212> TYPE: PRT
<213> ORGANISM: Artificial Sequence
<220> FEATURE:
<223> OTHER INFORMATION: IL-13 Cytokine

<400> SEQUENCE: 119

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala His Arg Glu Leu Ile Glu
        35                  40                  45

Glu Leu Val Asn Ile Thr Gln Asn Gln Lys Ala Pro Leu Cys Asn Gly
 50                  55                  60

Ser Met Val Trp Ser Ile Asn Leu Thr Ala Gly Met Tyr Cys Ala Ala
 65                  70                  75                  80

Leu Glu Ser Leu Ile Asn Val Ser Gly Cys Ser Ala Ile Glu Lys Thr
                 85                  90                  95

Gln Arg Met Leu Ser Gly Phe Cys Pro His Lys Val Ser Ala Gly Gln
            100                 105                 110

Phe Ser Ser Leu His Val Thr Gly Arg Lys Ile Glu Val Ala Gln Phe
                115                 120                 125

Val Lys Asp Leu Leu His Leu Lys Lys Leu Phe Lys Glu Gly Gln
130                 135                 140

Phe Asn
145

<210> SEQ ID NO 120
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 120

Pro Gly Pro Val Pro Ser Thr Ala Val Arg Ala Leu Ile Glu Glu
 1               5                  10                  15

Leu Ile Asn Ile Thr Gln Asn Gln Lys Ala Pro Leu Cys Asn Gly Ser
                 20                  25                  30

Met Val Trp Ser Ile Asn Arg Thr Ala Gly Met Tyr Cys Ala Ala Leu
             35                  40                  45

Glu Ser Leu Ile Asn Val Ser Gly Cys Ser Ala Ile Glu Lys Thr Gln
 50                  55                  60

Asp Met Leu Ser Gly Phe Cys Pro His Lys Val Ser Ala Gly Gln Phe
 65                  70                  75                  80

Ser Ser Leu His Val Arg Ser Lys Ile Glu Val Ala Gln Phe Val
                 85                  90                  95

Lys Asp Leu Leu Phe His Leu Arg Thr Leu Phe Arg Glu Gly Gln Phe
            100                 105                 110

Asn

<210> SEQ ID NO 121
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 121

Pro Gly Pro Val Pro Ser Thr Ala Val Arg Ala Leu Ile Glu Glu
 1               5                  10                  15

Leu Ile Asn Ile Thr Gln Asn Gln Lys Ala Pro Leu Cys Asn Gly Ser
                 20                  25                  30

Met Val Trp Ser Ile Asn Leu Thr Ala Gly Met Tyr Cys Ala Ala Leu
             35                  40                  45

Glu Ser Leu Ile Asn Val Ser Gly Cys Ser Ala Ile Glu Lys Thr Gln
 50                  55                  60

Asp Met Leu Ser Gly Phe Cys Pro His Lys Val Ser Ala Gly Gln Phe
 65                  70                  75                  80

Ser Ser Leu His Val Arg Ser Lys Ile Glu Val Ala Gln Phe Val
            85                  90                  95

Lys Asp Leu Leu Phe His Leu Arg Thr Leu Phe Arg Glu Gly Gln Phe
            100                 105                 110

Asn

<210> SEQ ID NO 122
<211> LENGTH: 114
<212> TYPE: PRT
<213> ORGANISM: Artificial Sequence
<220> FEATURE:
<223> OTHER INFORMATION: IL-13 Cytokine

<400> SEQUENCE: 122

Met Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Gln
            100                 105                 110

Phe Asn

<210> SEQ ID NO 123
<211> LENGTH: 117
<212> TYPE: PRT
<213> ORGANISM: Artificial Sequence
<220> FEATURE:
<223> OTHER INFORMATION: IL-13 Cytokine

<400> SEQUENCE: 123

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Asp Thr Lys Ile
        35                  40                  45

Glu Val Ala Gln Phe Val Lys Asp Leu Leu Leu His Leu Lys Lys Leu
50                  55                  60

Phe Arg Glu Gly Gln Phe Asn Gly Gly Ser Gly Pro Gly Pro Val Pro
65                  70                  75                  80

Pro Ser Thr Ala Leu Arg Glu Leu Ile Glu Glu Leu Val Asn Ile Thr
                85                  90                  95

Gln Asn Gln Lys Ala Pro Leu Cys Asn Gly Ser Met Val Trp Ser Ile
            100                 105                 110

Asn Leu Thr Ala Gly
        115

<210> SEQ ID NO 124
<211> LENGTH: 118
<212> TYPE: PRT

```
<213> ORGANISM: Artificial Sequence
<220> FEATURE:
<223> OTHER INFORMATION: IL-13 Cytokine

<400> SEQUENCE: 124

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
                20                  25                  30

Val Ser Ala Gly Gln Phe Ser Ser Leu His Val Arg Asp Thr Lys Ile
            35                  40                  45

Glu Val Ala Gln Phe Val Lys Asp Leu Leu His Leu Lys Lys Leu
    50                  55                  60

Phe Arg Glu Gly Gln Phe Asn Gly Gly Ser Gly Met Pro Gly Pro Val
65                  70                  75                  80

Pro Pro Ser Thr Ala Leu Arg Glu Leu Ile Glu Leu Val Asn Ile
                85                  90                  95

Thr Gln Asn Gln Lys Ala Pro Leu Cys Asn Gly Ser Met Val Trp Ser
                100                 105                 110

Ile Asn Leu Thr Ala Gly
            115

<210> SEQ ID NO 125
<211> LENGTH: 117
<212> TYPE: PRT
<213> ORGANISM: Artificial Sequence
<220> FEATURE:
<223> OTHER INFORMATION: IL-13 Cytokine

<400> SEQUENCE: 125

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
                20                  25                  30

Val Ser Ala Gly Gln Phe Ser Ser Leu His Val Arg Ser Ser Lys Ile
            35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Pro Gly Pro Val Pro
65                  70                  75                  80

Pro Ser Thr Ala Val Arg Glu Leu Ile Glu Glu Leu Ile Asn Ile Thr
                85                  90                  95

Gln Asn Gln Lys Ala Pro Leu Cys Asn Gly Ser Met Val Trp Ser Ile
                100                 105                 110

Asn Arg Thr Ala Gly
            115

<210> SEQ ID NO 126
<211> LENGTH: 118
<212> TYPE: PRT
<213> ORGANISM: Artificial Sequence
<220> FEATURE:
<223> OTHER INFORMATION: IL-13 Cytokine

<400> SEQUENCE: 126

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
                20                  25                  30
```

```
Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
50                  55                  60

Phe Arg Glu Gly Gln Phe Asn Gly Gly Ser Gly Met Pro Gly Pro Val
65                  70                  75                  80

Pro Pro Ser Thr Ala Val Arg Glu Leu Ile Glu Glu Leu Ile Asn Ile
                85                  90                  95

Thr Gln Asn Gln Lys Ala Pro Leu Cys Asn Gly Ser Met Val Trp Ser
            100                 105                 110

Ile Asn Arg Thr Ala Gly
        115

<210> SEQ ID NO 127
<211> LENGTH: 117
<212> TYPE: PRT
<213> ORGANISM: Artificial Sequence
<220> FEATURE:
<223> OTHER INFORMATION: IL-13 Cytokine

<400> SEQUENCE: 127

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
50                  55                  60

Phe Arg Glu Gly Gln Phe Asn Gly Gly Ser Gly Pro Gly Pro Val Pro
65                  70                  75                  80

Pro Ser Thr Ala Val Arg Ala Leu Ile Glu Glu Leu Ile Asn Ile Thr
                85                  90                  95

Gln Asn Gln Lys Ala Pro Leu Cys Asn Gly Ser Met Val Trp Ser Ile
            100                 105                 110

Asn Leu Thr Ala Gly
        115

<210> SEQ ID NO 128
<211> LENGTH: 118
<212> TYPE: PRT
<213> ORGANISM: Artificial Sequence
<220> FEATURE:
<223> OTHER INFORMATION: IL-13 Cytokine

<400> SEQUENCE: 128

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
50                  55                  60

Phe Arg Glu Gly Gln Phe Asn Gly Gly Ser Gly Met Pro Gly Pro Val
65                  70                  75                  80

Pro Pro Ser Thr Ala Val Arg Ala Leu Ile Glu Glu Leu Ile Asn Ile
```

```
                        85                  90                  95

Thr Gln Asn Gln Lys Ala Pro Leu Cys Asn Gly Ser Met Val Trp Ser
                100                 105                 110

Ile Asn Leu Thr Ala Gly
            115

<210> SEQ ID NO 129
<211> LENGTH: 153
<212> TYPE: PRT
<213> ORGANISM: Artificial Sequence
<220> FEATURE:
<223> OTHER INFORMATION: IL-4 Cytokine

<400> SEQUENCE: 129

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
        130                 135                 140

Arg Glu Lys Tyr Ser Lys Cys Ser Ser
145                 150

<210> SEQ ID NO 130
<211> LENGTH: 130
<212> TYPE: PRT
<213> ORGANISM: Artificial Sequence
<220> FEATURE:
<223> OTHER INFORMATION: IL-4 Cytokine

<400> SEQUENCE: 130

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
                20                  25                  30

Ile Phe Ala Ala Ser Lys Asp Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
                100                 105                 110
```

```
Phe Leu Glu Arg Leu Lys Thr Ile Met Arg Glu Lys Tyr Ser Lys Cys
            115                 120                 125
Ser Ser
    130

<210> SEQ ID NO 131
<211> LENGTH: 128
<212> TYPE: PRT
<213> ORGANISM: Artificial Sequence
<220> FEATURE:
<223> OTHER INFORMATION: IL-4 Cytokine

<400> SEQUENCE: 131

Lys Cys Asp Ile Thr Leu Gln Glu Ile Ile Lys Thr Leu Asn Ser Leu
1               5                   10                  15

Thr Glu Gln Lys Thr Leu Cys Thr Glu Leu Thr Val Thr Asp Ile Phe
            20                  25                  30

Ala Ala Ser Lys Asn Thr Thr Glu Lys Glu Thr Phe Cys Arg Ala Ala
        35                  40                  45

Thr Val Leu Arg Gln Phe Tyr Ser His His Glu Lys Asp Thr Arg Cys
50                  55                  60

Leu Gly Ala Thr Ala Gln Gln Phe His Arg His Lys Gln Leu Ile Arg
65                  70                  75                  80

Phe Leu Lys Arg Leu Asp Arg Asn Leu Trp Gly Leu Ala Gly Leu Asn
                85                  90                  95

Ser Cys Pro Val Lys Glu Ala Asn Gln Ser Thr Leu Glu Asn Phe Leu
            100                 105                 110

Glu Arg Leu Lys Thr Ile Met Lys Glu Lys Phe Arg Lys Cys Ser Ser
        115                 120                 125

<210> SEQ ID NO 132
<211> LENGTH: 134
<212> TYPE: PRT
<213> ORGANISM: Artificial Sequence
<220> FEATURE:
<223> OTHER INFORMATION: IL-4 Cytokine

<400> SEQUENCE: 132

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser
    130

<210> SEQ ID NO 133
```

```
<211> LENGTH: 134
<212> TYPE: PRT
<213> ORGANISM: Artificial Sequence
<220> FEATURE:
<223> OTHER INFORMATION: IL-4 Cytokine

<400> SEQUENCE: 133

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser
    130

<210> SEQ ID NO 134
<211> LENGTH: 252
<212> TYPE: PRT
<213> ORGANISM: Artificial Sequence
<220> FEATURE:
<223> OTHER INFORMATION: IL-4 Cytokine

<400> SEQUENCE: 134

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Arg Gln Phe Tyr Ser His His Glu Lys Asp
    130                 135                 140

Thr Arg Cys Leu Gly Ala Thr Ala Gln Gln Phe His Arg His Lys Gln
145                 150                 155                 160

Leu Ile Arg Phe Leu Lys Arg Leu Asp Arg Asn Leu Trp Gly Leu Ala
                165                 170                 175

Gly Leu Asn Ser Cys Pro Val Lys Glu Ala Asn Gln Ser Thr Leu Glu
```

```
                180             185             190
Asn Phe Leu Glu Arg Leu Arg Val Ile Met Gln Ser Lys Trp Phe Lys
                195                 200                 205

Cys Gly Ala Gly Gly Asn Gly Gly His Lys Cys Asp Ile Thr Leu Gln
            210                 215                 220

Glu Ile Ile Lys Thr Leu Asn Ser Leu Thr Glu Gln Lys Thr Leu Cys
225                 230                 235                 240

Thr Glu Leu Thr Val Thr Asp Ile Phe Ala Ala Ser
                245                 250

<210> SEQ ID NO 135
<211> LENGTH: 133
<212> TYPE: PRT
<213> ORGANISM: Artificial Sequence
<220> FEATURE:
<223> OTHER INFORMATION: IL-4 Cytokine

<400> SEQUENCE: 135

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Lys Cys Ser Ser Gly Gly Asn Gly
                85                  90                  95

Gly His Lys Cys Asp Ile Thr Leu Gln Glu Ile Ile Lys Thr Leu Asn
            100                 105                 110

Ser Leu Thr Glu Gln Lys Thr Leu Cys Thr Glu Leu Thr Val Thr Asp
        115                 120                 125

Ile Phe Ala Ala Ser
        130

<210> SEQ ID NO 136
<211> LENGTH: 178
<212> TYPE: PRT
<213> ORGANISM: Artificial Sequence
<220> FEATURE:
<223> OTHER INFORMATION: IL-10 Cytokine

<400> SEQUENCE: 136

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95
```

```
Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 137
<211> LENGTH: 219
<212> TYPE: PRT
<213> ORGANISM: Artificial Sequence
<220> FEATURE:
<223> OTHER INFORMATION: IL-12A Cytokine

<400> SEQUENCE: 137

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 138
<211> LENGTH: 328
<212> TYPE: PRT
<213> ORGANISM: Artificial Sequence
<220> FEATURE:
<223> OTHER INFORMATION: IL-12B Cytokine

<400> SEQUENCE: 138
```

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
                35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
            130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 139
<211> LENGTH: 162
<212> TYPE: PRT
<213> ORGANISM: Artificial Sequence
<220> FEATURE:
<223> OTHER INFORMATION: IL-15 Cytokine

<400> SEQUENCE: 139

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30
```

Val Phe Ile Leu Gly Cys Phe Ser Ala Gly Leu Pro Lys Thr Glu Ala
             35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 140
<211> LENGTH: 193
<212> TYPE: PRT
<213> ORGANISM: Artificial Sequence
<220> FEATURE:
<223> OTHER INFORMATION: IL-18 Cytokine

<400> SEQUENCE: 140

Met Ala Ala Glu Pro Val Glu Asp Asn Cys Ile Asn Phe Val Ala Met
 1               5                  10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
             35                  40                  45

Arg Asn Leu Asn Asp Gln Val Leu Phe Ile Asp Gln Gly Asn Arg Pro
 50                  55                  60

Leu Phe Glu Asp Met Thr Asp Ser Asp Cys Arg Asp Asn Ala Pro Arg
 65                  70                  75                  80

Thr Ile Phe Ile Ile Ser Met Tyr Lys Asp Ser Gln Pro Arg Gly Met
                 85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 141
<211> LENGTH: 157
<212> TYPE: PRT
<213> ORGANISM: Artificial Sequence
<220> FEATURE:
<223> OTHER INFORMATION: IL-18 Cytokine

<400> SEQUENCE: 141

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 142
<211> LENGTH: 261
<212> TYPE: PRT
<213> ORGANISM: Artificial Sequence
<220> FEATURE:
<223> OTHER INFORMATION: IL-13 Variant-H9

<400> SEQUENCE: 142

```
Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn Gly Gly Gly Gly Ser Gly Gly Gly Ser Gly Gly Gly Gly Ser
        115                 120                 125

Ala Pro Thr Ser Ser Ser Thr Lys Lys Thr Gln Leu Gln Leu Glu His
    130                 135                 140

Leu Leu Leu Asp Leu Gln Met Ile Leu Asn Gly Ile Asn Asn Tyr Lys
145                 150                 155                 160

Asn Pro Lys Leu Thr Arg Met Leu Thr Phe Lys Phe Tyr Met Pro Lys
                165                 170                 175

Lys Ala Thr Glu Leu Lys His Leu Gln Cys Leu Glu Glu Glu Leu Lys
```

```
              180                 185                 190
Pro Leu Glu Glu Val Leu Asn Leu Ala Gln Ser Lys Asn Phe His Phe
            195                 200                 205

Asp Pro Arg Asp Val Val Ser Asn Ile Asn Val Phe Val Leu Glu Leu
            210                 215                 220

Lys Gly Ser Glu Thr Thr Phe Met Cys Glu Tyr Ala Asp Glu Thr Ala
225                 230                 235                 240

Thr Ile Val Glu Phe Leu Asn Arg Trp Ile Thr Phe Cys Gln Ser Ile
                245                 250                 255

Ile Ser Thr Leu Thr
            260

<210> SEQ ID NO 143
<211> LENGTH: 261
<212> TYPE: PRT
<213> ORGANISM: Artificial Sequence
<220> FEATURE:
<223> OTHER INFORMATION: IL-13 Variant-H9

<400> SEQUENCE: 143

Pro Gly Pro Val Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn Gly Gly Gly Gly Ser Gly Gly Gly Gly Ser Gly Gly Gly Gly Ser
        115                 120                 125

Ala Pro Thr Ser Ser Ser Thr Lys Lys Thr Gln Leu Gln Leu Glu His
    130                 135                 140

Leu Leu Leu Asp Leu Gln Met Ile Leu Asn Gly Ile Asn Asn Tyr Lys
145                 150                 155                 160

Asn Pro Lys Leu Thr Arg Met Leu Thr Phe Lys Phe Tyr Met Pro Lys
                165                 170                 175

Lys Ala Thr Glu Leu Lys His Leu Gln Cys Leu Glu Glu Glu Leu Lys
            180                 185                 190

Pro Leu Glu Glu Val Leu Asn Leu Ala Gln Ser Lys Asn Phe His Phe
        195                 200                 205

Asp Pro Arg Asp Val Val Ser Asn Ile Asn Val Phe Val Leu Glu Leu
    210                 215                 220

Lys Gly Ser Glu Thr Thr Phe Met Cys Glu Tyr Ala Asp Glu Thr Ala
225                 230                 235                 240

Thr Ile Val Glu Phe Leu Asn Arg Trp Ile Thr Phe Cys Gln Ser Ile
                245                 250                 255

Ile Ser Thr Leu Thr
            260
```

-continued

```
<210> SEQ ID NO 144
<211> LENGTH: 651
<212> TYPE: PRT
<213> ORGANISM: Artificial Sequence
<220> FEATURE:
<223> OTHER INFORMATION: H9-IL-12

<400> SEQUENCE: 144

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Ser Arg Asn Leu Pro Val Ala Thr Pro Asp Pro Gly Met
145                 150                 155                 160

Phe Pro Cys Leu His His Ser Gln Asn Leu Leu Arg Ala Val Ser Asn
                165                 170                 175

Met Leu Gln Lys Ala Arg Gln Thr Leu Glu Phe Tyr Pro Cys Thr Ser
            180                 185                 190

Glu Glu Ile Asp His Glu Asp Ile Thr Lys Asp Lys Thr Ser Thr Val
        195                 200                 205

Glu Ala Cys Leu Pro Leu Glu Leu Thr Lys Asn Glu Ser Cys Leu Asn
    210                 215                 220

Ser Arg Glu Thr Ser Phe Ile Thr Asn Gly Ser Cys Leu Ala Ser Arg
225                 230                 235                 240

Lys Thr Ser Phe Met Met Ala Leu Cys Leu Ser Ser Ile Tyr Glu Asp
                245                 250                 255

Leu Lys Met Tyr Gln Val Glu Phe Lys Thr Met Asn Ala Lys Leu Leu
            260                 265                 270

Met Asp Pro Lys Arg Gln Ile Phe Leu Asp Gln Asn Met Leu Ala Val
        275                 280                 285

Ile Asp Glu Leu Met Gln Ala Leu Asn Phe Asn Ser Glu Thr Val Pro
    290                 295                 300

Gln Lys Ser Ser Leu Glu Glu Pro Asp Phe Tyr Lys Thr Lys Ile Lys
305                 310                 315                 320

Leu Cys Ile Leu Leu His Ala Phe Arg Ile Arg Ala Val Thr Ile Asp
                325                 330                 335

Arg Val Met Ser Tyr Leu Asn Ala Ser Ile Trp Glu Leu Lys Lys Asp
            340                 345                 350

Val Tyr Val Val Glu Leu Asp Trp Tyr Pro Asp Ala Pro Gly Glu Met
        355                 360                 365

Val Val Leu Thr Cys Asp Thr Pro Glu Glu Asp Gly Ile Thr Trp Thr
```

370             375             380
Leu Asp Gln Ser Ser Glu Val Leu Gly Ser Gly Lys Thr Leu Thr Ile
385                 390             395                 400

Gln Val Lys Glu Phe Gly Asp Ala Gly Gln Tyr Thr Cys His Lys Gly
            405             410                 415

Gly Glu Val Leu Ser His Ser Leu Leu Leu His Lys Lys Glu Asp
            420             425             430

Gly Ile Trp Ser Thr Asp Ile Leu Lys Asp Gln Lys Glu Pro Lys Asn
            435             440             445

Lys Thr Phe Leu Arg Cys Glu Ala Lys Asn Tyr Ser Gly Arg Phe Thr
450             455             460

Cys Trp Trp Leu Thr Thr Ile Ser Thr Asp Leu Thr Phe Ser Val Lys
465             470             475             480

Ser Ser Arg Gly Ser Ser Asp Pro Gln Gly Val Thr Cys Gly Ala Ala
            485             490             495

Thr Leu Ser Ala Glu Arg Val Arg Gly Asp Asn Lys Glu Tyr Glu Tyr
            500             505             510

Ser Val Glu Cys Gln Glu Asp Ser Ala Cys Pro Ala Ala Glu Glu Ser
            515             520             525

Leu Pro Ile Glu Val Met Val Asp Ala Val His Lys Leu Lys Tyr Glu
530             535             540

Asn Tyr Thr Ser Ser Phe Phe Ile Arg Asp Ile Ile Lys Pro Asp Pro
545             550             555             560

Pro Lys Asn Leu Gln Leu Lys Pro Leu Lys Asn Ser Arg Gln Val Glu
            565             570             575

Val Ser Trp Glu Tyr Pro Asp Thr Trp Ser Thr Pro His Ser Tyr Phe
            580             585             590

Ser Leu Thr Phe Cys Val Gln Val Gln Gly Lys Ser Lys Arg Glu Lys
            595             600             605

Lys Asp Arg Val Phe Thr Asp Lys Thr Ser Ala Thr Val Ile Cys Arg
610             615             620

Lys Asn Ala Ser Ile Ser Val Arg Ala Gln Asp Arg Tyr Tyr Ser Ser
625             630             635             640

Ser Trp Ser Glu Trp Ala Ser Val Pro Cys Ser
            645             650

<210> SEQ ID NO 145
<211> LENGTH: 305
<212> TYPE: PRT
<213> ORGANISM: Artificial Sequence
<220> FEATURE:
<223> OTHER INFORMATION: H9-IL18

<400> SEQUENCE: 145

Ala Pro Thr Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
            35              40              45

Lys Ala Thr Glu Leu Lys His Leu Gln Cys Leu Glu Glu Glu Leu Lys
        50              55              60

Pro Leu Glu Glu Val Leu Asn Leu Ala Gln Ser Lys Asn Phe His Phe
65              70              75              80

Asp Pro Arg Asp Val Val Ser Asn Ile Asn Val Phe Val Leu Glu Leu

```
                85                  90                  95
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Gly Ser Gly
        130                 135                 140

Gly Gly Gly Ser Tyr Phe Gly Lys Leu Glu Ser Lys Leu Ser Val Ile
145                 150                 155                 160

Arg Asn Leu Asn Asp Gln Val Leu Phe Ile Asp Gln Gly Asn Arg Pro
                165                 170                 175

Leu Phe Glu Asp Met Thr Asp Ser Asp Cys Arg Asp Asn Ala Pro Arg
                180                 185                 190

Thr Ile Phe Ile Ile Ser Met Tyr Lys Asp Ser Gln Pro Arg Gly Met
                195                 200                 205

Ala Val Thr Ile Ser Val Lys Cys Glu Lys Ile Ser Thr Leu Ser Cys
        210                 215                 220

Glu Asn Lys Ile Ile Ser Phe Lys Glu Met Asn Pro Pro Asp Asn Ile
225                 230                 235                 240

Lys Asp Thr Lys Ser Asp Ile Ile Phe Phe Gln Arg Ser Val Pro Gly
                245                 250                 255

His Asp Asn Lys Met Gln Phe Glu Ser Ser Ser Tyr Glu Gly Tyr Phe
                260                 265                 270

Leu Ala Cys Glu Lys Glu Arg Asp Leu Phe Lys Leu Ile Leu Lys Lys
                275                 280                 285

Glu Asp Glu Leu Gly Asp Arg Ser Ile Met Phe Thr Val Gln Asn Glu
                290                 295                 300

Asp
305

<210> SEQ ID NO 146
<211> LENGTH: 20
<212> TYPE: PRT
<213> ORGANISM: Artificial Sequence
<220> FEATURE:
<223> OTHER INFORMATION: H9-Fc Fusion

<400> SEQUENCE: 146

Met Tyr Arg Met Gln Leu Leu Ser Cys Ile Ala Leu Ser Leu Ala Leu
1               5                   10                  15

Val Thr Asn Ser
            20

<210> SEQ ID NO 147
<211> LENGTH: 120
<212> TYPE: PRT
<213> ORGANISM: Artificial Sequence
<220> FEATURE:
<223> OTHER INFORMATION: anti-PD-1 antibody

<400> SEQUENCE: 147

Glu Val Gln Leu Val Leu Ser Gly Gly Phe Val Gln Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Asn Pro Glu Arg Arg Leu Val Trp Val
            35                  40                  45
```

```
Ala Thr Ile Thr Gly Gly Arg Asn Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Thr Arg Gln Gly Tyr Asp Gly Tyr Thr Trp Phe Ala Tyr Trp Gly Gln
            100                 105                 110

Gly Thr Leu Val Thr Val Ser Ser
            115                 120
```

<210> SEQ ID NO 148
<211> LENGTH: 447
<212> TYPE: PRT
<213> ORGANISM: Artificial Sequence
<220> FEATURE:
<223> OTHER INFORMATION: anti-PD-1 antibody

<400> SEQUENCE: 148

```
Glu Val Gln Leu Val Leu Ser Gly Gly Gly Phe Val Gln Pro Gly Gly
 1               5                  10                  15

Ser Leu Lys Leu Ser Cys Ala Ala Ser Gly Phe Thr Phe Ser Ser Tyr
                20                  25                  30

Ala Met Ser Trp Val Arg Gln Asn Pro Glu Arg Arg Leu Val Trp Val
            35                  40                  45

Ala Thr Ile Thr Gly Gly Arg Asn Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Thr Arg Gln Gly Tyr Asp Gly Tyr Thr Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 149
<211> LENGTH: 112
<212> TYPE: PRT
<213> ORGANISM: Artificial Sequence
<220> FEATURE:
<223> OTHER INFORMATION: anti-PD-1 antibody

<400> SEQUENCE: 149

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Pro Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Glu Leu Glu Ile Lys Arg
            100                 105                 110

<210> SEQ ID NO 150
<211> LENGTH: 218
<212> TYPE: PRT
<213> ORGANISM: Artificial Sequence
<220> FEATURE:
<223> OTHER INFORMATION: anti-PD-1 antibody

<400> SEQUENCE: 150

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met Asn Trp Phe Gln Gln Lys Pro Gly Gln Pro Pro
        35                  40                  45
```

```
Lys Leu Leu Ile Tyr Ala Ala Ser Asn Pro Gly Ser Gly Val Pro Ala
         50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Trp Thr Phe Gly Gly Gly Thr Glu Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 151
<211> LENGTH: 447
<212> TYPE: PRT
<213> ORGANISM: Artificial Sequence
<220> FEATURE:
<223> OTHER INFORMATION: anti-PD-1 antibody

<400> SEQUENCE: 151

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Tyr Met Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
     50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 152
<211> LENGTH: 218
<212> TYPE: PRT
<213> ORGANISM: Artificial Sequence
<220> FEATURE:
<223> OTHER INFORMATION: anti-PD-1 antibody

<400> SEQUENCE: 152

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110
```

```
Thr Val Ala Ala Pro Ser Val Phe Ile Phe Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 153
<211> LENGTH: 113
<212> TYPE: PRT
<213> ORGANISM: Artificial Sequence
<220> FEATURE:
<223> OTHER INFORMATION: anti-PD-1 antibody

<400> SEQUENCE: 153

```
Gln Val Gln Leu Val Glu Ser Gly Gly Gly Val Val Gln Pro Gly Arg
1               5                   10                  15
Ser Leu Arg Leu Asp Cys Lys Ala Ser Gly Ile Thr Phe Ser Asn Ser
            20                  25                  30
Gly Met His Trp Val Arg Gln Ala Pro Gly Lys Gly Leu Glu Trp Val
        35                  40                  45
Ala Val Ile Trp Tyr Asp Gly Ser Lys Arg Tyr Tyr Ala Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Thr Asn Asp Asp Tyr Trp Gly Gln Gly Thr Leu Val Thr Val Ser
            100                 105                 110
Ser
```

<210> SEQ ID NO 154
<211> LENGTH: 440
<212> TYPE: PRT
<213> ORGANISM: Artificial Sequence
<220> FEATURE:
<223> OTHER INFORMATION: anti-PD-1 antibody

<400> SEQUENCE: 154

```
Gln Val Gln Leu Val Glu Ser Gly Gly Gly Val Val Gln Pro Gly Arg
1               5                   10                  15
Ser Leu Arg Leu Asp Cys Lys Ala Ser Gly Ile Thr Phe Ser Asn Ser
            20                  25                  30
Gly Met His Trp Val Arg Gln Ala Pro Gly Lys Gly Leu Glu Trp Val
        35                  40                  45
Ala Val Ile Trp Tyr Asp Gly Ser Lys Arg Tyr Tyr Ala Asp Ser Val
    50                  55                  60
Lys Gly Arg Phe Thr Ile Ser Arg Asp Asn Ser Lys Asn Thr Leu Phe
65                  70                  75                  80
```

```
Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 155
<211> LENGTH: 108
<212> TYPE: PRT
<213> ORGANISM: Artificial Sequence
<220> FEATURE:
<223> OTHER INFORMATION: anti-PD-1 antibody

<400> SEQUENCE: 155
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg
                100                 105
```

<210> SEQ ID NO 156
<211> LENGTH: 214
<212> TYPE: PRT
<213> ORGANISM: Artificial Sequence
<220> FEATURE:
<223> OTHER INFORMATION: anti-PD-1 antibody

<400> SEQUENCE: 156

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 157
<211> LENGTH: 440
<212> TYPE: PRT
<213> ORGANISM: Artificial Sequence
<220> FEATURE:
<223> OTHER INFORMATION: anti-PD-1 antibody

<400> SEQUENCE: 157

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

```
Ser Arg Leu Thr Val Asp Lys Ser Arg Trp Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 158
<211> LENGTH: 214
<212> TYPE: PRT
<213> ORGANISM: Artificial Sequence
<220> FEATURE:
<223> OTHER INFORMATION: anti-PD-1 antibody

<400> SEQUENCE: 158

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 159
<211> LENGTH: 117
<212> TYPE: PRT
<213> ORGANISM: Artificial Sequence
<220> FEATURE:
<223> OTHER INFORMATION: anti-PD-1 antibody

<400> SEQUENCE: 159

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
```

```
                    35                  40                  45

Ser Gly Ile Ser Gly Gly Gly Arg Asp Thr Tyr Phe Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Gly Glu Asp Thr Ala Val Tyr Tyr Cys
                    85                  90                  95

Val Lys Trp Gly Asn Ile Tyr Phe Asp Tyr Trp Gly Gln Gly Thr Leu
                100                 105                 110

Val Thr Val Ser Ser
            115

<210> SEQ ID NO 160
<211> LENGTH: 107
<212> TYPE: PRT
<213> ORGANISM: Artificial Sequence
<220> FEATURE:
<223> OTHER INFORMATION: anti-PD-1 antibody

<400> SEQUENCE: 160

Asp Ile Gln Met Thr Gln Ser Pro Ser Ser Leu Ser Ala Ser Val Gly
 1               5                  10                  15

Asp Ser Ile Thr Ile Thr Cys Arg Ala Ser Leu Ser Ile Asn Thr Phe
                20                  25                  30

Leu Asn Trp Tyr Gln Gln Lys Pro Gly Lys Ala Pro Asn Leu Leu Ile
            35                  40                  45

Tyr Ala Ala Ser Ser Leu His Gly Gly Val Pro Ser Arg Phe Ser Gly
        50                  55                  60

Ser Gly Ser Gly Thr Asp Phe Thr Leu Thr Ile Arg Thr Leu Gln Pro
 65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
                100                 105

<210> SEQ ID NO 161
<211> LENGTH: 444
<212> TYPE: PRT
<213> ORGANISM: Artificial Sequence
<220> FEATURE:
<223> OTHER INFORMATION: anti-PD-1 antibody

<400> SEQUENCE: 161

Glu Val Gln Leu Leu Glu Ser Gly Gly Val Leu Val Gln Pro Gly Gly
 1               5                  10                  15

Ser Leu Arg Leu Ser Cys Ala Ala Ser Gly Phe Thr Phe Ser Asn Phe
                20                  25                  30

Gly Met Thr Trp Val Arg Gln Ala Pro Gly Lys Gly Leu Glu Trp Val
            35                  40                  45

Ser Gly Ile Ser Gly Gly Gly Arg Asp Thr Tyr Phe Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
                100                 105                 110
```

```
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 162
<211> LENGTH: 214
<212> TYPE: PRT
<213> ORGANISM: Artificial Sequence
<220> FEATURE:
<223> OTHER INFORMATION: anti-PD-1 antibody

<400> SEQUENCE: 162

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30
```

Leu Asn Trp Tyr Gln Gln Lys Pro Gly Lys Ala Pro Asn Leu Leu Ile
            35                  40                  45

Tyr Ala Ala Ser Ser Leu His Gly Gly Val Pro Ser Arg Phe Ser Gly
 50                  55                  60

Ser Gly Ser Gly Thr Asp Phe Thr Leu Thr Ile Arg Thr Leu Gln Pro
 65                  70                  75                  80

Glu Asp Phe Ala Thr Tyr Tyr Cys Gln Gln Ser Ser Asn Thr Pro Phe
                 85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 163
<211> LENGTH: 121
<212> TYPE: PRT
<213> ORGANISM: Artificial Sequence
<220> FEATURE:
<223> OTHER INFORMATION: anti-PD-L1 antibody

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
            115                 120

<210> SEQ ID NO 164
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 164

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 165
<211> LENGTH: 447
<212> TYPE: PRT
<213> ORGANISM: Artificial Sequence
<220> FEATURE:
<223> OTHER INFORMATION: anti-PD-L1 antibody

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 166
<211> LENGTH: 214
<212> TYPE: PRT
<213> ORGANISM: Artificial Sequence
<220> FEATURE:
<223> OTHER INFORMATION: anti-PD-L1 antibody

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 167
<211> LENGTH: 118
<212> TYPE: PRT
<213> ORGANISM: Artificial Sequence
<220> FEATURE:
<223> OTHER INFORMATION: anti-PD-L1 antibody

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 168
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 169
<211> LENGTH: 122
<212> TYPE: PRT

```
<213> ORGANISM: Artificial Sequence
<220> FEATURE:
<223> OTHER INFORMATION: anti-PD-L1 antibody

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 170
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 171
<211> LENGTH: 118
<212> TYPE: PRT
<213> ORGANISM: Artificial Sequence
<220> FEATURE:
<223> OTHER INFORMATION: anti-PD-L1 antibody

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

```
Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser
                115

<210> SEQ ID NO 172
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 172

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
                100                 105

<210> SEQ ID NO 173
<211> LENGTH: 118
<212> TYPE: PRT
<213> ORGANISM: Artificial Sequence
<220> FEATURE:
<223> OTHER INFORMATION: anti-PD-L1 antibody

<400> SEQUENCE: 173

Glu Val Gln Leu Val Glu Ser Cys Gly Gly Leu Val Gln Pro Gly Gly
 1               5                  10                  15

Ser Leu Arg Leu Ser Cys Ala Ala Ser Gly Phe Thr Phe Ser Asp Ser
                 20                  25                  30

Trp Ile His Trp Val Arg Gln Ala Pro Gly Lys Gly Leu Glu Trp Val
             35                  40                  45

Ala Trp Ile Ser Pro Tyr Gly Gly Ser Thr Tyr Tyr Ala Asp Ser Val
        50                  55                  60

Lys Gly Arg Phe Thr Ile Ser Arg Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ala
```

-continued

115

<210> SEQ ID NO 174
<211> LENGTH: 118
<212> TYPE: PRT
<213> ORGANISM: Artificial Sequence
<220> FEATURE:
<223> OTHER INFORMATION: anti-PD-L1 antibody

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Arg Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 175
<211> LENGTH: 118
<212> TYPE: PRT
<213> ORGANISM: Artificial Sequence
<220> FEATURE:
<223> OTHER INFORMATION: anti-PD-L1 antibody

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Trp Ile His Trp Val Arg Gln Ala Pro Gly Lys Gly Leu Glu Trp Val
        35                  40                  45

Ala Trp Ile Leu Pro Tyr Gly Gly Ser Ser Tyr Tyr Ala Asp Ser Val
    50                  55                  60

Lys Gly Arg Phe Thr Ile Ser Arg Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 176
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 177
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Val Pro Trp
                85                  90                  95

Thr Phe Gly Gln Gly Thr Lys Val Glu Ile Lys Arg
            100                 105

<210> SEQ ID NO 178
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ala Pro Pro Trp

```
                    85                  90                  95

Thr Phe Gly Gln Gly Thr Lys Val Glu Ile Lys Arg
                100                 105

<210> SEQ ID NO 179
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Pro Trp
                85                  90                  95

Thr Phe Gly Gln Gly Thr Lys Val Glu Ile Lys Arg
                100                 105

<210> SEQ ID NO 180
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Asn Thr Phe
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Pro Arg
                85                  90                  95

Thr Phe Gly Gln Gly Thr Lys Val Glu Ile Lys Arg
                100                 105

<210> SEQ ID NO 181
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 181

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Val Pro Arg
                85                  90                  95

Thr Phe Gly Gln Gly Thr Lys Val Glu Ile Lys Arg
            100                 105

<210> SEQ ID NO 182
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Phe Thr Pro Pro
                85                  90                  95

Thr Phe Gly Gln Gly Thr Lys Val Glu Ile Lys Arg
            100                 105

<210> SEQ ID NO 183
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ile Thr Pro Thr
                85                  90                  95

Thr Phe Gly Gln Gly Thr Lys Val Glu Ile Lys Arg
```

<210> SEQ ID NO 184
<211> LENGTH: 107
<212> TYPE: PRT
<213> ORGANISM: Artificial Sequence
<220> FEATURE:
<223> OTHER INFORMATION: anti-PD-L1 antibody

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Pro Pro Thr
                85                  90                  95

Phe Gly Gln Gly Thr Lys Val Glu Ile Lys Arg
            100                 105

<210> SEQ ID NO 185
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Thr Pro Pro
                85                  90                  95

Thr Phe Gly Gln Gly Thr Lys Val Glu Ile Lys Arg
            100                 105

<210> SEQ ID NO 186
<211> LENGTH: 450
<212> TYPE: PRT
<213> ORGANISM: Artificial Sequence
<220> FEATURE:
<223> OTHER INFORMATION: anti-PD-L1 antibody

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Lys Leu Gly Thr Val Thr Thr Val Asp Tyr Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
 210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
         355                 360                 365

Thr Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly Lys
    450

<210> SEQ ID NO 187
<211> LENGTH: 216
<212> TYPE: PRT
<213> ORGANISM: Artificial Sequence
<220> FEATURE:
<223> OTHER INFORMATION: anti-PD-L1 antibody

<400> SEQUENCE: 187

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 188
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Leu Phe Thr Pro Pro
                85                  90                  95

Thr Phe Gly Gln Gly Thr Lys Val Glu Ile Lys Arg
            100                 105

<210> SEQ ID NO 189
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Tyr Thr Pro Pro
                85                  90                  95

Thr Phe Gly Gln Gly Thr Lys Val Glu Ile Lys Arg
            100                 105

<210> SEQ ID NO 190
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Tyr His Pro Pro
                85                  90                  95

Thr Phe Gly Gln Gly Thr Lys Val Glu Ile Lys Arg
            100                 105

<210> SEQ ID NO 191
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 191
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Tyr Ile Pro Pro
                85                  90                  95

Thr Phe Gly Gln Gly Thr Lys Val Glu Ile Lys Arg
            100                 105

<210> SEQ ID NO 192
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Tyr Thr Pro Tyr
                85                  90                  95

Thr Phe Gly Gln Gly Thr Lys Val Glu Ile Lys Arg
            100                 105

<210> SEQ ID NO 193
<211> LENGTH: 108
<212> TYPE: PRT
<213> ORGANISM: Artificial Sequence
<220> FEATURE:
<223> OTHER INFORMATION: anti-PD-L1 antibody

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Phe Ile Pro Pro
                85                  90                  95

```
Thr Phe Gly Gln Gly Thr Lys Val Glu Ile Lys Arg
            100                 105
```

<210> SEQ ID NO 194
<211> LENGTH: 118
<212> TYPE: PRT
<213> ORGANISM: Artificial Sequence
<220> FEATURE:
<223> OTHER INFORMATION: anti-PD-L1 antibody

<400> SEQUENCE: 194

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
            115
```

<210> SEQ ID NO 195
<211> LENGTH: 106
<212> TYPE: PRT
<213> ORGANISM: Artificial Sequence
<220> FEATURE:
<223> OTHER INFORMATION: anti-PD-L1 antibody

<400> SEQUENCE: 195

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Trp Tyr Ser
        35                  40                  45

Ala Ser Phe Leu Tyr Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Tyr Leu Tyr His Pro Ala Thr Phe
                85                  90                  95

Gly Gln Gly Thr Lys Val Glu Ile Lys Arg
            100                 105
```

<210> SEQ ID NO 196
<211> LENGTH: 448
<212> TYPE: PRT
<213> ORGANISM: Artificial Sequence
<220> FEATURE:
<223> OTHER INFORMATION: anti-PD-L1 antibody

<400> SEQUENCE: 196

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
50                      55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
                420                 425                 430
Leu His Asn His Tyr Thr Gln Lys Ser Leu Ser Leu Ser Pro Gly Lys
            435                 440                 445

<210> SEQ ID NO 197
<211> LENGTH: 214
<212> TYPE: PRT
<213> ORGANISM: Artificial Sequence
<220> FEATURE:
<223> OTHER INFORMATION: anti-PD-L1 antibody

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 198
<211> LENGTH: 192
<212> TYPE: PRT
<213> ORGANISM: Artificial Sequence
<220> FEATURE:
<223> OTHER INFORMATION: >HsBAX_Q07812-1(UniProtKB)

<400> SEQUENCE: 198

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
50                  55                  60
```

```
Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 199
<211> LENGTH: 211
<212> TYPE: PRT
<213> ORGANISM: Artificial Sequence
<220> FEATURE:
<223> OTHER INFORMATION: >HsBAK1_Q16611-1(UniProtKB)

<400> SEQUENCE: 199

Met Ala Ser Gly Gln Gly Pro Gly Pro Pro Arg Gln Glu Cys Gly Glu
  1               5                  10                  15

Pro Ala Leu Pro Ser Ala Ser Glu Glu Gln Val Ala Gln Asp Thr Glu
             20                  25                  30

Glu Val Phe Arg Ser Tyr Val Phe Tyr Arg His Gln Gln Glu Gln Glu
         35                  40                  45

Ala Glu Gly Val Ala Ala Pro Ala Asp Pro Glu Met Val Thr Leu Pro
     50                  55                  60

Leu Gln Pro Ser Ser Thr Met Gly Gln Val Gly Arg Gln Leu Ala Ile
 65                  70                  75                  80

Ile Gly Asp Asp Ile Asn Arg Arg Tyr Asp Ser Glu Phe Gln Thr Met
                 85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
        115                 120                 125

Val Ala Leu Leu Gly Phe Gly Tyr Arg Leu Ala Leu His Val Tyr Gln
    130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205

Phe Lys Ser
    210

<210> SEQ ID NO 200
<211> LENGTH: 159
```

```
<212> TYPE: PRT
<213> ORGANISM: Artificial Sequence
<220> FEATURE:
<223> OTHER INFORMATION: >HsBIK_Q13323-1(UniProtKB)

<400> SEQUENCE: 200
```

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Arg Leu Ala Cys Ile Gly
    50                  55                  60

Asp Glu Met Asp Val Ser Leu Arg Ala Pro Arg Leu Ala Gln Leu Ser
65                  70                  75                  80

Glu Val Ala Met His Ser Leu Gly Leu Ala Phe Ile Tyr Asp Gln Thr
                85                  90                  95

Glu Asp Ile Arg Asp Val Leu Arg Ser Phe Met Asp Gly Phe Thr Thr
            100                 105                 110

Leu Lys Glu Asn Ile Met Arg Phe Trp Arg Ser Pro Asn Pro Gly Ser
        115                 120                 125

Trp Val Ser Cys Glu Gln Val Leu Leu Ala Leu Leu Leu Leu Leu Ala
    130                 135                 140

Leu Leu Leu Pro Leu Leu Ser Gly Gly Leu His Leu Leu Leu Lys
145                 150                 155

```
<210> SEQ ID NO 201
<211> LENGTH: 195
<212> TYPE: PRT
<213> ORGANISM: Artificial Sequence
<220> FEATURE:
<223> OTHER INFORMATION: >HsBID_P55957-1(UniProtKB)

<400> SEQUENCE: 201
```

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

```
Phe Ile Asn Gln Asn Leu Arg Thr Tyr Val Arg Ser Leu Ala Arg Asn
            180                 185                 190
Gly Met Asp
        195

<210> SEQ ID NO 202
<211> LENGTH: 113
<212> TYPE: PRT
<213> ORGANISM: Artificial Sequence
<220> FEATURE:
<223> OTHER INFORMATION: IL-13 Cytokine

<400> SEQUENCE: 202

Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn

<210> SEQ ID NO 203
<211> LENGTH: 330
<212> TYPE: PRT
<213> ORGANISM: Artificial Sequence
<220> FEATURE:
<223> OTHER INFORMATION: IgG1

<400> SEQUENCE: 203

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 204
<211> LENGTH: 326
<212> TYPE: PRT
<213> ORGANISM: Artificial Sequence
<220> FEATURE:
<223> OTHER INFORMATION: IgG2

<400> SEQUENCE: 204

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190
```

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 205
<211> LENGTH: 377
<212> TYPE: PRT
<213> ORGANISM: Artificial Sequence
<220> FEATURE:
<223> OTHER INFORMATION: IgG3

<400> SEQUENCE: 205

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

```
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Phe Thr Gln
    355                 360                 365

Lys Ser Leu Ser Leu Ser Pro Gly Lys
370                 375

<210> SEQ ID NO 206
<211> LENGTH: 327
<212> TYPE: PRT
<213> ORGANISM: Artificial Sequence
<220> FEATURE:
<223> OTHER INFORMATION: IgG4

<400> SEQUENCE: 206

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
                325
```